US012441994B2

(12) United States Patent
Baltes

(10) Patent No.: US 12,441,994 B2
(45) Date of Patent: *Oct. 14, 2025

(54) METHODS FOR TARGETED INSERTION OF DNA IN GENES

(71) Applicant: BLUEALLELE CORPORATION, Oakdale, MN (US)

(72) Inventor: Nicholas J. Baltes, Oakdale, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,758

(22) Filed: Dec. 1, 2023

(65) Prior Publication Data

US 2024/0141319 A1 May 2, 2024

Related U.S. Application Data

(63) Continuation of application No. 17/830,011, filed on Jun. 1, 2022, now Pat. No. 12,054,706, which is a continuation of application No. 17/590,613, filed on Feb. 1, 2022, now Pat. No. 11,365,407, which is a continuation of application No. 17/366,290, filed on Jul. 2, 2021, now Pat. No. 11,254,930, which is a continuation of application No. 16/800,444, filed on Feb. 25, 2020, now Pat. No. 11,091,756, which is a continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
*C12N 15/10* (2006.01)
*C12N 15/86* (2006.01)
*C12N 15/90* (2006.01)

(52) U.S. Cl.
CPC ........... *C12N 15/102* (2013.01); *C12N 15/86* (2013.01); *C12N 15/907* (2013.01); *C12N 2310/20* (2017.05); *C12N 2800/80* (2013.01)

(58) Field of Classification Search
None
See application file for complete search history.

(56) References Cited

U.S. PATENT DOCUMENTS 6,228,639 B1 5/2001 Gaitanaris
6,740,503 B1 5/2004 Harrington et al.
7,005,299 B1 2/2006 Smith et al.
9,255,250 B2 2/2016 Gregory et al.
9,493,827 B2 11/2016 Von Kalle et al.
9,677,070 B2 6/2017 Allison et al.
9,765,404 B2 9/2017 Sastry-Dent et al.
9,873,894 B2 1/2018 Conway et al.
9,877,988 B2 1/2018 Rebar
10,240,115 B2 3/2019 Tang
10,648,001 B2 5/2020 Rebar
10,888,628 B2 1/2021 Wang et al.
11,091,756 B2 8/2021 Baltes
11,254,930 B2 2/2022 Baltes
11,268,086 B2 3/2022 Maeder et al.
11,365,407 B2 6/2022 Baltes
11,993,770 B2 5/2024 Baltes
12,054,706 B2 8/2024 Baltes
2004/0106566 A1 6/2004 Lin et al.
2005/0064474 A1 3/2005 Umov
2005/0208489 A1 9/2005 Carroll
2012/0046349 A1 2/2012 Bell et al.
2013/0280222 A1 10/2013 Kay et al.
2014/0130205 A1 5/2014 Bhyri
2016/0040155 A1 2/2016 Maizels et al.
2016/0102322 A1 4/2016 Ravinder et al.
2016/0281111 A1 9/2016 Cotta-Ramusino et al.
2017/0073664 A1 3/2017 Mccafferty et al.
2017/0119906 A1 5/2017 Riley
2018/0023075 A1 1/2018 Liang et al.
2018/0071406 A1 3/2018 Chuah et al.
2018/0110877 A1 4/2018 Wilson et al.
2018/0112213 A1 4/2018 Welstead et al.
2018/0119123 A1 5/2018 Gori et al.
2018/0273932 A1 9/2018 Bothmer et al.
2018/0296603 A1 10/2018 Gori et al.
2018/0362590 A1 12/2018 Monds et al.
2019/0032089 A1 1/2019 Townes et al.
2019/0032092 A1 1/2019 Gong et al.
(Continued)

FOREIGN PATENT DOCUMENTS

BR 102014027 448 A2 9/2015
CA 2906747 A1 9/2014
(Continued)

OTHER PUBLICATIONS

Intellia Therapeutics, “Q3 2018 Earnings and Corporate Development”, Powerpoint, 23 pages, presented Oct. 31, 2018, 1-23 (Year: 2018).*
Blueallele, LLC in connection with PCT/US2019/058857 filed Oct. 30, 2019, “The International Search Report and the Written Opinion of the International Searching Authority, or the Declaration”, 19 pages, mailed Jun. 23, 2020.
Robert, Francois, “Bidirectional terminators: an underestimated aspect of gene regulation”, Curr Genet, vol. 64, pp. 389-391, 2018.
Ouyang et al., “CRISPR/Cas9-Targeted Deletion of Polyglutamine in Spinocerebellar Ataxia Type 3-Derived Induced Pluripotent Stem Cells”, vol. 27, No. 11, pp. 756-770, 2018.
(Continued)

*Primary Examiner* — Anoop K Singh
(74) *Attorney, Agent, or Firm* — Arrigo, Lee, Guttman & Mouta-Bellum, LLP; Carla Mouta-Bellum

(57) ABSTRACT

Methods and compositions for modifying the coding sequence of endogenous genes using rare-cutting endonucleases and transposases. The methods and compositions described herein can be used to modify the coding sequence of endogenous genes.

19 Claims, 8 Drawing Sheets

Specification includes a Sequence Listing.

(56) References Cited

U.S. PATENT DOCUMENTS

| | | | | |
|---|---|---|---|---|
| 2019/0032156 | A1 | 1/2019 | Gong et al. | |
| 2019/0093114 | A1 | 3/2019 | Bower et al. | |
| 2019/0134221 | A1 | 5/2019 | Bumcrot et al. | |
| 2019/0136210 | A1 | 5/2019 | Cotta-Ramusino et al. | |
| 2019/0276850 | A1 | 9/2019 | Brinkmann et al. | |
| 2019/0330603 | A1 | 10/2019 | Ahlfors et al. | |
| 2019/0390189 | A1 | 12/2019 | Lee et al. | |
| 2020/0040362 | A1* | 2/2020 | Carlo | C12N 15/111 |
| 2020/0231974 | A1 | 7/2020 | Jarvis et al. | |
| 2020/0270617 | A1* | 8/2020 | Finn | C12N 15/113 |
| 2020/0270716 | A1 | 8/2020 | Finn | |
| 2024/0141317 | A1 | 5/2024 | Baltes | |
| 2024/0141319 | A1 | 5/2024 | Baltes | |
| 2024/0141320 | A1 | 5/2024 | Baltes | |
| 2024/0141321 | A1 | 5/2024 | Baltes | |
| 2024/0141322 | A1 | 5/2024 | Baltes | |

FOREIGN PATENT DOCUMENTS

| | | | | |
|---|---|---|---|---|
| EP | 2893025 | B1 | 7/2015 | |
| EP | 3114227 | A1 | 1/2017 | |
| EP | 3122880 | A2 | 2/2017 | |
| EP | 3344771 | A1 | 7/2018 | |
| EP | 3375877 | A1 | 9/2018 | |
| EP | 3426784 | A1 | 1/2019 | |
| EP | 3556858 | A2 | 10/2019 | |
| EP | 3592140 | A1 | 1/2020 | |
| EP | 3080274 | | 6/2020 | |
| ES | 2653212 | T3 | 2/2018 | |
| ES | 2699848 | T3 | 2/2019 | |
| ES | 2730378 | T3 | 11/2019 | |
| JP | 2020530769 | A | 10/2020 | |
| WO | 2010097437 | A1 | 9/2010 | |
| WO | 2012051343 | A1 | 4/2012 | |
| WO | 2013044008 | | 3/2013 | |
| WO | 2013075008 | A1 | 5/2013 | |
| WO | 2013169802 | A1 | 11/2013 | |
| WO | 2014011237 | A1 | 1/2014 | |
| WO | 2014089212 | | 6/2014 | |
| WO | 2014186585 | | 11/2014 | |
| WO | 2015017866 | A1 | 2/2015 | |
| WO | 2015089046 | | 6/2015 | |
| WO | WO-2015089351 | A1 * | 6/2015 | A01K 67/0276 |
| WO | 2015127439 | | 8/2015 | |
| WO | 2015153780 | A1 | 10/2015 | |
| WO | 2015173436 | A1 | 11/2015 | |
| WO | 2016073990 | A2 | 5/2016 | |
| WO | 2016109840 | A2 | 7/2016 | |
| WO | 2016161380 | A1 | 10/2016 | |
| WO | 2016172727 | A1 | 10/2016 | |
| WO | 2016182959 | A8 | 11/2016 | |
| WO | 2017048995 | A1 | 3/2017 | |
| WO | 2017123757 | A1 | 7/2017 | |
| WO | 2017155408 | A1 | 9/2017 | |
| WO | 2017158422 | | 9/2017 | |
| WO | 2018009562 | A1 | 1/2018 | |
| WO | WO-2018009534 | A1 * | 1/2018 | A61K 38/46 |
| WO | 2018131551 | | 7/2018 | |
| WO | 2018195555 | A1 | 10/2018 | |
| WO | 2018197020 | A1 | 11/2018 | |
| WO | 2019005851 | A1 | 1/2019 | |
| WO | 2019092505 | A1 | 5/2019 | |
| WO | 2019113149 | A1 | 6/2019 | |
| WO | 2019118875 | A1 | 6/2019 | |
| WO | 2019157326 | A1 | 8/2019 | |
| WO | 2019157326 | A2 | 9/2019 | |
| WO | 2019178500 | | 9/2019 | |
| WO | 2019183123 | A1 | 9/2019 | |
| WO | 2019210216 | A2 | 10/2019 | |
| WO | 020082042 | A2 | 4/2020 | |
| WO | 2020081438 | | 4/2020 | |
| WO | 2020082041 | A1 | 4/2020 | |
| WO | 2020082046 | A2 | 4/2020 | |
| WO | 2020082047 | A1 | 4/2020 | |

OTHER PUBLICATIONS

Blueallele, LLC in connection with PCTUS2019/056083 filed Oct. 14, 2019, "The International Search Report and the Written Opinion of the International Searching Authority, or the Declaration", 21 pages, mailed Dec. 19, 2019.

Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.

Gilles et al., "Efficient CRISPR-mediated gene targeting and transgene replacement in the beetle *Tribolium castaneum*", The Company of Biologists, vol. 142, pp. 2832-2839, Jun. 29, 2015.

Hahm et al., "Construction of retroviral vectors with enhanced efficiency oftransgene expression", Journal of Virological Methods, vol. 121, pp. 127-136, May 27, 2004.

Hildinger et al., "Design of 5' Untranslated Sequences in Retroviral Vectors Developed for Medical Use", Journal of Virology, vol. 73, No. 5, pp. 4083-4089, May 1999.

Intellia Therapeutics, "Q3 2018 Earnings and Corporate Development", Powerpoint, 23 pages, presented Oct. 31, 2018.

Ruan et al., "Highly efficient CRISPR/Cas9-mediated transgene knockin at the H11 locus in pigs", Scientific Reports, 10 pages, Sep. 18, 2015.

Suzuki et al., "In vivo genome editing via CRISPR/Cas9 mediated homology-independent targeted integration", Nature, vol. 540, 24 pages, Dec. 1, 2016.

Uno et al., "CRISPR/Cas9-induced transgene insertion and telomere-associated truncation of a single human chromosome for chromosome engineering in CHO and A9 cells", Scientific Reports, 10 pages, Oct. 6, 2017.

Yao et al., "Homology-mediated end joining-based targeted integration using CRISPR/Cas9", Cell Research, vol. 27, pp. 801-814, Apr. 6, 2017.

Sheng et al Canadian Journal of Microbiology, 445-454 (Year: 2014).

Ryu et al Plant Molecular Biology 54: 489-502 (Year: 2004).

Senis et al Nucleic acid Res. , 45(1), e3 (Year: 2016).

Kaiser Science, 317, 580 (Year: 2007).

Frank et al N. Engl. J Med. Jul 9;361 (2): 161-9 (Year: 2009).

Edelstein Journal Gene Med., 597-602 (Year: 2004).

High Nature, 435, 577-579 (Year: 2005).

Ramirez Nature Methods, 5(5): 374-375 (Year: 2008).

Li Nature, Jul. 14,, 475, 7355, 217-221 (Year: 2011).

Christian Genetics, 757-761 (Year: 2010).

Hauschild PNAS, 108( 29), 12013-12017 (Year: 2011).

Hsu et al Nat Biotechnology. Sep;31 (9):827-32 (Year: 2013).

Lee et al., (Drug Discovery Today: Disease Models, vol. 20, 13-20 (Year: 2016).

Kosicki et al Nature Biotechnology, 36, 765-771 (Year: 2018).

Robert et al Curr Genetics, 64(2):389-391 (Year: 2018).

Cox et al , Nature Medicine 21 (2), 121-13 (Year: 2015).

Kuscu et al Nature biotechnology, 32(7), 677 (Year: 2014).

Kleinstiver Nature, 523, 481-485 (Year: 2015).

Pluta et al. (Acta Biochimica Polonica. Nov. 23, 2009. 54(4): 531-595) (Year: 2009).

Kurosaki et al. (Journal of Human Genetics (2011) 56, 727-733). (Year: 2011).

Great Britain Search Report, issued Feb. 8, 2023, in connection with Great Britain Application No. GB2300487.2, 1 page.

Ohmori et al. "CRISPR/Cas9-mediated genome editing via postnatal administration of AAV vector cures haemophilia B mice", Sci Rep, Jun. 2, 20173, vol. 7, No. 1, article No. 4159 (11 pages).

Finn, Jonathan Ph.D. "Supra-therapeutic levels of transgene expression achieved in vivo by CRISPR/Cas9 mediated targeted gene insertion", 26thAnnual Congress of the European Society of Cell Therapy, Oct. 18, 2018, (14 pages).

Yew et al. Human Gene Therapy 8:575-584 (Year 1997).

Aschauer et al., Analysis of Transduction Efficiency, Tropism and Axonal Transport of AAV Stereotypes 1, 2, 5, 6, 8 and 9 in the Mouse Brain, PLoS One Sep. 27, 2013;8(9):e76310.

(56) References Cited

OTHER PUBLICATIONS

Auer et al., CRISPR/Cas9-mediated conversion of eGFP- into Gal4-transgenic lines in zebrafish, Nat Protoc Dec. 2014;9(12):2823-40.
Auer et al., Highly efficient CRISPR/Cas9-mediated knock-in zebrafish by homology-independent DNA-repair, Genome Res Jan. 2014,24(1):142-53.
Barket et al., Subretinal delivery of adeno-associated virus serotype 2 results in minimal immune responses that allow repeat vector administration in immunocompetent mice, J Gene Med Jun. 2009;11(6):486-497.
Bell et al., Inverse zonation of hepatocyte transduction with AAV vectors between mice and non-human primates., Mol Genet Metab Nov. 2011;104(3):395-403.
Bill et al., Genomic DNA double-strand breaks are targets for hepadnaviral DNA interogation, Proc Natl Acad Sci U S A Jul. 27, 2004;101(30):11135-40.
Brocchieri and Karlin Protein length in eukaryotic and prokaryotic proteomes, Nucleic Acids Res Jun. 10, 2005;33(10):3390-400.
Chen et al., Hemophilia A ameliorated in mice by CRISPR-based in vivo genome editing of human Factor VIII, Sci Rep Nov. 14, 2019;9(1):16838.
Chu et al., Efficient generation of Rosa26 knock-in mice using CRISPR/Cas9 in CB57BL/6 zygotes, BMC Biotechnol Jan. 16, 2016;16:4.
Chuah et al., Liver-Specific Transcriptional Modules Identified Genome-Wide In Silico Analysis Enable Efficient Gene Therapy in Mice and Non-Human Primates, Mol Ther Sep. 2014;22(9):1605-13.
Cui et al., A CRISPR/Cas9-Mediated, Homology-Independent Tool Developed for Targeted Genome Integration in Yarrowia lipolytica, Appl Environ Microbiol Feb. 26, 2021;87(6):e02666-20.
De Caneva et al., Coupling AAV-mediated promoterless gene targeting to SaCas9 nuclease to efficiently correct liver metabolic diseases, JCI Insight Aug. 8, 2019;4(15):e128863.
Diao et al., Plug-and-Play Genetic Access to Drosophila Cell Types using Exchangeable Exon Cassettes, Cell Rep Mar. 3, 2015;10(8):1410-21.
Finn et al., A Single Administration of CRISPR/Cas9 Lipid Nanoparticles Achieves Robust and Persistent In Vivo Genome Editing , Cell Rep (2018) Feb. 27;22(9):2227-2235.
Friedland et al., Characterization of Staphylococcus aureus Cas9: a smaller Cas9 for all-in-one adeno-associated virus delivery and paired nickase applications, Genome Biol Nov. 2, 20154:16:257.
Gabriel et al., An unbiased genome-wide analysis of zinc-finger nuclease specificity, Nat Biotechnol Aug. 7, 2011;29(9):816-23.
Geisinger et al., In vivo blunt-end cloning through CRISPR/Cas9-facilitated non-homologous end-joining, Nucleic Acids Res May 5, 2016;44(8):e76.
Guan et al., CRISPR/Cas9-mediated somatic correction of a novel coagulator factor IX gene mutation ameliorates hemophilia in mouse , EMBO Mol Med May 2, 2016;8(5):477-88.
Hashimoto et al., Electroporation enables the efficient mRNA delivery into the mouse zygotes and facilitates CRISPR/Cas9-based genome editing, Sci Rep Aug. 5, 2015:5:12658.
He et al., Knock-in of large reporter genes in human cells via CRISPR/Cas9-induced homology-dependent and independent DNA repair, Nucleic Acids Res May 19, 2016;44(9):e85.
Hocquemiller et al., Adeno-Associated Virus-Based Gene Therapy for CNS Diseases, Hum Gene Ther Jul. 2016;27(7):478-96.
Hu et al., In Vivo CRISPR/Cas9-Mediated Genome Editing Mitigates Photoreceptor Degeneration in a Mouse Model of X-Linked Retinitis Pigmentosa, Invest Ophthalmol Vis Sci Apr. 9, 2020;61(4):31.
Hung et al., AAV-Mediated CRISPR/Cas Gene Editing of Retinal Cells In Vivo, Invest Ophthalmol Vis Sci Jun. 1, 2016;57(7):3470-6.
Ibraheim et al., All-in-One Adeno-associated Virus Delivery and Genome Editing by Neisseria meningitidis Cas9 in vivo, Genome Biol Sep. 19, 2018;19(1):137.
Jarrett et al., Somatic editing of Ldlr with AAV-CRISPR is an efficient tool for atherosclerosis research, Arterioscler Thromb Vasc Biol Sep. 2018;38(9):1997-2006.
Jarrett et al., Somatic genome editing with CRISPR/Cas9 generates and corrects a metabolic disease, Sci Rep Mar. 16, 2017:7:44624.
Jiang et al., A non-viral CRISPR/Cas9 delivery system for therapeutically targeting HBV DNA and pcsk9 in vivo, Cell Res Mar. 2017;27(3):440-443.
Kawabe et al., Targeted knock-in of an scFv-Fc antibody gene into the hprt locus of Chinese hamster ovary cells using CRISPR/Cas9 and CRIS-PITCh systems , J Biosci Bioeng May 2018;125(5):599-605.
Jul. 8, 2024, Exhibit 4, Intellia Corporate Overview, Nov. 2022, 92 pages.
Jul. 8, 2024, Exhibit 5, Feb. 22, 2024 Intellia 10-K, 24 pages.
Jul. 8, 2024, Exhibit 6, ESGCT Presentation, 16 pages.
Jul. 8, 2024, Exhibit 7, Oct. 2021 Intellia Corp Overview, 36 pages.
Jul. 8, 2024, Exhibit 9, Civil Cover Sheet, 2 pages.
Jul. 8, 2024, Plaintiff's Complaint for Patent Infringement, 19 pages.
Sep. 12, 2024, Declaration re [20] Motion to Dismiss for Failure to State a Claim (of Daniel Hemming), 5 pages.
Sep. 12, 2024, Exhibit A, Jun. 26, 2021 Intellia Press Release, 6 pages.
Sep. 12, 2024, Exhibit B, 2018 ESGCT Stats, 3 pages.
Sep. 12, 2024, Exhibit C, 2018 ESGCT Abstract Book, 186 pages.
Sep. 12, 2024, Exhibit D, Oct. 18, 2018 Intellia Press Release, 4 pages.
Sep. 12, 2024, Exhibit E, REGN Phase 1 trial—clinicaltrials.gov, 18 pages.
Sep. 12, 2024, Exhibit F, Jul. 30, 2024 Intellia Press Release, 3 pages.
Sep. 12, 2024, Exhibit G, Blueallele Corporation—De Certified Docs, 8 pages.
Sep. 12, 2024, Exhibit H, Baltes 2021 CV, 5 pages.
Sep. 12, 2024, Exhibit J, Kuleon Bio—Forest Quote, 5 pages.
Sep. 12, 2024, Exhibit K, CMC-Information-Human-Gene-Therapy-IND-Applications_Jan_2020, 57 pages.
Sep. 12, 2024, Exhibit L, Human-Gene-Therapy-for-Hemophilia_Jan_2020)(Smith, Rodger), 18 pages.
Sep. 23, 2024, D25 so Ordered Stip for EOT to Resp to MTD or Amd Complaint, 1 page.
Oct. 16, 2024, D26 Order—Oral Arg on MTD, 1 page.
Oct. 23, 2024, D27 BlueAllele Ans Brief IOT MTD, 23 pages.
Oct. 28, 2024, D28 Stip and Prop Order for EOT, 2 pages.
Oct. 28, 2024, D29 So Ordered Stip and Order for EOT, 2 pages.
Nov. 8, 2024, D30 Def's Reply Brief ISO MTD, 16 pages.
Nov. 19, 2024, D31 Def's Mot for Exemption of Persons fr Standing order re Personal Electronics, 3 pages.
Nov. 19, 2024, D32 SO Ordered D31 Mot for Exemption of Persons fr Standing Order re Personal Electronic Devices, 3 pages.
Nov. 19, 2024, D33 Pltf's NOA of Warren Mabey, 2 pages.
Dec. 9, 2024, D035 Memo Opinion, 8 pages.
Dec. 9, 2024, D036 Order Denying Def's MTD, 1 page.
Dec. 16, 2024, D038 Order granting D37 Stip for EOT and Commencing Discovery, 2 pages.
Dec. 16, 2024, D37 Stip for EOT and Commence Discovery, 2 pages.
Dec. 20, 2024, D39 NOS of Pltfs 1st Set of Discovery Reqs, 2 pages.
Dec. 23, 2024, D40 NOS of Def's 1st Set of RPFs and Rogs, 3 pages.
Jan. 6, 2025, Exhibit 2, Q3 2018 Earnings and Corporate Developments, Oct. 31, 2018, 24 pages.
Jan. 6, 2025, Exhibit 3, Calyxt names Joseph B. Saluri as General Counsel & EVP, Corporate Development, 3 pages.
Jan. 6, 2025, Exhibit 4, Second declaration of Nicholas J. Baltes, PH.D., 22 pages.
Jan. 6, 2025, Exhibit 5, Transformative Technology for Correcting Gene Function in vivo, 5 pages.
Jan. 6, 2025, Exhibit 1, Intellia Therapeutics Announces Third Quarter 2018 Financial Results and Corporate Developments, Oct. 31, 2018, 6 pages.

(56) References Cited

OTHER PUBLICATIONS

Jan. 6, 2025, Exhibit 8, BlueAllele Presentation Apr. 2022, 13 pages.
Jan. 6, 2025, Exhibit 9, Our Pipeline—Intellia Therapeutics, 5 pages.
Jan. 6, 2025, Intellia's Counterclaims, Answer, and Affirmative Defenses To Blueallele's Complaint, 67 pages.
Jan. 17, 2025, Stipulation and [Proposed] Order To Extend Time and Proceed With Discovery From Blueallele, 2 pages.
Jan. 21, 2025, D43 Order setting Initial Pretrial videoconf for Feb. 21, 2025, 8 pages.
Jan. 21, 2025, D44 Order not approving Stip for EOT re D42, 1 page.
Jan. 27, 2025, [Proposed] Order Granting Plaintiff's Motion To Dismiss Defendant's Counterclaims, 1 page.
Jan. 27, 2025, Certification Regarding Motion To Dismiss Counterclaims Pursuant To Policies and Procedures of Judge John F. Murphy, 2 pages.
Jan. 27, 2025, Confirmation receipt for U.S. Appl. No. 62/747,393, Exhibit 3, 119 pages.
Jan. 27, 2025, Declaration of Jonathan A. Bell in Support of Plaintiff's Motion To Dismiss Defendant's Counterclaims, 2 pages.
Jan. 27, 2025, Exhibit 1, Office action summary, 15 pages.
Jan. 27, 2025, Exhibit 2, Bloomberg News Article, 3 pages.
Yang et al., A dual AAV system enables the Cas9-mediated correction of a metabolic liver disease in newborn mice, Nat Biotechnol Mar. 2016;34(3):334-8.
Yao et al., Homology-mediated end joining-based targeted integration using CRISPR/Cas9, Cell Res Jun. 2017;27(6):801-814.
Yao et al., 2 CRISPR/Cas9—Mediated Precise Targeted Integration In Vivo Using a Double Cut Donor with Short Homology Arms, EBioMedicine Jun. 2017:20:19-26.
Yin et al., Genome editing with Cas9 in adult mice corrects a disease mutation and phenotype, Nat Biotechnol Jun. 2014;32(6):551-3.
Yin et al., Therapeutic genome editing by combined viral and non-viral delivery of CRISPR system components in vivo, Nat Biotechnol Mar. 2016;34(3):328-33.
Yu et al., Nrl knockdown by AAV-delivered CRISPR/Cas9 prevents retinal degeneration in mice, Nat Commun Mar. 14, 2017:8:14716.
Zhang et al., Curing hemophilia A by NHEJ-mediated ectopic F8 insertion in the mouse, Genome Biol Dec. 16, 2019;20(1):276.
Zhang et al., Large genomic fragment deletions and insertions in mouse using CRISPR/Cas9, PLoS One Mar. 24, 2015;10(3):e0120396.
Zhao et al., In Vivo AAV-CRISPR/Cas9-Mediated Gene Editing Ameliorates Atherosclerosis in Familial Hypercholesterolemia, Circulation Jan. 7, 2020;141(1):67-79.
US Patent Office, TPS US20200289628, 32 pages.
US Patent Office, TPS US20200270618, 28 pages.
US Patent Office, TPS US20200270617, 35 pages.
US Patent Office, TPS US20200268906, 27 pages.
Eu Patent Office, TPO EP3867376, 14 pages.
Eu Patent Office, TPO EP3867378, 8 pages.
EU Patent Office, TPO EP3867380, 12 pages.
EU Patent Office, TPO EP3867381, 10 pages.
GB Patent Office, Examination Report 1, 4 pages.
GB Patent Office, Response 1, 3 pages.
GB Patent Office, Notification of Grant 1, 2 pages.
GB Patent Office, Notification of Grant 2, 2 pages.
DE Patent Office, Examination Report 1, 6 pages.
DE Patent Office, Response 1, 7 pages.
DE Patent Office, Examination Report 2, 3 pages.
DE Patent Office, Response 2, 2 pages.
DE Patent Office, Notification of Grant, 7 pages.
JP Patent Office, Examination Report 1, 6 pages.
JP Patent Office, Response 1, 4 pages.
JP Patent Office, Notification of Grant, 4 pages.
NZ Patent Office, Examination Report 1, 4 pages.
NZ Patent Office, Response 1, 3 pages.
NZ Patent Office, Notification of Grant, 1 page.
AU Patent Office, Examination Report 1, 2 pages.
AU Patent Office, Response 1, 10 pages.
AU Patent Office, Notification of Grant, 3 pages.
EA Patent Office, Examination Report 1, 2 pages.
EA Patent Office, Response 1, 5 pages.
EA Patent Office, Examination Report 2, 3 pages.
EA Patent Office, Response 2, 4 pages.
EA Patent Office, Notification of Grant, 2 pages.
EU Patent Office, Examination Report 1, 4 pages.
EU Patent Office, Response 1, 4 pages.
EU Patent Office, Examination Report 2, 5 pages.
EU Patent Office, Response 2, 5 pages.
EU Patent Office, Examination Report 3, 4 pages.
EU Patent Office, Response 3, 5 pages.
EU Patent Office, Examination Report 4, 3 pages.
EU Patent Office, Response 4, 4 pages.
EU Patent Office, Examination Report 5, 2 pages.
EU Patent Office, Response 5, 10 pages.
Jan. 27, 2025, Plaintiff's Motion To Dismiss Defendant's Counterclaims, 2 pages.
Jan. 27, 2025, Plaintiff's Opening Brief in Support of Its Motion To Dismiss Defendant's Counterclaims, 27 pages.
Feb. 7, 2025, D051 NOS of Intellia's Initial Discls, 3 pages.
Feb. 7, 2025, D052 NOS of BlueAllele Initial's Discls, 2 pages.
Feb. 10, 2025, D053 Intellia's Ans Brief Iot Mtd, 27 pages.
Feb. 14, 2025, D054 Jt Rule 26(f) Report, 13 pages.
Feb. 14, 2025, D054-01 Prop Scheduling Order, 14 pages.
Feb. 18, 2025, D055 Reply Brief ISO MTD CCs, 15 pages.
Feb. 18, 2025, D056 Request for Oral Argument, 2 pages.
Feb. 19, 2025, D057 Mot and Order for PHV_Nina Elder, 2 pages.
Feb. 24, 2025, D061 Order re Pltfs MTD is Granted in part and Denied in part, 1 page.
Feb. 24, 2025, D62 Sched Order, 12 pages.
Feb. 25, 2025, D63 Not of Withdrawal_Finn, 2 pages.
Feb. 27, 2025, D067 Stip for EOT to file Prop PO, 1 page.
Feb. 27, 2025, D64 Mot for PHV_Jennifer Esch and Manuela Burek, 4 pages.
Feb. 28, 2025, D068 Order Granting D067 Stip for EOT to File PO, 1 page.
Mar. 10, 2025, D071 Unopposed Mot to Extend DL to Ans CCs, 5 pages.
Mar. 10, 2025, D071-01 Prop Order Granting Unopposed Mot for EOT, 1 page.
Mar. 10, 2025, D072 Order Granting Unopposed Mot for EOT to Answer Counterclaims, 1 page.
Mar. 10, 2025, D073 BlueAllele's Ans to Cntrclaim, 45 pages.
Mar. 14, 2025, D074 Stip for EOT to File Proposed Protective Order, 2 pages.
Mar. 17, 2025, D075 Order Granting D74 Stip for EOT to File Prop PO, 2 pages.
Mar. 21, 2025, D076 NOS of Pltf's Para 3 Discls, 3 pages.
Mar. 21, 2025, D078 Jt Ltr to Jdg Murphy re Protective Order Dispute, 8 pages.
Mar. 21, 2025, D79 NOS of Pltf's 2nd Set of Discovery, 3 pages.
Mar. 21, 2025, D80 Pltf's Mot for Admission PHV_Rafferty, 2 pages.
Mar. 25, 2025, D078-01 Ex A to Jt Ltr to Jdg Murphy re Protective Order Dispute, 28 pages.
Mar. 25, 2025, D078-02 Ex B to Jt Ltr to Jdg Murphy re Protective Order Dispute, 5 pages.
Mar. 24, 2025, D82 Order Granting D80 Mot for Admission PHV_Rafferty, 1 page.
Robert F. Bidirectional terminators: an underestimated aspect of gene regulation. Curr Genet. Apr. 2018;64(2):389-391.
Sandford, Andrew J. "Alpha-1 Antritrypsin Mutations: Is One Too Many?" American Thoracic Society, Dec. 6, 2019 (2 pages).
EU Patent Office, Notification of Grant, 5 pages.
EU Patent Office, Third Party Observations Combined, 32 pages.
EU Patent Office, Examination Report 6, 2 pages.
Notification of Grant foreign counterpart German Patent 11 2019 005 166 on Sep. 16, 2024 with English translation. (14 pages).
Examination Report issued on Mar. 10, 2025 in Foreign Counterpart Australian Patent Application No. 2023202878 (3 pages).
Stipulated Protective Order issued Mar. 24, 2025 (27 pages).

(56) References Cited

OTHER PUBLICATIONS

Notice of Service Intellia's Core Technical Document Production issued Apr. 4, 2025 (4 pages).
Notice of Entry of Appearance on Apr. 4, 2025 of Q. Claire Xue, Ph.D. (2 pages).
Kong et al., Self-complementary AAV5 Vector Facilitates Quicker Transgene Expression in Photoreceptor and Retinal Pigment Epithelial Cells of Normal Mouse, Exp Eye Res. Feb. 4, 2010;90(5):546-554.
Kramer The structure and function of proteins involved in mammalian pre-mRNA splicing , Annu Rev Biochem 1996:65:367-409.
Laoharawee et al., Dose-Dependent Prevention of Metabolic and Neurologic Disease in Murine MPS II by ZFN-Mediated In Vivo Genome Editing , Mol Ther (2018) Apr 4;26(4):1127-1136.
Laoharawee et al., Prevention of Neurocognitive Deficiency in Mucopolysaccharidosis Type II Mice by Central Nervous System-Directed, AAV9-Mediated Iduronate Sulfatase Gene Transfer, Hum Gene Ther Aug. 2017;28(8):626-638.
Lee et al., In vivo genome editing for hemophilia B therapy by the combination of rebalancing and therapeutic gene knockin using a viral and non-viral vector, Mol Ther Nucleic Acids Mar. 21, 2023:32:161-172.
Lee et al., Nanoparticle delivery of Cas9 ribonucleoprotein and donor DNA in vivo induces homology-directed DNA repair , Nat Biomed Eng 2017:1:889-901.
Lee et al., A gene-specific T2A-GAL4 library for Drosophila, Elife Mar. 22, 2018:7:e35574.
Li et al., AAV-CRISPR Gene Editing Is Negated by Pre-existing Immunity to Cas9, Mol Ther Jun. 3, 2020;28(6):1432-1441.
Li et al., Inhibition of HBV Expression in HBV Transgenic Mice Using AAV-Delivered CRISPR-SaCas9, Front Immunol Sep. 11, 2018;9:2080.
Li et al., Intron targeting-mediated and endogenous gene integrity-maintaining knockin in zebrafish using the CRISPR/Cas9 system , Cell Res May 2015;25(5):634-7.
Li et al., In vivo genome editing restores haemostasis in a mouse model of haemophilia , Nature Jun. 26, 2011;475(7355):217-21.
Lin et al., Promiscuous patching of broken chromosomes in mammalian cells with extrachromosomal DNA , Nucleic Acids Res Oct. 1, 2001;29(19):3975-81.
Loser et al., Reactivation of the Previously Silenced Cytomegalovirus Major Immediate-Early Promoter in the Mouse Liver: Involvement of NFηB, J Virol Jan. 1998;72(1):180-190.
Mao et al., CRISPR/Cas9-mediated efficient and precise targeted integration of donor DNA harboring double cleavage sites in Xenopus tropicalis , FASEB J Jun. 13, 2018:fj201800093.
Mersmann et al., Aspartoacylase-LacZ Knockin Mice: An Engineered Model of Canavan Disease, PLoS One 2011;6(5):e20336.
Miller et al., Adeno-associated virus vectors integrate at chromosome breakage sites, Nat Genet Jul. 2004;36(7):767-73.
Miller et al., Non-Viral CRISPR/Cas Gene Editing In Vitro and In Vivo Enabled by Synthetic Nanoparticle Co-Delivery of Cas9 mRNA and sgRNA, Angew Chem Int Ed Engl Jan. 19, 2017;56(4):1059-1063.
Min et al., CRISPR-Cas9 corrects Duchenne muscular dystrophy exon 44 deletion mutations in mice and human cells, Sci Adv Mar. 6, 2019;5(3):eaav4324.
Nakade et al., Microhomology-mediated end-joining-dependent integration of donor DNA in cells and animals using TALENs and CRISPR/Cas9, Nat Commun Nov. 20, 2014:5:5560.
Nelson et al., In vivo genome editing improves muscle function in a mouse model of Duchenne muscular dystrophy, Science Jan. 22, 2016;351(6271):403-7.
Ohmori et al., CRISPR/Cas9-mediated genome editing via postnatal administration of AAV vector cures haemophilia B mice , Sci Rep Jun. 23, 2017;7(1):4159.
Orlando et al., Zinc-finger nuclease-driven targeted integration into mammalian genomes using donors with limited chromosomal homology, Nucleic Acids Res Aug. 2010;38(15):e152.
Ou et al., ZFN-Mediated In Vivo Genome Editing Corrects Murine Hurler Syndrome, Mol Ther Jan. 2, 2019;27(1):178-187.
Petrkova et al., Characterization of a Dmd EGFP reporter mouse as a tool to investigate dystopian expression, Skelet Muscle Jul. 5, 2016;6:25.
Platt et al., CRISPR-Cas9 knockin mice for genome editing and cancer modeling, Cell Oct. 9, 2014;159(2):440-55.
Qin et al., Efficient CRISPR/Cas9-Mediated Genome Editing in Mice by Zygote Electroporation of Nuclease, Genetics Jun. 2015;200(2):432-30.
Roy et al., Calcium phosphate nanoparticles as novel non-viral vectors for targeted gene delivery, Int J Parm Jan. 2, 2003;250(1):25-33.
Sakuma et al., MMEJ-assisted gene knock-in using TALENs and CRISPR-Cas9 with the PITCh systems, Nat Protoc Jan. 2016;11(1):118-33.
Sarra et al., Kinetics of transgene expression in mouse retina following sub-retinal injection of recombinant adeno-associated virus, Vision Res Feb. 2002;42(4)541-9.
Sharma et al., In vivo genome editing of the albumin locus as a platform for protein replacement therapy., Blood (2015) 126, 1777-1784.
Shinmyo et al., CRISPR/Cas9-mediated gene knockout in the mouse brain using in utero electroporation, Sci Rep Feb. 9, 2016;6:20611.
Singh et al., Efficient In Vivo Liver-Directed Gene Editing Using CRISPR/Cas9, Mol Ther May 2, 2018;26(5):1241-1254.
Stephens et al., Targeted in vivo knock-in of human alpha-1-antitrypsin cDNA using adenoviral delivery of CRISPR/Cas9, Gene Ther Apr. 2018;25(2):139-156.
Swartz et al., Sparking new frontiers: using in vivo electroporation for genetic manipulations, Dev Biol May 1, 2001;233(1):13-21.
Tabebordbar et al., In vivo gene editing in dystrophic mouse muscle and muscle stem cells, Science. Dec. 31, 2015;351(6271):407-411.
Talas et al., A convenient method to pre-screen candidate guide RNAs for CRISPR/Cas9 gene editing by NHEJ-mediated integration of a 'self-cleaving' GFP-expression plasmid, DNA Res Dec. 1, 2017;24(6):609-621.
Tiessen et al., Mathematical modeling and comparison of protein size distribution in different plant, animal, fungal and microbial species reveals a negative correlation between protein size and protein number, thus providing insight into the evolution of proteomes, BMC Res Notes Feb. 1, 2012:5:85.
TIPANEE Validation of miR-20a as a Tumor Suppressor Gene in Liver Carcinoma Using Hepatocyte-Specific Hyperactive piggyBac Transposons, Mol Ther Nucleic Acids Mar. 6, 2020:19:1309-1329.
Venkatesh et al., Retinal Gene Delivery by rAAV and DNA Electroporation, Curr Protoc Microbiol 2013:Chapter 14:Unit 14D.
Wang et al., Comparative Study of Liver Gene Transfer With AAV Vectors Based on Natural and Engineered AAV Capsids, Mol Ther Oct. 27, 2015;23(12):1877-1887.
Wang et al., CRISPR-Cas9-Mediated In Vivo Gene Integration at the Albumin Locus Recovers Hemostasis in Neonatal and Adult Hemophilia B Mice, Mol Ther Methods Clin Dev Jun. 30, 2020:18:520-531.
Wang et al., A mutation-independent CRISPR-Cas9-mediated gene targeting approach to treat a murine model of ornithine transcarbamylase deficiency, Sci Adv Feb. 12, 2020;6(7):eaax5701.
Wang et al., Mapping a functional cancer genome atlas of tumor suppressors in mouse liver using AAV-CRISPR-mediated direct in vivo screening, Sci Adv Feb. 28, 2018;4(2):eaao5508.
Wang et al., Systematic evaluation of CRISPR-Cas systems reveals design principles for genome editing in human cells, Genome Biol. (2018) May 29;19:62.
Wang et al., Unbiased detection of off-target cleavage by CRISPR-Cas9 and TALENs using integrase-defective lentiviral vectors , Nat Biotechnol Feb. 2015;33(2):175-8.
Wang et al., Large genomic fragment deletion and functional gene cassette knock-in via Cas9 protein mediated genome editing in one-cell rodent embryos , Sci Rep Dec. 1, 2015:5:17517.
Willems et al., Orange: A CRISPR/Cas9-based genome editing toolbox for epitope tagging of endogenous proteins in neurons, PLoS Biol Apr. 10, 2020;18(4):e3000665.

(56) References Cited

OTHER PUBLICATIONS

Xiong et al., AAV cis-regulatory sequences are correlated with ocular toxicity, Proc Natl Acad Sci U S A Mar. 19, 2019;116(12):5785-5794.
Xu et al., CRISPR-mediated Genome Editing Restores Dystrophin Expression and Function in mdx Mice, Mol Ther Mar. 2016;24(3):564-9.
Xue et al., CRISPR-mediated direct mutation of cancer genes in the mouse liver, Nature Oct. 16, 2014;514(7522):380-4.

* cited by examiner pBA1012-D1 (SEQ ID NO: 10); pBA1135 (SEQ ID NO:17)

METHODS FOR TARGETED INSERTION OF DNA IN GENES

CROSS-REFERENCE TO RELATED APPLICATIONS

This application is a continuation of previously filed U.S. Ser. No. 17/830,011, filed Jun. 1, 2022, which is a continuation of U.S. Ser. No. 17/590,613, filed Feb. 1, 2022, now U.S. Pat. No. 11,365,407, issued Jun. 1, 2022, which is a continuation of U.S. Ser. No. 17/366,290 filed Jul. 2, 2021, now U.S. Pat. Ser. No. 11/254,930, issued Feb. 2, 2022, which is a continuation of U.S. Ser. No. 16/800,444 filed Feb. 25, 2020, now U.S. Pat. No. 11,091,756, issued Jul. 28, 2021, which is a continuation of U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

REFERENCE TO SEQUENCE LISTING SUBMITTED ELECTRONICALLY

This application contains a Sequence Listing which has been submitted electronically in XML format. The Sequence Listing XML is incorporated herein by reference. Said XML file, created on Jan. 10, 2024, is named 1026_004-US8.xml and is 418,594 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
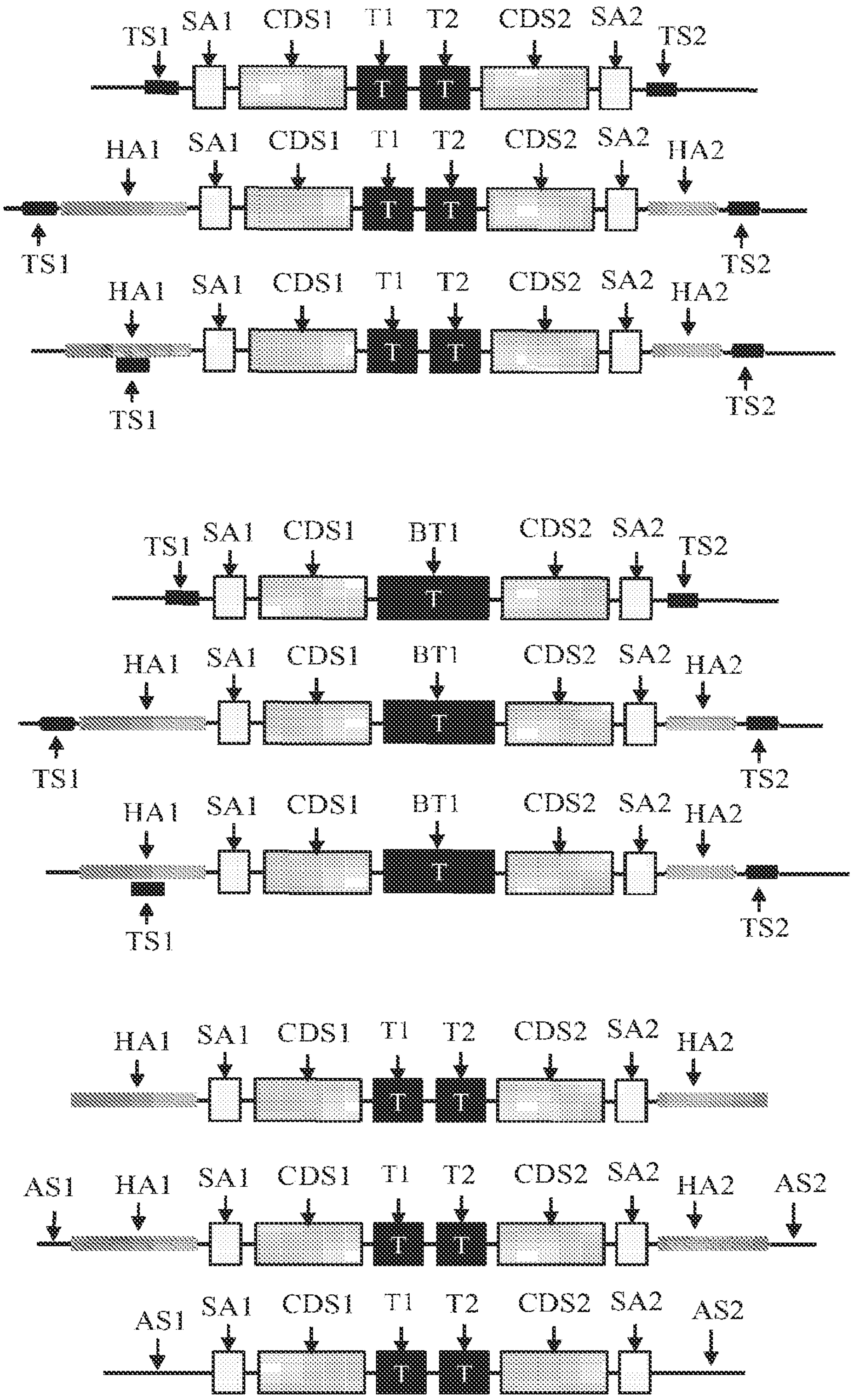
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HAL homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence, but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence, but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence, but encode the same amino acids. The transgene can be harbored on a vector, wherein the vector format is selected from double-stranded linear DNA, double-stranded circular DNA, or a viral vector. The viral vector iscan include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence, but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO: 41, and the right end can comprise the sequence shown in SEQ ID NO: 13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, “Chromatin” (P. M. Wassarman and A. P. Wolffe, eds.), Academic Press, San Diego, 1999; and METHODS IN MOLECULAR BIOLOGY, Vol. 119, “Chromatin Protocols” (P. B. Becker, ed.) Humana Press, Totowa, 1999.

As used herein, the terms “nucleic acid” and “polynucleotide,” can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms “polypeptide,” “peptide” and “protein” can be used interchangeably to refer to amino acid residues covalently linked together. The term also applies to proteins in which one or more amino acids are chemical analogues or modified derivatives of corresponding naturally-occurring amino acids.

The terms “operatively linked” or “operably linked” are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron’s 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally-occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequeence. For example, the product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "head-to-head" refers to an orientation of two units in opposite and reverse directions. The two units can be two sequences on a single nucleic acid molecule, where the 5' end of each sequence are placed adjacent to each other. For example, a first nucleic acid having the elements, in a 5' to 3' direction, [promoter 1]—[partial coding sequence 1]—[splice donor 1] and a second nucleic acid having the elements [promoter 2]—[partial coding sequence 2]—[splice donor 2] can be placed in head-to-head orientation resulting in [splice donor 1 RC]—[partial coding sequence 1 RC]—[promoter 1 RC]—[promoter 2]—[partial coding sequence 2]—[splice donor 2] where RC refers to reverse complement.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]—[partial coding sequence 1]—[terminator 1] and a second nucleic acid having the elements [splice acceptor 2]—[partial coding sequence 2]—[terminator 2] can be placed in tail-to-tail orientation resulting in [splice acceptor 1]—[partial coding sequence 1]—[terminator 1]—[terminator 2 RC]—[partial coding sequence 2 RC]—[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC1, GAL1, GALT, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG_008198.2 and corresponding SEQ ID NO: 42. The exon and intron boundaries can be defined with the sequence provided in SEQ ID NO: 42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alpha1A protein. A representative sequence of the CACNA1A gene can be found with NCBI Reference Sequence: NG_011569.1 and corresponding SEQ ID NO: 43. The exon and intron boundaries can be defined with the sequence provided in SEQ ID NO: 43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm nih.gov. Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq2.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. For example, the following command can be used to generate an output file containing a comparison between two sequences: C:\B12seq −i c:\seq1.txt −j c:\seq2.txt −p blastn −o c:\output.txt −q −1 −r2. To compare two amino acid sequences, the options of B12seq are set as follows: –i is set to a file containing the first amino acid sequence to be compared (e.g., C:\seq1.txt); –j is set to a file containing the second amino acid sequence to be compared (e.g., C:\seq2.txt); –p is set to blastp; –o is set to any desired file name (e.g., C:\output.txt); and all other options are left at their default setting. For example, the following command can be used to generate an output file containing a comparison between two amino acid sequences: C:\B12seq –i c:\seq1.txt –j c:\seq2.txt –p blastp –o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
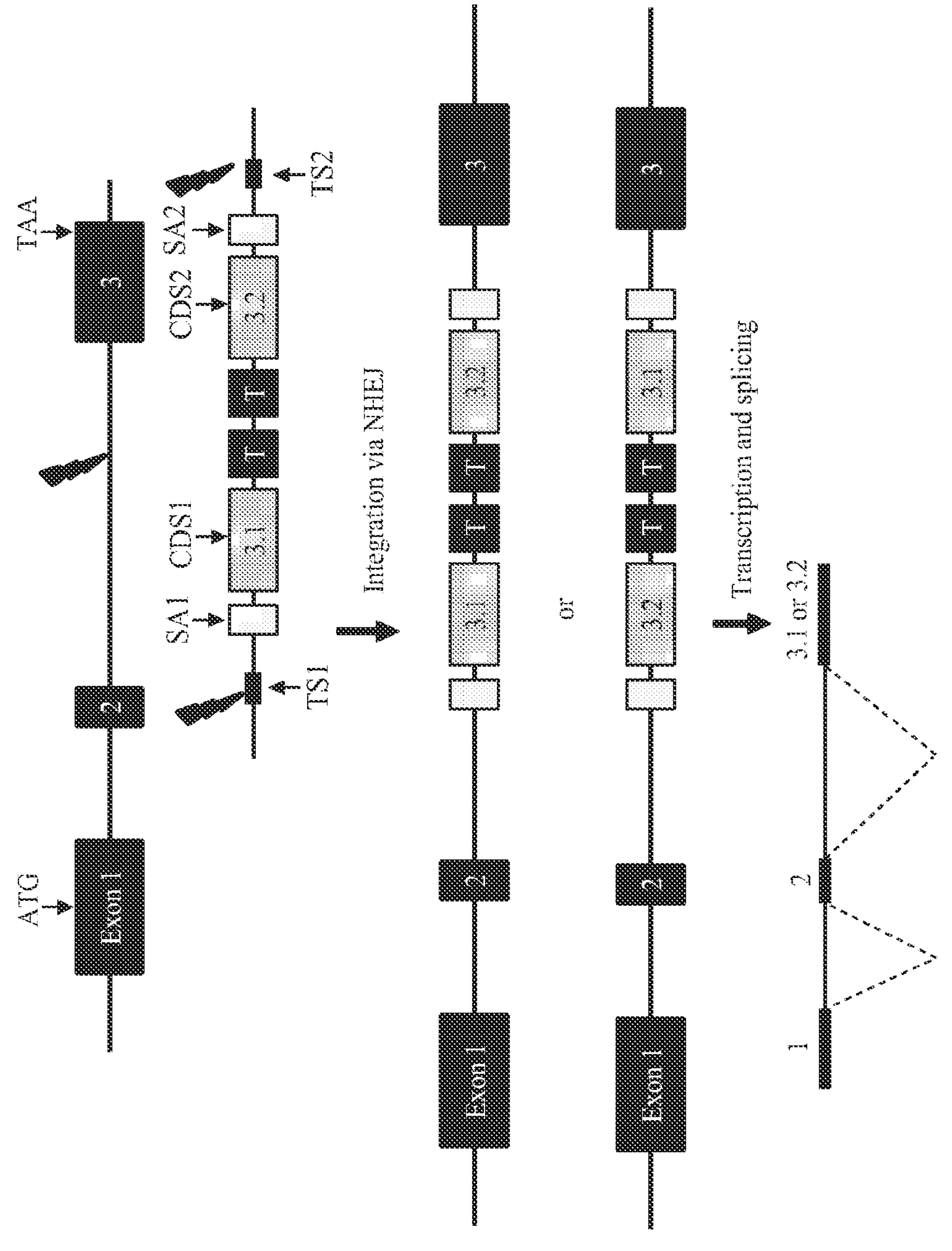
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
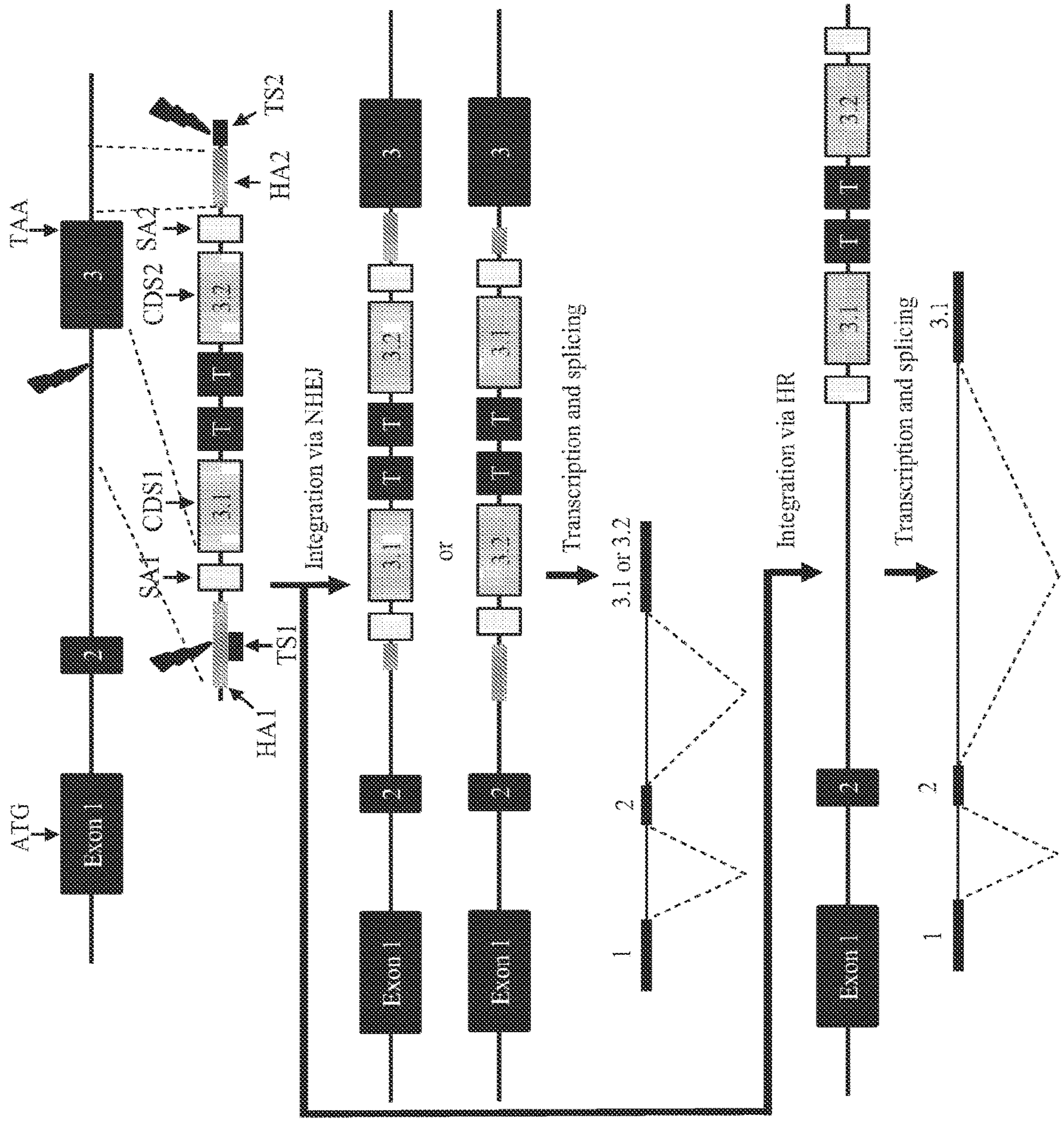
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., *Science* 10.1126/science.aax9181, 2019; Klompe et al., *Nature,* 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO: 30) or *Anabaena cylindrica* (SEQ ID NO: 31). In one embodiment, the transgenes described herein comprising a left (SEQ ID NO: 32) and right transposon end (SEQ ID NO: 33) can be delivered to cells along with ShCas12k, tnsB, tnsC, TniQ and a gRNA (SEQ ID NO: 14). Alternatively, the CRISPR transposase can include the Cas6 protein, along with helper proteins including Cas7, Cas8 and TniQ. In one embodiment, the transgenes described herein comprising a left (SEQ ID NO: 41) and right transposon end (SEQ ID NO: 13) can be delivered to eukaryotic cells along with Cas6 (SEQ ID NO: 37), Cas7 (SEQ ID NO: 37), Cas8 (SEQ ID NO: 37), TniQ (SEQ ID NO: 37), TnsA (SEQ ID NO: 37), TnsB (SEQ ID NO: 37), TnsC (SEQ ID NO: 37) and a gRNA (SEQ ID NO: 12). The proteins can be administered to cells directly as purified protein, or encoded on RNA or DNA. If encoded on RNA or DNA, the sequence can be codon optimized for expression in eukaryotic cells. The gRNA (SEQ ID NO: 12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]—[partial coding sequence 1]—[terminator 1]—[terminator 2 RC]—[partial coding sequence 2 RC]—[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[rare-cutting endonuclease cleavage site 1]. In another embodiment, the combination can be, from 5' to 3', [rare-cutting endonuclease cleavage site 1]—[homology arm 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1 +rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]—[splice acceptor 1]—[partial coding sequence 1]—[terminator 1]—[terminator 2 RC]—[partial coding sequence 2 RC]—[splice acceptor 2 RC]—[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]—[homology arm 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators, and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT 1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 15 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), herpes simplex, pox virus, hybrid adenoviral vector, epstein-bar virus, lentivirus, or herpes simplex virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAVS, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, algae, animals, fungi and protists. The eukaryotic organisms can also include plant cells, algae cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, tomato, alfalfa), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc), flowering plants (e.g., petunia, rose, chrysanthemum), conifers and pine trees (e.g., pine fir, spruce); poplar trees (e.g. P. tremula×P. alba); fiber crops (cotton, jute, flax, bamboo) plants used in phytoremediation (e.g., heavy metal accumulating plants); oil crops (e.g., sunflower, rape seed) and plants used for experimental purposes (e.g., Arabidopsis). The methods disclosed herein can be used within the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary algae species include *microalgae, diatoms, Botryococcus braunii, Chlorella, Dunaliella tertiolecta, Gracileria, Pleurochrysis carterae, Sorgassum* and *Ulva*.

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpf1). The CRISPR system can include variants which display broad PAM capability (Hu et al., *Nature* 556, 57-63, 2018; Nishimasu et al., *Science* DOI: 10.1126, 2018) or higher on-target binding or cleavage activity (Kleinstiver et al., *Nature* 529:490-495, 2016). The gene editing reagent can be in the format of a nuclease (Mali et al., Science 339:823-826, 2013; Christian et al., *Genetics* 186:757-761, 2010), nickase (Cong et al., Science 339:819-823, 2013; Wu et al., *Biochemical and Biophysical Research Communications* 1:261-266, 2014), CRISPR-FokI dimers (Tsai et al., *Nature Biotechnology* 32:569-576, 2014), or paired CRISPR nickases (Ran et al., *Cell* 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1

Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO: 17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO: 18. The individual elements within pBA1135 are shown in SEQ ID NOS:44-51. SEQ ID NO: 44 comprises the left homology arm, nuclease target site, and splice acceptor. SEQ ID NO: 45 comprises the partial coding sequence (exon 10 and 11) of a non-pathogenic ATXN3 gene. SEQ ID NO: 46 comprises the SV40 p(A) terminator sequence. SEQ ID NO: 47 comprises the BGH terminator in reverse complement. SEQ ID NO: 48 comprises the reverse complement, codon adjusted partial coding sequence (exon 10 and 11) of a non-pathogenic ATXN3 gene. SEQ ID NO: 49 comprises the sequence for the splice acceptor. SEQ ID NO: 50 comprises the sequence for the right homology arm. SEQ ID NO: 51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO: 19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO: 20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
|---|---|---|
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |

TABLE 1-continued

Primers for detecting integration of transgenes in ATXN3.

| Primer Name | Sequence (5' to 3') | SEQ ID NO: |
|---|---|---|
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
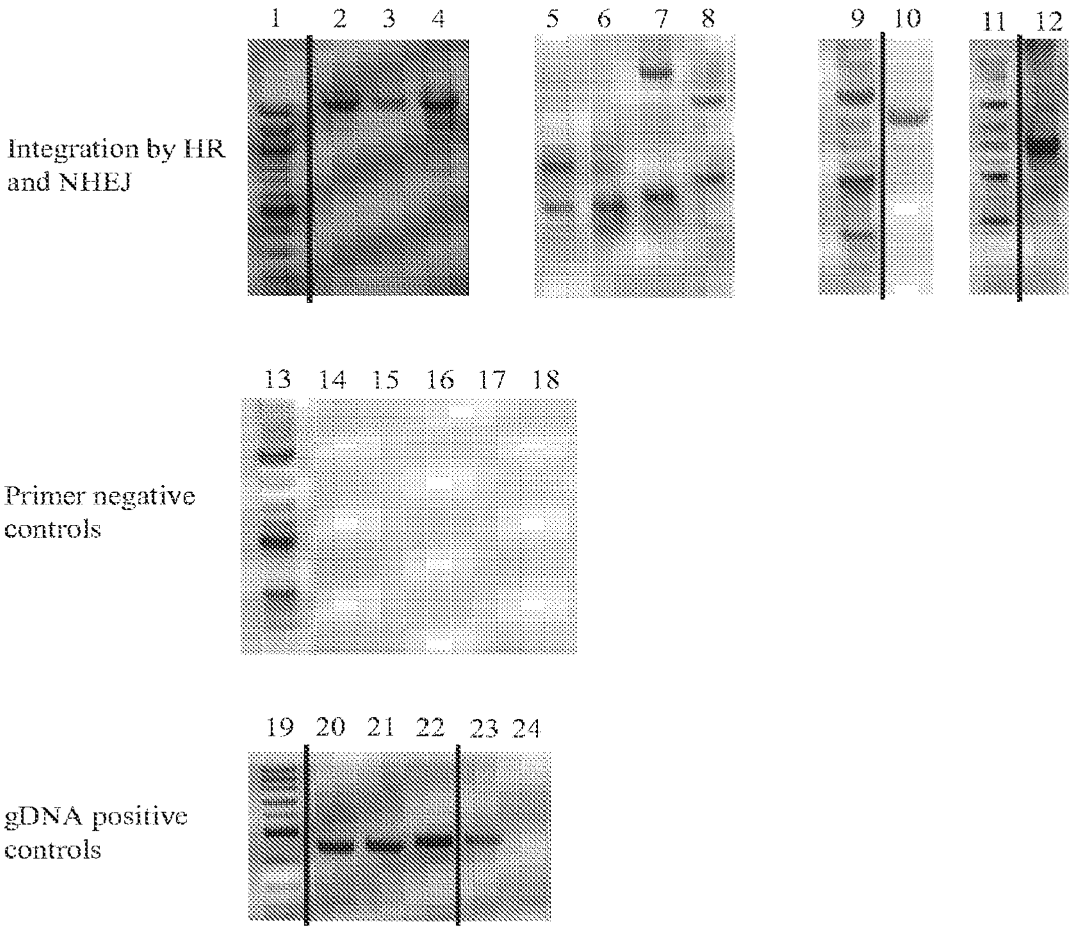
FIG. 8 are images of gels detecting integration of transgenes into the ATXN3 gene. 1, 100 by ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1kb ladder with darker bands running at 500 bp, 1,000 bp and 3,000 bp; 9, 1kb ladder with darker bands running at 500 bp, 1,000 bp and 3,000 bp; 10, pBA1135 inverted 5' junction; 11, 1kb ladder with darker bands running at 500 bp, 1,000 bp and 3,000 bp; 12, pBA1136 inverted 5' junction; 13, 1kb ladder with darker bands running at 500 bp, 1,000 bp and 3,000 bp; 14;, primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate size bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2

Targeted Integration of DNA in the CACNA1A Gene

Figure 4:
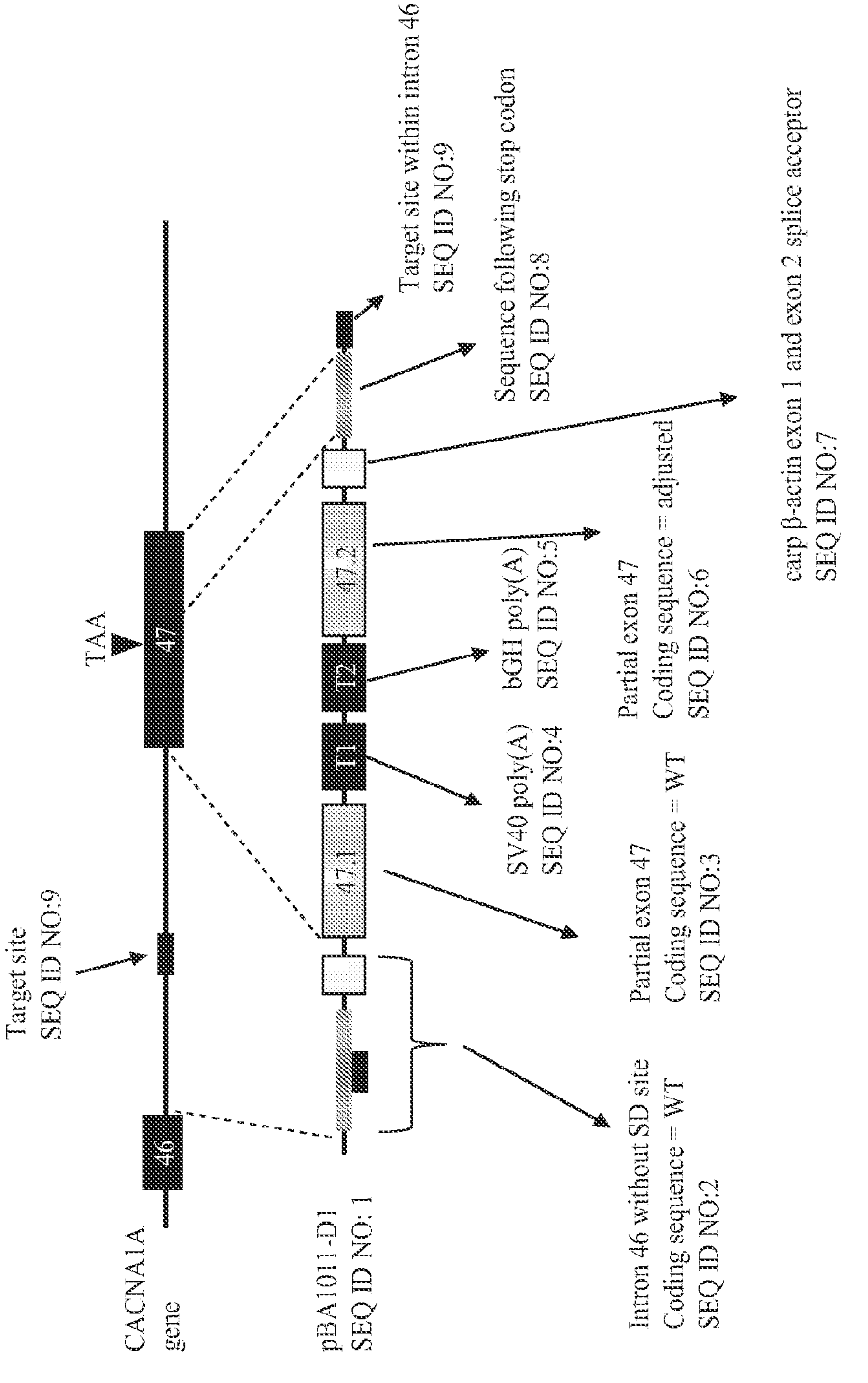
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO: 9) and a splice acceptor sequence. The first homology arm is followed by a first coding sequence comprising the CACNA1A exon 47 and a non-expanded CAG repeat sequence (SEQ ID NO: 3). Following the first coding sequence is a SV40 poly(A) termination sequence (SEQ ID NO: 4). In a tail-to-tail orientation, a second set of functional elements is present. The beginning of the second set of elements comprises a target site for the nuclease (SEQ ID NO: 9) followed by a second homology arm. The second homology arm harbors 446 bp which is homologous to sequence immediately following the stop coding (SEQ ID NO: 8). This sequence was determined to be free of consensus branch or splice acceptor sequences via in silico analysis. Following the second homology arm is a second splice acceptor from carp beta-actin intron 1 (SEQ ID NO: 7). Following the splice acceptor is a codon optimized version of the CACNA1A exon 47 (SEQ ID NO: 6) and a bGH poly(A) terminator (SEQ ID NO: 5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO: 9.

Figure 5:
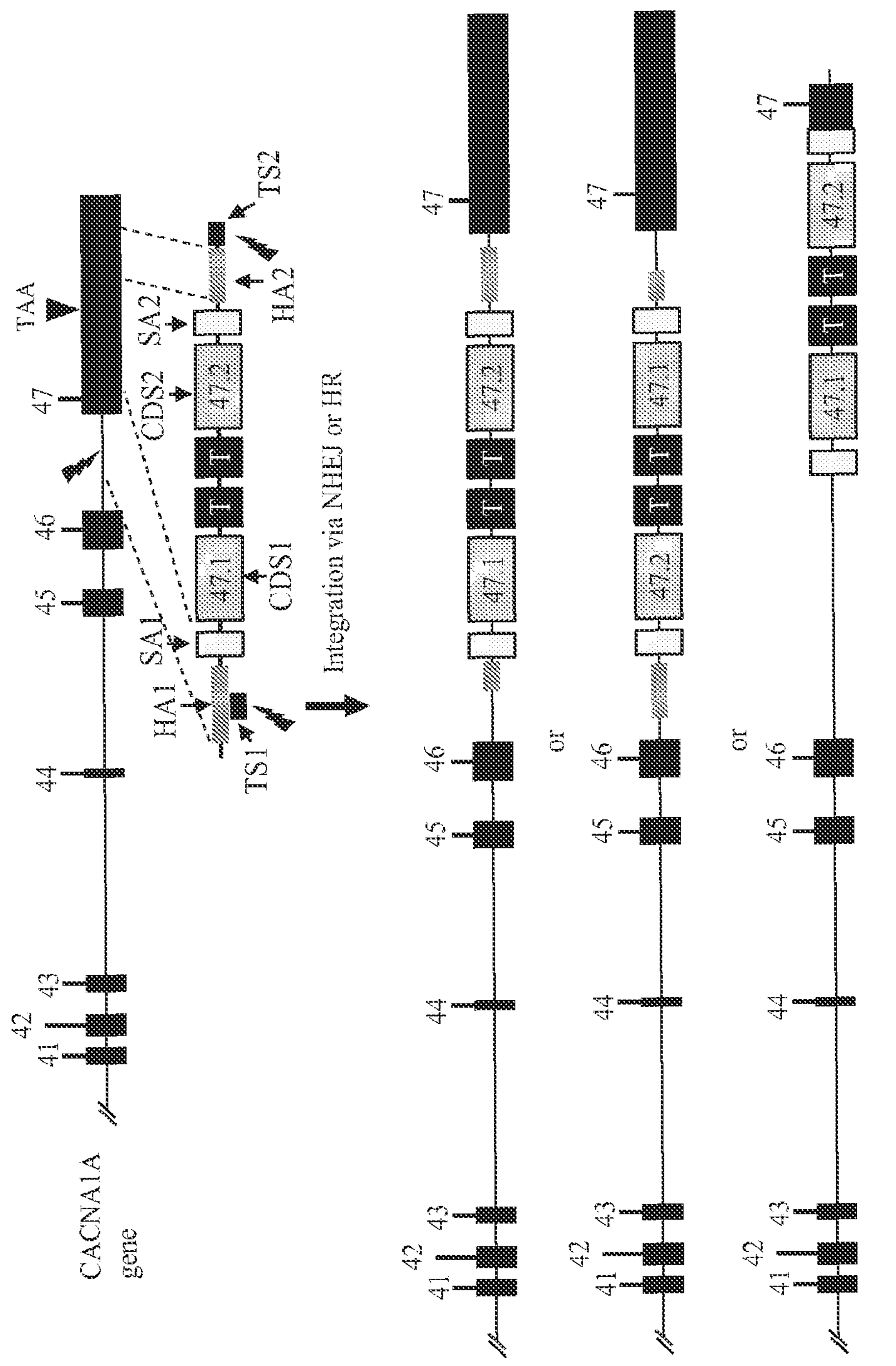
FIG. 5 is an illustration of the integration outcomes for the pB1011-D1 transgene within the CACNA1A gene.
Figure 6:
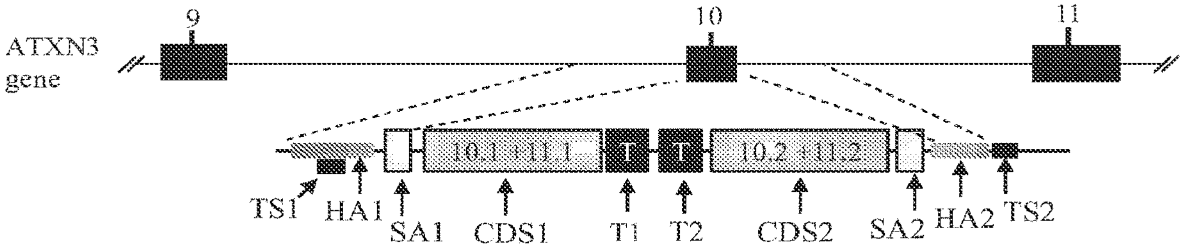
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3

Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO: 10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO: 11.

Figure 7:
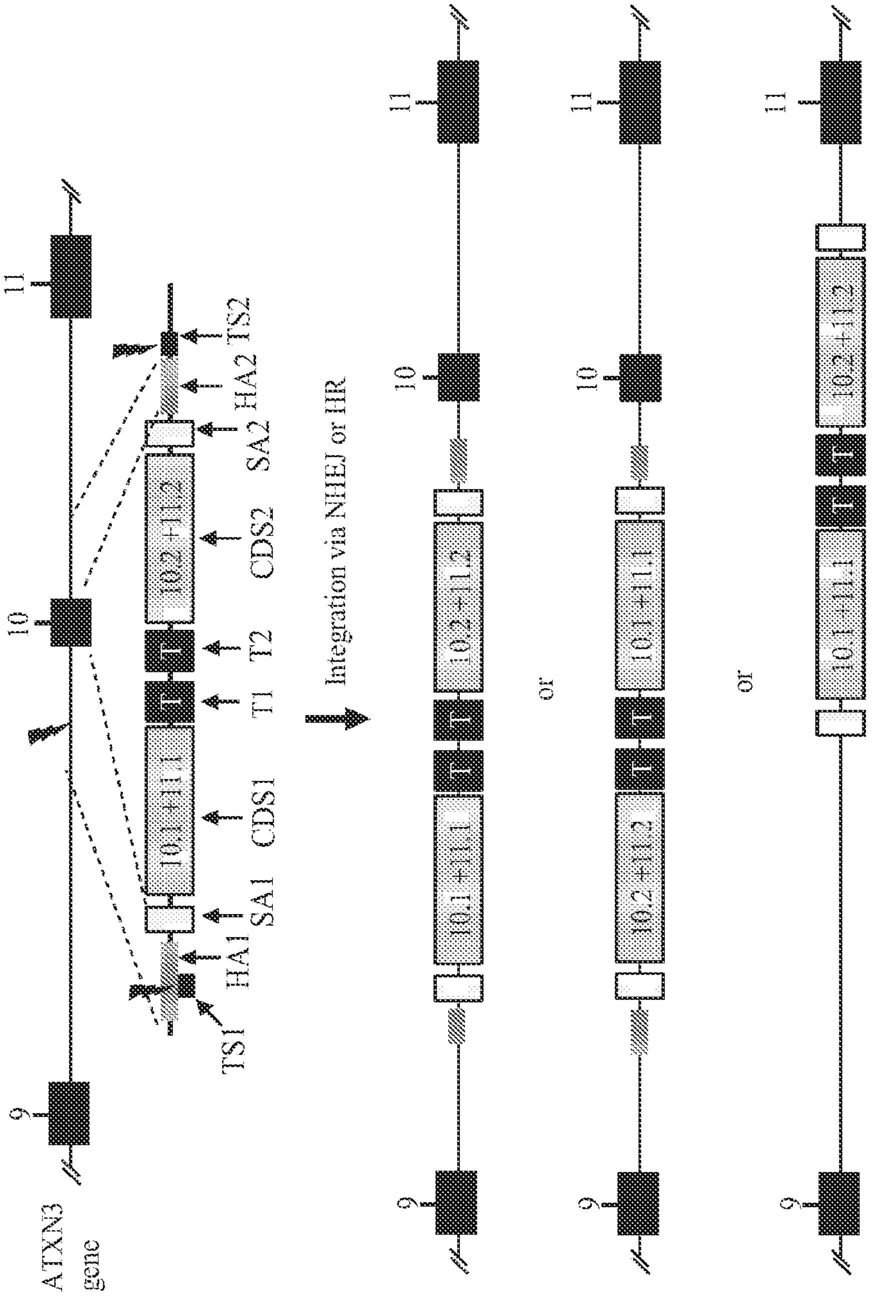
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4

Targeted Integration of DNA in the ATXN3 Gene Using Cas12k Transposases

An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the Scytonema hofmanni tnsB, tnsC, tniQ and Cas12k (SEQ ID NO: 30) using eukaryotic promoters. A second plasmid is engineered to express the corresponding Cas12k guide RNA (SEQ ID NO: 14). The guide RNA targeted sequence CCGCCCGACCTTTCACTTTC (SEQ ID NO: 15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5

Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the Scytonema hofmanni tnsB, tnsC, tniQ and Cas12k (SEQ ID NO: 30) using eukaryotic promoters. A second plasmid is engineered to express the corresponding Cas12k guide RNA (SEQ ID NO: 14). The guide RNA is designed to target sequence CCCG- GATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100X. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A vector comprising a transgene comprising in 5' to 3' orientation: a first splice acceptor, a first coding sequence, a first terminator, a second terminator reverse complement, a second coding sequence reverse complement, and a second splice acceptor reverse complement, wherein the first coding sequence is operably linked to the first splice acceptor and first terminator, and the second coding sequence is operably linked to the second splice acceptor and second terminator, wherein the first terminator is selected from an SV40 poly (A) or BGH poly (A), wherein the first and second coding sequences differ in nucleic acid sequence but each encode the same amino acid sequence, wherein said amino acid sequences encoded by the first and second coding sequences correspond to amino acid sequences having at least 80% identity to the amino acid sequence of an endogenous human ATXN3 gene, and wherein the transgene is equal to or less than 4.7 kb.

2. The vector of claim 1, wherein the second terminator is selected from an SV40 poly (A) or BGH poly (A).

3. The vector of claim 2, wherein the amino acid sequences encoded by the first and second coding sequences have at 100% sequence identity to the amino acid sequence encoded by the endogenous ATXN3 gene.

4. The vector of claim 1, wherein the amino acid sequences encoded by the first and second coding sequences have 98% sequence identity to the amino acid sequence encoded by the endogenous ATXN3 gene.

5. The vector of claim 1, wherein the amino acid sequence encoded by the first and second coding sequences have 99% sequence identity to the amino acids encoded by the endogenous ATXN3 gene.

6. The vector of claim 3, wherein the vector a viral vector.

7. The vector of claim 6, wherein the viral vector is selected from the group consisting of an adenovirus vector and a lentivirus vector.

8. The vector of claim 7, wherein the viral vector is incorporated into a viral particle.

9. The of vector claim 8, wherein the transgene does not comprise homology arms.

10. The vector of claim 9, wherein the first splice acceptor comprises a splice acceptor sequence from an intron of the endogenous ATXN3 gene.

11. An adeno-associated viral vector comprising:

(i) a transgene comprising from 5' to 3' orientation a first splice acceptor, a first coding sequence, a first terminator, a second terminator reverse complement, a second coding sequence reverse complement, and a second splice acceptor reverse complement, wherein the first coding sequence is operably linked to the first splice acceptor and first terminator, and the second coding sequence is operably linked to the second splice acceptor and second terminator, wherein the first terminator is selected from an SV40 poly (A) or BGH poly (A), wherein the first and second coding sequences differ in nucleic acid sequence but each encode the same amino acid sequence, wherein said amino acids encoded by the first and second coding sequences correspond to amino acid sequences having at least 80% identity to the amino acid sequence of an endogenous human ATXN3 gene, and wherein the transgene is equal to or less than 4.7 kb; and (ii) adeno-associated virus inverted terminal repeats flanking the transgene.

12. The adeno-associated viral vector of claim 11, wherein the first and second coding sequences encode amino acid sequences having 100% sequence identity to the amino acid sequence encoded by the endogenous ATXN3 gene.

13. The adeno-associated viral vector of claim 11, wherein the amino acids encoded by the first and second coding sequences having 98% sequence identity to the amino acids encoded by the endogenous ATXN3 gene.

14. The adeno-associated viral vector of claim 12, wherein the amino acids encoded by the first and second coding sequences having 99% sequence identity to the amino acids encoded by the endogenous ATXN3 gene.

15. The adeno-associated viral vector of claim 11, wherein the second terminator is selected from an SV40 poly (A) or BGH poly (A).

16. The adeno-associated viral vector of claim 15, wherein the viral vector is incorporated into a viral particle.

17. The adeno-associated viral vector of claim 15, wherein the transgene does not comprise homology arms.

18. The adeno-associated viral vector of claim 17, wherein the first splice acceptor comprises splice acceptor sequence from an intron of the endogenous ATXN3 gene.

19. The adeno-associated viral vector of claim 17, wherein the first terminator is an SV40 poly (A) and the second terminator is a BGH poly (A).

* * * * *

SEQUENCE LISTING

```
Sequence total quantity: 51
SEQ ID NO: 1            moltype = DNA  length = 3527
FEATURE                 Location/Qualifiers
source                  1..3527
                        mol_type = other DNA
                        organism = synthetic construct
SEQUENCE: 1
gtgcggctgc aagtgacccc aggctgggct cggccgggag gcggggagga gagaagggga  60
taccccatcc aacagccact ctaggcaaag gtccccggat cccggctgtg accacctccc  120
atcctgcccc caagccaccg ggtgcccgg cggccggagc ggacacggat ccccaccaca  180
ccagctgcct atgctgtccc cccagccccc ttgcccaccc gccgccccct ccccgccgcc  240
cgcagctgct tgctcctcgg ttgtggatca tatttgagtt ctgggccgtg ccgcccgacc  300
tttcactttc ctttaacccg gcttctgttt ttgtttcaat tatgatttct gtcctctgga  360
cgcctgtgag taatttttga aacttctgct atttttaacc ccgaaactta caaaactcca  420
tttctcattt ctcttttcac tttgttgtgt tggttttcga ctcctcccct ccctgtctca  480
ctccccctcc tcccctccct cctccctgtg gctgttgctt ttttccattc aatgtcctgt  540
gtccccccctc tcctcctcct cctcctcctc cccctccccc tcctccctct cctcccggcc  600
cctctccctt cgctccccctc tcttcctccc aatcccgtgt ctcctttgat tttgttgtat  660
cttttttttt gatttccttt gtttcaattt tcgtgtaggg cagtagttcc gtaagtggaa  720
gcccagcccc ctcaacatct ggtaccagca ctccgcggcg gggccgccgc cagctccccc  780
agacccccctc cacccccccgg ccacacgtgt cctattcccc tgtgatccgt aaggccggcg  840
gctcggggcc cccgcagcag cagcagcagc agcagcagca gcagcagcag caggcggtgg  900
ccaggccggg ccgggcggcc accagcggcc ctcggaggta cccaggcccc acggccgagc  960
ctctggccgg agatcggccg cccacggggg gccacagcag cggccgctcg cccaggatgg  1020
agaggcgggt cccaggcccg gcccggagcg agtcccccag ggcctgtcga cacggcgggg  1080
cccggtggcc ggcatctggc ccgcacgtgt ccgagggggcc cccgggtccc cggcaccatg  1140
gctactaccg gggctccgac tacgacgagg ccgatggccc gggcagcggg ggcggcgagg  1200
aggccatggc cggggcctac gacgcgccac cccccgtacg acacgcgtcc tcgggcgcca  1260
ccgggcgctc gcccaggact ccccgggcct cgggcccggc ctgcgcctcg ccttctcggc  1320
acggccggcg actccccaac ggctactacc cggcgcacgg actggccagg ccccgcgggc  1380
cgggctccag gaagggcctg cacgaaccct acagcgagag tgacgatgat tggtgctaaa  1440
acttgtttat tgcagcttat aatggttaca aataaagcaa tagcatcaca aatttcacaa  1500
ataaagcatt tttttcactg cattctagtt gtggtttgtc caaactcatc aatgtatctt  1560
atcatgtctg gatctcccca gcatgcctgc tattctcttc ccaatcctcc cccttgctgt  1620
cctgccccac cccacccccc agaatagaat gacacctact cagacaatgc gatgcaattt  1680
cctcatttta ttaggaaagg acagtgggag tggcaccttc cagggtcaag gaaggcacgg  1740
gggaggggca aacaacagat ggctggcaac tagaaggcac agtcagcacc agtcgtcgtc  1800
ggattcgctg tagggttcat ggagaccctt ccgagaccca ggtcctcttg gccgggccaa  1860
gccgtgtgca gggtaatatc cattggggag cctccggcca tgccgagaag gtgaagcgca  1920
cgctggtcct gacgcccggg gggtgcgagg agacctccct gtcgccccgg aagacgcatg  1980
cctaacggga ggcggagcat cataagcacc agccatcgct tcctcgccac caccactgcc  2040
gggcccgtca gcttcgtcat agtcagaacc ccgataatat ccgtgatggc gaggccctgg  2100
aggtccttcg ctaacgtgtg gcccagaagc aggccaccgc gcacctccat ggcgacatgc  2160
tctaggactc tcgcttcttg caggtccagg aacccgccgc tccattcgcg ggcttcgccc  2220
actactgtgt ccacctgtcg gagggcggtc tccggcaagg ggttcagcgg ttgggcctgg  2280
atagcgccgc ggaccggagg tagcagcccg accgggtcgt gctaccgctt gctgttgctg  2340
ttgttgctgt tgctgctgtt gttgttgggg tggcccgcta cctcccgctt ttctaataac  2400
tggtgaataa ctcacatgtg ggcgcggagt ggatggtgtc tgagggagtt gccttctccc  2460
tcggcggggt gtagacgtac cagatgttga aggcgccggg ctcccgctta ctgaactact  2520
gtaaatgaat gagaaaaccg gtttagaaag tgcacagctg tcagggaagt caacacttca  2580
gtgagcatgt gaccatgtgg agtcagcttc ctgtttcgtg ctgcaatcgc ccgggcgagg  2640
tggcgcccgc ccggcccccc acgcacccca cgcacacacc ccacccgagg agccgcgcag  2700
aggccgcggg ggcccagcac agagggcccg ggagagggcc agccgggaga ccccagactc  2760
tggagaggcc agggctgggc cacaagggtg tcccgcagag accctcggcc aaaagagacc  2820
ctcctgggca gccacggcgc cccccaacca gccccgatcc ccccacccac gacaggggct  2880
ctcgggtggg aggcagggag cagacaaacc acacagccaa gggatttgaa ttaactcagc  2940
catttttgga gaactttggg gaacatgaaa aaaaaaaaaa aaaaaaaaaa aaaaaacatt  3000
tttaaaagaa aaaacgggga gaaaaaaata gcttctattg atgagtttta tcatctcaat  3060
tgaatctttc ctttccctga tgaagacagc tggtggccga gtgcggcaaa gaagccagaa  3120
ggaaccagaa tcccagtgcc ctacacccac caccagacac actcacaccc acacacgttc  3180
tcagacacac acaagagtgc ttgccggtta taccaaaccc tactattact gcctgcagaa  3240
atcaatttaa aaaaataata ataacaataa acaattttaa aaaggacaaa aaaattaatg  3300
attgagaaaa gaggcatttt tttctgacat ttggtcctgc ttgaaacaac aaaagaagaa  3360
```

```
gaaaaaccca ccatcaccac cgattccttt gcttcttttt tcctttttc ctaccttgtt  3420
tgaaaaccgt gggcttggga ctgtgaatta ttgcatgaca ttcaaaaaga aaaaaaaaat  3480
aaaaaaaagt tgaatcaaat ttctgtcctc tggacgcctg tgagtaa               3527

SEQ ID NO: 2           moltype = DNA  length = 703
FEATURE                Location/Qualifiers
source                 1..703
                       mol_type = other DNA
                       organism = synthetic construct
SEQUENCE: 2
gtgcggctgc aagtgacccc aggctgggct cggccgggag gcggggagga gagaagggga  60
taccccatcc aacagccact ctaggcaaag gtccccggat cccggctgtg accacctccc  120
atcctgcccc caagccaccg gggtgcccgg cggccggagc ggacacggat ccccaccaca  180
ccagctgcct atgctgtccc cccagccccc ttgcccaccc gccgccccct ccccgccgcc  240
cgcagctgct tgctcctcgg ttgtggatca tatttgagtt ctgggccgtg ccgcccgacc  300
tttcactttc ctttaacccg gcttctgttt ttgtttcaat tatgatttct gtcctctgga  360
cgcctgtgag taatttttga aacttctgct atttttaacc ccgaaactta caaaactcca  420
tttctcattt ctcttttcac tttgttgtgt tggttttcga ctcctcccct ccctgtctca  480
ctccccctcc tcccctccct cctccctgtg gctgttgctt ttttccattc aatgtcctgt  540
gtccccccctc tcctcctcct cctcctcctc cccctccccc tcctccctct cctcccggcc  600
cctctccctt cgctcccctc tcttcctccc aatcccgtgt ctcctttgat tttgttgtat  660
ctttttttt gatttccttt gtttcaattt tcgtgtaggg cag                    703

SEQ ID NO: 3           moltype = DNA  length = 736
FEATURE                Location/Qualifiers
source                 1..736
                       mol_type = other DNA
                       organism = synthetic construct
SEQUENCE: 3
tagttccgta agtggaagcc cagccccctc aacatctggt accagcactc cgcggcgggg  60
ccgccgccag ctcccccaga ccccctccac cccccggcca cacgtgtcct attcccctgt  120
gatccgtaag gccggcggct cggggccccc gcagcagcag cagcagcagc agcagcagca  180
gcagcagcag gcggtggcca ggccgggccg ggcggccacc agcggccctc ggaggtaccc  240
aggccccacg gccgagcctc tggccggaga tcggccgccc acgggggggcc acagcagcgg  300
ccgctcgccc aggatggaga ggcgggtccc aggcccggcc cggagcgagt cccccagggc  360
ctgtcgacac ggcggggccc ggtggccggc atctggcccg cacgtgtccg aggggccccc  420
gggtccccgg caccatggct actaccgggg ctccgactac gacgaggccg atggcccggg  480
cagcgggggc ggcgaggagg ccatggccgg ggcctacgac gcgccacccc ccgtacgaca  540
cgcgtcctcg ggcgccaccg ggcgctcgcc caggactccc cgggcctcgg gcccggcctg  600
cgcctcgcct tctcggcacg gccggcgact ccccaacggc tactacccgg cgcacggact  660
ggccaggccc cgcgggccgg gctccaggaa gggcctgcac gaaccctaca gcgagagtga  720
cgatgattgg tgctaa                                                 736

SEQ ID NO: 4           moltype = DNA  length = 135
FEATURE                Location/Qualifiers
source                 1..135
                       mol_type = other DNA
                       organism = synthetic construct
SEQUENCE: 4
aacttgttta ttgcagctta taatggttac aaataaagca atagcatcac aaatttcaca  60
aataaagcat ttttttcact gcattctagt tgtggtttgt ccaaactcat caatgtatct  120
tatcatgtct ggatc                                                  135

SEQ ID NO: 5           moltype = DNA  length = 208
FEATURE                Location/Qualifiers
source                 1..208
                       mol_type = other DNA
                       organism = synthetic construct
SEQUENCE: 5
tccccagcat gcctgctatt ctcttcccaa tcctcccccct tgctgtcctg ccccacccca  60
ccccccagaa tagaatgaca cctactcaga caatgcgatg caatttcctc attttattag  120
gaaaggacag tgggagtggc accttccagg gtcaaggaag gcacggggga ggggcaaaca  180
acagatggct ggcaactaga aggcacag                                    208

SEQ ID NO: 6           moltype = DNA  length = 736
FEATURE                Location/Qualifiers
source                 1..736
                       mol_type = other DNA
                       organism = synthetic construct
SEQUENCE: 6
tcagcaccag tcgtcgtcgg attcgctgta gggttcatgg agacccttcc gagacccagg  60
tcctcttggc cgggccaagc cgtgtgcagg gtaatatcca ttggggagcc tccggccatg  120
ccgagaaggt gaagcgcacg ctggtcctga cgcccggggg gtgcgaggag acctccctgt  180
cgccccggaa gacgcatgcc taacgggagg cggagcatca taagcaccag ccatcgcttc  240
ctcgccacca ccactgccgg gcccgtcagc ttcgtcatag tcagaacccc gataatatcc  300
gtgatggcga ggccctggag gtccttcgct aacgtgtggc ccagaagcag gccaccgcgc  360
acctccatgg cgacatgctc taggactctc gcttcttgca ggtccaggaa cccgccgctc  420
cattcgcggg cttcgcccac tactgtgtcc acctgtcgga gggcggtctc cggcaagggg  480
ttcagcggtt gggcctggat agcgccgcgg accggaggta gcagcccgac cgggtcgtgc  540
```

-continued

```
taccgcttgc tgttgctgtt gttgctgttg ctgctgttgt tgttggggtg gcccgctacc  600
tcccgctttt ctaataactg gtgaataact cacatgtggg cgcggagtgg atggtgtctg  660
agggagttgc cttctccctc ggcggggtgt agacgtacca gatgttgaag gcgccgggct  720
cccgcttact gaacta                                                  736

SEQ ID NO: 7           moltype = DNA  length = 110
FEATURE                Location/Qualifiers
source                 1..110
                       mol_type = other DNA
                       organism = synthetic construct
SEQUENCE: 7
ctgtaaatga atgagaaaac cggtttagaa agtgcacagc tgtcagggaa gtcaacactt  60
cagtgagcat gtgaccatgt ggagtcagct tcctgtttcg tgctgcaatc             110

SEQ ID NO: 8           moltype = DNA  length = 446
FEATURE                Location/Qualifiers
source                 1..446
                       mol_type = other DNA
                       organism = synthetic construct
SEQUENCE: 8
gcccgggcga ggtggcgccc gcccggcccc ccacgcaccc cacgcacaca ccccacccga  60
ggagccgcgc agaggccgcg ggggcccagc acagagggcc cgggagaggg ccagccggga  120
gaccccagac tctggagagg ccagggctgg gccacaaggg tgtcccgcag agaccctcgg  180
ccaaaagaga ccctcctggg cagccacggc gccccccaac cagccccgat ccccccaccc  240
acgacagggg ctctcgggtg ggaggcaggg agcagacaaa ccacacagcc aagggatttg  300
aattaactca gccattttg gagaactttg gggaacatga aaaaaaaaaa aaaaaaaaaa  360
aaaaaaaaca tttttaaaag aaaaaacggg gagaaaaaaa tagcttctat tgatgagttt  420
tatcatctca attgaatctt tccttt                                       446

SEQ ID NO: 9           moltype = DNA  length = 24
FEATURE                Location/Qualifiers
source                 1..24
                       mol_type = other DNA
                       organism = synthetic construct
                       note = Target site
SEQUENCE: 9
tttctgtcct ctggacgcct gtga                                         24

SEQ ID NO: 10          moltype = DNA  length = 2288
FEATURE                Location/Qualifiers
source                 1..2288
                       mol_type = other DNA
                       organism = synthetic construct
SEQUENCE: 10
atttcattta tcaggtgttc agtgaatgct tactatgtaa cagcacagtt atcagcactg  60
gggaaataga tgagtaagat aagatttgca ctttcattag cttacatgcc ataaagaggg  120
aaataaagag aacaccagat gatgataagt ttatgctgag aattaaaatg aagtgatgaa  180
ataatgggaa tgtcaggtgg ctacttttgg tgggatggtc aggaaaggca tctctgggga  240
gataaatttt aagctcagac ctgagtgaaa agaatgagcc agccatggaa acattatgtt  300
aactcacatg gtagtttgaa atgctttatc tgatcaaagg tacttatttt tggtgacttt  360
caacaatatt aagggtctat aaaccaacac tcatttgcat aagaataact accagtgaat  420
ctttttgtat gataggtttt ttgtttgttg tttttttgag acagagtctc gctctgtcgc  480
ccaggctgga gtgcagtggc gcgatcttgg ctcactgcaa cctctacctc cccggttcaa  540
gtgattctcc tgcctcagcc tcccaaagta gctgggatta caggtgcctg ccaccacgcc  600
tggctaattt ttgtattttt agtagagatg gggtttcacc gtgttgtcca ggctcgtgtc  660
aaacttctga cctcaagcca tccacccgcc tcggcctccc aaagtgctgg gattacaggt  720
gtgagccacc actcctggcc atgataggtt attttgtgat gaaaatacct acctcttaat  780
ttgtctgata aatttaaatt ttatgtctag atttcctaag atcagcactt ccatatttta  840
aagtaatctg tatcagacta actgctcttg cattctttta ataccagtga ctactttgat  900
tcgtgaaaca atgtattttc cttatgaata gtttttctca tggtgtattt attcttttaa  960
gttttgtttt ttaaatatac ttcacttttg aatgtttcag acagcagcaa aagcagcaac  1020
agcagcagca gcagcagcag caggggggacc tatcaggaca gagttcacat ccatgtgaaa  1080
ggccagccac cagttcagga gcacttggga gtgatctagg tgatgctatg agtgaagaag  1140
acatgcttca ggcagctgtg accatgtctt tagaaactgt cagaaatgat ttgaaaacag  1200
aaggaaaaaa ataaaacttg tttattgcag cttataatgg ttacaaataa agcaatagca  1260
tcacaaattt cacaaataaa gcattttttt cactgcattc tagttgtggt ttgtccaaac  1320
tcatcaatgt atcttatcat gtctggatct ccccagcatg cctgctattc tcttcccaat  1380
cctccccctt gctgtcctgc cccaccccac cccccagaat agaatgacac ctactcagac  1440
aatgcgatgc aatttcctca ttttattagg aaaggacagt gggagtggca ccttccaggg  1500
tcaaggaagg cacgggggag gggcaaacaa cagatggctg gcaactagaa ggcacagcta  1560
cttcttgccc tcggtcttca ggtcgttgcg cacggtctcc aggctcatgg tcacggcggc  1620
ctgcagcatg tcctcctcgc tcatggcgtc gcccaggtcg ctgcccaggg cgccgctgct  1680
ggtggcgggg cgctcgcagg ggtggctgct ctggccgctc aggtcgccct gctgctgctg  1740
ctgctgctgc tgctgctgct tctgctgctg tctgtaaatg aatgagaaaa ccggtttaga  1800
aagtgcacag ctgtcaggga agtcaacact tcagtgagca tgtgaccatg tggagtcagc  1860
ttcctgtttc gtgctgcaat cgtaaggcct gctcaccatt catcatgttc gctaccttca  1920
cactttatct gacatacgag ctccatgtga tttttgcttt acattattct tcattccctc  1980
tttaatcata ttaagaatct taagtaaatt tgtaatctac taaatttccc tggattaagg  2040
agcagttacc aaaagaaaaa aaaaaaaaaa agctagatgt ggtggctcac atctgtaatc  2100
```

```
ccagcacttt gggaaaccaa ggcaggagag gattgctaga acatttaatg aatactttaa  2160
cataataatt taaacttcac agtaatttgt acagtctcca aaaattcctt agacatcatg  2220
gatatttttc tttttttgag atggagtctt gctctgtcac tttgagacag agtctcgctc  2280
tgtcgccc                                                            2288

SEQ ID NO: 11          moltype = DNA  length = 24
FEATURE                Location/Qualifiers
source                 1..24
                       mol_type = other DNA
                       organism = synthetic construct
                       note = Target site
SEQUENCE: 11
tttgagacag agtctcgctc tgtc                                          24

SEQ ID NO: 12          moltype = RNA  length = 60
FEATURE                Location/Qualifiers
misc_difference        9..40
                       note = a, c, g, or u
source                 1..60
                       mol_type = other RNA
                       organism = synthetic construct
                       note = gRNA
SEQUENCE: 12
ctgataacnn nnnnnnnnnn nnnnnnnnnn nnnnnnnnnn gtgaactgcc gagtaggtag  60

SEQ ID NO: 13          moltype = DNA  length = 47
FEATURE                Location/Qualifiers
source                 1..47
                       mol_type = genomic DNA
                       organism = Vibrio cholerae
SEQUENCE: 13
aattatcaat ttatgggtgt aattatcatt ttatggttgt atcaaca                 47

SEQ ID NO: 14          moltype = RNA  length = 258
FEATURE                Location/Qualifiers
misc_difference        236..258
                       note = a, c, g, or t
source                 1..258
                       mol_type = other RNA
                       organism = synthetic construct
                       note = gRNA
SEQUENCE: 14
tattaatagc gccgcaattc atgctgcttg cagcctctga attttgttaa atgagggtta  60
gtttgactgt ataaatacag tcttgctttc tgaccctggt agctgctcac cctgatgctg  120
ctgtcaatag acaggatagg tgcgctccca gcaataaggg cgcggatgta ctgctgtagt  180
ggctactgaa tcacccccga tcaaggggga accctccaaa aggtgggttg aaagtnnnnn  240
nnnnnnnnnn nnnnnnnn                                                 258

SEQ ID NO: 15          moltype = DNA  length = 20
FEATURE                Location/Qualifiers
source                 1..20
                       mol_type = other DNA
                       organism = synthetic construct
                       note = Target site
SEQUENCE: 15
ccgcccgacc tttcactttc                                               20

SEQ ID NO: 16          moltype = DNA  length = 20
FEATURE                Location/Qualifiers
source                 1..20
                       mol_type = other DNA
                       organism = synthetic construct
                       note = Target site
SEQUENCE: 16
cccggatccc ggctgtgacc                                               20

SEQ ID NO: 17          moltype = DNA  length = 2391
FEATURE                Location/Qualifiers
source                 1..2391
                       mol_type = other DNA
                       organism = synthetic construct
SEQUENCE: 17
atttcattta tcaggtgttc agtgaatgct tactatgtaa cagcacagtt atcagcactg  60
gggaaataga tgagtaagat aagatttgca ctttcattag cttacatgcc ataaagaggg  120
aaataaagag aacaccagat gatgataagt ttatgctgag aattaaaatg aagtgatgaa  180
ataatgggaa tgtcaggtgg ctacttttgg tgggatggtc aggaaaggca tctctgggga  240
gataaatttt aagctcagac ctgagtgaaa agaatgagcc agccatggaa acattatgtt  300
aactcacatg gtagtttgaa atgctttatc tgatcaaagg tacttatttt tggtgacttt  360
caacaatatt aagggtctat aaaccaacac tcatttgcat aagaataact accagtgaat  420
```

```
cttttgtat gataggtttt ttgtttgttg ttttttgag acagagtctc gctctgtcgc  480
ccaggctgga gtgcagtggc gcgatcttgg ctcactgcaa cctctacctc cccggttcaa  540
gtgattctcc tgcctcagcc tcccaaagta gctgggatta caggtgcctg ccaccacgcc  600
tggctaattt ttgtattttt agtagagatg gggtttcacc gtgttgtcca ggctcgtgtc  660
aaacttctga cctcaagcca tccacccgcc tcggcctccc aaagtgctgg gattacaggt  720
gtgagccacc actcctggcc atgataggtt attttgtgat gaaaatacct acctcttaat  780
ttgtctgata aatttaaatt ttatgtctag atttcctaag atcagcactt ccatatttta  840
aagtaatctg tatcagacta actgctcttg cattctttta ataccagtga ctactttgat  900
tcgtgaaaca atgtattttc cttatgaata gtttttctca tggtgtattt attcttttaa  960
gtttgtttt ttaaatatac ttcactttg aatgtttcag acagcagcaa aagcagcaac  1020
agcagcagca gcagcagcag caggggggacc tatcaggaca gagttcacat ccatgtgaaa  1080
ggccagccac cagttcagga gcacttggga gtgatctagg tgatgctatg agtgaagaag  1140
acatgcttca ggcagctgtg accatgtctt tagaaactgt cagaaatgat ttgaaaacag  1200
aaggaaaaaa ataaaacttg tttattgcag cttataatgg ttacaaataa agcaatagca  1260
tcacaaattt cacaaataaa gcattttttt cactgcattc tagttgtggt ttgtccaaac  1320
tcatcaatgt atcttatcat gtctggatct ccccagcatg cctgctattc tcttcccaat  1380
cctcccccctt gctgtcctgc cccaccccac cccccagaat agaatgacac ctactcagac  1440
aatgcgatgc aatttcctca ttttattagg aaaggacagt gggagtggca ccttccaggg  1500
tcaaggaagg cacgggggag gggcaaacaa cagatggctg gcaactagaa ggcacagcta  1560
cttcttgccc tcggtcttca ggtcgttgcg cacggtctcc aggctcatgg tcacggcggc  1620
ctgcagcatg tcctcctcgc tcatggcgtc gcccaggtcg ctgcccaggg cgccgctgct  1680
ggtggcgggg cgctcgcagg ggtggctgct ctggccgctc aggtcgccct gctgctgctg  1740
ctgctgctgc tgctgctgct tctgctgctg tctgtaaatg aatgagaaaa ccggtttaga  1800
aagtgcacag ctgtcaggga agtcaacact tcagtgagca tgtgaccatg tggagtcagc  1860
ttcctgtttc gtgctgcaat cgtaaggcct gctcaccatt catcatgttc gctaccttca  1920
cactttatct gacatacgag ctccatgtga ttttgcttt acattattct tcattccctc  1980
tttaatcata ttaagaatct taagtaaatt tgtaatctac taaatttccc tggattaagg  2040
agcagttacc aaaagaaaaa aaaaaaaaaa agctagatgt ggtggctcac atctgtaatc  2100
ccagcacttt gggaaaccaa ggcaggagag gattgctaga acatttaatg aatactttaa  2160
cataataatt taaacttcac agtaatttgt acagtctcca aaaattcctt agacatcatg  2220
gatatttttc ttttttgag atggagtctt gctcttttaa gctcagacct gagtgaaaag  2280
aatttgagac agagtctcgc tctgtcgcct ttcctaagat cagcacttcc atatttggtg  2340
actttcaaca atattaaggg tctataaacc aacactcatt tgcataagaa t           2391

SEQ ID NO: 18          moltype = DNA  length = 20
FEATURE                Location/Qualifiers
source                 1..20
                       mol_type = other DNA
                       organism = synthetic construct
                       note = Target site
SEQUENCE: 18
aatatggaag tgctgatctt                                               20

SEQ ID NO: 19          moltype = DNA  length = 1205
FEATURE                Location/Qualifiers
source                 1..1205
                       mol_type = other DNA
                       organism = synthetic construct
SEQUENCE: 19
tttaagctca gacctgagtg aaaagaattt gagacagagt ctcgctctgt cgcctttcct  60
aagatcagca cttccatatt ttaaagtaat ctgtatcaga ctaactgctc ttgcattctt  120
ttaataccag tgactacttt gattcgtgaa acaatgtatt ttccttatga atagtttttc  180
tcatggtgta tttattcttt taagttttgt tttttaaata tacttcactt ttgaatgttt  240
cagacagcag caaaagcagc aacagcagca gcagcagcag cagcaggggg acctatcagg  300
acagagttca catccatgtg aaaggccagc caccagttca ggagcacttg ggagtgatct  360
aggtgatgct atgagtgaag aagacatgct tcaggcagct gtgaccatgt ctttagaaac  420
tgtcagaaat gatttgaaaa cagaaggaaa aaaataaaac ttgtttattg cagcttataa  480
tggttacaaa taaagcaata gcatcacaaa tttcacaaat aaagcatttt tttcactgca  540
ttctagttgt ggtttgtcca aactcatcaa tgtatcttat catgtctgga tctccccagc  600
atgcctgcta ttctcttccc aatcctcccc cttgctgtcc tgccccaccc cacccccccag  660
aatagaatga cacctactca gacaatgcga tgcaatttcc tcattttatt aggaaaggac  720
agtgggagtg gcaccttcca gggtcaagga aggcacgggg gaggggcaaa caacagatgg  780
ctggcaacta gaaggcacag ctacttcttg ccctcggtct tcaggtcgtt gcgcacggtc  840
tccaggctca tggtcacggc ggcctgcagc atgtcctcct cgctcatggc gtcgcccagg  900
tcgctgccca gggcgccgct gctggtggcg gggcgctcgc aggggtggct gctctggccg  960
ctcaggtcgc cctgctgctg ctgctgctgc tgctgctgct gcttctgctg ctgtctgtaa  1020
atgaatgaga aaaccggttt agaaagtgca cagctgtcag ggaagtcaac acttcagtga  1080
gcatgtgacc atgtggagtc agcttcctgt ttcgtgctgc aatctttaag ctcagacctg  1140
agtgaaaaga atttgagaca gagtctcgct ctgtcgcctt tcctaagatc agcacttcca  1200
tattt                                                               1205

SEQ ID NO: 20          moltype = DNA  length = 1723
FEATURE                Location/Qualifiers
source                 1..1723
                       mol_type = other DNA
                       organism = synthetic construct
SEQUENCE: 20
atttcattta tcaggtgttc agtgaatgct tactatgtaa cagcacagtt atcagcactg  60
gggaaataga tgagtaagat aagatttgca ctttcattag cttacatgcc ataaagaggg  120
```

```
aaataaagag aacaccagat gatgataagt ttatgctgag aattaaaatg aagtgatgaa  180
ataatgggaa tgtcaggtgg ctacttttgg tgggatggtc aggaaaggca tctctgggga  240
gataaatttt aagctcagac ctgagtgaaa agaatgagcc agccatggaa acattatgtt  300
aactcacatg gtagtttgaa atgctttatc tgatcaaagg tacttatttt tggtgacttt  360
caacaatatt aagggtctat aaaccaacac tcatttgcat aagaataact accagtgaat  420
ctttttgtat gataggtttt ttgtttgttg ttttttttgag acagagtctc gctctgtcgc  480
ccaggctgga gtgcagtggc gcgatcttgg ctcactgcaa cctctacctc cccggttcaa  540
gtgattctcc tgcctcagcc tcccaaagta gctgggatta caggtgcctg ccaccacgcc  600
tggctaattt ttgtattttt agtagagatg gggtttcacc gtgttgtcca ggctcgtgtc  660
aaacttctga cctcaagcca tccacccgcc tcggcctccc aaagtgctgg gattacaggt  720
gtgagccacc actcctggcc atgataggtt attttgtgat gaaaatacct acctcttaat  780
ttgtctgata aatttaaatt ttatgtctag aaatcctaag atcagcactt ccatatttta  840
aagtaatctg tatcagacta actgctcttg cattctttta ataccagtga ctactttgat  900
tcgtgaaaca atgtattttc cttatgaata gtttttctca tggtgtattt attcttttaa  960
gttttgtttt ttaaatatac ttcacttttg aatgtttcag acagcagcaa aagcagcaac  1020
agcagcagca gcagcagcag cagggggacc tatcaggaca gagttcacat ccatgtgaaa  1080
ggccagccac cagttcagga gcacttggga gtgatctagg tgatgctatg agtgaagaag  1140
acatgcttca ggcagctgtg accatgtctt tagaaactgt cagaaatgat ttgaaaacag  1200
aaggaaaaaa ataaaacttg tttattgcag cttataatgg ttacaaataa agcaatagca  1260
tcacaaattt cacaaataaa gcattttttt cactgcattc tagttgtggt ttgtccaaac  1320
tcatcaatgt atcttatcat gtctggatcg taaggcctgc tcaccattca tcatgttcgc  1380
taccttcaca ctttatctga catacgagct ccatgtgatt tttgctttac attattcttc  1440
attccctctt taatcatatt aagaatctta agtaaatttg taatctacta aatttccctg  1500
gattaaggag cagttaccaa aagaaaaaaa aaaaaaaaag ctagatgtgg tggctcacat  1560
ctgtaatccc agcactttgg gaaaccaagg caggagagga ttgctagaac atttaatgaa  1620
tactttaaca taataattta aacttcacag taatttgtac agtctccaaa aattccttag  1680
acatcatgga tatttttctt tttttgagat ggagtcttgc tct                    1723

SEQ ID NO: 21          moltype = DNA  length = 19
FEATURE                Location/Qualifiers
source                 1..19
                       mol_type = other DNA
                       organism = synthetic construct
                       note = Primer
SEQUENCE: 21
caaaggtgcc cttgaggtt                                               19

SEQ ID NO: 22          moltype = DNA  length = 20
FEATURE                Location/Qualifiers
source                 1..20
                       mol_type = other DNA
                       organism = synthetic construct
                       note = Primer
SEQUENCE: 22
aggagaagtc tgccgttact                                              20

SEQ ID NO: 23          moltype = DNA  length = 22
FEATURE                Location/Qualifiers
source                 1..22
                       mol_type = other DNA
                       organism = synthetic construct
                       note = Primer
SEQUENCE: 23
ggacaaacca caactagaat gc                                           22

SEQ ID NO: 24          moltype = DNA  length = 20
FEATURE                Location/Qualifiers
source                 1..20
                       mol_type = other DNA
                       organism = synthetic construct
                       note = Primer
SEQUENCE: 24
taggaaagga cagtgggagt                                              20

SEQ ID NO: 25          moltype = DNA  length = 24
FEATURE                Location/Qualifiers
source                 1..24
                       mol_type = other DNA
                       organism = synthetic construct
                       note = Primer
SEQUENCE: 25
ccattatgtc tcagttgttc agtg                                         24

SEQ ID NO: 26          moltype = DNA  length = 19
FEATURE                Location/Qualifiers
source                 1..19
                       mol_type = other DNA
                       organism = synthetic construct
                       note = Primer
```

```
SEQUENCE: 26
ccagaccatc tcagacacc                                          19

SEQ ID NO: 27          moltype = DNA  length = 18
FEATURE                Location/Qualifiers
source                 1..18
                       mol_type = other DNA
                       organism = synthetic construct
                       note = Primer
SEQUENCE: 27
ggctgggctt ccacttac                                           18

SEQ ID NO: 28          moltype = DNA  length = 22
FEATURE                Location/Qualifiers
source                 1..22
                       mol_type = other DNA
                       organism = synthetic construct
                       note = Primer
SEQUENCE: 28
gtggtttgtc caaactcatc aa                                      22

SEQ ID NO: 29          moltype = DNA  length = 22
FEATURE                Location/Qualifiers
source                 1..22
                       mol_type = other DNA
                       organism = synthetic construct
                       note = Primer
SEQUENCE: 29
agtaactctg cacttcccat tg                                      22

SEQ ID NO: 30          moltype = AA  length = 639
FEATURE                Location/Qualifiers
source                 1..639
                       mol_type = protein
                       organism = Scytonema hofmanni
SEQUENCE: 30
MSQITIQARL ISFESNRQQL WKLMADLNTP LINELLCQLG QHPDFEKWQQ KGKLPSTVVS  60
QLCQPLKTDP RFAGQPSRLY MSAIHIVDYI YKSWLAIQKR LQQQLDGKTR WLEMLNSDAE  120
LVELSGDTLE AIRVKAAEIL AIAMPASESD SASPKGKKGK KEKKPSSSSP KRSLSKTLFD  180
AYQETEDIKS RSAISYLLKN GCKLTDKEED SEKFAKRRRQ VEIQIQRLTE KLISRMPKGR  240
DLTNAKWLET LLTATTTVAE DNAQAKRWQD ILLTRSSSLP FPLVFETNED MVWSKNQKGR  300
LCVHFNGLSD LIFEVYCGNR QLHWFQRFLE DQQTKRKSKN QHSSGLFTLR NGHLVWLEGE  360
GKGEPWNLHH LTLYCCVDNR LWTEEGTEIV RQEKADEITK FITNMKKKSD LSDTQQALIQ  420
RKQSTLTRIN NSFERPSQPL YQGQSHILVG VSLGLEKPAT VAVVDAIANK VLAYRSIKQL  480
LGDNYELLNR QRRQQQYLSH ERHKAQKNFS PNQFGASELG QHIDRLLAKA IVALARTYKA  540
GSIVLPKLGD MREVVQSEIQ AIAEQKFPGY IEGQQKYAKQ YRVNVHRWSY GRLIQSIQSK  600
AAQTGIVIEE GKQPIRGSPH DKAKELALSA YNLRLTRRS                     639

SEQ ID NO: 31          moltype = AA  length = 642
FEATURE                Location/Qualifiers
source                 1..642
                       mol_type = protein
                       organism = Anabaena cylindrica
SEQUENCE: 31
MSVITIQCRL VAEEDSLRQL WELMSEKNTP FINEILLQIG KHPEFETWLE KGRIPAELLK  60
TLGNSLKTQE PFTGQPGRFY TSAITLVDYL YKSWFALQKR RKQQIEGKQR WLKMLKSDQE  120
LEQESQSSLE VIRNKATELF SKFTPQSDSE ALRRNQNDKQ KKVKKTKKST KPKTSSIFKI  180
FLSTYEEAEE PLTRCALAYL LKNNCQISEL DENPEEFTRN KRRKEIEIER LKDQLQSRIP  240
KGRDLTGEEW LETLEIATFN VPQNENEAKA WQAALLRKTA NVPFPVAYES NEDMTWLKND  300
KNRLFVRFNG LGKLTFEIYC DKRHLHYFQR FLEDQEILRN SKRQHSSSLF TLRSGRIAWL  360
PGEEKGEHWK VNQLNFYCSL DTRMLTTEGT QQVVEEKVTA ITEILNKTKQ KDDLNDKQQA  420
FITRQQSTLA RINNPFPRPS KPNYQGKSSI LIGVSFGLEK PVTVAVVDVV KNKVIAYRSV  480
KQLLGENYNL LNRQRQQQQR LSHERHKAQK QNAPNSFGES ELGQYVDRLL ADAIIAIAKK  540
YQAGSIVLPK LRDMREQISS EIQSRAENQC PGYKEGQQKY AKEYRINVHR WSYGRLIESI  600
KSQAAQAGIA IETGKQSIRG SPQEKARDLA VFTYQERQAA LI                  642

SEQ ID NO: 32          moltype = DNA  length = 208
FEATURE                Location/Qualifiers
source                 1..208
                       mol_type = other DNA
                       organism = synthetic construct
                       note = Transposon left end
SEQUENCE: 32
tacagtgaca aattatctgt cgtcggtgac agattaatgt cattgtgact atttaattgt  60
cgtcgtgacc catcagcgtt gcttaattaa ttgatgacaa attaaatgtc atcaatataa  120
tatgctctgc aattattata caaagcaatt aaaacaagcg gataaaagga cttgctttca  180
acccacccct aagtttaata gttactga                                 208

SEQ ID NO: 33          moltype = DNA  length = 219
```

-continued

```
FEATURE                 Location/Qualifiers
source                  1..219
                        mol_type = other DNA
                        organism = synthetic construct
                        note = Transposon right end
SEQUENCE: 33
cgacagtcaa tttgtcatta tgaaaataca caaaagcttt ttcctatctt gcaaagcgac  60
agctaatttg tcacaatcac ggacaacgac atctattttg tcactgcaaa gaggttatgc  120
taaaactgcc aaagcgctat aatctatact gtataaggat tttactgatg acaataattt  180
gtcacaacga catataatta gtcactgtac acgtagaga                         219

SEQ ID NO: 34           moltype = AA  length = 394
FEATURE                 Location/Qualifiers
source                  1..394
                        mol_type = protein
                        organism = Vibrio cholerae
SEQUENCE: 34
MFLQRPKPYS DESLESFFIR VANKNGYGDV HRFLEATKRF LQDIDHNGYQ TFPTDITRIN  60
PYSAKNSSSA RTASFLKLAQ LTFNEPPELL GLAINRTNMK YSPSTSAVVR GAEVFPRSLL  120
RTHSIPCCPL CLRENGYASY LWHFQGYEYC HSHNVPLITT CSCGKEFDYR VSGLKGICCK  180
CKEPITLTSR ENGHEAACTV SNWLAGHESK PLPNLPKSYR WGLVHWWMGI KDSEFDHFSF  240
VQFFSNWPRS FHSIIEDEVE FNLEHAVVST SELRLKDLLG RLFFGSIRLP ERNLQHNIIL  300
GELLCYLENR LWQDKGLIAN LKMNALEATV MLNCSLDQIA SMVEQRILKP NRKSKPNSPL  360
DVTDYLFHFG DIFCLWLAEF QSDEFNRSFY VSRW                              394

SEQ ID NO: 35           moltype = AA  length = 640
FEATURE                 Location/Qualifiers
source                  1..640
                        mol_type = protein
                        organism = Vibrio cholerae
SEQUENCE: 35
MQTLKELIAS NPDDLTTELK RAFRPLTPHI AIDGNELDAL TILVNLTDKT DDQKDLLDRA  60
KCKQKLRDEK WWASCINCVN YRQSHNPKFP DIRSEGVIRT QALGELPSFL LSSSKIPPYH  120
WSYSHDSKYV NKSAFLTNEF CWDGEISCLG ELLKDADHPL WNTLKKLGCS QKTCKAMAKQ  180
LADITLTTIN VTLAPNYLTQ ISLPDSDTSY ISLSPVASLS MQSHFHQRLQ DENRHSAITR  240
FSRTTNMGVT AMTCGGAFRM LKSGAKFSSP PHHRLNSKRS WLTSEHVQSL KQYQRLNKSL  300
IPENSRIALR RKYKIELQNM VRSWFAMQDH TLDSNILIQH LNHDLSYLGA TKRFAYDPAM  360
TKLFTELLKR ELSNSINNGE QHTNGSFLVL PNIRVCGATA LSSPVTVGIP SLTAFFGFVH  420
AFERNINRTT SSFRVESFAI CVHQLHVEKR GLTAEFVEKG DGTISAPATR DDWQCDVVFS  480
LILNTNFAQH IDQDTLVTSL PKRLARGSAK IAIDDFKHIN SFSTLETAIE SLPIEAGRWL  540
SLYAQSNNNL SDLLAAMTED HQLMASCVGY HLLEEPKDKP NSLRGYKHAI AECIIGLINS  600
ITFSSETDPN TIFWSLKNYQ NYLVVQPRSI NDETTDKSSL                        640

SEQ ID NO: 36           moltype = AA  length = 352
FEATURE                 Location/Qualifiers
source                  1..352
                        mol_type = protein
                        organism = Vibrio cholerae
SEQUENCE: 36
MKLPTNLAYE RSIDPSDVCF FVVWPDDRKT PLTYNSRTLL GQMEAASLAY DVSGQPIKSA  60
TAEALAQGNP HQVDFCHVPY GASHIECSFS VSFSSELRQP YKCNSSKVKQ TLVQLVELYE  120
TKIGWTELAT RYLMNICNGK WLWKNTRKAY CWNIVLTPWP WNGEKVGFED IRTNYTSRQD  180
FKNNKNWSAI VEMIKTAFSS TDGLAIFEVR ATLHLPTNAM VRPSQVFTEK ESGSKSKSKT  240
QNSRVFQSTT IDGERSPILG AFKTGAAIAT IDDWYPEATE PLRVGRFGVH REDVTCYRHP  300
STGKDFFSIL QQAEHYIEVL SANKTPAQET INDMHFLMAN LIKGGMFQHK GD          352

SEQ ID NO: 37           moltype = AA  length = 199
FEATURE                 Location/Qualifiers
source                  1..199
                        mol_type = protein
                        organism = Vibrio cholerae
SEQUENCE: 37
MKWYYKTITF LPELCNNESL AAKCLRVLHG FNYQYETRNI GVSFPLWCDA TVGKKISFVS  60
KNKIELDLLL KQHYFVQMEQ LQYFHISNTV LVPEDCTYVS FRRCQSIDKL TAAGLARKIR  120
RLEKRALSRG EQFDPSSFAQ KEHTAIAHYH SLGESSKQTN RNFRLNIRML SEQPREGNSI  180
FSSYGLSNSE NSFQPVPLI                                               199

SEQ ID NO: 38           moltype = AA  length = 230
FEATURE                 Location/Qualifiers
source                  1..230
                        mol_type = protein
                        organism = Vibrio cholerae
SEQUENCE: 38
MATSLPTPSA ITTSALEYAF HTPARNLTKS RGKNIHRYVS VKMSKRITVE STLECDACYH  60
FDFEPSIVRF CAQPIRFLYY LNGQSHSYVP DFLVQFDTNE FVLYEVKSAY AKNKPDFDVE  120
WEAKVKAATE LGLELELVEE SDIRDTVVLN NLKRMHRYAS KDELNNVHNS LLKIIKYNGA  180
QSARCLGEQL GLKGRTVLPI LCDLLSRCLL DTRLDKPLSL ESRFELASYG              230

SEQ ID NO: 39           moltype = AA  length = 603
```

```
FEATURE                Location/Qualifiers
source                 1..603
                       mol_type = protein
                       organism = Vibrio cholerae
SEQUENCE: 39
MAKKGFSSFH RKAVSSQDTL ESIELVSSAN CLESVTYQDI SAFPETIAVE INFRLSILRF  60
LARKCETIVA KSIEPHRVEL QQNYSRKIPS AITIYRWWLA FRKSDYNPIS LAPNIKDRGN  120
RETKVSTVVD SIMEQAVERV ISGRKVNVSS AYKRVRRKVR QYNLTHGTKY TYPKYESVRK  180
RVKKKTPFEL LAAGKGERVA KREFRRMGKK ILTSSVLERV EIDHTVVDLF AVHEEYRIPL  240
GRPWLTQLVD CYSKAVIGFY LGFEPPSYVS VSLALKNAIQ RKDDLISSYE SIENEWLCYG  300
IPDLLVTDNG KEFLSKAFDQ ACESLLINVH QNKVETPDNK PHVERNYGTI NTSLLDDLPG  360
KSFSQYLQRE GYDSVGEATL TLNEIREIYL IWLVDIYHKK PNQRGTNCPN VAWKKGCQEW  420
EPEEFSGSKD ELDFKFAIVD YKQLTKVGIT VYKELSYSND RLAEYRGKKG NHKVQFKYNP  480
ECMAVIWVLD EDMNEYFTVN AIDYEYASRV SLWQHKYNMK YQAELNSAEY DEDKEIDAEI  540
KIEEIADRSI VKTNKIRARR RGARHQENSA RAKSISNANP ASIQKHEDEI VSADNDDWDI  600
DYV                                                              603

SEQ ID NO: 40          moltype = AA  length = 330
FEATURE                Location/Qualifiers
source                 1..330
                       mol_type = protein
                       organism = Vibrio cholerae
SEQUENCE: 40
MSETREARIS RAKRAFVSTP SVRKILSYMD RCRDLSDLES EPTCMMVYGA SGVGKTTVIK  60
KYLNQNRRES EAGGDIIPVL HIELPDNAKP VDAARELLVE MGDPLALYET DLARLTKRLT  120
ELIPAVGVKL IIIDEFQHLV EERSNRVLTQ VGNWLKMILN KTKCPIVIFG MPYSKVVLQA  180
NSQLHGRFSI QVELRPFSYQ GGRGVFKTFL EYLDKALPFE KQAGLANESL QKKLYAFSQG  240
NMRSLRNLIY QASIEAIDNQ HETITEEDFV FASKLTSGDK PNSWKNPFEE GVEVTEDMLR  300
PPPKDIGWED YLRHSTPRVS KPGRNKNFFE                                 330

SEQ ID NO: 41          moltype = DNA  length = 105
FEATURE                Location/Qualifiers
source                 1..105
                       mol_type = genomic DNA
                       organism = Vibrio cholerae
SEQUENCE: 41
tgttgatgca accataaagt gatatttaat aattatttat aatcagcaac ttaaccacaa  60
aacaaccata tattgatatc tcacaaaaca accataagtt gatat                  105

SEQ ID NO: 42          moltype = DNA  length = 48031
FEATURE                Location/Qualifiers
source                 1..48031
                       mol_type = genomic DNA
                       organism = Homo sapiens
SEQUENCE: 42
gtgggggccg ttggctccag acaaataaac atggagtcca tcttccacga gaaagtgagt  60
gtccgcgttc ggtggggagc tgtctgccgc gcggtggcgg gcgtggagcg cggcatcacc  120
gcctctcgga gggctgggtg gggcccgagt cgccccccatg ccgatctcgc ccggcgaggg  180
gcgacgccgc agcctcccgc ctcctcggct cgaggagggg agcatcacct acgcccctac  240
ttcccccgcg gcccccgccc tgggagccgg gagggagtat gggcggggcc gggggcgtct  300
cgggacacgg gagtggggtg gcgcccagtg ggtttgcttc tgcctttctc cgtcactttc  360
catcgctttt cggaggattc cttcacccct ccccaatcct tccctctccc tagggtctag  420
ctagagtcat ctctgggaca cctccctcaa cccctcctac cctaatcctg gcagaattaa  480
cttttcctcc tccggactgc tcaattctat attggagtct tccctacacg tagatctttg  540
gggtcttgtt cgtgtctttc ccctgcacta ggtccgcgag cctcccgagg gaggagacct  600
tggctcgccc actgtagggc ctgacattta ggaagtgaag taggaaaccc ggcgtgcccc  660
taaacaggga agtcgtcaca agagttttta ttacgggatg tttgggtttg gtttcttttg  720
gtactcccat ctttccggag caggcggcca gctttgtttt taggtattag gagtggactg  780
ggatgatttt gttgtagtct gcctagcctg ctgtcccttt aactcttccg tgaccatgca  840
cttgaagata ctgtttgtga tatgtaaaga aactcctcgt ttctctcata ctattatcca  900
gccatttgtg tgtgagtgaa gccttcccca ggacagcttt ggcacatggt atcatgtttc  960
ataatagttt cgtgtttgga aagagttgct ggtaaggctg ttatttaata ggaggagcaa  1020
agggtttttg ttttattaaa tacttataaa tgatcattta tcccagacat ttaaaattca  1080
cacacacaca acaaataaag caaagacaaa agaatacatt taccaaatgt aaatctgtag  1140
cataaatttt ttttaatttt tattttaaag atggggtctc attctgtcac ccaggcaggt  1200
gtgcaatgga gagatcatgg ctcactgcag ccttgatctc ctaggcacaa gcgatcctcc  1260
cgcctctgcc tccagagtag ctgggactac aggtgcatat cgccagggcc aggtaatgtt  1320
tttgggagag acggggtctc gctgtgttgc ccaggctggt ctcgaactcc tggactcagg  1380
tgattctccc acctcggcct ctcgaagtgc tgtgattaca ggcgtgagcc actgtgcctg  1440
gaacaaattg ttaagtacaa tgcttttcat tgtagaaaac atctcggaaa cttttgaaat  1500
aggctgatgt tcagtggggg aggaaggact cagtcgtata gttgtcacta attttttgac  1560
ttgattgaca tgactcgtaa atcatagaca atagagattt ggttgcttgg ctgagtagag  1620
tgcgtgaaaa atacacacgt actttttttt tttttttttt gagatggagt ttggctcttg  1680
tcacccaggc tggagtgcaa tggcgccatc atggctcact gcaacctccg cctccccgtt  1740
caagcgattc tcctgcctca gtctccccag tagctgagat tacaggcgcc cgccaccacg  1800
cccagctaat ttttgtattt ttagtagaga cagggtttca ccatgttggc caggctggtc  1860
tccaactcct gacaggtggt ccgcccgcct cggcctccca aagtgctggg attacaggcg  1920
tgagccaccg cacccggcca tatttttgtt attaatttc aaaggctttg gtgtgggacc  1980
acatttcaac atggaaggcc ttaaacatgt tccacactac ttcctgagaa ttagacaaga  2040
```

```
tttttaacaa tattgttacc tagttgggac acatttgtac tgacccatgg gatgaaaaaa  2100
agctgagtgc tagcctagtg aaaatctact tacccgaaag aaatccctct tagtctgggt  2160
gcagtggctc acaccagtgc tttgggaggc ccagacgggc ggatcatgag gtcagtagtt  2220
tgagaccagc ctggccaaca tggtgaaacc ccgtctctac taaaaataca aaaaattagc  2280
caggtgtggt ggcaggcgcc tgtaatccca ggtactctgg aggctgaggc aggagaattg  2340
cttgaacccg agaggcagag gttgcagtga gccgagaccg tgccactgca cttcagcctg  2400
ggcaacagag cgagactccg tctcaaaaaa aagaaaagga aaaaagagtc cctcttaatt  2460
atcagcatgt gtataggcct acagatactt caggaatacc tttaccatta tcatcaactt  2520
gtatctacat agcatgtgaa gattcaacaa tttagttttt tgggcgtcct caagagtacg  2580
cacctataac catatggccc aattgttaat ctcctataca gtccattctg ggaatgtttg  2640
ggcttactgt gccatttttc cgttcactgc cttcccctct gcaatatacc tttaaccctt  2700
gctaggtcct gggtttggag agccagagaa ccaactttgg ccctaaagaa gctgtgtagg  2760
tagcaatatc tgcctacgaa gggccttgca accatttcct cttggaacct tggtttcctc  2820
tttctgagta gtcactttga gtacccttta ttaagttaga atgtaaaaac agtttctcac  2880
tgatatatct gcagtgcctg agagagggcc tggcacagag taagtactca ataaatattt  2940
gaatggggcc gggcgtggtg agacctgtct ctacaagaat gaacaaaatt agctgggcgt  3000
gttagcacat gcctgtagac ttgggaggct gaggtgggag gattgcatga gtctgggagg  3060
tcgaggctgt agtgagccat gatcgcacca ctgcactcca gcctagggga cagagcaaga  3120
tcctgtctca aaagaaaaaa atgtatatat ttgaatggat aaagagatgg ctttgagttt  3180
ctgagatata tatggtgctg tttatctaaa gtaaacaagt tttctgtaaa tattttaagg  3240
ctttgcaggc cagctgtagt ctctgtcaca cattcttatt tgtgcatgtt tttcccaacc  3300
atgtaaaaat gtaaagtgca ttcttagcta ctggggcagg ttgaatttgg cccatgggct  3360
agagtttgcc aacccctaac ttaaaccttt gtactaactt tatgaccact actggatttt  3420
tgttgttgtt tgttttagtt ctggtgcctg ctttgttttt tttttttttt ttaatcctct  3480
tgctgatgtt tcttggtgca gttactgtgc catttgtatt ggtgctttta atgtaatgca  3540
aactggtaat aatatctaaa cttgctgggg ttgtacataa aattattgaa aagattgaaa  3600
agatgctgag cattgactct gtggcattca ttatgccctt ttgtgattgc tggattttag  3660
ccatctttag gacatttgag ctttaggaga agccaaattc tgtataaatg acttgaagtg  3720
ctaatagcac aggttttgaa acctctgcct gggtttgagt ctcagctctg cctttttacta  3780
cctgtgtgat cctgagcaag ttacttagta tccctgtcct ctagtttcct cctctgtagt  3840
gtggggataa taacatagac ataacctgag agttagagtg tagagaaggc tccctggcag  3900
atagtgctgt agaagtactg gccattgcca ttactcaggt gcttgtgttt gctgaacctc  3960
atagtaaggg ctcggagagc actaagagga ggtgagaaat gctgctagat tgacagcttg  4020
tccccagata gcccattccc gagagcacct taggtttata cctgatttgt gttgtagtta  4080
gtagtgtctc tggtaatttg aactagtttc aggttggtct tgaaaacctg gggaggttgg  4140
gggtaaatga tttggtagca gttctctttt gtgattttat acattatctt tgtagaactg  4200
cagtttgcta attctctgag cccaacacaa tgaagtctgg gcctaaaatc atagaatttc  4260
ttttattttt tttttttgttt ttaatttatt tattccctcc ctccctcctt tcttcctttc  4320
ttccttttct ttctttcttt ccttccttcc ttccttcttt cttttctttc tttcttttct  4380
ttctttggag tctcactctg tcaccaggct ggagtgcagt ggcacgaact ttcttcagag  4440
tctcactttg tcaccaggct ggagtgcagt ggcgcgaact cagctcactg caacctccgt  4500
ctcctgagtt caagagattc tcctgcctca gcctcccgag tagctgggac tataggcatg  4560
tgccaccatg cccagctaat ttttcttattt ttagtagaga cgaggtttca ccatgttggc  4620
caggatggtc ttgatctctt gacctcgtga tccacctgcc tcagcctccc aaagtgcggg  4680
gattacaggc gtgagctacc acgcccagcc tatttttttat tttttgaggc agagtctcac  4740
tctgtcaccc aggctggagt gcagtggtgc aatctcagct cactgcaacc tccgcctcct  4800
gggttcaggt gattctcctg ccttagcctc ctgagcacct gggactacag gcgcctgcca  4860
ccacacctgg ctaattctta tatttttagt agaggcgggg tttcaccatg ttggccaggc  4920
tggtctcgaa ctcctgatct caagtgatca acctgccttg gcctcccaaa gtgctggaat  4980
tacagccatg agccaccatg cccagccaaa tcatgagatt tcaataccgc tgaactttga  5040
ttatggcaaa gtgaacttct gctttgatta aagcttgatg agagaggtgg ctggggatag  5100
tttgagataa gggcaaggca ggaaaatgca taatcttacg tgggctcatt gtcattgtac  5160
aattcttttg gtccatgtgg aatttgatcc gtcctatgac ttaagttatg tttatttttg  5220
tttttatttt tatttatttt gtgtcttttt gagagacatg atgttgctct gtcacctggg  5280
ccagaataca gtggcacaat cttagctccg tgtagccttg aactcctggg ctcaagtgat  5340
cctcccacct cagcccctca aacagttgag attatagtat gaaccactgt gcctagcctt  5400
aagtgatttt taaatttgta ctgaacagtt tgtcctttcc ttccattaaa tcatattaga  5460
agtacagaac ttgatatttc ctgtagcaat acagtttttc tttgatgaag tttgatttca  5520
agtacttatt tttcataatt taaagctatt ttttatagag agaattttaa tcaaatattt  5580
ggatgtcact attgctatat atggtattaa gtatggtgac catagtttgt aaactccaaa  5640
ctgacagcaa gacaggaaat ttgtgttagc aaaggctttt ttcttactgt ttgaattttt  5700
taaaaattag atacaataca gagaggagca cacaaatcat taagagtaca gctcagcgaa  5760
ttttcacaca gtgaacatgt gtaaacagca agtaacaaaa gatttacctg catcctataa  5820
cctcccatta ttccctttttc taggtactgt ctctccactg cattcccacc aaatataacc  5880
actatgctga attctgacat cataaatgag ttttgcctga ttttgagctt ttgtgactgg  5940
aagtgtacag tgtatatacc ctttcgattc tgtcctcttt agtttaccat tgtttgagaa  6000
atttatccat actgttccag aattaactac tgttaattat tgttaattaa ctactgttgt  6060
agttaattca tcctcattgt tatctagtat tcttttgtga gtaaacacaa tttccattct  6120
actgtgatcc cagctatcca tttgggtcgt ttccagtttg gggtccatta caaatagtaa  6180
tgctatctgt aatgctattt tgtattacta caaatagtaa tgctatttgt ggcacaaaaa  6240
tactgctttt gtgaacattc ttatacatgt cttttgatga atgtatgttt gcattgctgt  6300
tgtttacatt atgtacctag taatggaatt gctagatcat aggagatgta tatattaagc  6360
tttagtggat gcattacata attattagtt attattggtt ataccaattt atcctctcat  6420
cagtagtata caacagtttc tgtatctcta atctccaaca ttttagccat tttagagttt  6480
gtgtactaac acattgtggt tttaatttac atttccctga tgactaataa agttgagtac  6540
ctcttttgtg ttctttatag ccatttgact gtcttgtgaa gtgcttgttt gtcttgccta  6600
tttttctttt ctttctttct ttttcttcct tccttccttt ctttctttct tctttctttc  6660
cttccttctt ttctttcttt ctgtctttct ttcttgtctt tcttgtcttt ctgtctttct  6720
tggtcttgcc ctgtcaccca tgctggagtg cagtggtgca gtctcagctt actgtagcct  6780
```

```
cgaccttttt ggggctcaag ttatcctcct ttctcagcct cccaagaagc tggactacaa  6840
gcacgcacca ccatgctcag ttaatttttt attttttgta gaaatggggt ttcaccatgt  6900
tgtccaggct ggtctcaaac ttctgggctc aagtaatcct cctgccttgg cctcccaaaa  6960
tgctgggatt acaggcatga gccaccgcag ccagccttgg ctatttttca aaaggatata  7020
agtagaacat ctgtatatcc cttcaatttg catattattc agtaagagtt gcactctggt  7080
agtagaaata tataaggagg agaaagaagt ggaaacaaaa agtctattct catgagaaga  7140
cttgggggat agtgttctct ctagctccaa gctacttatt ccttacgaaa agttgaagat  7200
aaacttatct cagactgagg ctgtctcaat gttgtcttcc tattccatta tacacatata  7260
acccatattt ttttcaccag ctgaattttg ctcctagaaa attgattcat caggaaaaat  7320
atccgtcttg caaggtggtt ctctttagag tctgctgtgt gacatagctc aggacaaatt  7380
gtgtgatgtc agataggttg ggttaaggaa tagaccttat tggggaaaga gagaacttgg  7440
agggccaagg ttagcaggag aaggaaatgt tctctcatct gccgtcaatt cagggagggg  7500
caaacctggt gtctgtgttc acagggaggg atccatccat ctgtgattct cccttcttat  7560
caggtagcat gggaaagcta cactgttgcg gggaggaggg tcacacgcag gctacttagt  7620
accaggcacc ctggacttgg attcaggttg ccagttgtgt gagaaactgc ccagcacctg  7680
aaggccctga acccatgaga agttgtacct acctcccatg aggaggaatc ctgtcatccc  7740
atgggagctg agcttgggtg cagtccctct tgctggcttg tccaggagtg agctccaggg  7800
ttgtttggga cagttctgct cattgcttta cactgtgtat acattatctg tagagttcca  7860
tgaagagaac ttcagcactg taactgcaag ttttaacatg gaacagaatt tttctcacct  7920
gtattaattc ttaagatttg aagttctatc aacaagcatt tagattgtgt ggagattttt  7980
ttatttttat ttttggagac agagtcttgc tctgttaccc agactggagt ggcagtggca  8040
tggtcttggc tcactgcagg ctctacttcc tgggttcaag cgattctcat gcctcagtgt  8100
cctgattagc taggactaca ggtacacacc accatgctgg ctaatttttg tatttttagt  8160
agagacgagg tttcaccgta ttggtcaggc tggtctcgaa ctcccagcct caagcagtcc  8220
acccacctcg gcctcccaaa ctgctgggat tacaggtgtg agccaccatg cttgactgac  8280
atcatcatgt taaaagaata aatgttctag ggagctgggc acagtgtcat gtttctgtag  8340
ttctagctgc tcgggaggct gaggcaggaa gatcccttga gccctggagt tcaagtccag  8400
cctgggcaac atagtgagat ctcttttttt aaataaataa ataactgttc tagggactaa  8460
aatttccttt caccattagt aatttactgt agaatctcca agaatgaact tattttaggt  8520
actgaaaatg agggagacta aatgttttat acagtagttt ttagtaaaat atgagatttg  8580
atgcatttga tagatgatgt ttgtttaaaa taattcttaa atttttgatc atgtaattat  8640
agtttcatta atggtagatt tgtaaaataa atgttaccaa atgaaaatgc atgtacctat  8700
gttaattatc cttatctaaa gctgaaagtt cagttcaact atgttaaaac atagtagggg  8760
cctggcaggg tggctcttgc ctgtaatccc agaacttagg gaggccaagg tgggcagatc  8820
acgaggtcag gagatcgaga ccatcctggc taacattgtg aaaccgtatc gctactaaaa  8880
atacaaaaaa ttagccgggc atggcggtgg gcacctgtag tcgcagctac ttggtaggct  8940
gaggcaggag aatggcgtga actcaggagg cagagcttac agtgagccga gatcatgcca  9000
ctgcactcca ggctgggtga cagagcaaga ctccatctca aaaaaaaaaa aaaagttggc  9060
caggtgtggc ggctcacacc tgtaatccca gcacttttgg aggccgaggc aggcggatca  9120
caagatcagg agtttgagac cagcctggct aacagagtga aaccctgtat atactaaaaa  9180
tacaaaaatt agccaggcat ggtggtgcat gcctgtagtc ccagctactt gagaggctga  9240
ggcaggagaa tcacttgaac ccgggaggcg gaggttgtgg taagctgaga ttgctccact  9300
gcactccagc ctggacaaca gagcaagact ctgtctcaaa aaaaaaaaaa attaatgatt  9360
aaattattta ggggagccgg gcgcagtggc tcacgcctgt aatcccagca ctttgggagg  9420
ccaaggcggg cggatcacga ggtcaggaga tcaagaccat cctggctaac acaggatgaa  9480
accccgtctc tactaaaaat acaaaaattt agccgggcgt ggtggcgggt gcctgtagta  9540
ccagctactc gggaggctga ggcaggagaa tggcatgaac ccgggtggcg gagcttgcag  9600
tgagccaaga tagcgccact gcactccggc ctgggtgaaa gagtgagact ccgtctcaaa  9660
aaaaaaaaaa aattatttag gggaagatac tatacaattc tgtttaacaa gtcacatttt  9720
aattttttct tttggaaata ttagcaagaa ggctcacttt gtgctcaaca ttgcctgaat  9780
aacttattgc aaggagaata ttttagccct gtggaattat cctcaattgc acatcagctg  9840
gatgaggagg agaggatgag aatggcagaa ggaggagtta ctagtgaaga ttatcgcacg  9900
tttttacagg tactgatttt aaactcacta agtcacattt cttttttttt tttttttttg  9960
agacggagtc tcgccctgtt gcccatgctg gagtgcaatg gcgcgatctc ggctcactgc  10020
aacctctgcc tcccgggttc aagcgattct cctgcctcag cctcccaagt agctgggatt  10080
acaggcacac ggcactatgc ccggctaatt ttttgtatct ttgttagaga tggggtttca  10140
ccatgttggt caggttggtc tcaaactcct gaccttatga tccacctgtc ttggcctccc  10200
aaagtgctgg gattataggt gtgagccacc acacccggct tacatttctt ttaaaaatgt  10260
ggataccatt tagaaaagga tgggccattc ttcctatagg gatctgactg gtgaattata  10320
actgtgctgt taactttgga aatgggaatg cacaagatat tgttttaaat atgcacgcta  10380
atgacagttt gtatccttct ttccccaccc ccacccttgc ttcaactacc tgtcaaaatt  10440
aacagcagcc ttctggaaat atggatgaca gtggtttttt ctctattcag gtaagtagtc  10500
acaagcatgt actatgtgtt gcttacatcc caggcaccgt ttcacagcct ttcaatagtc  10560
actgtaacaa ggcgaccttc ggaagttctt ctgtctacag agtatagatt atactctaga  10620
gtactagatt ttttttttct tgagacagag tctcgttctg tcacctaggc tggagtgcag  10680
tggcgtgatc ttggctcact gtagcctctg cctcccgggt tcaagcgatc ctcctgcctc  10740
agcctcccaa gtagctggga ttacaggcac ccgccaccac accagttaat atttgtattt  10800
ttagtagaga tagtggggtt tcaccgtgtt ggccagtctg gtctccaact cctgacctca  10860
gcctcccaaa gtgctgggat tacaggtgtg agccactgca cctggccaac tagagtacta  10920
gatttttata tagataaaca tgaaaggatt gtagaatctt catattagag tggggcattt  10980
aaaaattcct tcttgagaaa gattaatttg catctggatg ctaataataa ccttaattct  11040
ggccgggcgc ggtggctcac acctgtaatc ccagcacttt ggggaggccg aggtgggcgg  11100
atcacgaggt caggagattg agaccatcct ggctaacatg gtgaaacccc gtctctacta  11160
aaaatacaaa aattagctgg acgtggtgac acgtgcctgt aatcccagct actcgggagg  11220
ctgaggcagg agaatcgctt gaaccaggga gtcgtaggtt gcagtgagcc aagatcgcgc  11280
cactgcactc tagcctggtg acagagcgag actccatctc aaagaaaaaa agaaatcctt  11340
aattctaata agtcacaatg tctcaaactt accatctgtt gggtaaattt gagaaaatgc  11400
aataccttgc taccatcctt ttaaatcagc ctaccagact ggatttcctt attatggttt  11460
gtggcttttg attttttttt tttaatgtat agctctcttt gaattctttg gtggttatat  11520
```

```
atatatgtac tcgcaagatt cttttatctg tgggtctttc attctttttc taacactgtg  11580
agttgtatcc agagtacttt cggaacctct cctgagcgac ctatctctgc agatatcttt  11640
gtttatgttt cccttgtact gccctcctgg actcttcctc atccaccagc atttccatct  11700
agtgctttac cgtgccactg ctaacaggta atggctactg cagggctgaa atcagaggcc  11760
agagtaggcc cagcacttgg cgtttcctat ttgtgccttg ctgctcttgg tgcctgttca  11820
tgtgtgccca ctaccttgca ctcaatttct gtctttgctg gtacctggct cacttgcttc  11880
tttgttggct accttggagg gcagatagtg aattttcaga aatttccctt tttttgtcag  11940
acagattgaa ataaacaggt ttgcattttg ttttttctac aagcggcaag cccatgaccc  12000
tagaagtctg acatctatgg aacccttcagt ttaaatgccc agggagaact tattttggta  12060
gatatgattt ctgacattgc aggtagcaag ttgaatataa tttttctaaa gtagcaccca  12120
cagcagccaa attatcagat gtatatagta gactagtttt aagaaaagca cttatgggta  12180
gaatatacat ctggattttt gaggcagttt tatttaggaa ttgtgtggtt ttctggaaca  12240
tctcagagac ctggtatgaa aagcactctt ctaatatata tgtgtttttt tttatggatt  12300
tagtgatata tctatacaca cacacttttt aaaacctata gccggctggg cgtggtggct  12360
catgcctgta atcccagtac tttgggaggc ccaggcgggt ggatcacaag gtcaggagat  12420
tgagaccagc ctggccaaca aggtgaaacc ctgtctctac taaaaataca aaaatagctg  12480
ggtgtggtgg cgtgtgcttg taatcccagc tactcgggag cctcaggagg agaatcgctt  12540
gaacctggga ggcggaggtt gcagcgagcc gagatcgtgc cactatactc cagcctgggc  12600
gacagagcaa gactctgtca caaaaaaaaa aaaaaaaacc tatagccttc tagagaaatt  12660
tatatatgaa gtacacaact aacatagcta cacttcctaa atttggaatg gagtggttta  12720
gcttatgaaa agttgctatt tttcttaaca ggttataagc aatgccttga aagtttgggg  12780
tttagaacta atcctgttca acagtccaga gtatcagagg ctcaggatcg atcctatgta  12840
agattctgtt ttgcatttca tacatttctt ttcccaaatt tgatttttaa agttgtaatt  12900
tcttaaagaa gagaaataca ttttgaatac ttttgttttg atgttccctg tttcattcac  12960
tcagactttc ctatttcacc tttgtgatgt ccatgagcat ctgccctgta gccttcctgg  13020
caccccagtg tctgtggcag cacagagctg accccataag tggtgcatga ggccatcttg  13080
tggcacagca tcactaagct gctgcagaga cgttcatatg gttgtgtgat cttttaaaaa  13140
catcagtgac acttaactat aaatataatc ttaaattatc acaaatttta tataatattt  13200
gccagtagac aacataaata tgaattcaat atttcaagtt aatattgtct gttttctttt  13260
ttagaaatga aagatcattt atatgcaatt ataaggaaca ctggtttaca gttagaaaat  13320
taggaaaaca ggtaacattt cttacccttc cttgtctttt tttcttatat tgtaccccat  13380
ttaaaactaa aatgtgggcc aggtgtggtg gctcatgcca acagtttggg aggctgaggt  13440
gggggggatca cttgaagcca ggagtttgag accagcctgg gcaacaaagg gaggtcctgt  13500
ctcttaaaaa aaaaataaaa ataaaaataa aaataaataa aaaaaaaaac aaagagccag  13560
gcatggtggc tcacatctgt aattccagct tacttggaag gctgagtcag aaggatcact  13620
tgagctcagg agtttgaggc tgcagtgaac tatgatttg tcactgtacc ccagcctggg  13680
tgacagagta agactgttct ataaaacata aaaataaaaa aaatatattt aaaaattaaa  13740
aaaaaaaaag gattgctgac tttaaaatta ggaaactgac cagtaatgtg tgtgtgtgta  13800
gcatggttta tccttcttga tagatagaaa ttgtcatttt aaaagataat atcagttttc  13860
cttataaatt tatttgtgac aagtatatgc aatttaacta tatcataaga aaaattctat  13920
attaaagata atacaaatgt ggttactttt aagtgggttt ttatgtgatg actatgttct  13980
gtcagttaat tattacattt atagatttgt atttagcata gtgctgtcac aaagcctgaa  14040
atagtgtcaa gcatgaataa agcattcaat tatgtttgct ttagtgtaag attattcatt  14100
atgattccaa aagccatgta atacgtacgt ctacagaaaa tcacttctat tttttaaata  14160
aaacatgaaa tatgtcttga gcaagctatt ttaagaaaca atcatttaac gtccttgtta  14220
ttagaatttt gaatctttga aagagggtta ttgaaaacca gctaggacag taaaaaagaa  14280
taaactagtg atacatgcag caatatggat gaatctcaaa ataattatgc tgaaagaata  14340
acccacaaac aaaatactac ctgctgtatg gtatcattta ttaaaagtct agaaaagtgc  14400
agattcatct gtagtgatgg aaagcagatt gaccagcggt tgcctgggga cgagaaggct  14460
atggaggagt gagaggggag ggttacagag aggcacggga aacatggcaa tgaggaatgt  14520
gttcactatc ttggttgtag taatggtttc atgggagtac agtatacaaa tgtgaaaaca  14580
tttcagaggc cagatgcagt ggctcatgcc tgtaatccca gcacttttgg aggccaaggc  14640
aggaggattg cttgagctca aggagttcag gaccagcctg ggcaatggca caagacccca  14700
tctctaaaaa aaaaatgaaa gaaaaaaaaa ttggctaggc gtggtgatgc atggccgtag  14760
tcccaggtgc tagggaggct gaggagggag cacagaggtc aagcctgcag tgaatcatga  14820
tcgtgctact gcactccagc ttgggtgaca gaaggagatc ctgtctcaaa aaaaaagttt  14880
caaattatac actttaaata tgtgcagttt attatatgtc acttataccc caataaatct  14940
gtttttttta aaatgtaaat acaagccaaa aaaggtataa gtcaagaaaa tatattgaat  15000
taaatctgta agagataatt caaaaacaaa aaccctattg ttatctttta agtcacccaa  15060
atcaaatttg ggaaaagtca cctacttagc ttcatcctaa gttggttctt tctttctttc  15120
tttccttctt ttgagacgga ttcttgctct atcgcccagg ctggattgca gtggcgggat  15180
cttggctccc tgcaacctcc gccacctggg ttcaagcaat tctcttgtct cagcctccca  15240
aatagctgtg tctacagcca cgcaccacca cacccagcta atttttgtat ttttagtaga  15300
gacggggttt cgccatgttg gtcaggctgg tcttgaactc ctgacctcag gtgatccgtc  15360
cgtctctgcc tctcaaagtg ctggggttac aggcgtgagc caccatgccg agccctaagt  15420
tggttctttc ttaaagttct tcctgaggag ccaagagcaa gttaaggaga tgtaacctag  15480
aagcttacag tggaggctag ctgggtgcag tggttcacgc ctgtaatccc agcactttag  15540
gaggctgagg cagggagatc actgaggcca ggagcttgag agcagcttgg cccaacacag  15600
tgacaccttg tctctacaaa aaaaaaaaaa aaaaaaggca gcttacagca gtagaggctg  15660
atgcgagtgg gaatcacctc taggtaaaaa ccagtgtagc gtactgctga gattatttaa  15720
cctctgggtt ttatttatgt gtttttaaaa attatgatcc agtatttttt actttttttt  15780
gtataaagta agcactgaat ttttaaggtt gtattaattt gcaaataaat gtctatctta  15840
ttattttgag agatttaaaa aattttagtt cttcaaaatt gcattttcac attttgaatt  15900
acgttatctt tgacaaatac agaagatgtc aaattttggt ttattttctt tggttctaat  15960
ttatattttt gtttaaaact atatttttca ctatagactc tttctgtctc tcgaggtccc  16020
tgtataatga aaaagaaggc tggaaaaagt attaacattg tcaaaatcca ggaaaagtag  16080
ttggtcatga tattgatcgt taactttaga aactttttgt atcttgtggg ttaaattagg  16140
attactatgt ggtagtgata aatgatgtta attagggccg agtgcagtgg ctaacacctg  16200
taattccagc atgtagggag gctgaggtgg gaggatgtct tgaatccagg agtttgagac  16260
```

```
cagcctgtac aacatagtgt aagacccctt ctccacacaa aaaaattaga aaatttgtca  16320
agcatcttgg tgcacacctg tagtcccagc tgcttgggag gatgaagcga gagaatcact  16380
taagcccagg tgttcgaggc tgcagtgagc tatgattgca ccactgcact ccagactaga  16440
tgaccatctc ttttaaaaaa atgtgtttat atgttatatg tgatagtgct ttttaaaaac  16500
atttttaaat tatagagaca gggtctcact atgttacagc ccaggctggt ctcaaattcc  16560
tgggctcaag caatcctccc accttagcta acctcccaaa gtgctcggat tataggcatg  16620
agctgcatgc ccagctaatt tagtgatttt taaaaactga gctggtaatt ataaattctc  16680
ttcctggaac ttctgacttt ctcacaattg gaatcttttg acaaaaatta tcagtaatgg  16740
gaaaactttg tgtagttgtc atttttcctc ccatcagtgt gatagatatg attggagtta  16800
tgttggactg atattttgaa aaaagattta attatagcta ttaataaaga catttaaact  16860
actgactatg catttttatt cttttgggag ggtttaatgt ttatagttta aagcaaactg  16920
ttgtttttaa aaaagtatct aacagggccg ggcgcggtgg ctcacacctg taatcccagc  16980
actttgggag gcctaggcgg gcggatcaca aggtcaagag atcaagacca tcctggctaa  17040
catggtgaaa ccctgtctct actaaaaata caaaaaaata gctgggtgtg gcggcgtgcg  17100
cctgtagtcc cagctactcg ggaggctgag gcaggaggat ggcatgaacc cgggaggcgg  17160
agcttgcagt gagccgagat cgcgccactg cactccagcc tgggcgacag agcaatactc  17220
tgtctaaaaa aaaaaaaaaa aaaaaaaaaa gagtatttag cagaggccag gtgcagtggc  17280
tcatgtttgt aatcccagaa ctttgggagg ctgaggcggg cggatcattt gaggtcagga  17340
gtttgagacc agcctggcca atgtggcaaa tgtgctgtct ctaactaaaa atacaaaaat  17400
tagctgggtg tggtggtgca gacctgtagt cccagctact tgggaggctg aggcaggaga  17460
atcacttgaa cctgggaggc agaggttgca gtgatccgag atcatgccac tgcactccag  17520
cctgggttac agagtgagac tcttctcaaa aaaaaaaaaa agtatttaat agtgataaat  17580
ctgcagtatt ctcttgtagt ttttaagatc atattattca gtcaaagaaa agagctcaac  17640
ttgaaatatt tccagagttt aaacaatctt actaagcttt gatgggttgt atctattctt  17700
aacatgtgaa acttccttat tacctataat atacactaac ttaaatattg acaatttttt  17760
tccagtggtt taacttgaat tctctcttga cgggtccaga attaatatca gatacatatc  17820
ttgcactttt cttggctcaa ttacaacagg aaggtaagta acggctgaac attttgtaat  17880
gttacctttc gaagtagtta aataaccagg cacattagat gacagtgtga taaaactgtt  17940
tttctggcag tggcagtgaa acaatcttta gttttgacgt ggtgataggc tgtgatttgg  18000
gtgacgctgt tcagttagag ttctcactga cacctggccc ttcctcttct gaggatgctg  18060
ctttctttgc agcccttcta agtaatggct ttttctttta tacatcacat atcacacggc  18120
tgagaggagg gatagatgtt tttcttcttt gcctcttcta ggccactgtt cttccttata  18180
aactccagtt tctttgaaat acatgcccct aacggctggg cacggtggct cacgcctgta  18240
atcccagcac tttgggaggc tgaggcaggc ggatcacgat gtcaggagat cgagaccatc  18300
ctggctaaca cggtgaaatc ctgtctctac taaaaataac aaaaaattag ccggggtgtg  18360
gtggcggacg cctgtagtcc gagctactcg ggaggctgag gcaggagaat ggcgtgaacc  18420
caggaggcgg agcttgcagt gagctgagat cgcgccactg ccctccagcc tgggcgacag  18480
agcgagactc cgtctcaaaa aaaaaaagaa aagaaaaaaa aaagaaatac atgcccctag  18540
attaaactat cccttgtcct tttgcactca tccacaagtc tcttttcatc agtgatttta  18600
ggatctgact cgttgtcttt ttctctactt caactacttt tatcattctt aattatttct  18660
gtatcgtcaa tcaatccagt acctgcctct tagtttcaaa atcacttact cttgcttagc  18720
tattaccagt aatcataacc actgtcaaat ctcaattgca agcatattac tctttaacta  18780
ccacctccta tctttaaacc atgttttgtc tgttttttta ttccagccat tctttaaacc  18840
ctactgtggg gcccaagcat ttcctttata cgcattcttc ctttcttcta ctgcttattt  18900
tctgtaatcc gtcatcataa tcactccatt gcattcttca acgtgtttcc cctctctccc  18960
tccatcatac ttgaatgaca aaaatctcaa ccctggttaa accacatctt ggccttgtcc  19020
attcctgtac cagagtagct ggacgtggct aaaaaataac ataaaacatg atgattggtt  19080
ttactttttt cttaaatgat ctatccatcc attcacccat ccatctatca aagtgactag  19140
gcctatttct gaagcccagg ctggagtgca gcagcataat cacagctcat tgcagctcca  19200
aactcctggg ctcaagtgat tctcttgcct tagcctgttg agtagctggg actacaggct  19260
tgtgctacca cacctagcta aggttttact ttaaatttat tataatcaca aaattcagat  19320
gagcctttag tgctgtctga tatttctact atgttttctt agtgatgtac caccctccaa  19380
ggtgtttata aaaaattatg taccactctc caagaagttt ataaaaaata atgtgccacc  19440
ctccaaggtg actaatttca cagcttatgt ctttaaacct ttaagcactt tcctctccct  19500
tacacacctt ccttgtggct ttccgttaca ttctgctgag aacatagaag caattaaaat  19560
tatgttcttt ctaccagcaa atttatcaat ttgcttatat cttcacctgt gctttgagcc  19620
tatttaaata gatgaatggt cccctacctc taaccaaaac cagtccctca cttgtgggct  19680
ggatcccagc tcttctcacc tactcaagat gttcctgctt tcatctctcc actctcttat  19740
ataatcagtt cccccccccct ttttttgtaa tattcctata agcagtaaaa taagcttttt  19800
atttccattg attaaaaata aaaatcctct cttaattcca tgaaactcca gctgcctccc  19860
catttttatt ttttccttag gattgtctct agtgtgcctt ctcctttctt tgaactctgc  19920
ctcctgggtt caagcgattc tcctgcctca acctcccgag tagctgggat tacaggcgtg  19980
caccaccatg accggctaat tttttttttt ttttttttgag atggagtttc cctcttgttg  20040
ctccggctgg agtgcaatgg cgtgatctcg gctcaccgta acttctgcct cctgggttca  20100
agcgatttc ttgcctcagc ctcccgagta gctggattta caggcatgtg ccaccatgcc  20160
tggctaattt tgtattttag tagagatgga aggggtttct ccatgtttgt taggctggtc  20220
tccaactcct gacctcaggt gagccgccca cctcggcccc ctaaagtgct gggattacag  20280
gcatgagcca ctgcgcctgg ccccggctaa attttttttt ttttttttttg tatttttagt  20340
agagacaggg tttcaccata ttggccaggt tggtctcgaa ttcctggcct cgagtgatcc  20400
acctgcctca gcctcccaaa gtgctgggat tacaggcgtg agtcaccttg cctagccatc  20460
ttttagtaat ggtatttgga gatcacaatt tgagtgctgg catgcttatt gctgctgggt  20520
ttgttatgta gttattgtga attcacattt aggaatatag ggtttttaat tctttgattt  20580
tagatacttg tatctttttt cttttatatt taaaaccttg gttcctgatg atatcccttc  20640
ttagaaaccc tgtctacctt tggccttcag cccaccatgc tgtggttttc ctaacttgct  20700
gcctgcactt ttcagattcc tttcatggat cttaaatatc atctgtaaat aagatctatg  20760
tgtcaataat taccaaactt ttatctttag tcttgacatc taccctgaac acctagcttt  20820
gactaactcc tagctttggc atctccactt ggaaatccaa aaagtgtttc aaactgaaca  20880
tgtctatgaa agacttattt ttttctctct atccatgcta tccatcaggt tttccatttc  20940
cataagggtg actcttgtac tctggttcct atatattata ccgacagagc agcccagagt  21000
```

```
gcttcttaac cagtgtaagg cctgttatgt cccaccctca ctctttgtcc ttcagtggct  21060
tcccagcaca cttagaataa aatctgaagt cttaggccgg gcttggtggc tcatgcctgc  21120
aatcccagca ctttgggagg atgagggggc agatcacttg aggtcaggag ttgatgagac  21180
cagcctggcc aacatggtga aaccctgtct ctaccaaaaa atacaaaaat taactgggtg  21240
tggtgttgtg cacctgtagt cccagctact cgggaggctg agataggaga atcacttgaa  21300
cccgggaggc agaggttaca gcgagccaag atcataccac tgcactccag cctgggtgac  21360
agaacgagac tctcaaaaaa aaattaaaaa aaaaaaatat gtgaagtctt gaataaaacc  21420
caagatcttt accatggccc ctgaacaggg cagagtatcc attcttcaga cactcttcat  21480
agaataccat ggtgagctgg catatttatt atacaataca gaaacaattt tactggcaga  21540
aaacacatta aaccgtctaa actctgaata cagttgtcct cataaaaaat gttcaacata  21600
ctattttgag gttttccatt aatagttctt ataatctttg tcccattatg tgttaatcca  21660
acaaaggata tccaataaca aacaccaaag tttaagaaaa atgtgctagg cgcggtggct  21720
cacacctgta atcccagcac tttgggaggc cgaggtgggc agatcacctg aggtcaggag  21780
ttcgagacca gcccagccaa catggtgaaa ccctgcctct cctaaaaata caaacattaa  21840
ctgggtgtgg tggtgggtgc ctgtaatccc agctactcag gaggctgagg caggagaatc  21900
gcttgaacct cctgggaggc agaggttgca gtgagctaat attgcaccac tgcactccag  21960
cctgggtgac agagtgagac tccatctcaa attaaaaaaa aaaaaaaatt aatgatagag  22020
aaacttaaat cagttagatt gttttaggta tagcccatcc ttggtttttg tgtgtagcat  22080
ctagcttggg gaaaccctgg atttctggaa tcatatttag acacagtcac actagactaa  22140
tgtaattctt ttgggatgca aaccacacgt ttgacacctt aaatagcttt taggtatttg  22200
gcttcccagc ccctattttt agttacaagg ggtgtacatg tgtgggtcag ggtgggggta  22260
gctctttccg cagatgatta gttttagcca tgttactagt tattgcacac attatctgtg  22320
tcctcacagc agccctgtga gtaagtgtat tagggttctc tagagggaca gaactaataa  22380
ggtagatgta tatatgaagg gtaatgtatt aaggagtatc gactcgtatg atcacaaggt  22440
gaagtcccac aataggctct ctgcaggctg aggaaccagg aagccagtcc aagtcccaaa  22500
acctcaaaag tagggaagct gacagtgcag ccttcagtct gtggcaaaag gcctgagagc  22560
ccctggcaaa ccactggtgt aagttcaaga gtccaaaaga tgaagaactt ggagtctgat  22620
gtttgagggc aggaagcatc cagcatggga gaaagatgaa ggctcagcaa gtctagtact  22680
tccacactct tatttctgcc tgctttattc tagctgagct ggcagctgat tagatggtga  22740
ccacccagtt tgagggtggg tctacctctc ccagttcact ggcttaaatg ttaatctcct  22800
ttggcaacac cctcgcagac acacccagaa acaataattt gtagccttca atccaatcaa  22860
gttgataata ttaaccatca caggaaggta ctagtatcat atgtttaaca gtagaaacca  22920
agacaaatgc agctaggaag tgggagaact gggatcagat gcaggcagtc tgattctaaa  22980
tcagttgctg ttacccactc tgacaacagt aagtgagtag cctgctcagt caagtactat  23040
attagtaggg ccctttacag acatatttat ttctcacagt cactcaatga gacggctctt  23100
ccagtcttac aatggagaaa gtgaggctca gagactttaa gtaacttacc ttagacgact  23160
ttactagtaa gtataagaat cattatttgg actaaagtct ttctgaatcc tcagcttgta  23220
tttttttcca gtgttctgtg ctgccttttt atctactagt gttttacatc aattttgaat  23280
ctctttacta actggttagg ttgatttttg ccttttttttt ttaggttatt ctatatttgt  23340
cgttaagggt gatctgccag attgcgaagc tgaccaactc ctgcagatga ttagggtcca  23400
acagatgcat cgaccaaaac ttattggaga agaattagca caactaaaag agcaaaggta  23460
aaaatgaggc ctgcagtatg gaatatatgg tagtatttca ttatgagaat taaattttca  23520
tgcttagatt gaatatgtgg tccttgtgtt gttggcgact ctattttgga ccttatattt  23580
tagtgaagtt tattagttta aacttgaatc aactctttga aatacttaaa tatattaact  23640
tagttagctg gtatggtata ttcctagcac ttcgggaggc tgaggcaggc tgattgcttc  23700
aacccaggag ttcgagacca gcctgggcaa catggcaaaa cctcatctct acaaatagta  23760
caaaaattag ccagatgtgg tggtgtatgc ctatagtccc agctacttgg gaggcagagg  23820
aagaaggatc acctgaaact ggggaggtag agactacagt gagccataat cacactaccg  23880
cactccagcc tggtcgagag agtcagaccc tgtctcaaaa aaaaaaaaaa aaagaaacgg  23940
aaaaaaaaaa cttagttgga ttcaaattgc aacacaatca ttatattact agagcttatt  24000
tgccagaaaa cattttaagt tttgacttac ttaaagcctt tacattacaa atgcctttat  24060
gttatgtcta aaatagaaga ttggttgcag ttattaccag tgcttttgtt ctttagagtc  24120
cataaaacag acctggaacg agtgttagaa gcaaatgatg gctcaggaat gttagacgaa  24180
gatgaggagg atttgcagag ggctctggca ctaagtcgcc aagaaattga catggaagat  24240
gaggaagcag atctccgcag ggctattcag ctaagtatgc aaggtaaaga cattctgatg  24300
tgtgttgtat tcattgctga agaattgatt ccaattattc ttagatttca tggaagttaa  24360
tgtactctta gaggtgtttt gacaattact gcagaagcaa tagctatata gtgggctttc  24420
cctttagatt tcttataatg gaaatcactt tttacaacct atattttatt aggagtagtt  24480
atatttttac tcctggttat tttatttggt ttcaacactg tactaacaca atagtaaatt  24540
gtggttttaa tctttgtggg tatcagttga cccttatcca aatcagctgt tacataaata  24600
tgtgccatta gacactatgg aagggcctgg acagggaata taaactgatt ttacaaaaac  24660
ccaacattta ttggctatgc aacttaaacc gtaagcccac tttggtgggc ccagtttttt  24720
agtgatataa actatcaata gagaaaagcg aaaacatatc ccctagacaa tctaggcaaa  24780
gaaaaatgtt aagacatagc tcaaagtagc ttaattaaaa gtttgaagtg ggtttttttgt  24840
tttatttttt tctaactcat atgtatttgc ttctactttc taatgaaatt atttatcagt  24900
tgatttcctt agatatctaa ataaaattga aatttcatta atgggaagat tatttttatc  24960
ctgaactttt cttgcctcta tgcatgcctc tgagtactcc atatggtgtg caatcccatt  25020
tttgattaat agagtcctgc tggattagca gggacagaaa tcagctttag atttctttct  25080
tttttttttt tctttctttt tttttttttt tttttttgag tcagagtctc actgtcgccc  25140
agcctggagt gcagtgatct tggctcactg caacccctgc ctccgaggtt caagcgattc  25200
tcctgcctca gcctcctgag tagctgggac tacaggcgcc taccaccacg cccagctaat  25260
tttttgtact tttagtagag atagggtttt gccccttttgg ccaggctggt cttgaactcc  25320
tgacctcagg tgatccacct gccttggcct cccaaagtgc tgggattaca tgtgtgagcc  25380
accacgccca gccagaagag tagaatattc ttaaagagaa aacgttttaa aggcttactc  25440
aaatgagtat aaacaaacat attgttgctt gaattggtaa atacagtgat tggtttttgt  25500
tgtgttgtgt tttgttttca ggtagttcca gaaacatatc tcaagatatg acacagacat  25560
caggtacaaa tcttacttca gaagagcttc ggaagagacg agaagcctac tttgaaaagt  25620
aaagtagttg gtacaagtta aagtagcatg tttaatattt gctttggcta ttttgtctat  25680
ttgtaaatgg ttactgcctg aatcctgtga atatttgaat gtatttttta aaaatttaca  25740
```

-continued

```
gcaaatagga cgggcacggt ggcttacgcc tgtgatgcta gcagtttggg aggccaaggc  25800
gggcagattg cctgaggtca ggagttcgag accagcctgg gcaacacagt gaaaccccat  25860
ctctactaaa aatacaaaag aatcagctgg gcatggaagc gtgcgcctgt agtcccagct  25920
gcttgggagg ctgagccagg agaattgctt gaacccggga cgtggaggtt gcagtgagcc  25980
gagatcgcac cactgccctc cagactgggt gacagagtga gactccgtct ccaaaaatat  26040
atgtatatat atataaataa aaataaaaat ttacggcaaa taacatgaaa caaaaaaacc  26100
ttgccccaat actggataaa ttttttaaac tgagtgaagg aaaccttata aaatttcatt  26160
tattaaaaga aaaatgaaat taggacaaga caagaagaat gccaattgat cctttggatg  26220
tacttcttgc ttacctgatt aaccctgcaa aattcctcta ccaatcagta cgaaaaacag  26280
ctttggaggt atgggagcgc attcccaaat agacgtggta gttcatttag ctgctcatgg  26340
ccgcttcagg cagtcctgta agcctgttag catcagggga atggatgcaa accataaatc  26400
tggatcaact cctaaaacct taccttgtgc ccagccttgt aagtgcttgc taaataggaa  26460
ttccaccata tgaaaataca ttcttttcaa gtaactatca ttcagacttt tgtcccccac  26520
tttttttttt taaagaaaaa taaaaggctg ggcacggtgg cttacgtctg taatcccacc  26580
attttaggag gccaaggcag gtggatcacc tgaggtcagg aattcaagac cagcctgacc  26640
aacatggtga aacctcatct ctactaaaaa tacaaaaatt agccgggcat ggtggtgggt  26700
gcctgtaatc ccagctactt gggaggctca gacaggagaa tcgcttgaat ctgggaggca  26760
gaagttgcag tgagctgaga taacgccatt gcactccagc ctgggggaca agagcgagac  26820
ttcgtctcaa aaaaaaagag aaagaaaact tcatgttaaa gattacaaga taaataatca  26880
gacccactga tcctaggtca gaaaacagag tcatagctca atctgactta ctatttgctg  26940
tatttcatcc attctgagat gcacatagtt tcacatttca atgtctctga aattgagaag  27000
catcttacag tcataattga cagtatatta gcagcaccta taaatattgg ctcattttac  27060
atttgatggt ataatgaaga aaatatttac cttttttttct gttttgtttt taagtcacaa  27120
ctcagaagta gatgaaggaa aattctgatc agctgacatc ctcttaatgt gagatatttc  27180
tagtctttat tcagtataga ttaatggcta attatatgtt aaatttcaaa gtagtgctta  27240
ttagtgcttt ttacttttaa gtttcaaaat taacttttta attataataa actccaaatt  27300
tatacaaaag tagaaaaact agcatactcc tgtttatgac ccagattcaa caaatactag  27360
cacacggcca atcttgcttt tttttttttt tttttttgag atggagtctt gctctgttgc  27420
ccaggctgga gtgcaatggc acaatttctg ctcactgcaa cctctgcctc ctgagttcaa  27480
gcgattctcc cacttcagcc tcccaagtag ctgggattac aggtacacac caccatgcct  27540
ggctaattct tgtattttta gtagacacgg gatttcacca tgtcgtccag gctggcctta  27600
aactcctgac ctcaagtgat ccacctgcct cggcctccca gagtgctggg attacaggca  27660
tgagccactg agcccggccc aatctcgttt tataatactc ccatctccca ttctttccac  27720
tgtcccacct gcaagtttgg attattttgt aacaaatctc aatcatcata ttattctata  27780
accattttaa tatgtgtctc taaaatatat tagctttatt tttaacatag ttaaatgcta  27840
ttgtcataaa ataataatca taataattaa ttgtaattct atatcatcaa ttatctagtt  27900
aatgtaaaaa ataaatctaa ggccaggcgc ggtggctcac acctgtaatc ccagcacttt  27960
gggaggctga ggtgggcaga tcacctgaga tcaggagttc aagaccagcc tgaccaacat  28020
ggagaaaccc catctctact aaaaatacaa aaaattagcc aggcgtggtg gcgcatgctt  28080
gtaatcccag ctacttgaga ggctgaggca ggagaatcac ttgaacccgg gaggcgaggt  28140
tgcggtgagc cgagatcgtg ccattgcact ctagcctggg caaaaagagt gaaactccat  28200
ctcaaataaa taaataaata aataataaaa aataacttaa atctacttaa ttagaaaaac  28260
taacattcta aaaattttat tttaagaaat atcaaaattg gctgggcacg gtggctcacg  28320
cctctaatcc ctgcactttg gaaggctgag gtgggcggat cacctgaggt caggagggtc  28380
aggagtacaa gaccagcctg gccaacatgg cgaaaccctg tctccactaa aaatacaaaa  28440
attagccagg catgatgatg ggcacctgta atcccagcta ctcaggaggc tgagacagaa  28500
gaatcgcttg aacccaggag gtagaggttg cagtgagctg agatcacccc actgcactcc  28560
agcctgggtg acagagtgaa actccgcctc aaaaaaaaaa aaaagagaaa agaaatatag  28620
aaattaaagc atacatggcc aggcgtagtg gctcatgtct gtaatcccag cactttggga  28680
ggctgaggca ggcagatcac ttgaggccat gagttcaaga ccaacctggc caacatggcg  28740
aaagcctgtc tctactaaaa atacaaaaaa attagttggg catggtggtg cacacctgta  28800
atcacagcta ctttggaggc tgaggcagga gaatcgtttg aacccagagg tggaggttgc  28860
agtgagccga gattgtgcca ctgcactcta tcctgggtga cagagcgaga tactgtctca  28920
aaaagaaaaa aaaaaggctg ggcgcggtag ttcatgcctg caatcccagc actttgggag  28980
gccgaggcag gcagattacg aagtcaggag atggagacca tcctggctaa tacagtgaaa  29040
ccccgtctct actaaaaaat acacaaaaat tagctgggtg tggtggcagg cacctgtagt  29100
cccagctact ctggaggctg aggcaggaga atggcatgaa cccgggaggt ggagcttgca  29160
gtgagcagag atcacaccac tgcactccag tctgggcgac agagcgaggc tctgtctcaa  29220
aaaaaaaaaa gaaagcatac tctcacctcc ttcagtgact gatgttagta ttttggcaca  29280
ttctttttct gtgacatata cacacttacc ttgtaagtgt tgtactcatt tcctatgaca  29340
gtaaatagtc tttgtaacag gctgcatgat atttcataaa atgaatggat gtggcataat  29400
ttatatgtga gccttttgaa ttctgctatt ataattaata ttgcaatgaa caattcttat  29460
attgcctcta cacctcaaat gtcttatcat ttcttctagt ttttctgagg atgtcagatt  29520
attgggttaa aggatatgaa catttttaag gccttggaac agatttctaa attgctttcc  29580
agaataattc ccatgtgata ctttcaccat gtttatttca gacttttttt tttttttttt  29640
tttgagacga aatctcactc tgtcacccag gctggagtgt agtggcatga tctcggctca  29700
ctgcaacctc cgcctcctga gtttaagcga ttattctgcc tcagcctccc aagtagctgc  29760
ggttacaggc aagtgcctcc atgcctggct aatttttgtg tcttttgtag acatggggtt  29820
tcaccatgtt gcccaggctg gtttcgaact cctgagctca ggcaatctgc ctacctcggc  29880
ctcccaaagt tctgggatta caggcgtgca ccaccgcgcc cagccatcag agtctttttt  29940
gtcaaaataa aatggtctaa agacatacat catagagaaa ctataataca aaatttacag  30000
gtatatctaa gaaaagaaaa gtatatttaa agcataaaaa taaactgctc ttttacttaa  30060
aatttttttaa aaactggatt aaaaatatga aacttccaac aaattgagct tttttttttt  30120
tttttttctt ttttgagacg aggtctcgct tttgtcaccc agtctggagt gcagtggcgc  30180
gatctcggct cactgcaacc tccacctccc tggttcaagc aattcccctg cctcagcctc  30240
ccaagtagct gggattacag gcgcatgcca ccacgtcggg ctaatttttt tgtattttta  30300
gtagagaggg ggtttcacca tgttggccag actggtctcg aactcctgat ctcaggcaat  30360
ctgccagcct gggtctccca acatgctggg attacaggca tgagccactg cactcggcct  30420
gaacttttta tagtagtaac gataattcag taatgtccaa taatgactaa gtaagttata  30480
```

```
acaagtacaa tgtcagcaat aactagtgct ttttagtaaa cagggtcagg caaccttgta  30540
ccctttaaa aatgttcgaa tatcgatata cctccttcct acttggtgga ggattgattg  30600
aggaggaaag tgtgcagtga tggttaccag cttcagcctc ttggcttgac tttgcaaata  30660
ctggtgagaa tttggaaaga gcttgagaat atcttacata gtcacatgtt gctgagaaga  30720
gttaagaact aacttcttga tgttcatttt taacaatggc ttgcattcaa aaccttgtag  30780
agctcattag taggagctaa gaagctaata tttgcctttc actaaaattc ctgattactt  30840
agcctaggta gttcgttgtc tctctaggtt ctgtctttgg gagcttgggt ctaaggttat  30900
caagctaact ctttcttccc tctcaccctt cccaaattga ccctggtgct gatttgttat  30960
tcatacgatt ttctagtttt tcttttccct ttttgagtat ttgaagcttc atactgaata  31020
tagtaatcat agtattcatg cataaagaaa atcataaagt aattgcataa atgcataaag  31080
taatcatagt tttcatgcat taaaaaaact agttttggct gggcgctatg gctcacgctt  31140
gtaatcccag cactttcgga ggccaaggca ggcgaatcat ctgaggtcag gagttcgaga  31200
ctagcctggc caacatggcg aaacctcttc tctactaaaa atacaaaaaa attagccgag  31260
tatggtggcg ggcgcctgta atcctagcta tttggcaggc tgaggcagga gaatcacttg  31320
aacctgggag gcagaggttg cagtgagccg aggttgtgcc attgcactac agcctaggcg  31380
acaagagcaa gactccatct caaaaaaaaa aaaaaaaaaa aaaaaactcc ctattacaga  31440
ttcataattt atgagtcatt aaataatatt ttcaagccat gacatttttt ccagcagtag  31500
tctctaaatc tgttttacca tcataaaacc ccaagcaaaa ctctactaca tcagctgtgt  31560
cactgtaaaa cctgccttaa ctcacagaag catgaaatta agcaatgtgt gtgaaactat  31620
tttataaact gtaaagtatt ccatacatac atgttggcag ttattaatgt cttctctagg  31680
tgtggctttg aaatggatgc agatgctttc tgttacaaaa aacataagtt gcaaatgttc  31740
tataacaagg agagacacaa atatcttcat ggacatggat tgctatgagt gtttgattgc  31800
ctaatacttg agccaccact tcagtgatat ggtataattt atcaaacagt gttgagaaac  31860
agaaactact ggggatgttt taaagaggaa aatacttaat atagaaatta ggggtttaca  31920
taatcttaag aaaggatgaa ggtgcagctc ttagccaggc ctccacagta ccacaaacca  31980
acttgcagga agagctgtaa ccactgcccc agttgggaca atgggtaatg aggatattaa  32040
atttaagaac atactgctat agcaatgatc cttggcatag aaagctgcca ccacaattgc  32100
ctagagatgg gaacatgaag tctggccccc attgcaacag cagtgaagca gaattttggg  32160
actggcatct cccaaatggc tttgcttgcc accagagaac aaccaaagtg gagggagatg  32220
gctaggcctc atttctgcct attttatttt attttttgag acggagtctt gtctgtcgcc  32280
caggctggag tgcagtagtg tgatctcggc tcactgcagc ctccgcctcc cagcttcaaa  32340
caattctcct gcctcagcct cctgagtagc tgggattaca ggcacccgcc actgtgccca  32400
gccaattttc ttatttttag tagaggtggg gttttgccac gttggccagg ctggtcttga  32460
actcctgacc tcaggtgatc tgcccgcctc agcctcccaa agtgttgtga ttacaggtat  32520
gagccaccat gcctggccca tttctccctt tttttttttt tttttttttt gaggtggagt  32580
ctcactctgt tgcccagact ggagtgcagt ggtgcaatct tggcgcattg caacctctgc  32640
ctcccagttt caagcaattc ttctgcttca gcctcctgag tagctgggac tacaggtgtg  32700
tagcaccaca cctggctaat tttgtttttt gttttgtttt ttttgagaca gagtctcact  32760
ctgtcaccca ggctggagtg tagtggcatg atctgggctc actacaacct ccgcctcccg  32820
ggttcaagca attctcctgc ctcagcctcc agagtagctg ggattacagg tgtgcgccaa  32880
cacacctggc taattttttt gtatttttaa tagagatggg gtttcaccat gttggccagg  32940
ctggtctcga actcctgacc tcgtgatccg cccgcctcgg cctcccaaag tgctgggatt  33000
acaggcatga gccaccgtgc ccagacaagg tttgtatttt tagtagagac agttttgcca  33060
tgttggccag gctggtcttg aactcctcac ctcaggtgat ccgcctgcct tggcctccca  33120
aagtgctggg attacaggcg caagccactg tgcctgaccc gtttctgctt tttaaagctc  33180
atgtgagcac ttaatttgta accagaatcc tacttgtaaa ataatctaag acatgtagct  33240
tttagctttg taacctctat aatattgatg gcacagtggg agtggatgct gagtaccact  33300
tgaacatgtt ccacctcagt gtcttcacag ctggaaggtg tctacattgt ttcaaggtgg  33360
acaattgatt tacttctcat ttttcataaa ctaaaagtag aataaaggct attcctctaa  33420
aattgctatc tcacctgtca ctcccttgca ttctcacata ccttcttgag tggaggggca  33480
gagggcatgg agtgatagca gatgtgccag gaattctcca taactcagtc cgtccctctt  33540
gtgctatgtt gcagcatcag gatttgctaa tgggaggata ctgcccttac gtgcatcatt  33600
agccatgcac actaaggtct tacacctaca cacaggtcag tattctggct cagagaccaa  33660
cagggagaaa ttgcagttct cattagttga actttcttta ttgttcacag ttttaaaaca  33720
caaaattgag aggaactcta taaaaaatgt gccattctat taataattgt tgctggtaat  33780
ttaaaaatcc ttgttccttt tcaaattctt atataccttt tttttttaaa cacttgatct  33840
tagccaaaag accgagaagc aatctttttt tttttttttt ttttttttaa cctatagctt  33900
ctcactgaga ttgtcagctg tttgtaagtt ttggtttttg gtttctgtg tttgtattta  33960
catatatgaa atacagattg agtatccctt atccaaaatg cttaagactg gaagtgtttt  34020
agatttgggg ttttttagga tttgtgaata tttgcactat acttaccagt taagcattcc  34080
aaatccaaaa tttcaaatct gaagtgttcc actgagcacc tcttttgagt atcatgttgg  34140
tgctcaaaaa gtttctgatt ttggagcatt tggatttctg attctcggat ttaggatgct  34200
tgacctgtaa tttcagattt acataaaagc agaaatagta cacagagctc cttatatcct  34260
tcacccagat tccccaatta ttggcctttc tgaaccattt gggaataata tgcagatatg  34320
attttccatt atgtctcagt tgttcagtgt atattttcta agtacaagaa tatattccta  34380
catatttaca tgataaccgt catgtttaaa cattttaaaa tggggatttg tattacattg  34440
tttctctttt tgaaaaaatt acagaggagc ttaatgcaat cagtattact taaaatctga  34500
taatgtgtgt taaatagtag ttttcattta tttcatttat caggtgttca gtgaatgctt  34560
actatgtaac agcacagtta tcagcactgg ggaaatagat gagtaagata agatttgcac  34620
tttcattagc ttacatgcca taaagaggga aataaagaga acaccagatg atgataagtt  34680
tatgctgaga attaaaatga agtgatgaaa taatgggaat gtcaggtggc tacttttggt  34740
gggatggtca ggaaaggcat ctctggggag ataaatttta agctcagacc tgagtgaaaa  34800
gaatgagcca gccatggaaa cattatgtta actcacatgg tagtttgaaa tgctttatct  34860
gatcaaaggt acttattttt ggtgactttc aacaatatta agggtctata aaccaacact  34920
catttgcata agaataacta ccagtgaatc tttttgtatg ataggttttt tgtttgttgt  34980
tttttgaga cagagtctcg ctctgtcgcc caggctggag tgcagtggcg cgatcttggc  35040
tcactgcaac ctctacctcc ccggttcaag tgattctcct gcctcagcct cccaaagtag  35100
ctgggattac aggtgcctgc caccacgcct ggctaatttt tgtattttta gtagagatgg  35160
ggtttcaccg tgttgtccag gctcgtgtca aacttctgac ctcaagccat ccacccgcct  35220
```

```
cggcctccca aagtgctggg attacaggtg tgagccacca ctcctggcca tgataggtta  35280
ttttgtgatg aaaataccta cctcttaatt tgtctgataa atttaaattt tatgtctaga  35340
tttcctaaga tcagcacttc catattttaa agtaatctgt atcagactaa ctgctcttgc  35400
attcttttaa taccagtgac tactttgatt cgtgaaacaa tgtattttcc ttatgaatag  35460
tttttctcat ggtgtattta ttcttttaag ttttgttttt taaatatact tcacttttga  35520
atgtttcaga cagcagcaaa agcagcaaca gcagcagcag cagcagcagc agggggacct  35580
atcaggacag agttcacatc catgtgaaag gccagccacc agttcaggag cacttgggag  35640
tgatctaggt aaggcctgct caccattcat catgttcgct accttcacac tttatctgac  35700
atacgagctc catgtgattt ttgctttaca ttattcttca ttccctcttt aatcatatta  35760
agaatcttaa gtaaatttgt aatctactaa atttccctgg attaaggagc agttaccaaa  35820
agaaaaaaaa aaaaaaaagc tagatgtggt ggctcacatc tgtaatccca gcactttggg  35880
aaaccaaggc aggagaggat tgctagaaca tttaatgaat actttaacat aataatttaa  35940
acttcacagt aatttgtaca gtctccaaaa attccttaga catcatggat atttttcttt  36000
ttttgagatg gagtcttgct ctgtcaccca ggctggagtg cagtgtcgcg atctcggctc  36060
actgcaagct ctgcttcctg ggttcatggc attctcctgc ctcagcctcc tgagtagctg  36120
ggactacagg cgcccgccac atcgcctggc taattttttg tatttttagt agagacaggg  36180
tttcaccatg ttagccagga tggtctcaat ctcctgacct catgatccgc ccgcctcggc  36240
ctcccaaagt gctgggatta caggcgtgag ccatcacgtc cggccagaaa tcatgaatat  36300
tagtaggtga aaaataaaca cattttacca cctggaaaat gaaaaatact tgagtataat  36360
ctaaataaca atgggaagtg cagagttact ttccaggtct cggtttaaat atgtcttaaa  36420
ctttggccaa ttagtagtag aagttgagag aaaaagtaac tatctgacaa agaaattata  36480
agcagaatat ataaagaact cttaaaactg aataatcaga aaacaactca ataaaaaggt  36540
gaaggatttg aaaagatatt tcaccaaata agacataggg atgacaaata agcacatgaa  36600
aagactctca gcatcactag tcacagggaa atgcacgata aaaccacagt gagacaccat  36660
ggcacccctg taggtatggc tttaatgaag aaataaaact gacaatacca agtgttggca  36720
aggatccaag cagctgagac tcatatactg ttaatgggaa tgtaaaagtg tacagctttg  36780
gaaaacagtt tggcattttt ttgataaatg tatacttagc catgtgatcc agcagtccca  36840
atcatgtata tataaccaaa agaaaagaaa acttaggttc acataaaaac ttatatcaaa  36900
tgcttatagc tgaccaggca tggtggccca tgcctataat cccagcactt tgggaggccg  36960
aggttggcag atacctgaag tcaagtgttc gagaccagcc tggccaacat ggcaaaaccc  37020
tgtctctact taaaatacaa aaattagcca ggcgtgatgg caggcacctg tagtccagct  37080
attcaggagg ctgaggcagg agaatcacgt gaacccggga ggcagaggtt gcagtgagcc  37140
gagatcgtgc cactatactc cagcctgggt gacagagcaa aactctgtct caaaaaaaaa  37200
aaaaaaaaaa agggctggac acggtggctt acgcctgtta tcccggcact ttgggaggcc  37260
aaggctgatg gatcacctga ggtcaggagt tcaagaccag cctggccaac atggtgaaac  37320
cccatctcta ctaaaaatac aaaaatttgc tgggcatggt ggtgggcacc tgtaatccca  37380
ggaggctgag gcaggagaat cacttgaacc cgggaggcgg agattgcagt gagccaagat  37440
tgtgccattg aactccagcc tgggtgacaa gaccaaaact ccttctcaaa aaaaaaaaag  37500
attatagcat ctttattcat cattgcccaa aattacaaac tgcctaaatg tagaccttca  37560
tttagttaat gaatgcacaa actgtggtat atccaaacaa ttgaataaaa aaaggaatga  37620
actggtactt ttttctattc ctcctgttta agtacagcca aaacacctca acatttgtat  37680
aaaacatgag ctgggctggg tgcggtggct cacacgtgta atcccagcac tttgggaggc  37740
tgaggcgggt ggatcaccta aggttgggag ttcaagaccg gtctgaccaa catggagaaa  37800
ccctgtctca actaaaaata caagattagt cgggcatggt ggcgcatgcc tgtaatccca  37860
gcttcttggg aggctgaggc aggagaattg cttgatcccg ggaagcgaag gttgcagtaa  37920
gctgagattg caccattgca ctccagcctg ggcaacaaga gcaaaactct gtctcaaaaa  37980
gaaaaaaaaa accattcagc tgaatctcaa aggcagagag aagacagact ggctagggac  38040
cttggaacca gaggagcagt gtggtgggga gtggactgga ttttcttttt gcctcattta  38100
tcctggactt ggtgctggag aagctatggg ttcagaccaa gagaaaaccc catgaaaagc  38160
ctgctctctc tagccaaaag aggcaaccta gcaagataaa aacctttaga taataagcac  38220
ttgactccag tcaaacaaaa cagaataaac tggccccatt cacccctgtc agcaaaggcc  38280
aagtgggagc caagatatgt accccaacct ggaagtcata aggtacactt ctcccctttc  38340
ccagccaagg tggtgttaga gaaggctgac tggggagctg ggattctcat tccctccagg  38400
aggtgataac actcctttca catggtgtca gtggtcacag ggaggctgaa cttccaccca  38460
gtaatacata ggcatctctc tggctcctat atgggtgatg ttggagaaga ggccgagtag  38520
agaatccaga ctgttgctga cacccagcag taacaaggac acctccacaa tgtccgtgga  38580
ggccatgtgg agatcagtaa caaggcactg ctctccctcc cagtcagaga gatgtcagtg  38640
gaggactagg gggctagaac tcccatgtgc gttcagcagt aatccccatg accgccactc  38700
cttgacatca caggccttga agaaacctgg actttcactc ccctctggtt gtagcgaggt  38760
ggcactccct tttccctgtt gccagtgctg tgtcagtgga ggcttgctaa attggaagat  38820
gtaaataaga ttcacattct cataacataa taccccaaat tttcaggatt taattgaaaa  38880
tcactaagct gggcatggtg gctcacacct gtaatcccag cactttggga ggccaaggtg  38940
ggccaaacac ttaaggtcag gaattcaaga ccagcctggc cagcatggtg aaaccctgtc  39000
tctactaaaa atacaaaaat tagctgggcg tggtggcaca tgcctgtaat cccagctact  39060
gggaaggcta aggcaggaaa atcactggaa cctgggagac ggaggttgca gtgatccaag  39120
atcgcactag tgtactgcag cctgggcaac agagcaagac tccatctaaa tttgtgtcag  39180
gattcccaga aggagatgag aaagggtggg gctgaaaaaa attgaggaag aagtcatggc  39240
tgaaaatttc ccaaatttgg caaaagtcag aaacctacag attgaaaaag ctgaatgaag  39300
ctcaaatatg ataaactcaa agaagttcac acagagacac atcacagtca gatttctgaa  39360
cactgcagac aaaaaatgaa gatctcgaaa ttagcaagaa atgaccttac ctaagcaatt  39420
tgaatgacag cagatttccc atcagagatc ataaaggcca gaaggaaggg gtacatacaa  39480
catttttct agtgctgaaa gacaaaaact ctaggctggg cacggtggca cacacctgta  39540
atcccagcac ttttggaggc tgaggcaggc agatcacctg aagtcaggag ttcgagacca  39600
gcctggccaa catggggaaa ccctgtctct actaaaaata caaaaattag ccaggtgtgg  39660
tggcacgcac ctataatcct agctacttgg gaggctgagg caggggaatc gcttgaacct  39720
gggaggcgac ggttgcagtg agccaaggtc gcgccactgc actccagcct gggcagttga  39780
gcgagactcc atctcaaaaa aaaaaaaatt atccaggctt ggtggtgggc gcctatagtc  39840
ccagctactt gggaggctga ggcaagagaa ttggttgaac ccaggaggtg gaggttgcag  39900
tgagccaagc tcatgccact gtactccagc ctgggtgaca gagcgagacc ttgtctcaaa  39960
```

```
aaaaaaaaaa aaaaaaaaaa acaagaaaaa aactctaaac ccagagttac atatccagtg  40020
aaatatcctt caggagtgaa gggaaaatta acgatttgtc ttcaggagac ctaccctaaa  40080
agaatggcta aaggaatttc tctaaacaga aaagaaatga taaaagaagt aattttggaa  40140
catcaggaag gaagaaagaa caataaaaag agtaaaatat gggtaaacac aatagacttt  40200
cccctccttt tgaattttct aaattgtatg atggttgaag caagaattat agcactgatt  40260
tggttttcag tatatatatt ggaaatattt aaggcattat gttacagatg aaggagggtc  40320
aaaggatata aagggaggta acctttctat atttcttttg tactgatgca ggcactttgg  40380
aaaataattt cactatttgt ttaaaaactg aacataccct gaccatatga catagcatct  40440
atactcctgg gcatttatcc cagagaaaca gaaatttatt tatttttttt ttagtattac  40500
actccgtaag tgctgtaata ctagcactta gggaggctga ggcaagcaga ttgcttgagc  40560
ccaggagttc aagaccagcc tgggcaatgc tgcacagtca aaaaagaaaa acaaacattt  40620
agaaaactat tttaaaagtc tttaattgct gaatgcctct ttggctaata tttggaagat  40680
cattattatt atttttcttt tttaggcaga gtcttgctct gtcactgagg ctggagtgca  40740
gtggcgccat ctcggcttac tgcaacctct gcctcccggg ttcacgccat tctcctgcct  40800
cagcctcccg agtagctggg actacaggcg tgtgccacca tgcccggcta atttttgtg  40860
tttttagtag agatggggtt tcactatgtt agtcaggatg gtctccatct cctaacctcg  40920
tgatccgccc acctcggctt cccaaaatgc tgggattaca ggcgtgagcc actgtgccca  40980
gcctggaaga tcattattta gtcctacaac tgacacattg ttccactgac gcaattgccc  41040
aggctggtct tgaactcctg ggctcaagca atctgcctgc ctcggcctcc ctaagtgcta  41100
gtattacagg cttgagccac tgtgcccagc caaaaaataga aatttatatt ctcacaaaaa  41160
catgtacatg aatgtttata gcagctttac ttgtcataat caaaaactgg aaacaaccaa  41220
aatgtcctac agtgaaacaa actgtagtac atccatagca tgtaatactc tactgtcagg  41280
attaaaaaga aacccactgt tggcacaggc agcaccgtgg ctggatctca ggggcattat  41340
gctgagtgca aaaaagcctc aaagggtctt acactgtatg attccacttg ttcaactaaa  41400
aatgacagct gtatagagat agagaacata ttagtggttt ccactagtta gagaaagtgg  41460
gtaaaagata ggtgggtggg aatataaatc gatagcaggg agatctttgt ggtattataa  41520
cacttctatg tcttgattgt agtggtggtg gttacatgaa tacacgtgtg ataaaatgcc  41580
atgtagaact acatataacg ttgtgccaat gtcaatatct aggttttagt ttgatcttta  41640
gttacataag atgtaactat tgggtgaaat tgggcaaaag agtacacgaa acctctctta  41700
aatatcttta caacttcctt tgaattgaca gtttttcaaa atagaaagtt gggtttttgt  41760
aaatacatga attgttgata tacacaacaa atctcaaatg cattatgcta cgtgaaagaa  41820
gccatattca aaaggctaca tacctactga tgccttttat atgacgtgca ggaaaagata  41880
aaactgtagg acagagaata tactggtggc tatctgggat taggaaatgg ggatcgacca  41940
caaaggggca gcatgggggga atttctgggg gcaatggaat ggttgtgtat cttgatggtg  42000
tatttgtcaa aatatataga actataaaag taaattttgc tttatatgta ttaaatcaaa  42060
aaaagaaact cgtgctcaaa tagaaataca ttttctgaga acttgccttt tgatgacttt  42120
gagaattttc tggaaatttt aaagaaatgt ggttttgttt cccaacaggt gatgctatga  42180
gtgaagaaga catgcttcag gcagctgtga ccatgtcttt agaaactgtc agaaatgatt  42240
tgaaaacaga aggaaaaaaa taatacottt aaaaaataat ttagatattc atactttcca  42300
acattatcct gtgtgattac agcatagggt ccactttggt aatgtgtcaa agagatgagg  42360
aaataagact tttagcggtt tgcaaacaaa atgatgggaa agtggaacaa tgcgtcggtt  42420
gtaggactaa ataatgatct tccaaatatt agccaaagag gcattcagca attaaagaca  42480
tttaaaatag ttttctaaat gtttcttttt ctttttgag tgtgcaatat gtaacatgtc  42540
taaagttagg gcatttttct tggatctttt tgcagactag ctaattagct ctcgcctcag  42600
gctttttcca tatagtttgt tttctttttc tgtcttgtag gtaagttggc tcacatcatg  42660
taatagtggc tttcatttct tattaaccaa attaaccttt caggaaagta tctctacttt  42720
cctgatgttg ataatagtaa tggttctaga aggatgaaca gttctccctt caactgtata  42780
ccgtgtgctc cagtgttttc ttgtgttgtt ttctctgatc acaacttttc tgctacctgg  42840
ttttcattat tttcccacaa ttcttttgaa agatggtaat cttttctgag gtttagcgtt  42900
ttaagcccta cgatgggatc attatttcat gactggtgcg ttcctaaact ctgaaatcag  42960
ccttgcacaa gtacttgaga ataaatgagc attttttaaa atgtgtgagc atgtgctttc  43020
ccagatgctt tatgaatgtc ttttcactta tatcaaaacc ttacagcttt gttgcaaccc  43080
cttcttcctg cgccttattt tttcctttct tctccaattg agaaaactag gagaagcata  43140
gtatgcaggc aagtctcctt ctgttagaag actaaacata cgtacccacc atgaatgtat  43200
gatacatgaa atttggcctt caattttaat agcagtttta ttttattttt tctcctatga  43260
ctggagcttt gtgttctctt tacagttgag tcatggaatg taggtgtctg cttcacatct  43320
tttagtaggt atagcttgtc aaagatggtg atctggaaca tgaaaataat ttactaatga  43380
aaatatgttt aaatttatac tgtgatttga cacttgcatc atgtttagat agcttaagaa  43440
caatggaagt cacagtactt agtggatcta taaataagaa agtccatagt tttgataaat  43500
attctcttta attgagatgt acagagagtt tcttgctggg tcaataggat agtatcattt  43560
tggtgaaaac catgtctctg aaattgatgt tttagtttca gtgttcccta tccctcattc  43620
tccatctcct tttgaagctc ttttgaatgt tgaattgttc ataagctaaa atccaagaaa  43680
tttcagctga caacttcgaa aattataata tggtatattg ccctcctggt gtgtggctgc  43740
acacatttta tcagggaaag ttttttgatc taggatttat tgctaactaa ctgaaaagag  43800
aagaaaaaat atcttttatt tatgattata aaatagcttt ttcttcgata taacagattt  43860
tttaagtcat tattttgtgc caatcagttt tctgaagttt ccccttacaca aaaggatagc  43920
tttattttaa aatctaaagt ttcttttaat agttaaaaat gtttcagaag aattataaaa  43980
ctttaaaact gcaagggatg ttggagttta gtactactcc ctcaagattt aaaaagctaa  44040
atattttaag actgaacatt tatgttaatt attaccagtg tgtttgtcat attttccatg  44100
gatatttgtt cattaccttt ttccattgaa aagttacatt aaacttttca tacacttgaa  44160
ttgatgagct acctaatata aaaatgagaa aaccaatatg cattttaaag ttttaacttt  44220
agagtttata aagttcatat atacccctagt taaagcactt aagaaaatat ggcatgtttg  44280
acttttagtt cctagagagt ttttgttttt gtttttgttt ttttttgaga cggagtcttg  44340
ctatgtctcc caggctggag ggcagtggca tgatctcggc tcactacaac ttccacctcc  44400
cgggttcaag caattctcct gcctcagcct ccagagtagc tgggattaca ggcgcccacc  44460
accacacccg gcagattttt gtatttttgg tagagacgcg gtttcatcat gtttggccag  44520
gctggtctcg aactcctgac ctcaggtgat ccgcctgcct tggcctccca aagtgttggg  44580
attacaggca tgagccactg cgcctggcca gctagagagt ttttaaagca gagctgagca  44640
cacactggat gcgtttgaat gtgtttgtgt agtttgttgt gaaattgtta catttagcag  44700
```

```
gcagatccag aagcactagt gaactgtcat cttggtgggg ttggcttaaa tttaattgac  44760
tgtttagatt ccatttctta attgattggc cagtatgaaa agatgccagt gcaagtaacc  44820
atagtatcaa aaaagttaaa aattattcaa agctatagtt tatacatcag gtactgccat  44880
ttactgtaaa ccacctgcaa gaaagtcagg aacaactaaa ttcacaagaa ctgtcctgct  44940
aagaagtgta ttaaagattt ccattttgtt ttactaattg ggaacatctt aatgtttaat  45000
atttaaacta ttggtatcat ttttctaatg tataatttgt attactggga tcaagtatgt  45060
acagtggtga tgctagtaga agtttaagcc ttggaaatac cactttcata ttttcagatg  45120
tcatggattt aatgagtaat ttatgttttt aaaattcaga atagttaatc tctgatctaa  45180
aaccatcaat ctatgttttt tacggtaatc atgtaaatat ttcagtaata taaactgttt  45240
gaaaaggctg ctgcaggtaa actctatact aggatcttgg ccaaataatt tacaattcac  45300
agaatatttt atttaaggtg gtgctttttt tttttgtcct taaaacttga tttttcttaa  45360
ctttattcat gatgccaaag taaatgagga aaaaaactca aaaccagttg agtatcattg  45420
cagacaaaac taccagtagt ccatattgtt taatattaag ttgaataaaa taaattttat  45480
ttcagtcaga gcctaaatca cattttgatt gtctgaattt ttgatactat ttttaaaatc  45540
atgctagtgg cggctgggcg tggtagctca cgcctgtaat cccagcattt tgggaggccg  45600
aagtgggtgg atcacgaggt cgggagttcg agaccagctt ggccaaaatg gtgaaacccc  45660
atctgtacta aaaactacaa aaattagctg ggcgcggtgg caggtgcctg taatcccagc  45720
tacctgggag tctgaggcag gagaattgct tgaaccctgg cgacagagga tgcagtgagc  45780
caagatggtg ccactgtact ccagactggg cgacagagtg agactctgtc tcaaaaaaaa  45840
aaaaaaaatc atgctagtgc caagagctac taaattctta aaaccggccc attggacctg  45900
tacagataaa aaatagattc agtgcataat caaaatatga taattttaaa atcttaagta  45960
gaaaaataaa tcttgatgtt ttaaattctt acgaggattc aatagttaat attgatgatc  46020
tcccggctgg gtgcagtggc tcacgcctgt aatcccagca gttctggagg ctgaggtggg  46080
cgaatcactt caggccagga gttcaagacc agtctgggca acatggtgaa acctcgtttc  46140
tactaaaaat acaaaaaatta gccgggcgtg gttgcacaca cttgtaatcc cagctactca  46200
ggaggctaag aatcgcatga gcctaggagg cagaggttgc agagtgccaa gggctcacca  46260
ctgcattcca gcctgcccaa cagagtgaga cactgtttct gaaaaaaaaa aatatatata  46320
tatatatata tatgtgtgta tatatatatg tatatatata tgacttccta ttaaaaactt  46380
tatcccagtc gggggcagtg gctcacgcct gtaatcccaa cactttggga ggctgaggca  46440
ggtggatcac ctgaagtccg gagtttgaga ccagcctggc caacatggtg aaaccccatc  46500
tctactaaaa atacaaaact taagccaggt atggtggcgg gcacctgtaa tcccagttac  46560
ttgggaggct gaggcaggag aatcgtttaa acccaggagg tggaggttgc agtgagctga  46620
gatcgtgcca ttgcactcta gcctgggcaa caagagtaaa actccatctt aaaggtttgt  46680
ttgttttttt ttaatccgga aacgaagagg cgttgggccg ctattttctt tttctttctt  46740
tctttctttc tttttttttt tttctgagac ggagtctagc tctgctgccc aggctggagt  46800
acaatgacac gatgttggct cactgcaacc tccacctcct gggttcaagc gattctcctg  46860
cctcagcctc ccaagtacct gggattacag gcacctgcca ctacacctgg cgaatatttg  46920
tttttttag tagagacggg ctttaccat gttaggctgg tctcaaactc ctgacctcag  46980
gtgatctgcc tgccttggcc tcccaaagtg ctgggattac aggtgcaggc caccacaccc  47040
ggccttgggc cactgttttc aaagtgaatt gtttgttgta tcgagtcctt aagtatggat  47100
atatatgtga ccctaattaa gaactaccag attggatcaa ctaatcatgt cagcaatgta  47160
aataacttta tttttcatat tcaaaataaa aactttcttt tatttctggc ccctttataa  47220
ccagcatctt tttgctttaa aaaatgacct ggctttgtat ttttttagtc ttaaacataa  47280
taaaaatatt tttgttctaa tttgctttca tgagtgaaga ttattgacat cgttggtaaa  47340
ttctagaatt ttgattttgt tttttaattt gaagaaaatc tttgctatta ttattttttc  47400
caagtggtct ggcattttaa gaattagtgc taataacgta acttctaaat ttgtcgtaat  47460
tggcatgttt aatagcatat caaaaaaacat tttaagcctg tggattcata gacaaagcaa  47520
tgagaaacat tagtaaaata taaatggata ttcctgatgc atttaggaag ctctcaattg  47580
tctcttgcat agttcaagga atgttttctg aattttttta atgctttttt tttttttgaa  47640
agaggaaaac atacattttt aaatgtgatt atctaatttt tacaacactg ggctattagg  47700
aataactttt taaaaattac tgttctgtat aaatatttga aattcaagta cagaaaatat  47760
ctgaaacaaa aagcattgtt gtttggccat gatacaagtg cactgtggca gtgccgcttg  47820
ctcaggaccc agccctgcag cccttctgtg tgtgctccct cgttaagttc atttgctgtt  47880
attacacaca caggccttcc tgtctggtcg ttagaaaagc cgggcttcca aagcactgtt  47940
gaacacagga ttctgttgtt agtgtggatg ttcaatgagt tgtattttaa atatcaaaga  48000
ttattaaata aagataatgt ttgcttttct a                                  48031
```

```
SEQ ID NO: 43           moltype = DNA  length = 300019
FEATURE                 Location/Qualifiers
source                  1..300019
                        mol_type = genomic DNA
                        organism = Homo sapiens
SEQUENCE: 43
gatgtcccga gctgctatcc ccggctcggc ccgggcagcc gccttctgag cccccgaccc  60
gaggcgccga gccgccgccg cccgatgggc tgggccgtgg agcgtctccg cagtcgtagc  120
tccagccgcc gcgctcccag ccccggcagc ctcagcatca gcggcggcgg cggcggcggc  180
ggcgtcttcc gcatcgttcg ccgcagcgta acccggagcc ctttgctctt tgcagaatgg  240
cccgcttcgg agacgagatg ccggcccgct acgggggagg aggctccggg gcagccgccg  300
gggtggtcgt gggcagcgga ggcgggcgag gagccggggg cagccggcag ggcgggcagc  360
ccggggcgca aaggatgtac aagcagtcaa tggcgcagag agcgcggacc atggcactct  420
acaaccccat ccccgtccga cagaactgcc tcacggttaa ccggtctctc ttcctcttca  480
gcgaagacaa cgtggtgaga aaatacgcca aaaagatcac cgaatggcca tatccttttg  540
cccgaacccc agcagcagct gcgcctcccc ctcctccctc cgcctcccct cttccaggct  600
gggagagaga cccgggggtt gatgggaggt ggggaggagg ggggtcttcc aggggctggg  660
agaggggca ccgggaggag tgtgaaagaa tctctccacc ccgagctggg ttgagctacc  720
ctggaggctt gggaatgggt ttgtgggggg ctggggggtg ggcagcggag agtggatcct  780
tcccaaggac cgactctaga atgagatctg gggcctgggg tcgtgcagga gccttggtgg  840
gggctttcga gccaagtccg gagggtttgg agttctacgg agtgagcttg gagcgggctc  900
gggcctgggc gcttctggcc agggcagggg aactatgggg gccttggttg ggttttcttg  960
```

-continued

```
gccgtcgctc actggagtcc acgcagggga agctggacag cctctccact actgctttcc  1020
ccaaggtggg gggccgccgc acttttaggg cagggcgctt gggggctccc agggctaaga  1080
gcaagaggga gtccatgtgg ccttcacact gagaagccag cactggccga agtgagtacc  1140
ccagggtggg ccgctgttcc tatctggaga ggatagtgat gggctggggg gcgcttatgt  1200
ttccctcatg tgtgcaggtc ccattgcctt taaccgctga ttggggaacc tcatcatctt  1260
tgggggtgtc gagaaagaga tcccacttgc tttatctggg cccctggcct gggaagacct  1320
gatctggaca ctttcagtaa gaaagacagg gcaacagcaa atgaggtggt gggtccattt  1380
tagagcacca tgtccagctt ttcctacccc gagtagccga gagggaacac caggagaatc  1440
agcacccatg tggacatctt aggtaggtaa atgcctttta aatttttttt tttttaatca  1500
aagatccaga ggaaaaaggt gaagcccaca ttttcttctg tggagatgct atcaaaatgc  1560
agatcttctg tgtttcttta aatccctgcc tgcttgaaat aaaccttgag gagggcttaa  1620
catctatcga gatgtaggca ggcaagggtg ggtaattagt cgggctttct agcagttatc  1680
taagcatgac ccagattcca ggaggggggga cacaccctgc tgcccaggct ggctggccac  1740
tgtgccatgc ccagatgtgc cgcttctccg cacagttcca accagctgcc ctctgtgtaa  1800
aaatgaacgg gctggatggg tccctggggc tcagcgatga gtcccctatc ccttttgtat  1860
gtggttttgc agttatagac taaacggggc tgggccctgt gtggtctccg gggttgctg  1920
tttgaggagc atggcgggtg gtagagggac tcacttcagg ggggttcaaa atcgagcctg  1980
gcgcttggat cctgggtgct gggattgcaa cagagggcac tgaggttttg gagtgtgtga  2040
gtggtctact ttgagggtgg ggaaaattaa gaagttcagc agaggtgctt ttgaggggag  2100
catacctcta actacgatgc catctccgtt ggtgcccaaa gcaggtgcca ggtctttgct  2160
tcctaagttt cagactctta aagaggctgg ttcttaaggt tagcaattcc tcaccatccc  2220
aggcccattg aagtgctcag gggtggcttg attactctgc ctatcaacag agtgaggagt  2280
gggagtgcct tgcaggagga cagggtattc atgggtgcac acccagttag ctccaggagt  2340
gagagggctt tgctcggctg acaggtttcc tcattgaaaa tggctttaga tcgccttctg  2400
gagcctggat ttggagactt ctaagaggaa aggaaggagg tggggagccc ttctgctgtg  2460
tccttagctt acctctgtcc agcctgaatc ctgcagattg gagggctgtt gggggagagg  2520
gggattgcag tggcccctcg gaagggggaa tcgtgggaga gggaggcagg tgaattgcga  2580
gtgttgcttg ccacttcatc tattctctgg ccagctcgcc cggggctttc ttgctcttat  2640
gatgagtttg tgcattatgc tctctgcaga ctgtttttgt tctctttgac ccgaggtaac  2700
aaacacatta tacagcccta ctctggaagg gaaaactccc cacctcacaa tctgtcatcg  2760
agctgggtca tccaggactg agctttctct gtcctggatg gagcggaggg cggtggcggg  2820
gtgggtggga gggttggaga tgagagggga tggacagaga cctggggagg gaggtagtga  2880
ataaaagaat tcaggccagt gtaaagagaa agacacgtgg aatgtcagag tcacgatacc  2940
agggcagaac attctacttt ttaatctaaa tatttctgcc attaaaaaaa aatgtttcag  3000
catatcctga gagtgaaaaa aaaagtgtgt aggtacttaa ataaagtcta atatatgtac  3060
aggcaagtac atatattcag atgcatagat ttttacaaaa tgaacacacc cacgtatcca  3120
gcacccaggt cccgatcagt gccctggaag tccccctccc cataccgcct cctagttgct  3180
cccccaacaa gggtaccgct cacctgactt ctaaggttca ttttgcctct tttaaacatg  3240
taaatggagt cacacagtac gttcttttgc cactggcttc ttttgctcac atctgtgtat  3300
gtgactctac tacaatctat ccattctact gttgatgggc atttgtgtca tttctgtttg  3360
tgccactggg aacattcttg tgtcttctat tatttttttc ccacagttct cttagatagg  3420
agtggaatcg cccctgctac tttttgatgc atgtgttgtg ggatgtgtat ttggaaatgg  3480
tgttgactaa gggttgcagg tcgatatgga aagcaggttc ctccctgtct tgtttaagag  3540
aagtgagtga atgatccatg aacttgtcgg tatgctcaca gggcctaaga gtgctacttc  3600
caaatgtaaa ttctggcatg gtacactggt gaaggatgca gtcttgcttt ctccacactc  3660
ggggcaattt gtcactatga tttcttcctc tttcatccct cagtgggtca aacttgaagc  3720
catcaatgac aattaagaat cctcatttat ttcatttttt cccctcttcc taagtgagga  3780
aacccaaatg gaagtctttg atgttcaaat ttacattgcc gtgtttttct catgccaggc  3840
agcaagccgt cttgaccaca caccttggtt tcatgtttttc attgactgga attgtgattc  3900
aaatagggcc atgagggtct ctgatgattg ccgaagagct cagatctgtc agctcaaaaa  3960
ggagcatctg tcagccttcc tagagttccc tccccactta atgccactca ctccttctac  4020
caagtgccaa ggtgaatgtc atctttccag ccctccctgt gccaccaggt ctcccactga  4080
acatgatgta gaaactcagg ccatcggagg aacactggaa gcaggtcagt gtattatcac  4140
gcacagttgc ctgaattaca cgtagaattc cagcttttca tccggtttgc agaaatctta  4200
acaagacacc taaagtcaca ttgacatcag gtgacatcac tttgacatct gtggacattg  4260
gctgattggc actcctctca tttttttttt tttttttttt tttaagaaaa gctctctaaa  4320
gagaaacttt ctgcatgaga agcgctggga gacatgggag caggttatca gactcttggc  4380
ctgtcctgag agatagaatg ttctagaagg tactgccgta gagggcagga tggtgtcact  4440
tacgtgatcc ttgtactaga ccggcttggc tggtatttcc agaggagcaa aattctgcga  4500
agtaaaattt agcacggctt ttccaatggg agtattttca aaaagggtgc aatttcttat  4560
ccacaattcc ccaatccaaa aagctccaaa aaccaaaaga cgagctcata tagaggtaaa  4620
acctaacctg aactgacttc agtttgaagt cttaatttac agttttcatt cattctactt  4680
ggtgtgcatt tgagtatgtt ttgcagcaga aatgttagat gtgcttgatg atgaggtgct  4740
gcttcagctc ctgactgtta ggtctgcatt gtagtcctgt caaactttca ggtgtatgga  4800
agttgtcttg ttaacaggat ggttctggtc cagcaggatt tgggtggggt ctgggattct  4860
gcttttctag ctagcttcta gggattcccc atgtggtaag ttcatgggct agggttggag  4920
tatccaggtt agatcataga gacatcttgt tatcattttt cttttcctta aaaatcaggt  4980
ttatagggc cgggtctggt ggttcacgcc tataatccca gcactttggg aggctgaggc  5040
cggtggatca tgaggtcagg agttcgagac cagcctggcc aacatggtga aaccccgtct  5100
ctactaaaaa tacaaaaatt agccaggcgt ggtattgtgc gtctataatc ccagctactc  5160
gggaggctgg caggagaatc atttgaacct gggaggcaga ggttgcagtg agccgagatt  5220
gcaccactgt actttttttt gagactctgt ctcaaaaaaa aaatagattt attgatgtat  5280
aatttatttg tagcaaaatt caccctttttg acatactggt ctgcaagctt tgacaaatgg  5340
atgtagttgt ggccaccacc caaatcaaga tatgggacag tttcatcaac cctaaaatac  5400
ccccacagtg cccctcttga gtcagcaccc cacttctcca gccccttcaa ccactgatct  5460
gttctccatc cctacagctt tgccttttgc cgaaggtcat ataaatgtaa tttcacagta  5520
tatagccttt tgaatgtgga ttcttttact cagactttga gattcattca tgctgttgcc  5580
tgtgacagta gcgccttcct ttttggtgtt gagcaggatt ccatgatatg gatggaccag  5640
agtttgcttc ccagccgaag gacattggga tgcttccagt ttcaatgatt atgaatagag  5700
```

-continued

```
ctgctataaa cattggctta tgggttttag tgggaacatt tcatttcata catttcattt  5760
ctcttgggta aattaaccca ggagtgagat tgctgagttg tgtggtaggt gtatgtttaa  5820
ttttataaga ggctctcaaa ctgttttcct aagtggttgt accattttac attcccatct  5880
ttgcaatgcg tctaaaagcc ctgagttctg aattccaaag cacgtctggc ctcgatggct  5940
taggattaag gatgtggatc tatggaaagg agtggaagta atagtgttaa atcccggtca  6000
gagaaataag aaagattaag gatgtcattc aaagctatgt gcctgcacta gagagagaga  6060
aagaaggggt tctcttgggt ggggttccac ccctccctgg tagttctacc attccccagg  6120
aaaaagtcaa gctctgaggc tgtgagaccc atgatcttta ccctgttctt caccactgca  6180
accccagtgt gtgggacaaa gcaggcgtcc tataaacgtt tgctgagcaa atgagaaaag  6240
gtacctgtct tcacccatta actaaattgt ataacatcta tctgatctac ccttgtgcca  6300
acgttttagg attttgatgg gttttagttg caggggggttg agagactgtc catgagatta  6360
tcagaccaat gaaagtttct gaaatgttag tgcttgagta gattggatgc agcggcccct  6420
tgagaatgaa gtctttcttc agggacttgg agtgggaggc atctgttggg tgcgtagggc  6480
ttatgcttcc ccctccctgt ttcccccccca gtagcaagca cacatataca ctttctcagc  6540
aataaaaagc accgccggga aggtggactc catccagaaa tgatcagagc ctaagagccg  6600
tgcagtaacg catttccgag aatgccagct cagctcctga gaaaagggcc ggatgggatg  6660
gtgcctgctc tgaaagaggg cagagaggag agggaaaaca ctccggactc tgggtcagac  6720
tggcccaggt tcacattatt caccagccat gttatcttgg gcaccagagc ctatttcttg  6780
acatgcatga tgaggatatt ccttctagta gcatctccct tggagggctc tcaggagatt  6840
aaatggggtc gtgcgtgaaa aatggccagc acagtctcca gcacagagaa aaaccccaaa  6900
acgccagagc cgtaatacta tggagtcatt taggttccag tgttcttttt ttggaaaccg  6960
gccagaaaag aggctttctg ggtgggaatg ggagcgaagt gccccccccc accacccccct  7020
gcgactggtc agtgtggatt gattaacctg atcgtggcgc tctttaaagc cacctttgga  7080
cattttgcat tctccgttct ctctggaagc tttcagggga aaaaaaattc gtggccactt  7140
gacccatttt tctattccct tgagtctaag gtaaaaatta attctctttc ctcctttggt  7200
ccctccctct ctctgtgggt gacaaggtga gggagtttta aagtatataa ttagcttccc  7260
tcttcccctt ttgcactccc tgtctcttcc tttggggccg gtcgagagtg cagcccagga  7320
tggccacccc aggtgtccac tgcaaactcc acagaaaaac tttgctcaac ttttggttta  7380
gaatttaggt acccccctcc ccttccaaac tttggtcttc tttctcctca ctccctaaaa  7440
aaataggaaa aacaaggaac attcctggcg agggaaccat gagtgggcac agcaacttag  7500
gtttcaaaaa ccactgggcc tcagttctta tctgagtagg gtgacccttc agccagggtt  7560
gcctgggact atcctgggtt tagcatctct ggaaactcac agtcctgggc aaactgggac  7620
gctggtcacc ctaatggtga gttcttaaca cctgagagag aagaatggtg caagagatgg  7680
tgccgttgac caagaaaggg ggagagtcag ttacttattc cctctgaaaa gccaagactt  7740
tttattggaa tgaatgcagc ttttagaagc cgtctttaag gcagctaata caagagagat  7800
tccagctatg aagggaaatg cctgagttaa gtccggatca agttttgaca tctcgcttcg  7860
gtcagacacg gctttatctg ccgttcagac tgggagcagc cgtgagtctt ccttaaaggt  7920
gcctgttgct caggcggcac ctgcagttag aaattagcag cctcccaccc ccagccccca  7980
aataacagga ttcaagagtc ccctctctga agccatgagg gaaacccaac ttagtcaccc  8040
acttgccagt aaataatatt catgctgtta agttctgttc tcattttagg cctatgtgta  8100
aaaaatatat gtaattttaa actgattttt aaagtatttt catacgaaca gcatttgcag  8160
gagggcgaag tctggatgtt accttttttgt aaaagtggat ggatttgtct tcaatgagac  8220
tctggggcag acttaaaact tggcccgcag tggtgttaca tggattctga tcttccagag  8280
tctgtcacgt tcttttatct ccatgatctt tattatcttc tttattgaga atgatgggca  8340
tggtgtgtgt gggtgggagg gctatgctga ccatcactgc agtgaaatgt gttcgtggca  8400
tgttgtggcg tctgcatagg aatgtgtctg tttgattaac agcacaagca gtggaggctg  8460
taaggaggaa aagaggaggg aaggtgatat tggatggagg ggagacatat agagcttggg  8520
aacagtccac cctggctgca aatctcagct ccagctcaca gttgtggagc ctcagtcttc  8580
tcctctgtaa aacggggaca gtagtcctat gtccgaggaa ttgtaagaag gttaaaagat  8640
actgtaccca gaaagcacat ggcatatata atcatcctgt gaagtagcca actcaatgaa  8700
ttttatttta tttattttga gtcagagtct cactctgtca cccaggctgg agtgcagtgg  8760
catgatcatg gctcactata gcctcgacct cctaggctca agcgatcctc ctgccttagc  8820
ctcccgagaa gctgggacta taggcatgca ccaccgtacc cagctttaac aacataaatt  8880
tatatatata tatatatata tatatatata tatatatata tatatatata tatatatatt  8940
ttttttttttt ttttttttttt ttttttttttt ttgagatgga gtttcattct tgttgcccag  9000
gctggagtgc aatggcgcga tctcggctca ctgcaacctc cgcctcccgg gttcaagcag  9060
gacgatgggc atttgggatg tttctagttt ggggtggggg attgtttgtt tgtttgctgt  9120
tatgaacaat gctgctgtaa ggaatcaata attttgaatg aatgaattcg aggtgttaat  9180
tttagtctgt gtacttggaa atctagcttc acctagaatc agctgagatt catcagcatt  9240
tatggcagga gctaagacat ttcacagctt actcatcatt ttctctaaga ggctgggtca  9300
accggttagc tcttggtcct gcttgtattc tgagagtcag aacctgtggt ttagacactg  9360
gcaattgata tggttgtaga gaagcagcat ggttgagttg agagcatgga ttctggagct  9420
aggtggctgg ggttcaaatc ccagctctac tagtcactgg ctgcgtgatc ttgggcaagt  9480
cacttaagtg ttctgtgctt cagtttccca gtctgtccca gtggtgattc taatagctcc  9540
atggggatcc taatagctcc tatctgggag gattaaatga gttaatacat ctgatgttta  9600
gagtggtgcc tgacacttag gaagcactat atgtgtttat acatggaaga gtggatagat  9660
ggatggactt atgtgggtgg ccatatttgg gcttctctga tccactgctg agaatagtgt  9720
gtggcacaca gtaggtgctg cataagtgtt aatattctgc tctttcttgc caagtctctc  9780
aactcccttg atctctgtta tttttggcgt ctgtgttgtt aacccattct tctgaatgat  9840
cagctgaatc actgttgctc caatatataa gccaaggaga acacaatcac aaggtctcat  9900
tgattgtcca tactagaatt ccatgattcc taggcccaag taggattttc cccacgtctc  9960
agcaatcctt cttccatgtt tctaatcttt ttctctcatt tgttatgccc cattgccaga  10020
ctctccaatc tccccacagc ttccccttcc tctaactata ctgtctctag tcttaccttc  10080
tccctaaggg caccgtcttt gaagacatca aatacttcag agcaccaaat ataggttagc  10140
ttctctgagg gccttacaag gacatggagt gtttgggtct tacacaaatt ggaatggtca  10200
gaaatgttta gagacttgag ttgtctttga aagagttgtc agaatgcaaa tttttgactt  10260
gtggcctgtt tctgatcaca acgcagtctt ttaagttatg gatcatagct ggatgtttgt  10320
ggtttagagg ggatggaggc atcctctgca gttagtgttg gatgtctggg tggatggatg  10380
gatggatgga tggatggatg gatggatgga tggatggttg aacagatgca tggatgagtg  10440
```

```
gatggatgga tggatgggat gaaggaagga aggaaggatg ggtgattgga gggtaggtgg  10500
gtggataagt agattggtag atgactcgat gggtgggtgg acaaatggat gggtgaatgg  10560
atgactggat ggatgactgg atggattggt gtatgagtga atatatggct ggatgaataa  10620
ataggcagat gactagactg gattgagggg taaaaatatg gatgactgga tgggtggatg  10680
agtggatgat agatggttga atgggtgggt ggatgggtgg atgttggata taagggtgta  10740
tggtagggta gctgtctatg tgtgggtctc cctgatattt ggtgttctgt ttgacttggg  10800
aatgaccaag tctctccgct taccacctta tttgtacctt ttccagtatc aagtgaattt  10860
tgcacacttt tgtaaaaatc aataagattg tatgtttagg actttgggag gccgaggcag  10920
gcagatcaca aggtcaggag atagagacca tcctggctaa cagggtgaag ccccatctct  10980
actaaaaata caaaaaatta gccaggcgtg gtggcgggca cctgtagtcc cagctacctg  11040
ggaggctgag gcaggagaat ggcatgaacc cgggaggtgg agcttgcagt gagccaagat  11100
catgccactg cactccagct tgggcgacag aacgagactc catctcaaaa taaataaata  11160
aataaatatt atatgcttag gttttaccta tgtaattaga aagctccttg agggtagggg  11220
acagtgattt gccttcctca catcccccca aagttcctgc actatatcat gcataagtat  11280
ttaattgagt aatggtgagg aaagtaaaca gtgttattga acaaagatta ttaaaattct  11340
ggaaacacct ggttttgttt cagcactggg actgaaagtg gaattccttg gattttgctc  11400
cattggtgga taggatagca tgtggtggtg gactggtaga ctctttctct tccaagcaga  11460
ttgggtaaat gccccagatt cttacccact agtcagagat tacagattac tgattgatat  11520
ggtttttctc tgtgtcccca cccaaatctc atctcaaatt gtaataccca catgtcatgg  11580
gagggacctg gtgaaggtga ctggatcatg ggggtgattt cccccatgct gttcttgtga  11640
tagtgagttc tcatgagatc tgatggtttt aaacttgtgt gggcctcttt cctctctctc  11700
ctctcctgct gccatgtaag acgtgccttg ctttcccttt gccttctgcc atgatttgta  11760
agtttcctga ggcgtcccca gccatgcaga actgtgagtc aattgaacct cttttcttta  11820
taaattactt ttatagcagt gtgaaaacgg actaacacac tgatgtagca aggtccttta  11880
aggccccatg tgatctggtc cctgttttgt ctttgatctc atctctttca ttgtctacct  11940
tcctttcatt gtctattctg tctcagccct gctgaccatt ttactcacac ccatgtcatt  12000
tgcattacat gacattcctt ctgttcagca taagctattt cctctgcctg catcactgtt  12060
tctccaggtc tccccatggc taactccttc tcttcattta ggtctcagcc caaaagttac  12120
ctcctccaag aggcctatcc ttttcattta ctgaacatct catgtacaaa aaagaatata  12180
aaatatatgt atactctctc atccacaaaa aaatctctga agacatttta atgtatttca  12240
tcccatacct ttttatgcat gtaaactttt aggaacacat ttccatgcca ctaggtatcc  12300
ttgaaaaaat aagggccacc atgtatagtt gcacaggttg tgcactgcac aaagatagca  12360
tgtcacatat cttaagtatc atggagcttg tatgtctact atttcagtac cccagctgat  12420
aaaagcttaa gtatcttgtt ctagcaagat gaagctatta tgacaatttt tgacagagaa  12480
aggggtgttt tgtttaagtt cacaatcaga gaaatgggtg tcttgtttaa tttcacaacc  12540
agagaaaggg gtgtcttgtt taaattcata cagtggtgct gtatgggttg gtggcaaccc  12600
cagaaaagac tgttgttaat atctgataat gttccacttt atacgtgtat tatattcatg  12660
taacaatctc tggctgtttg ttttgccatt ataaataaca gtgcagtaaa catctttgtg  12720
tgtgaatctc tgtccaaggt tctgatagtt ttctgaatga aattcctgtc tatatatggc  12780
actccaagcc cataattgaa actctgctgt taccacttta tttgaatctg tagaaggaat  12840
tttgagaaca ggtgactggt atattcagga tgttgatgac aaggaacaga gaaagaacag  12900
ttaaatggtt tggaattttt cctgggctgc atgtaaagca gtgcttttga actgggagca  12960
atttttcccc caaggggact tttggcaatg tctggagacg tttttggttg tcacgaatgt  13020
agggggaggg ggcaagatgc tactggcatc tggctggtag aaaccaggga tgcagttcag  13080
catcttaaaa tgcacaggac agcctttctc agtaaagaat tatccagctc caaatgtcag  13140
taataccaag gttgagaaat cttgatgtaa tcgatgtcat gggtttcttc aagaggagtg  13200
ggtggattta gggtttttgg gtgacttaaa tttaatttac agtttgtctt cctagctggg  13260
tgtctaagcc agctttctgt gaactttaga tcccacacaa gaagcaacag gcttgctacc  13320
gacagattcg ttgatgtaaa tatagatgag tgtatagaag gaaatctcac ccagagctgg  13380
aaaatgttgg aatgaaaact gcggcggcct ccccttctct ctccttcccc ttctgttgcc  13440
ctgtttgaaa atcgtgcctt actttctttg gtctcctggc atggtgaatg ctgctggtat  13500
ggactgtgtt tctatatccc cttgatcccc acacccttag gaacgtacag gagagagacc  13560
ctggagcata tcagcttaga gatggagggg aatgggaagg agtgcgttca ttcattcata  13620
aatgttgact gagcacctac tgtatgctag gtgaatggga ggacgtgagg gcagggaggt  13680
gacaaggttg gcttattctg ggctttgtga actatggtga ggattttgtt tttttccaaa  13740
ggaaatggaa taaccactcc tttttttccc ccgatatacc taaacttttt gattttcata  13800
acaaaaatgg gcttcctttt gtatatttgt tttgagacca gccgtttttc caccaacact  13860
gatcacactg cagtgagcat cctggtagag aagtctttgc acacttctgt cactgtttcc  13920
ctaggacaga ttcctggaaa tggtatggca aggttgtatg tcaggctttt gggccaggtt  13980
gcaagaaaca ggaagtctgt gccctttcaa attccaaggt ccccctttccc tgacgacgtg  14040
gcccaatcag gcttgccctc ccttgatttt acatcttcac caatcagata agtgaaagtg  14100
aaatcctgtt gtggtatcct gtgcatttct ttggtgactt aagacataga gcattttcca  14160
gatctctgtg ggctgtttgg atatcctttc ctctgttttc tcaggcacat tctttaccga  14220
tgtctttgag ggattgagca agtttctgtt gaaattgagg catgtcatgg ctctgtgtgg  14280
ggcttgaggc agtccagtgt agtggaggga gggaggctgt ggagcctggc tgcctaggtt  14340
caaataccaa ctctgcttat ttccattcat atcattttag gcaaatcact tagcccctg  14400
ggcctgcctt tcctcatcag taaaagtggt ataacattag tgcctgcatt gtggggtggt  14460
tgtgaggaaa gcagcactca aaacagtacc tgacacacag tgggtgccaa ataagagtct  14520
gatgtattag tgttataggt atcggcctcc tccctcccca gtgcaatagt gtgtgtgcgc  14580
ctctgtgtac ctctgttggt gctgacaagc cctttttaaa atttagaggt gaggtctcac  14640
tctgtcccct aggctggagc acagtggtgc aatcatggct cactgcagcc tcaaccgcct  14700
gggctcaagc aatcctccca gcttagcctc ctgagtagtt gggactatcg gtgtgcacca  14760
ccacacctgg cccttagaca gcccctttat ttcaaagcga aatggcagcc acaagattta  14820
gtgcaagctc tccaagcttt aggaccagct gcaactcctc taactgacca aacaggatcc  14880
cccatgtccc caacccccaa aacctgatga aaagcaaaca gaccattttc cacattcatg  14940
acggaaaggc ccttttcttg gctcctgccc ttgctcatgt caggatttca ctccatccct  15000
gataaagagg aagcaccatg tcccaggagg acatggaaac tctctgcttt gtggtgaata  15060
gttacagtaa cagtagctcc tctctgtggg gagcttatga gcccctaagc tttatagaac  15120
tgccctggca gtttatgaga acttcatccc agcccccaga gctcatggca cttatttttg  15180
```

```
cccccagttt gcagatgtgc acactgagac tcagagagct aacactgctt gccaaggtca  15240
cacatctagc aaatggagaa actttatgag acaggtgaag gcacagcaag gataaaaacc  15300
cagagggaaa aatactcaag ttttctccgg gaaaccattt gcattccaga gaggttggtg  15360
tgcgagtggg caagagatgt cgcgggacga tggttaaggg acagagtctg agctcaacta  15420
ggactaggtt tcttcctttc cttccttcct tcctttcttc cttccttctt cctttccttt  15480
gtctttctct ccctcccttc cttcttcctt tccttccttt cctttctctt tccctccctc  15540
cctcccttcc ttcttccttc cttactcctt tccttccttc ctcctttcct tcctttcctt  15600
tctctttccc tccttccctc cctcccttct tccttccttt ctttccttcc ttcctttttc  15660
ctttctcttt cctttctttc ctttccttcc ttcctctctt cttccttctt ttctttcttt  15720
cttttctctt tctttctttc tttctttctt tctttctttc tttctttcct ttctttctct  15780
ctctctctct ttctttcctt ctttctcctt ccttccttcc ttcttttctt ttcttttcct  15840
ttcttttctt ttgtttttttg agatggagtc tcgctctgtt gcccaggctg gagtgcaatg  15900
gcacaatctc agctcactgc aacctctgcc tcccggttca agcaattttc ctgccttggc  15960
ctcccaagtg gctgggacta caggcacgcg ccaccacacc cagctaattt ttgcattttt  16020
agtagagatg gagtttcacc atgttggcca agctggtctc gacctcttga cctcgtgatc  16080
ctcctgcctc agcctcccaa agtgctggca ttacaggcgt gagctaccac gcctgggcta  16140
ggactaggtt tctatcggtg gtgtggcttt tgggaagcta cctaatctta accactctgt  16200
ttcgtcatct ataagataag cagtgtagca ttttcttgca ggaatgttgc aaggattaag  16260
tggatggtga ctgtaaaaca tcatgcgtgg cacatagtaa attctcagca ggtagtcatt  16320
gctggtcatt tacttttctc taatgaccag caagctctta atttcctcct tggcatgggc  16380
actgggacgt agatggacaa aacacagaga gaaataaaca cacggacaaa aatccccgcc  16440
ctggtgtggc tgatattctg ggtggggaga gagagggagt ccaaggacca gataaacagg  16500
taaaggatag tttgagtgtg gtaagtacta aggctcaaaa ataaagatct cccaggtgat  16560
cttagctgca tttggaggtg acaggagata caactgagaa actgagatag gaggaaaccc  16620
aaggggagat gtgggcttga tttagggtga tctgaggagt aggagaagtc aggggctggt  16680
gtggggaggc tctgatggtt ctctctgggg agtgaagcag ggattcgttg gggagaccca  16740
aggggacagg tgaaggcccc tgaacaggtg gccagtgctg agaaaggaaa ggtggaggac  16800
ccaagtgagt tcctaatttc ttcattgctc ccctaaggtg tttgtctcac ccttggccat  16860
agtcttggat cacttacaga tgcagaccag gctgggctca atggcttgtg cctgtaatcc  16920
cagcactttg agaggctgaa cccaggagtt tgagagcagg ctgggcaaca tggtgaaacc  16980
ccgtctctac aaaaaaatac aaaaattggc cgagggtgtt ggcacatgcc tgtagtccca  17040
gctacttggg aggctgaggt aggaggatct cttgagcccg ggagacctat gctgccaaat  17100
aaggtaggca gtagccacac atggctattg caattttaga aattaattac aggccacatg  17160
tggtggctca cacctgtaat cccaacactt tgggaggccg aggcgggcag atcatgaggt  17220
caggagatcg agatcatcct ggccaacatg gtgaaacccc atctctacta aaaatacaaa  17280
aattagctgg gcatggtggt gcacacccgc agtcccagct actcgggaga ctgaggcagg  17340
agaattgctt gaacccagga ggcagaggct gcagtgagct gagattgcac cactgcactc  17400
cagcctgggc aacagagaga gactccgtct caaaaaaaaa aaaaaaaaaa aaaaaaagaa  17460
aagaaaagaa attaattaca ataaaaacag tccctgagtt tcactggcca catttgaagt  17520
gcccgatgac cctgtgtggc ttagtgacca ctgtgctgaa tagtgcagat ctagagcatc  17580
ctactggaca tgttgccagg gtccctgaac caacagaatt agcatctcct gggagcttgt  17640
tggaaatgca gaatctcatc ccctacccca gacctgctca atcccaatct gctcttcagt  17700
gagattcctc aggtgatctt gactgcacct tctaatcact tggaagcttt aaaaatgctg  17760
aggctgggca cggtggctca cgtgtgtaat cccagcactt taagaggcca aggcgggtgg  17820
atcacctgag gtcagaagtt tgagaccagc ctggccaaca tggtgaaact ccatctctac  17880
taaaaattac aaaaattacc caggtgtggt ggcacacacc tgtagtccca gctacttggg  17940
aggctgaggc aggagaactg cttgaacctg ggaggtggag gttgcagtaa gctgagatgg  18000
cactgctgca ctccagcctg ggtgacagag tgggactctg tctcaaaaaa aaaaaaaaaa  18060
aaaaaaaaaa gaaaagaaaa aggaaaatgc tgatgcccca agctccaccc ccacagatgc  18120
tggagagatt tgtccagggc ttcccctgga gtggggaatg tttgaaaact ccccaagggt  18180
ttctaaagtt cagccagagt tagcagaaag cccattaggt ggctaagcag gtagactgaa  18240
gttggagctg tgtgaccttg ggcaagccac ttaccctctc tgaaccacaa gctcccttct  18300
ctctaaaact agagacctgc tggcacctcc ctcccagggc tgtgagaagt aaatgatggg  18360
atgattcaaa gtgctgagta gggtcagatg cagtggctca cacctataat cctagcactt  18420
tgggacgctg aaatgggagg attgcttgaa gccaggagtt tgagaccagc ctgggcaaca  18480
tttaaacatt acccaggtgt agtggtgcat gcctgtagtc ctagctgctt gggaggccga  18540
ggtgggggga tcccttgagc ccaggagttc aaggctgcag tgaacaatga tggtgccact  18600
gcactccagc ctgggggaca agagtgagac cctatttcta aaaaagaaag aaacccaaaa  18660
tgctgagcga gtgccttgga ttgatagtaa gcagtgcctg tgtaataagc atgaatttta  18720
aaaaatgagg tcagcagcct tagagctaat ggttaatggg tttgggtgtg ggattttttt  18780
tttttaatt tttaaaacat tgagataaaa ttcccataac ataaaattga ccattaacca  18840
ttttaaagtg tacagtttgg tggcatttaa tacactcagt gttgtgcaac catcacctct  18900
ctgtagttca aagaccccaa aaaggagacc ccgtactcac tgagcgctca ctccctgtct  18960
ctccccgctc ccccagcccc tggcaactac taatcttctg tctgtataga ttgacctatt  19020
ctgattttgg gggtttttga actcgccttc cctggctgac aacctctcgc catccaggtg  19080
agactgtgtg aaagcccagc tccctgcatt tctgggtctt cctctcccca ctgggggctg  19140
cccccacctg tttccccctc tgggcaccct ggttctactc atcagcctgg cttaatccca  19200
gcagcaggtc catgttctgc tctcctgtgg ctgccacaaa tgagaggttt catctcagct  19260
gggtttctcc tagttaaata tttaataaat aagacctaca acttgtgatg ctgggagtgt  19320
ttgatagtga aattaatgat ggggagagag tggcaggcgg cccacaggtc catgctggag  19380
ctgggatgag gcgccctggg caggcgtccg tgccactgat gcttgggaac cacggtgggc  19440
catgccatcc catttccccc agccagggcc tcttttttag cactgtgtcc agcacagggt  19500
agccacctga taaataagtg ttaaaagaaa gagaggctgc gtgtgtaggg aagaaggaag  19560
agacagagga gacaaagagg agacacagag agagagagag agatgagaga gaaagaaaag  19620
tggaaggtga gaaagagaca gagatggaag gggagagaag gacctggatg gaggaagtgc  19680
aaggaaggca atggtgaggg aaaagagaga gagacaaaga tggaagggat gaaggagagg  19740
gagagatatg gaggtagaga aagagagaca gaaagaagag agagaatatt gcttcttgta  19800
tcttcccctt ctcctgttat ccttgaccat cttattattt ttttcttttt tctgtctctc  19860
cagttctcat ttccttaccc tcgccgtctt gccaactcgt catctctttt catttcctgt  19920
```

```
gtctatgtta tcttttaatt ttctgtctgg gtattttccc cttttctctt tctcagcata  19980
aactgttggt tggtgtatgt gtcttctttc ttttttagtc tttaactgac gtgtgtgtgt  20040
atgtgtgtgt gtgagagaga gagagacaga cagacagaga gagagagaga gagacagaac  20100
aaacctagag agcagtgtag gaacatagat gaacatttta aagaccaaac catgaagcgt  20160
acacccattt tacccaggtc aagagccaca gggccaccat cagattctcc ctcatgctca  20220
tcctcaatca cagccactcc ttccctcctg gaggaaccac tattggagat tgtatgggaa  20280
ccattcgctt gctttcttgt gtggttgtac cacctaagta cgcatcctga agcaatatag  20340
tcagatatta tgtggttttg agttttatat gaataaaatc atgtgagagg agttgttttg  20400
tattttgctt cattggtttg cagttacctt tgtgagattt catcctcatt gtggtcactg  20460
cagctccttc atgatcttgt ttattcattg atgatgagca tgtgactttg ttctcttttg  20520
ggcactggca taagcagctt tgttggttgt ttatggattc tgctgctcgc ttgcaggggt  20580
ctctctggag cacatcgctc tgtgtgaaat tgttggatac taagatttgt acattttcac  20640
cttgactaaa cactgccaaa caattttcca aagtgcttgt gctaatttac actcctgccg  20700
gtggtgggtg agcattcaag atgcttcaca accttgccaa cacttggtat tgtcaggttt  20760
ttaagttata gcctttctca tggtgatttc tcattgtgat tttagtttgc atcccccgat  20820
tgcaaattag agtgaacata gtttaaaata tttattgact attcaagctt gctttttttgt  20880
gaagtgcctc tacatgctct gtccattttt gattaggtca cttttaaaaa aaaaatattg  20940
atttgtgggt gatccttaca tagcctggaa actgattctt catcattata tgttgtgcaa  21000
tattttctct tggcttggct tttgatcttt tttataatgt cttttgatca ccaacagttc  21060
ttaattttga tgtggttgat tttagaaatc ttttccttta tagtttgtgg gctttgtatc  21120
ttatttaaga aaatcatttc taccctgagg ccatggatat attttatgtt atttctgaaa  21180
gttttacagt tgtgttcact gtatgtcttt aatcagcttg ggattgattt ttatatgtgg  21240
tggtaggtag gggtccaatt tcctttttat tccataagaa ttgtcccagc atcatttatt  21300
aaaaagccca ttcttgcccc aatgatctgc aagacaacct cttgactgtt taacttttac  21360
cttctttcat ctggtctgtt tttatactca acctttgaag ccacaaatat ttattgagtg  21420
ccaactgtgt gccaggcact gagttacagt gacggatatg acagatgcaa tcatggcttt  21480
catggagttt acagtctggc aaggatgaca tgtaaatagt tattactact tataatttaa  21540
aatgttatag gccttgcaaa aagggacaag tctggcttgc tctaaaagaa acatgtgaaa  21600
caacatcttc cagggaagtg ctgataaact gagtctttag tgggcctctg ctattgtagg  21660
ggtgggaatg gtggaaaaga tgttttggcc acagggaaca gcatgtgcaa aggtcctgtg  21720
gaaggtgctt aggagtttga tatttatcct aaaggcactg tcaggctact gaagcagtaa  21780
tacaatgatt ttatgtctgt gaatagttcc actggttgct gcatggagaa tgtattggaa  21840
tacagcaaga ataaaaagcc atgagaccaa ttaggaaatg atttcactca ttcagggaag  21900
tgtgccttgg gctggcatgg tggctgtgga gatggaaatc attgatcaga ttaaaagaaa  21960
ttttgagctg gcatgatttt tcccctctct cccctctctc tatctctgtt tcttttctgg  22020
ttgtgttttc tgggtgagaa aagcagtttg tgatcctgcc aagggtatgt gctctggagg  22080
atgtatttgc cacagatggt ctttggaatt ctggccaaga gagtcactgg acagcccctg  22140
gcccccaggg tttctggagc caattcaaca atgactgttt attaacaaca gcaaggatga  22200
gttgctagcc tttccttcag agcacctttt aactgttacc ttactttgtt acccaaaccg  22260
acactatgga attggtgggg gagaagtgga agggttttta tctccatttt ttatagaacg  22320
ggggaagtta attggcactc ttgaaatcat acaaaagatg ttggtttcag gattggtttc  22380
tggactttca gcccaatccc aattactcaa gctcacacac ccaatcccca aacatactct  22440
tttgcaaata atttccctac tgaggtgctc ctggccaatt taaaaggtcc ccatttcctt  22500
gcctataaaa tgggaattaa agtaaaaata tctacctgtt gacttgctgt gaggtcagtg  22560
ggcctgacac atggtgtgga ctcattatat ttacctatgt gaatccctta gttcccttta  22620
cttggaagag gtggaaaact caaaggggct taaacaagaa gtggggattg tattggctca  22680
tgagactgaa gagtctcagg agtgtccagc ttcaggcttg tttggatcta gggatcagat  22740
aacaccatta ggcctctgtt tctgtttctt ggctctactt tttgcagctg gctccattat  22800
ccatgactta gctgcacttc cagccctcca gtctgcccaa gaccatattc agagagagat  22860
tcttctctct ttttcagcta tcttcccgga attttcagca aatgctttct tgcttttgat  22920
tggctgttgc tgaggtcgtg tgctcatgcc agaaccaatc actgtgggga aatgggaggt  22980
ggagaacggg gtgctctgat tggcttaggc ttgggtcaca tgactttatg gagttggggt  23040
ggagccaact tctccaagtg gggaagagca gtcttcttaa aggtgtatta ggatatgctt  23100
gctgctgtaa caagcaaccc ccaagtctgc agtagcttaa ggcaatacga atgtacttct  23160
cactcaccct aaatccaatc agataatcag caagtggcat tccatgtggt gatttcagga  23220
cccggctctt tccatctgtg gctccaccat cccctaagat cagaaagtcc ttcacttccg  23280
gcctgtagga aaagagtatg aaggctcaca caggaagttt tgggaggcca catatagaag  23340
tagtgaacct tacttctgcc tgcattctgt ggactggaat ttcatcccat ggtgtatgag  23400
agagggtccc agtaggaaac ggaagacaca gaccaagaat caaattaaga gatagcttaa  23460
gaatcaaatt aagagatagc ttacaaaggt gtgggccctt actgaaatag agaaggagga  23520
agagaggaag gaggcagaga cagagagaga ctgagactca caaagacaca cacacacaca  23580
cacacacaca cacacacaca cacacacaca caagttgaga gaaagaaggg gggagagaaa  23640
gagagagagg gagcatttcc taacaggaag ctggcagaat aaatgtcccc cattgtccaa  23700
agccagaggg ctgggagccc agtgagccca tccacacagg tcagcccccc atgtgacagt  23760
cctagaaggg taaagaagga aggagagtgg atttggggta atggaagaca gccaataccc  23820
atggtccatc tgactgcagg gggaactgag aaattcagtc catggagaag aaggtttagt  23880
ggacacgtca ctttgtcttt ttcacaaagt gaaactaggt tctcaggtgg aaaaaagaaa  23940
aagaaggttt gccttgctgc tattcttttt ttttttttga gacggagtct cactctgtca  24000
cccaagcggg agtgcagtgg cacgatctcg gctcactgga agctctgcct cctgggttca  24060
cgccattctc ctgcctcagc ctcccgagta gctgggacta caggcaccca ccaccacgcc  24120
cggctagttt ttttgtattt tagtagagac ggggtttcac tgctagccag gatggtctcg  24180
atctcctgac ctcgtgatcc gcccgcctca gcctcccaaa atgctgggat tacagacgtg  24240
agccaccgca cccggcctcc ttactgctat tcttattatt ggtggtagca gtggtggtga  24300
tggttattgg ttcttagttc cctctacatg ccagtatctg ctctcttctt tttttctccc  24360
ttacttcttt ccttgttctg caaattcttt ccctttaagt gaaaatcttt ccgtgttctc  24420
caagggagat aaattctatg ccaagcttga gtgtggggtc ctctgcttgg atagctgtct  24480
tctccaggag atgaggtaga actgagatag tgggggtctc tgcaggcagt ctgtgcccct  24540
ggcaagcccc tcaccttaac ctgaggctgg gtggggaaag atgccttgat ggagtcagaa  24600
cagaaagcaa gtgatcgctg cctgaaccaa gcagtcactt tcctggaggt gaaacctaga  24660
```

```
aacggtccct caggctgggt ccagggaggt ggacttgggt cccaggggca ggaagcaacc  24720
tgcccctcac ctgctcctac ctctttgtag cctatcttgg caaccagaag taggtataca  24780
agtgacgttg aagctgggca tgttaacaat ggtgtgagcc cgcctgactc caatctggtc  24840
cagctgtact ggccgtgcat cctcatctcc agcccccagg gtcagcccag cggctgtaac  24900
aatggtctgt cccctccccg ccccacccac ttctttgaac tcctccaagg atctgtgatg  24960
atagggctgt cactgtctta gcttccacca ttcaagctta accggccttc ttcccctcca  25020
tggagaacgg aagagcaacc cctcattgcc tctggcagct gaccagcagg tccctgcctt  25080
ctgcccactc ccaggtctag gacaatgagg tgagaggtag acaggaccaa gttccccagt  25140
gctgtcttct aggtccacct atcatgagag ccgtgattcc tagtttttat caccctctcc  25200
ccaactttgc cagctctcca cttctggcag tggtggctgc ccatgacttc accttcccgt  25260
gcctcagttt cctcatctgt aaaataagga cagccatggt aatgagagtt ctggtcaata  25320
tgccaggcac ctcgcttgca tcaatttagc tcatcctttc agtgccctga ggggtgggta  25380
ctgttatcat cccgtgtaac aaaaagagaa aaccgaaaca gagagagaga ctcactatct  25440
gaggtcttgc acccctcaag caacaaaagt gggatttcag cctaggctat ctagattcgg  25500
agtccacggt ctcaatgaat aataacaaca ataataatat tgtcctaatc tgatgagttt  25560
ttgatcagat tcaatacaag agcataggca gaaaagctta gcccagtgcc cagcacatgg  25620
taagaactca gcatgttatt tataatagta ataaaccatt ttatgttatg taattatata  25680
ttcatagata aatatagttg actcttgaac aacatagggg ttggggcaat gacctcctgt  25740
gcagtcaaaa atgtgtgtgt aacttttttt ctctattttt tagaaatttt aaaattagag  25800
acaaggtctc gcttttgttg ctcaggttga tctcgaactc ctgggctcaa gtgatcctcc  25860
tgcctcagcc tctcaaagtg ctaggattac aggtgtgagc ccccgcaccc agcctgtgta  25920
taacttctga ctcccccaaa gcttaactac taacagtcta ttcttgacca gaagccttac  25980
cagtaacata aacagtcgat gaagacagat tttatatgtt atatgcatta tatactgtat  26040
tcttacaata aagtaagcta gggaggagaa agtattattt taagaaaatc ataaggaaga  26100
gaaaatatat ttactattca ttaattggaa agggatcatt ataaaggtct tcatcctcat  26160
tgtcttcaca ttaagtaggc tgaagaagag gaggagttgg tcttgttgtc tcaggggtgg  26220
cagaggtgga ggtggaaggg gaggccagaa agacaagcac gcttggtgta actgttattg  26280
gaaacaaatc tacataagtg gacccataaa attcaaacct gagttgttca ggggtcaact  26340
atatatgcta caaatacgta atatgctaat atagttgtat gttattgtta tagtacgggg  26400
atcagaaaat gttttctgca aaggattagc tagaaaatgt ctagtaaata ctgtctcttt  26460
gggaccactc tactctgcca ttatagcaaa ggcagctaca ggcaatacgt aaatgaatgg  26520
gcatggccat ttgccaataa aactttgttt acacaaacaa gccatgggcc agagtttgtc  26580
aacggctggt atagtatatg ttattatata ttagctttac tttttctgtt gctttgttta  26640
tgttcttctt tgcccttcct ttcttaaagg ccagcctttc tttctctctg ttggtctgtc  26700
ttttaggaca gcatggcagg ccactgggac atgggctctc ctgactccag gcttgtttgt  26760
ctgataagac atgaagagtg aaggtggcag gactctgagc tcaggcctgt cctcctcctc  26820
ttccctctct tcgtttttttc tttcctcttt cctcttttct tcccaagctc cagaagttgc  26880
cattttcctt tcccattgct gattttctct gccttgggag aaagcccgag aagatcactt  26940
ggaaaagccc acgagcatct ctggcctcac tcacccagct cctgccattg tctttactct  27000
tcctcagaca caccaggcac agtcctacct cagggccttt gcactggctg tttcctctgt  27060
ctgcattgtt cttctctcag gtgacctcat ggcttctccc tcctctcctt caggacttca  27120
ctcaaaggcc accttctcag catttgcctc ccgcccttct gccttatttt cccctttgga  27180
acttttcacc ttcttactta ctcatctgtc tgctatctgt caccctacat cactatgatc  27240
tccacaaggg aaggtgattt tattcgtttt ttgttctgtt ttgttgaaga tgaggttttg  27300
ctcttgttac ccaggctgga gtgtggtggc acgatctggg ctcactgcaa cctccacctc  27360
ccggattcaa gtgagtctcc tgcctcagcc tcctgagtag ctgggattac aggcacccac  27420
caccatgcct ggctaatttt tgtattttta gtacagatgg ggtttcacca tgttggccag  27480
gctgatctca aactcctgac ctcaggtgat ccacccacct cagccttcca aagtgctggg  27540
attactgtga gccaccacac ctgatctttt ggttttaccc accaatgtgg actagaacag  27600
cctagatcag caggtggcat gcagtaagca gttgataaat atgtgttgga tgagtgagca  27660
ctgtggcttc tgtcattctg ttgctcaata gcattcatct ggaaataacc acagtttgtt  27720
tatccattta cctgttgatt ggcatttctg ttgattctcg tttgggccat tatgaacaaa  27780
gctgctgtga aatacttata cctttgccca attcttcact tggtgaaccc ttataaatcc  27840
tttaggccag gtgtggtagc tcacgcttgt aaccccagca ctttgggaag ccgaggtagg  27900
aggatcgctg gaggccagga gttcaaaacc agcctgggta acatagcaag acccgtctct  27960
acaaaaaaat aaaaaattgg ctggacgtgg caatgcatgc ctgtagttcc agctacttag  28020
gaggctgagg tgggaagagt gcctgagccc aggagttcaa gaccgcagtg agtgatcgcg  28080
tcctgcactc caggctgggc gatagagtga gaccctgtct gtaaaaatga cagcaacaac  28140
aacaataata aaacctttag gtttcctctt aaaaggaaca tccttagagc ttttcctgac  28200
ccagcaactc accccaagtc tgaattagac ttcaccccat ttctttcata acatttatca  28260
caatgacatg tttattttgt gggggcgggt ggcattctgg ccagaactgt cgacttccag  28320
agtgaaaata cggaagaacc aaataaaaca caacacacac atttgcacag cagctcgagg  28380
gaggtgctta gttctttgag tttccaagaa cagagagacg aagatttgtc tggggaggaa  28440
aaatcaggga ctgcttcttg gaggaggtgg actgttgctg ccccatccac ccacacattt  28500
gcagatgtgg tgatgagaag atgactgtca cgaggtctct gagcccaggg ggcccatggt  28560
tgagtgcaaa gatagtgggg ttgacaaata atcgtcgtat aacaaaagaa aagccaccac  28620
agttgcataa tggaaaggcg gcttctatag aacattcaga tcatagttga aggcatgtca  28680
cactgtgtta ctcagaggcc actgtcagag ccaaaagtga gagtggatga gagtttgggc  28740
aggaaacaac tgaaccagat acagcatcac ctccatgagg gctcagcttt atctattttg  28800
tcttctgttg catccccagc ccttagaaca ctgcctggtc catctttgct gtgtgaataa  28860
taataaggaa cgatcgctgt gttgagtttg ggctgtgaat tcagacagtt tgctgctgca  28920
tacctgatta tgagtctcag ttttcctcct ccataaaatg ggcaaaacag tccttgcctc  28980
atggggctgt gcatttgttt agcaaacact gaaggagtat acatggtggc caaggcactc  29040
ttcaagacac aggaagcaga caaaagtccc tgccctctgg gagcttacat gctcatgggg  29100
agagatgtat gataagaaac aaaaatagta ggtaagttgc atagtacttt agaagattat  29160
aagggtaatg ggaagagaac agcagagaaa gggctgggga ggcagttgct gtattagata  29220
gagctttatc gaggcgatgg cattggagcc aagacttgag gaagctgtga ggatgtctag  29280
agaaagaagg aacagctggt gcaaaggccc tgaggtaggg gtatatgtga catgtgtgac  29340
agtgaggagg cagatgtggc tgaagccagt gagcaagaga gagggaaggt gcaaggataa  29400
```

```
ggacagagag gtgacgggac aggttttgga gggccttatg ggctgcgggg aggactttgg  29460
cttttgctct gagggagctg ggagccacgg agggcttttg agcagaggag ggacgtgacc  29520
tgactcagat attcataggc tcctctggct gctgtgaaaa gaacagactt tgaaggttgg  29580
gggcaggcag ggcagaagct ggggaattag gaaggaggtg acagtgttgg tcctggcagg  29640
taatagtggg ggtggaacca ggttgttgtc tgtggagata ataatgagtg gctggattct  29700
ggttataatt tttaagtttt tttattgtga taaaatgaat ttttttattg tgataaaatg  29760
aaatttacca ctttgaggtg tgcaattcca cagcacttac tacagtcacc ctgttatgca  29820
acagtcacct ctatttaatc tcagaacatt tcatcccccc taaaggaaac cctgcaccca  29880
ttagtagtta cttccagttt ctcccttccc ccagcttctg gaaactacta attctggata  29940
taagttgaaa gttgaccagt aggatttcta ggcagacagg tggtgagggc tcaatgcatt  30000
catgcacaga aagtactcag gtggcatatc ataggtgctc aaaactgaaa tggtgatgat  30060
gagttggcaa tgatggtgag tccttccaga atccctgctc tagtgctaaa ctgacctacc  30120
tggctgtgta gaattctcac ctgctggccg ggagggtggc agaaccagga tcccttctta  30180
cttccagtct ggcttgggtt agggataggg gaggaatgat cagaagaacc aagctagcac  30240
catctgttct ggaacatcat ccaactcttg tccagatttc ccagaactga gcaggaaaat  30300
gtccagggag gaacagtgca gctgatggaa gtcctggtaa gccctggccc cagcttcctg  30360
agctgctgtt gcaccaacta gcatttgttg gaccttcagt ctgagccaag atggcagctt  30420
cagaggaaga acaagaagtg tacaagtttc tttcatggtt gtgtccccgc ctccttatat  30480
agcctcatat aaacccctgc actatcccgt tactgtttgc ctctccctga aaagagtgta  30540
aaactccccc actttttccc tacttttcac aatgtgtttt ggtttctaaa gatgaaactc  30600
ctttaattat gttctggttg taattttctg gctcctttta tttctccctt acttgatgta  30660
ttattttccc ttgttccttc tgccccctgc ctccattgat gtttctcttc actgctatct  30720
agatttaatt ctcaactcct gccaagttca gggtgatagt gcaaaaagac atggaccatt  30780
tagtcttgaa ttcaggtccc acttctgaca ccttcaaagc tgctttactt tgggcaagtc  30840
atatgatctt cctgaggggg tatcctttac cttgttcagc taacatttct tgtttttctc  30900
tgggcacaga gtagagtgtc attttcccca cctccctgaa gttaggtatg gctgtgtgat  30960
ttggtttcat caatgaaatg tgaggggaag tgacgtgagt ccttccggac agaagcctta  31020
agggtgagca tgggattcac catgtttcct ttttcctgcc tccactgtca tggatgcaca  31080
aagatggacc ctctctcaaa gtaagtgctg gagagaggat gacatagatc agtccccatc  31140
ccacttcata gcatgagtag aaaaatagac ctggggtgtg ttcaaccact gagatctggg  31200
gattgtttgt tactgcagca ggacatagac taggctgact gtatacctca ttatctgcat  31260
tttggggctg atatctaatc acagtgtctc caggaagatt atgttgatgt atgttttagg  31320
gatggatatt catattttcc tataagggct caataggttt ggaaatgtca catgcatgta  31380
aacttctgat taacaaatat ttcttgcttt ccaatttctt cctatagtgc ttctaatttt  31440
cctgtttttc aatcttgaat aaaatgtgag aagtgtttga cttctccttc gaggagatta  31500
atggtttcta aagcctgggg cattgattta gtcattctca acctccttgt ttctatgacc  31560
tttttttctc cttctctggt cacttagtgt ctgctaaggg gtgaaggaat gtctgtttta  31620
actcattgca tttttttttt ttttgagacg gagtctccct ctgttgccca ggctggagtg  31680
cagtggtgtg atgttggctc actgcaacct ctgcctcctg ggttcaagtg attctcctgc  31740
ctcagcatcc caagtagctg ggactacagg tgtctgccac cactcccggc taatttttgt  31800
atttttagta gagacggggt ttcaccatat tggccaggct ggtctcgaac tcctgacctt  31860
gtgatccgcc cgccttggcc tcccaaagtg ctgggattac aggcgtaagc caccacacct  31920
ggcaaactct ttgcattttt aactcttgac atcttcatct tctttttccc acctcccctt  31980
tgcctgttcc tcccctgctc accccaccag ggagtttata atcaggttct agaacctgca  32040
atgtttttct gttgttgtct tccatcttcc ttgagtctta tgggaatcgg ccatagtcgc  32100
aaattaacaa atagctctga agcgcctcaa gcttggaggc atttcctttt gctcacctaa  32160
gcaagatcct ggagctgttg caaatatcct gccccctact gtaaatctgt cttcatggtt  32220
gtaagagatt cagtcggggt cagtgaagac ccgagcagga gatcttggcc gaggctcctt  32280
gatgttctgt ctgcgctggg tgttgtcata ttgattaagc tcctgggact gctgccagca  32340
gcctctagga ttaaatcaat agagtttgca aaagtaaaag cttcttttgg agacacagaa  32400
tatgtgggtt tattttttaa tgataaagct tcaaggagaa tcttcatgga tggcagaacc  32460
agtgatggaa aaggcgaggc agacccaaat atttggggaa gtgcagtggg gagcaagtga  32520
gggaggtttc attgggaggc cggggctttc cagaaaatct gtttaactgg agttgctaat  32580
gcaacagctc agagttagaa gtgaaggtgg aagatgcaag aaggactgcc gctgagatgt  32640
aaagagaaat gaaggagagg tggatccatt tgctcattca ataaacattt tgggaggcag  32700
gggggtgggg gggagcctgc catgtgcctg gaactgggat gtacatggtg gggacatgac  32760
agtgggcagg acagatgtgg ttcctcctgg ccctcctgga acttgtaaca ggaaaagaag  32820
gcataaaata aggaataggc aaatacagac ataattacta attgtggtaa gtgtttggga  32880
gaaaaccagc agggtcctgt gtttgtttcc tagggctgcc aggacaaatt gccatgaact  32940
atatggctta aaacaacata aatatattgt cacccagttc tgaaggctgg aagaccaaaa  33000
tcaaggcatc agcagtgctg agctcccttg gacggctcta gagaagaatg cttccttgat  33060
tcttccagtt tctggtagtt gttagcatac attggcttga ttggcttgtg gctgcatcac  33120
tgcagtctct gcctctgtct tcacatggcc ttctccttca tgtcagtgtc ttctcttcct  33180
cttctctctc tctcttttt tttttttgt cagggcctca ctctgtcacc ctgtacaaga  33240
gtacagcagt gcaattatag ctcactgcaa ctgctgcttc ccagcatcaa acaatcctcc  33300
cacctcagcc tcctgagcag ctgggactta caggcgtgca ccaccatact cagctaattt  33360
ttaaattttt gatagagatg ggatctcact atattgccca gactggtctt gaacttctgg  33420
gctcaagtga tcctccctcc tcagcctccc gaagtgctgg gattacaggt gtgagccact  33480
gcacctggcc tcttctgtct cttataagga tctttgtcga tggattttga gcccgtcaga  33540
taatccagga caatctcatc ttgagatctc taatttaatt atacttgcag aggccgtttt  33600
actaaataag gtcatggcca gaggctccag aggctaaagc atgggtatga ttgcaccact  33660
gcactttagg ctgggtgaca gagcaaggcc ccatctctga aaaataaaat aaaataagta  33720
acctactaca ggccctttgc gtagaggata attagaagta caggggtacc acgtaagtga  33780
agacctgaag gttgttaagc acagagcaga gtgtgaacag aatgagacag agggaggaag  33840
agaatcccag gcagagggaa cagcatgtgc aaaggccctg gggaaggaac aagttcatca  33900
tgttaaaaat gagccagtgt agctagagtc tgatgagcaa agggactcac aggtgggaag  33960
acacccaaga agttggcaga gacaggtcac acaagacctt ctaggtcaag ttccggaggt  34020
gaactttatt ctacatgcaa tgagaagtcc tcagagaagc ttaagtggga tgggacagaa  34080
ctgctttact ttaaatatat atacatatat acaaacatat aatattacat atataaagca  34140
```

```
tatatatgta tacatatata catatctatc tacctgtcta tatatttttt agctgggcat  34200
ggtggctcac acctgtgatc ctagcacttt gggaggctga ggtgggagga tcacttgagc  34260
ccaggagttc aagaccagcc tgggcaacat agggagaccc catcactaca aataaaaata  34320
aaaattaaaa attagctggg tgtgatagtg tgcacctgta gtcccagcta cccgggaggc  34380
tgaggtagga ggattgctgg agccccaaag gttgaggctc cagtaagccg tgattgtgcc  34440
cctgcactct agcttgagca acagagtgag atcctgtctc aataaaataa tttttgtatt  34500
gaggtgaaat tcatgcaaca taagttaacc attttaaaat gagcaattca gtggcattca  34560
gcgcattcac aatattgtac aacctccacc tctttctagt gctgaaatat tttcatcacc  34620
acccctccag aaaaccctgt atccatgagg cagttgctcc tcatcctccc ctcccggtat  34680
ccccccaacc cccaccactc ctggtaacta caaatttgtt ttctgtttct atggatttac  34740
ctatactggc tctttcatat aaatgaattc aggcactgtg tgacctttcg tgtctggctt  34800
ctttcactta gcataatgcc ctggcttctc tctggagaat gaaatggata gaccactttg  34860
gagtctactg agattataga tatttctgtg ggaagggaca gtggcttgac cttgggtggt  34920
gctgaagagg caatgctgag caggaggatt caaagtctaa tttcggaagt agaattggtg  34980
gggtctgatg atacatcagc tgtaggggga ggaagatgta ggaactggga aggtctctta  35040
gggtaacctt acctgattga gctccttact aggcagctgg tggtacaatt cataacaaag  35100
gttaatagag aaagagacat gggattaggg agggaatgga agagtttggg ccttggacac  35160
tgtagtggtt tgaatcctgt ccaccaaaaa ttcagatgca tttggaactt cagaacctga  35220
gacctcattt gaaagtagga tctttgcaga tgtcattgag tcagggattg agatgaggtc  35280
atcctggatt acagtggact cgagattcca tggtaagtgc ttttatatga gaaggtacag  35340
gggagaaagt catgtggcaa tagaagcaga gaatggagtg ctgcagccac aagccaaaag  35400
acatgtagag gcaccaaaag cgggaagagg caaggaagga tcctccccta gagcctttga  35460
agggaaaccc cctaatttca gaaccttgcc tccaggatga cgagagaata aatttctgtt  35520
gttttaagcc acccaatctg tggcaatttg tcatgactgc cctaggagac taatatagac  35580
actcctatga gatgctctaa gaagacacag agtggtatag ctattgctaa gaccacacac  35640
tgtagcaggg aggaaatcaa atggagaaat gccccaactc cccctcctct ctgatctctt  35700
gctggtgcct cccgttggcc aagccaaccc agaaggcaga agatgtggtg gagggcagcg  35760
ttgcagggct tggatgatgc agtcacagaa gtcagccctg cctctaccag gatgccaaac  35820
agggcaatga gtggatattt tagggagaaa gggcaacaag agaatggcaa aatacatcga  35880
aatgcatgca agctctagaa agaggataga gatagataaa gggtgattac ctaggattaa  35940
gccccaggga agaccaacat ttagagattg gatagaaaaa gaggagcaaa aagggaagat  36000
tgagaagtag agaccaggag gataggagga aaactagaac aacattaaga agggcatggt  36060
caagtaatct gggcacagaa aaatggccct gggatttggc agcctggggg tctttggtga  36120
tcctctttgg aagagttttg gttgagtgat gggggctaga aaccagcctg gggagggtag  36180
gagaagaatg tgcagtgagg aagtggcagg aacacgtgaa ggcaactctt catgaagggg  36240
agtagagaaa ttggttggtg gctgaaggaa aattttcagt caagggtgga ggttttaatg  36300
atggaagaat attgatttct gtaaattggg tcattcccat ccattatacc aatatgcacg  36360
ggtgtcttct ctgatatagg atgctgggat tctcaaatgc ccatttgagt ttagcatcat  36420
gaatttaatg tcaccagccc agatagttga tctcattcag gaatgctcca ctgcccaggt  36480
atggggaagg caactagttg agttcatgca gggatggatt ttttccagga gagaaacagg  36540
aggcaagaaa gtgcgatata atcaacctat gtaaggttga caaggcagga gagggtcctg  36600
agaaatggcg gggtcagtgg gttgcagggc tcgatgggat ggacgttggt ttgcatttaa  36660
gggagttagt gagctgggag gtggttaaag aggaggtggt tcagccgggc gcggtggccc  36720
acacctgtaa tcgcagcact ttggggagcc gaggcgggcg gatcacaagg tcaggcgatc  36780
gagaccatcc tggctaacac ggtgaaaccc tgtctctact aaaaatacaa aaaaaaaaaa  36840
aaaaattagc caggcgtggt ggcgggcgcc tgtagtccca gctactcagg agcctgaggc  36900
aggagaatgg cgtgaacccg ggaggcggag ctgctgtact ccagcctggg cgacagggcg  36960
agactccgtc tcaaaaaaaa aaaaaaaaaa aaaaaaaaaa gaggtggttc aagacaagga  37020
tgctggaaac aggtgttttg gaggtggctg gtgtagcttc tgagcatgca tagctggagt  37080
ggcttggagg agacattggt tattgatgaa gaggtaggga catcctccag tgatcaagga  37140
agcaggggac cagcatggac aatggtctct ccacagggaa attggaggtc atcaaatgtt  37200
aacaggttcc gtcggagtct tagctcccag cttctgtttt cctgtggatc tcaggatctt  37260
ggctgctggt gctacctctg actttggact tcccattgag cccagcagca ctgggaggga  37320
ccttcatggc attggctggt ttaaggaaga cttccttggc tttgctgact ttcttggggg  37380
ccttcttggc tacacctgct tttgagggag ccctcctcac ctcacctgac ttcttggggg  37440
caccttttcc accttatctg agttgggaag gtctttcttt gattctcttg ctttcttggg  37500
gcccttctca ctggttttc tgggggccat gatggtggac atattccaga gctgagcttt  37560
ccttttgttc ttaggaacta atttgaggct gccagtggcc ccaccttggt cttagagttg  37620
atggtctgca gggaatttcc aggttaaagg ttttttattt gtttgtttaa ttttgagaca  37680
gagtcttgct ctgtcaccca ggttggagtg cagcggcacg atcttggctc actgcagcct  37740
ccgcctcctg ggttcaaaca gtttcctgc ctcagcctcc taagtagctg ggattacaag  37800
cacgcaccac catgcccagc taacttttgt atttttagtg gagacagggt ttcaccatgt  37860
tgaccaagct ggtctcaaac tcctgatctg aagtgatccg gccaccttgg cctcccaaag  37920
tgctgggatt acaggtgtga gccactgcgc ctgacctcca ggtttaagtt taaaccatga  37980
agtagatgga ctgtgtagag agagaccagg gaaatggagg attttactga ccactgaaca  38040
gggatgtcac tattgccaga gaggaaaagg attcccctt ggtagagtga acatataagg  38100
gaaagtggtt gaaaattgaa tcaggagaca gagacctcac accactcaga ggtccctaga  38160
gaactttact gacctagaaa aaaagataaa cagggagaag gtcttcagtt cttgtttgga  38220
atctgacact gaagcatcct cactcctcac tctcttcccg accccgagag tctgaaattg  38280
attaatactt tttgtttaaa acttggcttg ttgttttgtt ttttctttct gttttcatca  38340
agggatcttt attttacttt tgtgtatttg tgtgttttcc atgagtcatg ttaattcttc  38400
catgtttaaa ctttttggcc cagaggaatt tatacattta aattatggat ttaatttcag  38460
aaggtacata cacacacaca cacacacact cactcatctc actttttaaa aactgtaaaa  38520
tatagccctg taaatatcca gaaaatatct aatgtgggcc gggtatggtg gctcatgcct  38580
gtaatctcag cactttggga ggccgaggtg ggtggatcac ctgaggtcag gagttcgaga  38640
ctagcctggc caacgtggtg aaaccctatc ctcactaaaa ataaaaaaat tagctgggca  38700
tggtggcagg tgcctgtaat cccagctact cgggaggatg agacaggaga atcacttgaa  38760
cccaggaggc agaggctgca gtgagccgag atcaccccac tgcgccccag cctgggcgac  38820
agactgagac tctgtctcac aaaaaaaaaa aaagaaaaga aaaagtcagt gtgcatcccc  38880
```

```
tctgacatcc agcaacttca catcttggaa tttatgctgc aggaaaatta tcacaagtgc  38940
acaaggatgt atggtgagat agttattatt atcattttaa aagatagggt ctcactgtgt  39000
cacccaggct ggagtgcagt gaagtgatca cagctcactg cagccttgac cttctgggct  39060
cgagtgatcc tcgtgcctca gcctccccag tagctgggat tacaggtgtg agccaccatg  39120
cctggcatcc cccttttttt aaaaaaaggt tttaattatg aaaagaatat gggcttgttg  39180
ttttgtgtgg tttttaaaa gcttaaaaaa tgtgtagtgt gtcatttaga aggtgaaaag  39240
cccttacccc atcccacctc ccagagataa cctctgctag caatttcgtg tttgtctttc  39300
aaattttttc ccacacacat tctttgtact ggctgcttcc cctcctgggt tactcttctc  39360
ccagacagaa acagggctca ttcccttgcc tcctccagct tttattaaaa cattaacttc  39420
cctgtagctg gatgcagtgg ctcacgcctg taatcccagt gttttgggag gtggggaggc  39480
aggaggatag cttgagccca ggagtttgag actagcctgg gcaacatagc gagacccatc  39540
tctacaaata aataaataaa taaataaata aataaataaa taatggaaat ttaaaagaga  39600
gagggaagga ctcttgaaaa ccgtccatat catgcttctc taaatggttg agggctcaga  39660
ggaaaaaaaa tcagcaattt cacatcacgg aatttattct gcagaaaaat tctcacaagt  39720
gcacaaggat gcgtggtcag atgatgatga tgatgattat tattattatt attgaagaaa  39780
gtagcagcag cagcagcagt attttaaaag acagagtctc ggatgggcat ggtggctcac  39840
gcctgtaatc ccagcacttt gggaggttga ggtgggcaga tcacttgagg tcaggagttc  39900
gagaccagtc tggccaacat ggtgaaaccc caactctact aaaaatgcaa aaattagcca  39960
ggtatggtgg tgggtgcctg cagtcccagc taccagggag gctgaggcac gagaatagct  40020
tgaacccagg aaatggaggc tgcagtgagc caagatcgtg ccactgcact ccatgcactc  40080
cagcctgggt gctgacccag gttaggtgca agactccgtc ttaaaaaaaa agaaaaggaa  40140
aaaaaaaaaa aaaggacaga gcctcactgt gtcgcccagg gtaaagtgca atgagtaaag  40200
gcccatgatg ggaaccctga ggagagagtc aaggggaaag aaaaaaaaaa aagcaaaacc  40260
aaaatggaat ttaaaaaaaa tcaggtgcaa tttgcataac agaaaattaa ccattttaaa  40320
gtgaacggct ctgtggcatt tactgcactc caactgttat gtaactacca cctctgtcta  40380
gctccagaac attttcacca cccctaaagg agaccttgta cccattaagc agtctctctc  40440
cttctcccct ccccaccacc ttcctccagc ctctggcaac cacccatctg cattctgtct  40500
ctatggattt acctattcta ggtagtcaac aggatgagat atcccaaaag tccatccatg  40560
gatgaacaga taaaccaagt gtgatatgcc ttcctcagat attagtctgc cttaaaaagg  40620
aatgaaatac taatctttgc tacaacatag atgaacctca aaaatatgat gtggctggac  40680
acagtggctt acacctgtaa tcccagaact ttgggaggct gaggtgggcg gatcgcttga  40740
gcccaggtgt tcaagaccac cctgggtaac atagcaaaac tccatctcta caaaacaatt  40800
tacaaaaaac tagccaggtg tggtgacatg tgcctgtagt cccagctatt caggagactg  40860
aggcgagagg atcgattgag cccaggaggc cgaggctgca gtgagccatg atcataccac  40920
tgcactccag cctaggcaac agagtgagac cctatctcaa aaaacaaaac aaaacaaaac  40980
aaaaaagttg atgctgagtg aaagaagcca gacacaaaag gcaacatcgt gtttaattcc  41040
atttacatga aatgtccaat gaagattttt tttggcaaca tttattttga gtataatatt  41100
cagtgagtgg accacacata tgcatgcact gcagtatgtt cttggaaaca tttcagattt  41160
gagaggtctg ttcagctatg atgacggtag gtattgtccc ttccctccct ccttgaagaa  41220
aaggaactaa ggctggacgc ggtggctcat gcctgtaatc ccagtacttt gggaggctga  41280
ggtgggcaga tcacttgagg tcaggagttc aagactagcc tggccaacat ggtgaaacca  41340
tgtctctact aaaaaataca aaaaattagc caggtatggt gctgcacgcc tgtagtccca  41400
gctactcggg aggctgaggc aggagaattg ctcgcaccca ggaggtggag gctgcagtca  41460
accgagattg caccattgca ctccagcctg ggtggcagag caagactctg tctcaaaaag  41520
aaaagagaag agaagagaaa agaaaagaaa ccaaaagaaa aggaaagaaa agaaaaggaa  41580
ccaagaccta gaagggcaaa aataggaaaa gttggccggg cgcagtggct cacgcctgta  41640
atcccagcac tttgggaggc caaggtgggc agatcacaag gtcaggagat cgagaccacc  41700
ctggctaaca cggtgaaacc ccgtctctac taaaaatact aaaaattagc cgggcgcggt  41760
ggcaggcgcc tgtaatccca gctactcggg aggctgaggc aggagaatgg cgtgaacctg  41820
ggaggcggag cttgcagtga gccgagatag caccactgca gtctggcctg ggcgaaagag  41880
caagactcgg tctctaaaaa aaaaaaaaaa aaaaaaattg gaaaagttat ttactattag  41940
cagcaattgt cataaagtaa tgaacattta ttgcatgatt acaatgagat aaattgtatc  42000
ctgtttttat aagcatatta agttttcttt tttaaaaaaa tgtatgtatt tatttatttt  42060
aagagatagg gtcttgctct gttgcccaga ctggagtgcc atggtatgat catagctcaa  42120
tgcagcctca aattcccagg ttcaagcaat cttcttgcct cagtctctcg agtagctagg  42180
actacaggca tgtgccaaca tgcctggcta gttttcttat ttttaaatgt atttttgtag  42240
agacaggatc ttgctgtgtc gcccaggctg tcctcaaact cctggcctca agcgatcctc  42300
tgccttggcc tcccaaaggg ctgagatgat aggcatctac ctctgcattt ggcccacatt  42360
aaattttcta gtcatcatgg gaaccaaaat aaacaatata aaacactcac attccttgag  42420
cacttactat atgcagggcc ctgtaataga ttattgtgtg tatcagctca ttccattctc  42480
acacaaccta tgaggttgat gctattttct accttttata tatgaggaaa ctgaggctca  42540
gagaaggaaa ctgccttgcc caaggtcaag gccacgtctg atccccaaat cctttcaact  42600
cctctgcact actatttttt agtgcagata ttgccagttt tctaagcaga agcatgattt  42660
agcagccctg agtagacttc tcatttcaga accaaagtgt tggacattgt tggataatat  42720
gaaaaacaaa tgacacacaa acctatttga tactgttttt aattttctct tcatttgatt  42780
ttcctgatga catgattaat ctttttttgcc tctaccctgt atgtgaaatg taggtctttg  42840
cagatgtctc agagagtgtt aatagttgct gctggttttg ttttctctcc ccggggattc  42900
ccatccctgg gtgcaagtga aattaaactt gtgcctcttt gccgctggcc gtggtgctga  42960
aaacatcccg ggcagcgcta gggttgccct tgttagcatg ccatccctgc taagagtctt  43020
aggctgatca gcgagtggag agatcttttc caggcttcat tttggttaga actgtgtgtt  43080
gaagatttta aagcccatgt ctgggaactg gagactgttt ggattgtttg aagttgaaat  43140
agtcatgaat aattcctact tgagatgggc ttatgagggc gtggactagc atgcaatggt  43200
tggcctttac taaactgtgg ccattggttg ggacttgggt gaggtgtaac ccatttggtc  43260
taatccatat ggttagggcc ccaagtgcac ctgcattcta tttttttttt tttttaaata  43320
aaggcaaacc catctatctt ctaaccagga tagctcctga gtggtctttg gggaccacca  43380
gcttaaaagc atagactgtg ggctgggcac agtggctcat acctgtaatc ccagcacttt  43440
gaaaggccaa ggtgagagga tcgcttgagc ccaggagttc aagaccagcc taggcaacat  43500
ggtgagaccc tcatctctac aaaaatgtta aaagttagcc aggtgtgttg gcatgcacct  43560
atagtcccag ctactcagga ggctgaagtg ggtggatcgc ttgagcctgg gaggtcaagg  43620
```

-continued

```
ctacagtgag ctgtgatcgt gccactgtat ttcaccctgg gcaacagagc aagaccctaa  43680
ctcaaacaaa caaacaaaaa aaggcataga ctgtggagtt gggcagacct gggtgtgagc  43740
cccagctctg ccagtacctc ctatgtgacc ttgaaaattt gtttaatctc tctgagcctg  43800
gattttcttg tgtggaaaat gaggcttacc acagaaccca ccttgtagaa atgttgcaag  43860
gaattaactg aaacaaagtg cttaccacgg tatctgccca aagaagcagt tggaaacaag  43920
gcagctgtaa ttatggtcgc tgtgcttgtt aatggcccca taatagttga tcatattgca  43980
gagtgaaatt ggggtatgtg tttaatggac caaggaatat gtcttaaacc catatatcta  44040
gggttctggt accctctact ctttttcctg gtgattgtga tgagcatgga acttacatga  44100
aaatgaggtc tgtttggctt cttcacacaa gctcaatgac ctggctaact gctacaagta  44160
tctgtttcct tagaacccac ccatcagcag tccccatagt ggagacaagg tcacaaagag  44220
ttgacaaacc tgatttgatt tccgcaccaa ccacaggagg cttgaaatga gatgagggtg  44280
aagggcacca cagagggatg caaggattac ttggacactg caaggtcttg ctaagggatg  44340
ggaaccatca gccacgccca ctttgagaat tttccttcat gttctgaatc tgaagagcaa  44400
ggtcctgttc tcagatgcaa gccctccttc ttccctacgc agagtcaaac ttggtctttt  44460
ccagggtcac atacagcctc tctctggggc ctctgcaggt cctgatcaat ttcattgtgt  44520
atagagctct gtgtctcctc acctgcctgc agggctgtct gctatcctga cttccgagag  44580
ccatttcgga agccagcttt tcctcccatc agggatgctt ctcttctttc agcccccgcc  44640
ccgctttggc ctcctaggat ggctgatttt tctggatccc gctgacacag gtgctttctc  44700
tccgagccaa tcagggagca gaaaggctca gctcagctaa cagaggcatt gctcaccgca  44760
gctgtgagtt agaactcagg ctttctaaat cgggaggatc aggcatgact tgaggttggg  44820
ctgagaaagc ctcgcctgcc ccccagctcg actacccagt gaaacctttg gcttctgcct  44880
cgggcgaggc atctcttacc atgccaagaa ctcagcagcc catctttctt tcatctgggc  44940
accaagtaca tcattgcata tttcaggggg tttcattgtg tccttaacat gctcatggag  45000
acttggcttg agatgaagtc ggggtttcta ggcagcagga cccatgtccc cttccttcat  45060
ttcctccacc ggtgattttt gttttgtttt gttttgtttt gttttgtttt gttttgtttt  45120
tgagacggag tctcgttctg ttgtccaggc tggagtgcag tggcgttatc tcggctcact  45180
gcaaactctg cttcccgggt tcaggtgatt ctcctgcctc agcctcccaa gtagctgaga  45240
ttacaggcgt ctgccactat gcccagctaa tttttgtatt tttagtagag acggggtttc  45300
accatgttgg ccaggctggt ctcgaactcc tgacctctgg tgatccaccc gcctcggcct  45360
cccaaagtgc tgggattaca ggtgtgagcc accgcaccag gcccttccac tggtgttttt  45420
tgagcatcta ctatatagag aatgctctcc tgggcacaga ggatgaagca gtgaacaaag  45480
tagacaaaaa atccccacgt gcatagagtg tgcagtctcg tgggagagac agggaacaag  45540
ataaagaagg aaaaaaatag cagatgcttg actggggacg gggactaaag aaagaaaaaa  45600
ataagcaggc taagggggtt gatggatgtg acctttgagt aaaggcctaa aggaagtgag  45660
ggagggagtc atgtggatgt ctggggaaag actattccag gagaatgaac agcaggtaca  45720
aaggcccctg ggtacaaatg tgcctgggga gtttggggaa taaaagggag gccggcgttg  45780
ctgtagctga gtgactaagg gagagaatag aggagatgag gggagggagg taatgggagc  45840
aggtcatgca ccttgctggt gctggaagga ctttgttttt gcttttgagt gagatgggat  45900
ccatgggaag gctttgaata cttccacatg cattaggctg aaatttttctt ttctgctttt  45960
gtcgcattcc aacattgctt ttatttcatc aaaatcttcg gtttcttctc aggctcttta  46020
cccaagtggg agcagaaggc tggtacccag ggctgttcag ttctccccct ggggtcagaa  46080
cgtggaggag aaagcttgga ggagaaacag gaaccccccac ctctttctgg atgactcaaa  46140
accgcaatta cctgagctcc tcctcctatc cctgaaatag aggcacttag cacttcctaa  46200
acttcccggt gcacacaaat cccctggcga tctttttaaa tgcaggttct gactcagcag  46260
gtggatgcaa ggtctaaggc tgcattccta accggtgctg gttctgggac cacactttga  46320
gtagcaaggg tctgaggtca ttgttgcaga tgtccatctg gggcatgtct gtggacactt  46380
gcgggggtgc gggtgagcag agggaggggg gatgatgttg gaaaagcagt gtgagtatct  46440
gtgtttgata agaagtaaga aaatgaagca aggtgggaga gtagaacctc tttatttttg  46500
cctacgtgct aaggttttat tgccataccc agagagccct gggtctgaaa tccaggcaac  46560
actggccagt tgaaaccctg atattgcagc ccataaaagt gctgcatgct gcatggtgga  46620
cttctgggac tcttcctgga accttcagtg ccagagccgg tccaaaggaa gtcacatccc  46680
tgccattgag gggcaggaga ccagggaacc ggaggagtgg gatggcagaa gcgcgtgtaa  46740
ggaggctgag ttggcaggga gagaaagcga agtcagcttc aaatcatagc gagaggagac  46800
cagggaaggg cttggcgttg ctgctctgtg tacaaatatt gtctcttatt ttccaggctg  46860
cagggtgagg cagagtggag tatttgtgca acacagccca gctttgttct ctgggctcct  46920
aatgcctgtc agctcagagg cagaaagcca atcagagatg atcgtcggca aggccggctt  46980
ttgttggctc cccaaattgc cctgagtctc ggattttgct tttcagagtg tgctttcagc  47040
tggaggcaaa ggctgaagct ggtgacaaaa ggaagcctgg ttttcctggc tttccgagac  47100
ttttactgag gggtttcta tttcagactc cgttttccca cctggaaagc aggttccact  47160
ctccctccgg cctggaaggg atggttttat ggtgcttcca aaatgccaaa cctaactcca  47220
gggcagaaga ggagactgaa accaattaat tttccaaagg ttagagctac gaggagggga  47280
gaggtttagc atggtcaagt tccccaagac atactaattg atctctctac agaatgcggg  47340
atttcagtgc ccccagggga cactcagcaa tgtttagaga ccacttgagg ttgtcatcac  47400
tggacaggag gggctgctac tggcatctag cacacacagg ccagggatac tgttgaacat  47460
gctgcagtgc ccagacagcc ccaccaagga gaatgatcca cccctaaacc tagtgctgag  47520
gttgggaaat cctgctccgg agtaaccaac accctatggc tttttcactc aagcagccgc  47580
ttctccagcg cttacacctc ctcagagatt gccagatcca tatgcagagc ctgttggcgt  47640
gggacacttc tgaggggtgt ggcagggaga cagcggacat tcccatttac cagctgatca  47700
gcaggttagg agctaatatg aaatgaacaa gatagaccct ccccacctgc cctgcagatc  47760
ctctggtggg acactaggga gggaggcctc ctaaacccaa atgacagttc ccaggatgca  47820
gggaggagtt tacctatgca aactggagag aatgcaaatg gggcatctag agatacttac  47880
tggacgaccc ctcccctgcc tcgggtcttg gaagaacaga ttctcagagg tctgccctga  47940
tcactgtaat ttttttttta ttgaggtaaa attaatataa cacaattaac catttttaaag  48000
tgacatttag ggctgggcac agtggctcat gcctgtaatc cccgcacttt gggaggctga  48060
ggaagaaagg tcgcccagga gttcaagacc accctgggca acaaagtaag actctgtctc  48120
ttacaaaaaa aaaattaggc acacatggtg ttgtgcacct gtagtcccag ctactcagga  48180
ggctgaggca ggaggatcgt ttgagcctag gaattcaagg ctgcggtgag ctatgatcat  48240
gccactgcac tccagcctgg gtgacagagc aaaattgtgt ttctttaaaa aaataaaagt  48300
aaaaataaat aagaaaagaa aggagagggg aggggagagg cgtttagtac actcacaatg  48360
```

```
ttgtgtaact gtcaccttca tctagttcta aaacattaag cagccactcc catttccctt  48420
gccattcccc aggaacaaca aatctgctgt ctgtctctgg atttgcctgt tcgggatatt  48480
tcatatacat ggaatcatac aatatggggt attttatgtc tgcttctttc gcttggcata  48540
atgttttcaa ggttcattcc tgttctatca tgtatcagta cttcattcct tttttttttt  48600
ttttttgaa acggagtttt gcttttgttg cccaggctgg agtgcaatgg cacaatcttg  48660
gctcactgca acctccgcct cccgggttca agcaatcctc ctgcctcagc ctcctgagta  48720
gctgggatta caggcatgcg ccaccacacc cagctaattt tgtacttttt ttagtagaga  48780
tggggtttct ccatgttggt catgctggtc ttgaactccc aacctcaggt gatctgcctg  48840
cctcggcctt ccaaagtgct gggattacag gcgtgagcca ctgcacccgg cctacttcat  48900
tcctttttat ggctgaatac tattccattc tatgagtaga ccacatttg tttatccatt  48960
cacccactgg tgaaatttag gttgtttcca tcttttggct gttgtgaata gtgctgctgt  49020
gaatatttgt gtatgagtgt tcgttggaat acctgtctta cgatcctttt gtgtttatac  49080
cttggagtgg agttactgtg tgtcacatgg taactctgtg attaactttt tgaggaacca  49140
aggaatggtt ttctatggca gttgcactgg tgttttttg ttgttgttgt ttttgttgtt  49200
gttgttttga gacagggtct cactcccatt gcccaggctg gagtgcagtg gtgcagtcat  49260
ggttcactgc agcctcaacc tcctggggct caagcaatcc tctctcctca gcctcccaag  49320
tagctggcac tacaggcctg cgccactatg cccggctaat tttcatatt ttttgtagag  49380
atagagtctc agtttgttgc ctaggctggt ctcggactcc tgtgctcaag taatcctcct  49440
acctcggcct cccaaagtgc tgggattaca ggcatgagcc accgcatctg gccagctaca  49500
ccattttata ttcccaccag catgagggtt tcaatttctt cacatcttca ccaacacttg  49560
ttttctgttt gtttgtttgt ttttaatagc tatcctagtg gatgtgaagc agtatcccgt  49620
tggggtttga tttgcacttc cctgatcact aataccctca tgtacatatt ggccatttga  49680
ctgtcttctt tggagaaatg tctattccag cctcctgtcc atttttcaat tggattatct  49740
ttttgttgtt gtgttgtaaa tgttctctct ttatttttta ttttttgag acagagtctc  49800
gctctgtcgc ccaggctgga gtgcagtggc acgatcttgg ctcactgcaa gctccgcctc  49860
ccaggttcac gccattctcc tgcctcagcc tcccgagtag ctgggactac agatgcccgc  49920
taccacgccc ggctaatttt ttgtattttt ttagtagaga tagggtttca ccgtgttagc  49980
caggatggtc tcgatctcct gacctcatga tccacccgcc ttggcctccc aaagttctgg  50040
gattacaggc gtgagccacc acacctggcc gtaaatgttc tttatatagt actagaccct  50100
tatcagatac atgatttgca aatagcttct cctattctgt tacttgcctt ttaactttct  50160
tgataacgtc ctttgatgca caaaaggttt aaattttgat aaagcccagc atatctgttt  50220
tttcttctgt ggatcatgca ttaggtgtca aatctgatca taatgtttta tttatttatt  50280
tacttattta tttattattt tatttatttt tgagatggag tcttgctctg ttgcccaggc  50340
tagagtgcag tggcatgatc tcggctcact gcaacctcca cctcccaggt tcaagcgatt  50400
ctcctgcccc ggcctcccaa gtagctggga ctacaggtgt gtaccaccac gcctggctaa  50460
tttttgtatt tttagtagag acagggtttc accatgttgg ccaggctggt ctcaaagtcc  50520
tgaccgcaag tgatccaccc accgcagcct ctatctattt ttaatttatc tcttttttt  50580
ttttttttt tgagacaggg cctccttctg tcacccaggc tggagtgcag tggtatagtc  50640
attgtacact gcagcctcta cctcctcggc tcaagcaatt ctctcgcctc agcctcccaa  50700
gtacctggga ccacaggtgc ctgccatcat gctggccctg ccaccatatt tgaaattgca  50760
gccctgaccc cttccactgt ctatagtctt caccatctta ctacataaca tagcatatat  50820
gatgtactgt ataacatggt atatgcagtg tactgtatag catagtatac atgatgtagt  50880
catctcattt atttgcttct cctctgggaa gcaggaggaa gcttctcctc ttgtctgctt  50940
tgctctcaac tgtgtcccta gcccagaaca gagtctggca cacagcaggt actgaatgaa  51000
tatgtgttca gtgaatattg tgggtgagat agaaggtgaa tatccacatt tccctttaga  51060
agtcacctga tctgggtttg agatctgcag ggatctactc cagacaggag aacgaataat  51120
tccacctgtg ctgatgagtt ggaaggatct agagggcttg agatctttcc actggggtca  51180
gtgggggtgg gtgcacctcc aacacccttc ttttctttga acaagatttt tccttaattc  51240
cccaatactc cctttgaata tatgatttta gccaccatca tagcgaattg catcgtcctc  51300
gcactggagc agcatctgcc tgatgatgac aagaccccga tgtctgaacg gctggtgagt  51360
gatgtctttt ctcagggtct tctccttggc tttagcagga cattaatttt tgggggagtg  51420
gagcagggca cagaggaggc tctcagtcct ggagcccaga gccagatcat gggaagccta  51480
aatttccttt tcattttttc ttgaaccaga gtctcgctct gtcacccagg ctggagtgca  51540
gtggttcagt catagctcac tgcagcctcc acctcctggg ctcaagccat cctcccactg  51600
cagcctcctg agtagcaggg actacaggtg ccaccatgcc cagttaattt tcttattttt  51660
atcttttttt gtagagatgg ggatctcact aggttgctta ggctggtctc aaactgccca  51720
ctttggcatc tgacataatt tcaggcagta tactcaaatg aacattgtta atgttaataa  51780
ttatgtcttg gccagacact gtagctcatg cctgtaatcc cagcagtttg ggaggccaag  51840
gcaggtagat cacttgaggt caagagttcg agaccatcct gaccaacatg gtgaaagccc  51900
gtctctacta aaaaaataca aaattagctg gatatggtgg tgcacacctg taatcccagc  51960
tacttgggag gctgaggcag gagaatcgct tgaacccggg aggcagaggt tgcagtaagc  52020
caagatcgca ccattgcact ccagtctggg caacaggagt gaaactccat cttggtgggg  52080
gggaggcgaa aaaaaagaaa caagaatatt acaaaggata cagatgaaga gatgcaaagg  52140
gtgagatata ggagaagggt gtggctggca gcttctaggt agcttcagga gggggactgg  52200
tcaccagaaa gaccaaggca tgattcgagg gttgcgactt tcagccccac cccccaacct  52260
ctgggagggc agaggggctg aaaatcaagt tgatcaccaa cggtcaatga tttaaatcca  52320
aacctctaat catgccttgg ttttcccggt gaccaacccc catcctgaag ctacctagaa  52380
gctgccagcc atcagtcaat ccttagcctg caaaaagaca tccctttgga gatcccaagg  52440
gttttaggag ctgtacacca ggaaacagtg tcaaagacca aacatacatt tcacaatgtc  52500
acagtcttct aaaaactata actagcctag caaacctatg atttctagat ctttgcattt  52560
tcacttaaaa taaagctaaa taaaaagcgt ccattgaaag actggtaagc aagtagaagt  52620
accagtggca agctaatgtg gaaaaaaaaa atcattcagg cagagtgaaa atgattgtag  52680
ctcgagaaac gttgctgtaa cagatgggaa aacattcaca ttggggctct gatggagaag  52740
agcttgtagc ttaatttcaa atatgataga ttagcagctg gaagccagaa ccagccggag  52800
gttctgcaga ggaactggag gtgaggatac tggccactta tcagccagta cagaagtcct  52860
attccaaacc tttaacaatc tacatgccag ctgagaacca tcctaagggg tcagatttag  52920
gagtgaggtc aatgcacaag ctctagcctc aaataccttg aacgctgcat gtgacaagta  52980
aattctctaa accaatgctt tccattagaa ctttctgcag tcacagaaat gatctccatc  53040
tgccctgtcc aataggattg tcacttgaaa tgtagccagt gtgactgcag aactgtgttt  53100
```

```
tttattttat tgcatttaaa ttaattttaa ttgaaatagc cacatgtggc ctgtgactgt  53160
cgtattgaat aagacaggtg caaacaaata attctgttta gctgagtgat atgtgaggtt  53220
ggcccaaaag gaatgaagga ggaaggtgcc ttctctaggc attggctttg ctcgcaaaag  53280
gctttggaca agagaactct gcaagaggca gtgaggggtg gtgagtgcag gagggtcagg  53340
ggaagtgaga gggtgatagg tactgatttc taggtgggct ggttccctga tcttgtcaac  53400
atctgcccag cccaagacgc tgaccttgcc ttctctccct tccaggatga cacagaacca  53460
tacttcattg gaatttttg tttcgaggct ggaattaaaa tcattgccct tgggtttgcc  53520
ttccacaaag gctcctactt gaggaatggc tggaatgtca tggactttgt ggtggtgcta  53580
acggggtaag tggcgcgtgc tatacgcttt ggatttaact agctgaagga ttacgaggct  53640
tttggttggt gtggtccggg ccaggctcag gaaggctgag cccttgtgtt ctccctcccc  53700
ttgttatgcg cctgcctcct ttctgccaac accccacctc catgtctcag ctgtatatta  53760
cagcagatgc tttctgttac aattaaaata atagctcatt attgttggct gcttccagag  53820
tgctttatgc ccattctcta atttaatcct tgcaacaacc cactgaatta ggaaatatta  53880
atattcccat ctgaccactg aggaatcaga aactcagagt gtaacttgct taaggccacc  53940
cagcaagtaa gtgatggaac tgggagatga acagaagatt atgcattcca gaactcaagg  54000
ttttaagtgt tgtacgtgca tgggtctctt gatttgcttg aggatatctt gcttttattt  54060
caacttggtg aatgtttttt gagaatgtct gggtgcaagg gattgtgatt atgacaaagg  54120
agaaaagcaa gctaaataag gtacagttac tgtcttcaag gagttttcag atccatatat  54180
gatgaactgt ggttgaaatg tgtatatgct ttcctctaag caccctgtat gaggtagcac  54240
ttgctggtat aacaaaagat ccaaagctag gaaatgactt aaacacggca gaagtttatt  54300
tgtcactcat agaaaattca aaattgagct gggtgtggtg gtgcatgcct gtaatctcag  54360
cactttggga ggctgaggtg ggaggatcac ttgagctcag gagttcaaga ccagcttggg  54420
caacacagtg agaccacccc cccatctgta aaacataaaa taaaataaaa attaaccagg  54480
catggtggta catgcctggg agaattgctt gagctcagga gttggagggc acagtgagct  54540
atgatcatcc aaccgtgctc cagcctgggc aacagagcaa gaccccatct cgaaaaaaaa  54600
aagtccaaaa taattgttcc tagttgacag gctcatctcc tccaatgact gacggaccct  54660
gacccttgcc atattgtggc tcttcattgt cagcccacat catccaataa ctccatgctt  54720
gtctgtatca aaccaggaag gagaagtgag catagaaggt gatacttgga aaggtttatg  54780
agtttggaag gggtgtgacc catacctgtt ccattcatat cctattggct agaactcggt  54840
cacatgacca cacatcactg caagggaagc tgggaagtat cagattgtgc ttagaagaaa  54900
agggaaatgg atttggagaa tgacctacta gtctgtcagg gaccttaaaa acttttatta  54960
gattccagta gggacattag tatctggtac caatggctgg ttcctcctct tcccactctc  55020
tactctcctc tcagctaagt ctgggctctt ctattctaag acccttcttc actggacacc  55080
tttttcatag taatcattta caggatcata gctttccatg ttttgttgct gctccaggtt  55140
ctgtctctct tggcggatgt gatgggttgc agcacccaca ctgtgctggc cgggctctca  55200
caatgcagat ttgtttcaga gcaatgttgc ctctcacaga aggagctgtg gcctattggg  55260
ctgtttctgt agaggccttc agatgtcagc agtctgttgt aaggactctg ggctagctct  55320
catgggcttg ggtgttcaca gagggatctt tgttggctgt gctcacagtt cggtggcttg  55380
ggaccttggt gggttccaag ggcatattat ggtactgggc acttttctct tagtctacta  55440
ggaaactcat ctagaaacag cctagtggct aactttttta ttgtttaaaa aatgtaaagc  55500
tgggcagggt ggctcatgcc tgtatcccag cacattggga ggccaaggtg ggaggattgc  55560
ttgggcccag gagtttgaga cgagcctgag caacatagca agaccacatc tccacaaaat  55620
aaaaattaaa agtgtataaa gctgggtaca gtggcacatg cctgtaaccc caattactca  55680
ggaggctgga gagagaggat tgcttgagcc taactagttt gagaccagct tgggtaacct  55740
agcaagatcc catgcaaaac taagtagaga ataatagagc aaacacctgt gtatacattc  55800
atttattcaa tgactattta ttgaacactt ctgtgtgcca ggtcctgttc taggctctgg  55860
gacacagcag taaacaaaat agaaaaatcc cctgtcctca tggagctgag agtctactga  55920
tggagatgga cacaattgat gaatgaatct agtgtgtcag atggcggtga ggggtacaga  55980
ggaaaaataa agcaggggag ggatgggatg tgtggcaggc aggggtgagg ggtgctggaa  56040
gccagggaag acttcactgg gcatgtgaca tctgaatgaa aacctaaggg aggtgagtga  56100
gtgagccatg aggagagctg gaacagagtg tcaggcaaag ggaacagcca gtgcaaaggc  56160
tctgaggctg gactgtatct gacatgtttg atcaacagta agaagaccca catggctaga  56220
gaaggtgacc agaagaatgg ggagaattgg ggatagagaa gtaatggagt aacctgctat  56280
caaaacacaa cctttctctt tttttttttt tttttttttt tgacaagagt ctccctctgt  56340
cacccaggct ggagtgcagt ggtacaatct cagctcactg cagcctctgc ctcccagttt  56400
caagtgattc tcctgcctca gcctcccaag tagcttggat tacaggcgtg taccacaaca  56460
tctagctaat ttttgtattt ttagtagaga cgggtttacg ccatgttggc caggctggtc  56520
ttgaactcct gacctcaagt gatccacctg gcatggcctc ccaaagtgct gggattacag  56580
gcgtaagcca ctgtgcccag caaaacaaaa cctttctaac ctttctaatc cctgttttct  56640
ccctccctag acccattcct ttctctcccc catccagggg cactttcctg aattttatgt  56700
ttattatttg catttatgta ttcacacttt ggctgcctaa gtatataaga aatatatgct  56760
acctattttt acacttcaaa atattttta aatagcatca gagtgagaat agtttacact  56820
ttgactacat gcatagataa gaaatatgtg ggctgggaat ggtggctcac acctgtaatc  56880
ctagcaattt tggaggcaaa gatggaagga ttactttagg ccagaagttt gagaccagcc  56940
tggccaatgt agtgaaaccc tgtctctaca aaatgaaata aaatgtaata aaatattcag  57000
ctgggcatgg tggtgtgctc ctgtggtccc agctactcag gaggccaagg cgggaggatc  57060
acttaagccc ataaggtcga cgctgtagtg agctatgact gcactccagc ttgggcaaca  57120
gagcaagacc ctgtccctaa aaaatgtttt ttgttgttgt tgttgttttt tgttttttg  57180
tttttttaat aaaggccagg tgtgatggct cacacttgta agcctagcac tttgagaggc  57240
cagggcagga agactgcttg agtccaggag tttaagacca gcctgggcaa catggtgaaa  57300
ccccatctat aaaaaaaatg caaaaaatta gccaggcatg atgacgcacg cctgtagtcc  57360
cagctactca ggaggctgag gtgggaggat cacgtgagcc caggaggtcg aggctgcagt  57420
gatccgtgat tgcaccactg cactccaggc tgggcaacaa agtaagacct tgtctcaaaa  57480
aaataaaata aaataaaaaa taaaaaaaag aaaagagaaa gaaaaaaaga gatatgtggt  57540
actgtttttc aaacttcaca tttctctaac ctgacttttg tgttcaacat gagataaatc  57600
tgattaataa aaatagtttc catgcatcca ttttcatgac tgcatagtat tctgtggtag  57660
gagtatgctg ccgtgtattt atctatttgg attgtttcca gctttgggct attttgaccc  57720
aaagtgtccc tgctttctcc caagtgagtt tctctagggc acgtacccag gagtggaact  57780
gctgagttgt atactgtgtg catcctcagc cccactaggt attgccaaat tgctctgcaa  57840
```

```
agtggttgtg ccaattcatg ctccctgggg gctggcttct gctggctgag gctggcttga  57900
ccttgctggc aggaaggagc cttaaaaatc cctgtgtggt ttttttttgtt ttacttttat  57960
tttaagttta ggggtacaag tgcagatcta ttacatgggt aaacttgtgt cttgggggtt  58020
tgttgtacag gttatttcat cacccacgta ttaagcctag tacccattag ttatttttct  58080
tgatcatctt cctcctcccg ccctccaccc tccaaaaggc cccagtgcgt gttgttcacc  58140
tctgtatgtc catgtgttat catcatttag cccccactta gaacacgcag tatttggttt  58200
tctgtttctg cattagtttg ctaaggataa tggcctccag ctccgtccgt gttcctgcaa  58260
aggacatgat cttgttcttt ttcttggctg catagtattc catggtgtat atgtaccaca  58320
ttttctttat ccagtctatc attgatgggc ttttgcagcc ctgttttttt ttttttttca  58380
taataacacg gttatgggaa cacttaggga agctcatata ttattgagca gtgtgatggt  58440
taatattgag catcaacttg atcagcttga aggatgcaaa gtcttgttcc tgggtgtgtc  58500
tgtgagggtg ttgccaaagg agattaacat ttgagccggt gaactaggag aggcagactc  58560
acccccaatc tgtgtgggca ccatctaatc agctgccagt gtggccagaa taaaagcagg  58620
cagaagaagt tggaaagagt agacttgctg agtcttctgg ccttcatctt tgtcctgtgc  58680
tgaatgcttc ctgccctcta aaatcagatt ccaagttctt cagcttttgg actcatggac  58740
ttacaccaat ggttagccag gagctctcag gcctttggcc acagactgaa ggctgcactg  58800
tcagcttccc tacttttgag gtttgaggac tctgacggat ccaccactgg cttccttgct  58860
cttcatcctt cagatgggct atcgtgggac tttaccttgt gattgtgtga gtcaattctc  58920
cttataaact ccctttcata tatacatcta tcctgttagt tttgtccctc tgaagaacct  58980
tgactaatac agacacctag tgggtcccaa taagtgatca ttaaactgaa ggcagtcatt  59040
cagtaggtca gtttgtcact tgtgtttgta tctccctgct tacaacaagg tggcctttct  59100
tctagtttcc tgtcatctga tggaagagat tctagactca ttcctctaga ggagaaatac  59160
ttcatctaga acagataggt cctaagggtg agagctcatc gttgggatga atgaacccac  59220
tgaaatttta tgcaagaaga aaattgtgta tatgtatatt ttttttctg gtctgtagtt  59280
tttattagat tctcagggaa tcctgatcct atcatgaaga ccttctattc tagattgggt  59340
tcctttcaca tccccttctc ctttcttgtt gaattctcca tgcatttctt tcacttgctt  59400
ttcttgctct tatttctctg gtagtcagtt atcctttttg tctggtggtt ctatctcctt  59460
caaatgaggc acattgctca aattttatta ctccaaattc caaggtgctg tttagtgtcc  59520
tgttgggttg taagctagga acagggaggg gaaagtaaaa cattctgcat gagctgggtg  59580
cagcgggcaa gcacctggaa ttccagctac tggaagctga ggtgggagga ttccctgagc  59640
ccaagggttt aaggccagcc tgggcaacaa agtgagattt tgtcttaaaa aaaaaaaaaa  59700
tcccagctgg gctctgtggc tcatacctgt aatcccagca ctttgggagg cagaggcggg  59760
cagatcgctt gaagtcagga gttccagacc agcctggcca acgtggtgaa accccatctg  59820
tactaaaaat acaaaaaaaa aaaaaaaaaa gcctggcatg gtggtgtggt gtgcactggt  59880
aatcccagtt atttgggagg ctgaggcagc agaatcactt gaatccagga ggcagaggtt  59940
gcagtgagct gagattgtgc cactgcactc catcctggat gacagagtga gactctgtct  60000
caaaaaaaaa aaaaaaaaga aagaaaaaac acgcgcgcac acacacacac atcatgcaga  60060
cctagccttc tgccaatgtc aatggtagag aaacacagta gacacttaat tctatgtttc  60120
agagaggagg ggactcaaat atattaattt gacattgaga cagtgatgac tttaatgagt  60180
actttctttc cttttttttt tttttttttt cgggacagag tgcagtggtg ggattttggc  60240
tcactgtagc ctccacctcc tgggttccag cagttctcct gcctcagcct cctgagtagc  60300
tgggactaca ggcatgcact gctgtgcctg gctaattttt gtatttttag tagagacggg  60360
gtttcacact atcagccaga ctggtctcga actccggacc tcaggtgatc tgcccacctc  60420
ggcctcccaa agtgctggga ttacaggcat gagccaccgt gcccggccta atgagtactt  60480
tctgattaac ctgttgccct ctcagattcc tgaagcaaac cacagcgtta aaacgtgatt  60540
cattttgtgt ggaccaccac ggtgtttacc ttcttcttgg gtgaagtttg gtggaaaaga  60600
tcttaccccg gacatctgtt tgttctttgt aactcagagc ctcagagaaa tcctaacttt  60660
ataatgttgt caaacccttg taaggcatgt ttttattgta tttgtgttct gatcatgaaa  60720
ctgaaaatgt gtaagaggaa gatttcagaa gcttggctgt atgtctgaga tgacagttct  60780
tttactgtca ttctcaaata tatataaata ttgaagagat caaataacac aaatcgtgca  60840
tgttaagaaa agagactgtg aacctcacca gagaggggtg agcacaattt tttttctttt  60900
ttattcacag ggttagcact gtccctttca cataataaat gctcagtaaa ataaatggtt  60960
gttaagccgg aaaagggtaa cacttctgat aatgagtgtc ctgggaaatt tactaagctg  61020
tttagaagat gggaccaaca cactgataga aatagtcaga tagtccagaa gtctatggca  61080
gatgccctga acatcagatg agatataaga cagagaagct ctgggtcttt gccagctctg  61140
acattttatg actctatgaa acggaaggtt ccttttttaga agggtctata aactgtctca  61200
ggctttgggc cattttgttg aagatcagag gcaaggaaaa gacacaacta cacaggaacc  61260
atcagggaaa gatgttgttt tttggtcttg aagcatcatt gaattttttt tttttttttt  61320
gagacggagt ttttctcttg ttgcccaggc tagagtgcaa tggcatgatc tcggctcact  61380
gcaacctccg cctcccaggt tcaagtgatt ctcctgcctc agccttctga gtagctggga  61440
ttacaggcat gtaccaccaa gcccgggtaa ttttttttgta tgtttagtag agacgaggtt  61500
tctccatgtt ggtcaggcta gtctccaagt cctgccctca ggtggtccgc ccacctctgt  61560
ctcccaaagt gctgagatta caagcgtgag ccaccgcacc gggccgcatc attggatttt  61620
aaggctccat ggattctggc aggtccagcc cttctgtttt actcacaaac aagtggtttg  61680
tccaaagtca cacagagatg gtggcaagag atctagaata agaaggtgtc ttcaagtcat  61740
ggagccagga accctggctt tttgggcaat ggaagtggta taaatgttta atatcacccc  61800
tcaggttctg ccactagagc ccagctctct cttccttcct cttgccccct gactagccta  61860
tggcctcttt ccagagaata agaaagggat cctcagagaa taatcccagt tcctcgcttt  61920
ttattatata gttgaggaaa ccaagtctca gaggggtcag tgtcttgacc atacacctct  61980
catgtcctct ctcctttttg attaattgaa taaatacatg tagttgcttc ttacctcctt  62040
tctttcttca cccctgcccc atgcacctgc tcttagttgc cttcacatgt aaacagcatt  62100
ccaacaacaa caacaaaaca caaccagcat tctaactcat gagaccagca acagttccta  62160
taaataccag cagcatttta ttttaatgtc tctctgcagt agtttctccc ctccatggat  62220
cagtcatcct tggtaccaaa aggattcccc actgtgacac aaatgctttt tgtcattctc  62280
agtgagttat accattgaga gagcatcgat ctttttattg ttcaaagctt ttggttgtca  62340
tgatatttgc tggaccatgt ttcaccagga accacatcac ttcctagcag caggagctat  62400
tttcttccat cttctaacaa caccagcagt gacagtgata ataatgatgt tagctgccat  62460
ggtcgttatt cttatcattt attgagtact tactatgtgc cagggactac attaagagtt  62520
ttatgtgtat tatcacattg agcctcgcta gcctttgtac agatgaatct gaggctcaga  62580
```

```
gaggttaagc tgctcacaag ggagtcacac agctggtaag gggtggatca ggatctcagc  62640
ctctctgcta ggacacttct ctaaacctag aataatactg ggcctgtgtt aagttcagca  62700
aagagctgta ttcaacccag tgtccttagg aatgtaatgc ctgttattaa caacagtggc  62760
aacattgata agctgaaact tatgaggtgc ttacaatatg atatactata tattatatac  62820
atacataggc acccacctat aatctcagca ctttaggagg ccaagtcagg aggatcactt  62880
gagcccagga gttcgagacc agcctgagca gcatagcaag atcctgtctc tgtaaaaagt  62940
ttattttttc agttggccag gtatgttggt acatgcctat agtcccagct aatgaggagg  63000
ctgaggcagg aggattgctt gagcccagga atttgaggct gcagtgaact atgatcacac  63060
cactgcactc cagcctgggt gacagagcaa gactgtctct aaaaataaaa ataaaaataa  63120
aattatttca actctcaagg ttaaataaat actattatta ttcccattta cagatggagc  63180
aactgaggct caaagacatt aaatgcttac tgtcttagtc tgttttctgt tgcttatagc  63240
agaacacctg aaactgagta atttataaag aaaaagcaat ttatttctta cagttatgga  63300
gactggaaag tttaagatca aggctgcatg agctataatg cacacacact attgcactcc  63360
aggctgggtg acagggtgag accccgtgtc aataaataat aatataaaat aaataaaaca  63420
aatttcaaca tgagtttttgg aaggtttgaa atattcaagc cagagcatct gtctcataag  63480
tggtggaccc aggatttgaa ctaaggcaga tctggatcta gaacccattt tcttgaatcc  63540
tacgctattt ctctaaggtc aagtttgcca aggaaaataa acttgagaat ttgaatagag  63600
ctctctgaca tgggaagtca gggtgatcct tccttcccct ccctgatctt gggttccact  63660
atggctgggg gaaaacagga gcagaagaga tttcaagaaa tgagagattg gcctagcgcc  63720
atggttaaga cctggacttc agagtcagag gaagctcctc cctctatgac agtgagaatg  63780
tgggttgaac tcactgaacc tcagttttct cacctggaaa aagggagtaa aactagtgcc  63840
tagctcctag ggtttgcatc acacacgaaa gttggtgaac tgaaggaaaa aaacttaaat  63900
tcttgtgggg gagcatgtga tagatgctac aaattctcca tgccttattt acctagctta  63960
cgtctaagtt cacctgcagc ttcctcttgg tacactccca tctctctaca tctctgttgg  64020
agggcagtct ctggcatcac agagtttgct gagccagatg cttaacaacc tcggtagcat  64080
ccctcaacca gtgagctagg gagtcagtgt ataaataccc tggcttcccc attgctcagt  64140
gggaaaacac tgaaatatgt tatacagcat catagaggtg cctcagtaaa attgaatcct  64200
agttgttcac ataaaaccca ttcactagtg taccctttac caatctctct cttcctcatt  64260
cctcacttgt aattccttgc attacctccc aaattaacca ttggacccta gtttttgcct  64320
tggggtctac tcggcgctaa ctcaaggagc ggaagttgga agcttagcgg gttacaggtt  64380
tcagcaccct ggacagctcc cagcacaccg tattgtgcta aaatgttctc ttccctccct  64440
ctgcctccag ctggggtgga gagggactga gtaaaggcca gatggccagg tgaccttgtt  64500
ccatactgag cttcttggcc attttccctg tggggctgga gaagaccttg ccatccatct  64560
ctccgcaggt ttgggggccg actgaggtct tgttttctcg aattgctatg acaaatgcca  64620
gcctgcctcc aaggggcatc tgtcccactg cctctacagt ttgcatgcct aatgactcct  64680
ctcctctcac cagggcaggg aggtggctgc ctggtgggcc gcttgaagcc gggagaccaa  64740
gatcatgcca ctggactcgc aacaaaccga gactcttttt tttttttttt tttcctcgag  64800
acagggtctt gctctgttgc ccaggctgga gtgcagtggc gcgatcttgg ctcactgcag  64860
cctccgcctc ccaggttcaa gcactcccac ctcagcctcc caagtagctg ggattacagg  64920
cgcacaccac catgcctggc taatttttgc atttttagta gagagggggt ttcaccatgt  64980
tggccaggct gatctcgaac ttctcccctc aggtgatcca ctcgccttgg cctctcaaag  65040
tgctgggatt gcagctgtga gccaccatgc ctggccaaca gaataggact ctgtctcaaa  65100
aaataatttt ttttaaacat tgctttgcaa cccagctgct tcttgtgcag gcatctctaa  65160
atgaggacag ccagtctaca tagacacgta aggaagcata gtggttaaga cctggtcttt  65220
ggggttagag tggattccca acctgactcc actgtttcca agctgtgtga ccttgggcaa  65280
gttactgtac ctccctgaat cttccatttc ttcatctgga aaatgagagt agtagcatcc  65340
cctgacttgg tggggcatgg tggctgatgc ttgtaatcca aacactttgg gaagccaagg  65400
tgggtgaatc gcttaaactt gggagttcaa ggccattctg ggcaacatgg tgaaactcca  65460
tctctacaaa aacaaaacaa agcaaaaatt atctgggtgt gatagtgtgt gcctgtaatt  65520
ccagctactc aggaggctga ggtgggagaa tcacttgagc ccaggaggtc aagtctgcag  65580
tgagccgtgc ttgcaccact gcagtccaac agagcgagac cttgtctcaa acaaacaaaa  65640
caaaacacaa aacaacaaca aaatactacc accttatgga gttgttttca aggttcaatg  65700
agttaatgtc tgacccatgc tgggctgggt ttatggatgt tacttgccca gggacagtct  65760
gaagaaagag aaagtgatat agtccattgg gcctcagctt cctcatctgt ggaatgggaa  65820
taataattgc acctacctca aaaggtaaaa gtcagtgaga tacatataag gcattcagaa  65880
caaaaactgg cacagaataa gtgctcaatt atattagcta ttgtaagact aataactatc  65940
attataatga tgataataat tattactact tccccaggcc cagttccata gaccagttag  66000
ttaactgtag ggaacgtttg ctattattag ttgggttccc aatatctgac ctccctttcc  66060
aatttaggga gaatcctccc ctttctataa agtactgctg gtctatggga tcccaccctc  66120
actaataagt tgaaggtgaa agggattcat tgtcacccca tcacctggta gtcagggcat  66180
gtgatttaaa caaccagggc caggcgcagt ggctcacgcc tgtaatccca gcactttggg  66240
acgccaaggc aggaggatag cttgagccaa gcccaggagt ttgagaccag actgggcaac  66300
atagtgagac ccctatctct taaaaatttt ttaattagct gggggtggta gcacaggctt  66360
gtagtccccg ctactcagga ggctgaggca ggaggattgc ttgagcccag gaggtcaagg  66420
ctgcagtgag ccgtgatagt gccactacac tccagcccag cctgggcaac agggcaagat  66480
cctgtctcaa aaaacaaact aataaaaaac tcaaccagtc acgttttcct acccaggaat  66540
ttgaaaatgg accaagtgat ccaaacatga tggtttggac tctttcatgg cctcctgcta  66600
caggagaagg tcaggctggc tacattgttc ctgctgattt cccaaatccc ctcttctggc  66660
cccctgttga ttatctgagt ttcctaaaaa tccctttttat gcctaagata gccggtcagt  66720
gtttggtttt gcaatcaaga acccagactg ggccaggcac ggtggcccac gcctgtaatc  66780
ccagcacttt gggaggccga ggcgggcaga tcatgagatc aggagatcga gaccatcctg  66840
gctaacgtgg tgaaaccccg tctctactaa aaatacaaaa caaaaaaaaa aaaattagcc  66900
aggcatgatg gcggtcacct gtagtcccag ctactgggga ggctgaggca ggagaatggc  66960
gtgaacccgg gaggcggagc ttgcagtgag ctgagatggc accactgcac tccagcctgg  67020
gcgacagaac gagactccgt caaaaaaaaa aaaagaaaaa agaagaaccc agaacccaga  67080
ctgatcctga gacaaagatt tgagggcaac gaatcacgag gtcaggaaat cgagaccatc  67140
ctggctaaca tggtgaaacc ccgtctttat taaaaataca acaaattagc tgagcgtggt  67200
ggtgggcgcc tgtagtccca gctactcggg aggctgagga aggagaatgg cgtgaacctg  67260
ggaggcggag cttgcaataa gccaagatcg caccactgca ctccagcctg ggtgacagag  67320
```

-continued

```
caagactcca tctcaaaaaa aaaaaaaaaa aatttgagga caagtggttt gtttggcaat  67380
accaggaaac aggggaacag gatagtcaga aaagaaagag aaagctgggc atggtggctc  67440
actcctgtaa tctcagcact ttgggaggcc aaggcaggtg gatcacctga ggtcaggagt  67500
ttgagaccag cctggccaac atggtgaaat cccgtctctg ctaaaaatat aaaaattagt  67560
cgggtgtggt ggcgtgcacc tataatcaaa ataaaataaa atcaggatat tttattttaa  67620
aactctgtct tagtgtaact catatttacc tcttctgtat gctcctttgc atcagttata  67680
tattgccata atacggctgt gtaacaaaca atccccaaga cccagtggct tataatgaca  67740
agcatttatt tagctcatga ttctgaaggg tggcagttta ggctgggccc agttgggtgc  67800
tttatctggt ctcagttgag ctcattcatg catctttggt cagctgcggg tcagctgggt  67860
ggctcttctg tttggctgtt agctggctgc agactggtcc aggatgacct cggctggaat  67920
gactgtgctc cactccctat ggtctttcac cctccagcag gctagcctga gctagttcac  67980
atggcagctt ttcatcctcc agcaggctag cctgagctag ttcacgtggc agcaatggga  68040
ttctaagaga aagaggaagt gttcagcctt cttaagggct agtcccagga atggcacaac  68100
atcgtgttgg ccactgttgt ccaaagcaag caatgaagct ggtccagatt caaggaatgg  68160
ggcaacagag cccatctggt atttacctgg ggccactggg gccccattcc tgttccctgg  68220
ggccttttgc cctgacttct gtgggccctc agagcatatt ttcagattcc tttccatccc  68280
tgaccctcag caatcaatgt agatgacgtg tcattactgt gtcacttgca cagagaaaag  68340
gaggaaaaaa tgtcagcaaa aactctgctg agagcagagg gcccatcata cagcaagctg  68400
gaaagaaaag tgggaatgat tacacagcct cctcagatgc ttccagcttt tatcaaatct  68460
cactgtgata tctgagttct gaaccctcac aggtggttgg cgtgcaaggg aagagatttc  68520
ttgtctgcca tgctgacatg cacagacacg caacctggct ccctctgtcc actggggctt  68580
tggattttgt ttgttgaaat gttacccact cctgatcaga gctggatgga aacctggctc  68640
tgattccatt ggctcagggg ctcaggtggg ggcagaggcc aggctggttg ggtgtctatg  68700
tggagacctt aactcttctc cctcccgccc caactctttt tgtttctttt tttttttttt  68760
tttttttttg agatggggtt tcactcttgt tgcccaggct ggagtgcagt ggcgtgatct  68820
tggctcactg caacttctgc ctcctgggtt caagcaattc tcccacctca gcctcctgag  68880
tagctgggat tacaggagca cgccaccata cctggctaat ttttgtattt ttagtagaga  68940
cagggtttcg ccatgttggc caggctggtc ttgaactcct gacctcaggt gatccaccct  69000
cctcagcctc ccaaaatgct gggattagag gcgtgagcca ccacacctgg cccttttctt  69060
ttcttagctg cctccacctc tcttcccttc tgcagtgtta ggtttatgga aaccgaggcc  69120
ggcgtagaga tcaacttcag agagcatgaa ctgagcatct gctgggtctt agatccttta  69180
catagcttat catcttcaaa ccttctcaca gttctgtgtg gctagagcca ggatttggac  69240
acagctctgc cccactgtag aaccaggctt ccttctgtcc actgtcaaat tttagaggga  69300
gaaaataggg aaagggacac cagccttctc cacgagcagc ttctgcccac tcaccccagg  69360
gactttgcac atgctgtgtg cctgtgtctg agatatgctc cctcctctgt atctgcttaa  69420
ttcttaccca gacatgatac ataaagtatt taacatccag gtggcaggga caccagctaa  69480
cctgaaaaga ggttcccctg ttgtgccaca tgtgtactca ttgtttgctg cattgtgggg  69540
gcagtccagg ggccttgaag aggggccaag gtgccaaagg ggcactctca ggcctcaagg  69600
aagtacatgt ttactgatat gatactgtct cttcctccag gaaggaagcc ttccctgatc  69660
tccccactgc atgcccacta tgataccagt ttaggtcccc tctttatggc catctgtggc  69720
atcagtgtga atcctcttaa tgttgtctat ttggttaatc atctgtctcc ttcctctggg  69780
gggtaaagac agaaccacag agcctcgtgt agaacttgag aatggggttc agtaaaaatc  69840
tgttgaatgc ataaatgggt gattgagtga atgaatgaat gagtgaatga atgagtgagt  69900
ggatgaatga atgagtgaat gaatgagtga gtgaatgaat gaatgagtga attaatgaat  69960
gaattcatag ctgataatac aggcttcatg gcttttgtta ggcttgccca gacattgcta  70020
ggggatggac agaaggaaga agagctatac ttaattccag tcctgttgtt ctgtagcagg  70080
aggagaaaaa cagggactgc ccagcctgct ctgggtggat tcaggagcag ctgaggttcc  70140
tctcttattt gcaaacaggg aattcaaaaa gccccaacct cagaatcaca ctcgcctcag  70200
cagctgtacc agccaagggg acaatgtggg aagccttggg caccaggaat gctgagtgct  70260
tcgaaaaagc gaaggctcag ggaacaatcc ctgatttttc attcccttgt cctttctgaa  70320
gaaacaggca aaggcaggcc aggcacggtg gctcacacct gtaatcccaa cactttagga  70380
ggccgaggct ggtgaatcac ttgaggtcag gagttcaaga ccagcgtagc caacatcatg  70440
aaatcccatc tctactaaaa atacaaaaat tagctgggtt tggtggtgca tccctgtaat  70500
ctcagctact cgggaggctg aggcatgaga atcacctgaa ctggggaggt ggaggttgca  70560
gtgagctgag tctgcgccac tgcactccag cctggatgac agagtgagac tccatcttaa  70620
aacaaaacaa aacaaaaaca agtaaagcct tgtgtgtttt taaattgtag gttcagcagc  70680
aaagctctgt aataaggagc tggaccctgc agtcagacag tcatgggctt ctccagtgcc  70740
cagccgagtg acccgaggga gttatgataa acaccaacat tcatccacaa tttgtaccta  70800
gtgctattct caatatcttg agtaaattat ctcatttaat cctccaggca catctttctt  70860
ggtaggtgcc gtcattgtcc ccagtgtaca tctgggaaaa tgaggacagg ctggcagagc  70920
acccttcctg ctcacctctg ctgctctgct gacctctggc aagactgttg tctctctgag  70980
cctcagtttc cccatctgaa aattggggcc tgtattagcc cgttctcaca ttgctataac  71040
gagatgcttg gctggggctg ggcgtgatgg cttatgcttg taatcccagc actttgggag  71100
gctgagttgg gcagattggg agtgtgagac cagcttgggc aatatagcaa gaccccatct  71160
cttctaaaaa aaaaaaaaaa ttagccaggc atggtgatat gcacctgtaa ttccagctac  71220
ccaggaggct gaggcaggag aattgcttga acccaggagg cagaggttgc agtgagccaa  71280
gattgcgcca ctgcactcca gcctgggaga cagagtgaga ctccatctca aaaaacaaat  71340
tatttttaaa aaattaaaaa aaaaaatgcc tggctgggca cagtggctca cacccataat  71400
cccagtactt tgggaggcca aggtgggaag attgcttgag cccaggagtt ccagaccagc  71460
ctgggcaaca cagtgaaatc ctgtctctac taaaagtaca aaaattagcc aggtgtggtg  71520
gcacgcgcct gtggtcccag ctactcagga gggtgaggtg ggaggattgc ttaagcctgg  71580
gaggtcaagg ctgcagtgag caatgattat gccactgcac tccagcctgg gcgacagagt  71640
gagaccttgt aaaaataata ataataataa taaataaata aaaaccctga gactggggta  71700
atttataaag aaaagaggtt taattgactc acgattctgc aggctctaca gaaagcatgg  71760
cagcatctgc tcagcttctg ggaaggcctc aggaaactta caatcatggc agaaggtaaa  71820
gctggagcag gtgtcctcac atggccagaa caggaggaag agagagagtg gggagatgct  71880
acacaccttt aaatgtccaa tctcacaaga actcactcac gatctcgaga atagcaccaa  71940
ggcggaaatc tgcccccatg atccaattac cttccaccag gccccacctc caacattggg  72000
gattacaatt cgccataaga tttggttgcg gacagacaca gatccaaagt acattaaaag  72060
```

-continued

```
taatggcaaa aaccacaatt acttttgcac caacctaata tctcaggggc tcattgtacc  72120
tatttcacag gacaaatgaa ggtatcagta ataacagtag cctgtagtcc cagctattca  72180
ggaggccgag acaggaggat cacttgaacc caggaggtcg aggctgcagt gagctatgat  72240
cacgccactg cactgcaccc tgggtgacag ggcgaaaact tatctctaaa aataataata  72300
acaacaacaa tagtgaacac agatataaca tgtgtgtggc caggctgtgc ccttagggct  72360
ttgcagggat tatttcattc actctcaatc tccccatttt acagatgaga aaactgacgt  72420
tcagaaaagc tagaggactt gccccaagcc acacggctag gaagtggtgg aattggggtt  72480
taaatgagga agcttgactt cagtgtcgaa gctcttaact gccacactca atacatggag  72540
tagaggttgc tgattctgtg attatctgat tctggaaagt aaagaccctg tttccagacg  72600
tttgctgctt gacttagttc ccaggggatg gccactggat gatgcagtgt tgcccaggag  72660
aggttagcta gacacactgc aaccattcca ttgctaatac ttatacttgc tcttgttctg  72720
ctgggtgcta tgcagggaag ggctgtctga gccctttgca agaattctcc cattggtgcc  72780
tcccagagat tctgaggttg gggctttttg catcccttat tagcagatga gacaccaaag  72840
cccaggtcaa taatctgacc tgcatccccc gcctaccagc cagaccaagg tcacttcccc  72900
acaatgcagg ccctgatcca aggctctggg tgcaaaccag tttccatgtc cctgggggtc  72960
catcttcttc agctgacttt tttttttttt tttttttttt gagacagcgt cttgctttgt  73020
tgccgaggct ggagtgcagt ggtgtgatca tggcttattg cagccttgac ctcccaggct  73080
caagcaatcc tcccacgtca gcctcctgag tagctaggac tatgggcaca cgccatgatg  73140
cctgggtaat tttttttttt ttttttttga gacagagtct cgcactgtag cccaggctgg  73200
agtgcagtgg cgcaatctcg gctcactgca agccccatct cccaggttca tgccattctc  73260
ctgcctcagc ctctcgagta gctgggatta caggtgcctg ctacctcgcc tggctaattt  73320
tttgtatttt tagtagagac ggggtttcac cgtgttagcc aggatggtct ccatctcctg  73380
acttcgtgat ccgcccacct cagcctccca aagcgctggg attacaggca tgagccagat  73440
gcctggctaa tttttaagtt tttttataaa ggcggggtct tgctatgttg cccaagctgg  73500
tctcaaactc ctggcctcaa aaagtcttcc tgcctcagcc tcccaaagtg ctaggattac  73560
agacatgagc cactgcaccc agcctgactt tttttctaac tgaaaaatta attatatata  73620
ttcatggagt acaatgggat gttctgatat atgtttacat ttttgaatga ttaaatcaag  73680
ccaattaaca tatccactac atcgcatact tattttttgt ggtgagaacg cttaaaatct  73740
actcttttag caattttgaa atatacaata ccttatgttg tatattacat tatgttgtat  73800
agtacgttga aacatacact acaatacgtt atcattaatt gtggtcacca tgctgtgcaa  73860
aagatctcta aaacgtattc ctcctgtctg actgaaactt tgtatccttt gcctaatatc  73920
tccccaatcc ctccaccacc agcccctggt aaccaccatt ctctctgctt ccatgggttc  73980
aaatttttta tttttttgaaa tttttaattt ttatttattt atttatttat ttatttattt  74040
atttttgaga tggagtctcg ctctgtcacc cagtctggag tgcaatggtg ccatcttggc  74100
tcactgcaac ctccgcctcc tgggttcaag cgattctcca gcctcagcct cccgagtagc  74160
tggggttaca ggtgcttgcc accaggcccg gctaattttt gtatttttag tagagacggg  74220
gtttcaccat gttggctagg ctggtctgga actcctgacc tccagtgatc cacccacctc  74280
ggcctcccaa agtgctgaga ttacaagcgt tgagccactg cacctggcct aaaatttttt  74340
tttttttttt tttttttgag acggagtctc actctcttgc taggctggag tgcagtggca  74400
tgatctcagc ccactgcaac ctcagcctcc cgggttcaag cgattctcct gcctcagcct  74460
cctgagtagc tgggactaga ggtgtgcacc accacgccca gctaattttt gtatttttag  74520
tagggacagg gtttcaccat gttggccagg atggtgtcaa tctcttgatc tcgtgatctg  74580
cctgcctcgg gcttccaaag tgatgggatt atgggccacc acgcccggcc tcaaattttt  74640
tagagctcac atataagcga gattgtgtac tatttgcgtt tctgtgtctg gcttgtttca  74700
tcttagtata atgtcctcca ggttcatgca cgttgtcgca aaagatggaa tttgctcctt  74760
tttaaagact gaatagtact tcattgtgta catatacacg ccatattttc ttcatccatt  74820
cctttactga tggacatttg ggttgtacct gcatcttggc tattgtgaag agtgctgtca  74880
tgaacatggg tgtgcagctg actctgaggt gttagaggga ttacagctcc tccaaaagac  74940
caccgtcacc caaacctgct cctcctgccc tattttctgt ttaggtaaag gcggctttaa  75000
ccccctgcag tgctctggcc tcagacctcc agatcttcct ctatgcctct atgcctcttt  75060
ttctccaccc cctgcatcca atctgttagc acatcttatt ggctctacct tcagaatcta  75120
cccagaatcc accacccacc tctcaccacc ttcacagccc caccccggtc cagcccccat  75180
ctttgctggc ctggactaaa ccagttgccc ctccacccca atctggtctc ttaacttcag  75240
tccttgcccc acccccagga ctgttcccca cacagcagcc agagggcacc tgtgagccac  75300
tgagtcagga cctggctcct ctttgctcac aacctcactt ggagaaaaag cccaaattct  75360
cctcacaggg acccacaaac tctgcccctg tgatccccca tccccctcta ttcccactct  75420
cctctccact cactcggctt cagctacaca agttccctgc tgtcccttac acaccaagca  75480
ctccccagcc tcagggcctt tgcacaggct gttccctctg cctggaacac tcttccccca  75540
gatatctgct tggctccccc ctcacttcct ttgggtcttt gctcaagtgt ccttctaaca  75600
tgtaactgcc tcacctgcac tgtgccaccc cactccccgc ctctaggctt aatttccctc  75660
tacacccctg aagagcatct gccaagctat atttacttgt ttattggtta ttgccaatcc  75720
cctgccccca ctagaatgcc agctccatga gggcagggac ttctgtctgt tttgttcact  75780
gctattcccc cagagcctag aacacagcct ggcacatagt aagtattcac taaataattt  75840
gtaatatgaa ttgtgccagt aaaatcttcc aggggcatca agcccctgcc atgactaggt  75900
ggtaacatcc tcacccccctg tccatgtgct atctcctcct gacctgcttg tctcattgtt  75960
ctaatggtgg ctcacgcctg taatcccagc acttggggag gccgaggcgg gcagatacct  76020
gagttcagga gtttgagacc agcctggcca acatgatgaa accctgtctc tactaaaaat  76080
acaaaaatta gctgggcgtg gcattgcacg cctgtagtcc tagctactcg agaggctgag  76140
gcaggagaat cgcttgaacc cgggaggtgg aggttgcagt gagctgagat catgccattg  76200
caatccagcc tgggccacaa gagcgaaact ctgtctcaaa aaatatatat atatatttca  76260
ttgtggtaac atatgcataa cataaaatgt accatttttt aagtgtttag ttgagcggcg  76320
ttaagtacat tcatattgtt gtgcaaccag gaccgccatc catctccaga actttttgcat  76380
cttgcaaaac tgaagctctg cccccaggaa actctcactc cccgctcccc cttcccctct  76440
ccccgactcc cccttccccc ctccccactc cccccaccct actccacact ccccactccc  76500
ccagcccctg gcacccgccg ttctagtttc tatctctgtg aatttggcta ctttgggtcc  76560
cccctgtgag tagaatcata cagtatttgt ctttttgtga ctggtttgtt tcgtggagca  76620
taatgtcctc cagtctcatc catattgtag catgagtcag aatttccttc ttttccaggc  76680
cgaatcgtat tccattgtgt ggatggacca cactttgctt atctgttcat ccagatgggc  76740
acttggcttc cacctttttgg ctattgtaaa taatgctgct gtaaacctgt gtgtacaaat  76800
```

```
agctgagtcc ctgctttcaa ttcttttgga tatagaccca gaagtggaat tttttttaaa  76860
tcaagatttg acccactggg gcccttagag gtctcattgg ctctgaagct ttttttttt   76920
ttttttttg gacgctttga aactaaaaat aggagtgagg ggcacagtga ggggggcaca   76980
catctctcgt gtcagcgttt tttaaaaaca ccccgggagg aagatgtgtg aaatccctcc  77040
cttcccccg ctcccacccc ctccaagatc tcaaaatacc tcttgtttta ggaagcggct   77100
gtgacatcag gcaggcagcg tgtggcatct gagacacaat atcgcaagtg gctgggagcc  77160
cagagaaacc aggacaggcg tgctggggat gtggactaga gatggagcta attttagtgg  77220
ctgaagaggc tgcaagaaga gagagaaaga ggggtgtgtg tgtgtgtgtg tgtgtgtgtg  77280
tgtgtgtgtg tgtacgcaca gtgatagagg ctggaggggg agaaatgaca gataaatcag  77340
cttgggcaaa gaaagctaat gggcagagga gcgagaccca gctcagaagg tggtcagcaa  77400
atctaaagat gtgtgcccga gggtcaaggt ggtgggggga ttcataggca agtggtagag  77460
aggctattcc atttgcagag gctctctctg tttgaggcgt gattcacctg tgccgtcctc  77520
aaggccattc tgagaacacc actgttgttt tcctcctttt atgagtaggg aaactgaggc  77580
attgaactgc ttctattctt cagtaagaag caggggggaac atatggtaga agcaaagaaa  77640
tacaaacatg agggctctcg gggtctacgt gattggctgt gacatccatg agagcggatc  77700
gcaggttgaa ggaaacactg gtggcagaaa gtagctgaac atttggattt gggaatccca  77760
gtggacgtgg cgaaaattct ggcttttccc ttcacaggct gcggggccac tctgacctgc  77820
ggtttcctta tctgtgaaat ggaacgatgc cacctgtctc agcgttgttt tgaggatgcg  77880
aggagatgat ccgtgtaata tgcccactag gggcctgct ccagggtaga ttctcagcaa   77940
atggtagtca tggtttttgt tacatttggg gatattggca ggtaaaaagg aaatacttca  78000
ttcattccaa aattgctcac tgaggttcta ctatgtgcta ggccctgatg acacatcggt  78060
caacaagaca ggcctgcttt ctgcccttgt aaaacttcag ttcaactgca ttgcactcat  78120
cagcctaata atccaggtaa attgtgatga gaataacaac tagcatttac tatgagccct  78180
ttacaaatat taacccattt aatcttctaa agagcctata agataagagc tcttgccctg  78240
cgcagtggct cacgcctata atcccagcac gtcgtgaggc caaggcaggt ggatcacctg  78300
aggtcaggag ttcaagaata gcctgaccaa cagggtgaaa ccctgtctct gctaataata  78360
caaaaattag ccaggcatgg tggcaggtgc ctgtaatccc agctacttgg ctgaggtagg  78420
agaatcgctt gaacccagga ggcggaggtt gcagtgagtc gagatcactc cactgcactc  78480
caagagtgaa actctgtcac acacacaaaa aaaaacaacc tgttattatc cacattttac  78540
ctatgaggaa accgatgccc agagaggtta agtaactgtc caaaggtcac acagctacgg  78600
agtggtagag ctgggattca gacccaggag tgtgatccca gagtgtgtgt gtatgtttgt  78660
ttgtttgttt gtttgtttgt ttgtttttac cactgtgttt tcctgcttct gcaatagaag  78720
taatcaccag taacactgag cagttgttat gtgccatgcc cttaacacac atctccttgg  78780
atctttggaa agaatcctaa aagggttgtt tttcatgatc cacattttat ggagagagag  78840
agatcaaagc atagagagag gaagtaactt gcccaagatc ctgcagctga agactctagg  78900
gttgcaaatt tgggacggcc ctggaccctg cattccagct tctagcagct catagggga   78960
actctttatt tatttattta tttatttatt tatttattta tttattttga gatggagttt  79020
cgctcttctt gcccagcctg gaatgcaatg gcatgatctc ggctcactgc aacctccgcc  79080
tcctgggttc aagtgattct cctgcctcag cctcctgagt agctgagatt acaggcatat  79140
gccaccacgc ctggctaatt taatttttt tagtagagac ggggtttctc catgttggtc   79200
aggctggtct cgaactcctg acctcaggtg atccgcccat ctcggccccc caaagtgcta  79260
ggaatacagg cctgagccac cacgcatgcc ctggggggga ccacttttat cggtgcattt  79320
cttccatttt ccctgtgtct gtgtaaagat aaacaccccc aagcccttg actatgaact   79380
gtgggccata attagttaat ggaaggtaaa tgttttagag acggaaattg ctgtgccatt  79440
tttccccgct aggcattgtt gcctgcatgc taatgcaaca caatgtgcct ttcttctgtc  79500
aggcattttt agacaaattc tattttccct aaaatatttt gccaaagaaa atagcaaatg  79560
gggaagacat tcagaggctc aggcagagag aggacaccat tcccttgggt ttaaacagaa  79620
tggcagagtg gataacagca cagatcttga gttaggtgga tgccaatttg tgatttattt  79680
cccagcaaac caagatgctg gctctctgtg tgcctcagtt tacttatttg tcaaatgagg  79740
agaataatgg tacctgtctc tcaccagctt accagttgcc tctttagcta tgtctaatct  79800
gctattaacc acgcccacta tgtctttaat tccaagtatt agaattgttt tcttcctaca  79860
agctgtctga tctttttaa tcctgcttca tcttttgcag tattgtttc ctacagcagg    79920
atttctcaac cttggcacaa ttgacatttt gggctaggta attcttggcc gtgagctacc  79980
accctgtgct aagatactta gagcatccct ggcctctcac cctactaaat gccagtagca  80040
gcccctcccc agttgtggca gccaaaaatg gctcagacat tgccaaacga aatgtcccat  80100
ggagggtaga aacgccccca cttgagaatt gttctatagg tattttcaag catgtcttac  80160
atttctttaa gtataatatg caaaagaaaa ggctaaatct aaaaaaagcc cataatatgc  80220
gaagaatttt tataatcagt gtccaataac ttaagtatct aaaattgtta tggcttttt   80280
tctgctgtct cttgtttcct gtgattcctc attctggtgc cttgttttct tgaatgtctt  80340
gttatctttg gttgtgtgaa gctcattttc catgggacac tattttttgt tttgttttgt  80400
tttgagacag agtctcgctt ggttgcccag gctggagtgc agtggtgcaa tatcagttca  80460
ctacaacctc agcctcccag gcccaaatga ttctcctgcc tcagcctcct gagtagctgg  80520
gattacaggc gtgtgccacc acacccagct aattttttg tatttttagt agaggcaggg   80580
tttcaccacg ttggccaggc tggttttgaa ctcctgacct caagtgatca acccgcctcg  80640
gccccccaaa gtgctgggat tacaggtgtg agccaccgtg cccggcatcc atgggacact  80700
gttgaaggga gttcattgag gcctgcgatg aaggcgaacc ctccatggac aatttgcatt  80760
tactttttcc aggtgtctgg gaaactccca gtctaggacc atcttagact tttagaccaa  80820
caatgtgttg agaatttagg tcaccagtgt ctgcaaaagc cagcttgtgg tttataatttc 80880
tcaaaaactt ttgtttttct ccttttctgc aaagtgccaa agtaacttcc tcaaaaatct  80940
ctgggaatgg aaagacggga gtaaattaac ttcaggtttc ttacctgaaa gtgatagcct  81000
attggggccc catcctactt ggggagtggt gtgtctcctt tgagactttc taacacgtgt  81060
gtaccctgga ctttgcccca cccctgctcc ctaggaggcc ataaaacttg aagcagcagt  81120
tccatgggtt agacagatgc ccttggggca aaagtggttt taatgctctg gtagatgctc  81180
aggttacctc tgggaaattc ttgacttcac ttatttattt ggggctgata actactaatt  81240
gtcaggcctt tcttgtttca acaacatgga cttcagattt tatgcaggat ttgtcatcgt  81300
tttcagcaag agagtcagtc ttattaccca gcttactgca ttagaaatag atgtctgggc  81360
caggcgcagt ggctcacacc tgtaatccca gctgtttggg aggctaaggt gggcggatca  81420
tgaggtcagg agttcgagac cagcctggcc aacatggtaa aaccccatct atactaaaga  81480
tagaaaaaat tagctgggtg tggtggtgcg tgcctgtaat cccagctact tgggaggctg  81540
```

```
aggcaggaga attgcttgaa cccgggaggc agaggttgca gtgagccaag atcgcaccac  81600
tgcactccag cctgggtgac aggacgagac tctgtctcaa aaaaagaaat agatgtctgt  81660
tgtgtggatt atttaaaaga gtagatggcc aagaactatg acttatgcct gtcatctcag  81720
cactttgaga ggctaaggtg gagggatcac ttgaggccat gagttagaga ccagcctggg  81780
aaacatagca agaccccat ctctgcaaaa gtaaaataaa ataagttagt gtgcatgatg  81840
gtgcaggcat acctctagtc ctagctactc aggaggctga ggcaggagga tcacttgagc  81900
ctaggagttt gaggctacag tgatctatga tcatgccact gcactccagc ctgggtgaca  81960
gatcaagacc ctgcctctaa aacataaaaa taaatacaaa ttaagttaaa aaataaaata  82020
aataagtaat agaacatcca gcacagttct tggcatgcat tgactgttgt tgtttgtttg  82080
tttgtttgtt tgtgacggag tctcactctt gttgcccagg ctggagtgca atggcatgat  82140
cttggctcat cataacttcc acctcccagg ttcaggtgat tctcctactt cagcctcctg  82200
agtagctggg attacaggca cgtgccacca ctcctagctg ttttgttttg tttgtttgtt  82260
tgttttgtat ttttagtaga gatggggttt ctccaagttg gtcaggctgg tctcaaactc  82320
ctgacctcag gcgatctgcc agcctcggcc tcccaaagtg ctgagattac agacgtaagc  82380
caccacgcct ggccagctgt tttgattgtt aaatgaaggt ggtatgaaag ggaaggaaga  82440
acagtgacat ttgcaaggga cactccctgg agggcagggc aagggggctg tggaggggag  82500
aagtcagaga gtatgataca ggttgccttg ggtgatgttt tagattttag ccaacattgg  82560
caaagagcct catttatctc tcagagtagc tctggctact ggaaatgctg cacaacttca  82620
ggcggacttt ctagaagaaa actcttggcc aggtgcagtg actcacacct gtaatcccaa  82680
cactttggga ggctgaggca ggtggatcac ttgagctcaa gagtttgaga ccagactggg  82740
caacgtggca aaacctcatc tctacaaaaa aaaatacaaa aattaaccag gcgtggtggt  82800
gcatgcctgt atcccagcta cttgggaggc tgaggtggga ggattgcttg agcctgggga  82860
ggtggaggtg gtagtgagcc aagattgcac cactgcactc ccatttgagt gacagagcaa  82920
gaccttgtct caaaaaagaa aaaaagaaaa gaaaagaaaa gaaaattctc tctgggattc  82980
aatcctggcc cacacagcat tggcttcact tcacctcctt ctcccctgag atacacagca  83040
ccattccccc aagcttcatc aacttaatct ctgatctggg tgctgtgact tgtccccatt  83100
cctggccaga atttaaggta gggatgaacc cactagccct ccatcacgca ctctgccata  83160
aaagcacacc acgtgctgat tgctgtcttt ggtctccttt ctgccttgcc ctctagactc  83220
tgagctgctt ggagacagag gccagttttg tccatctcca aatcccctaa agtcctgtgg  83280
ccagcaagca ggtaggacat ctgaaagttc gtcagagagg gaattgcttt tctcttgaga  83340
tgcaactaga acaagaatct tattgacctg gagtagcttc aaggttgtaa gagtatgtgt  83400
cagggttctc caagaccact ctcaggtttg aaggtttgct aaaagggctc acgggaccca  83460
gaaaagctgt gaaattcagt tatggtttat tacagtggaa gaatacagat aatacagatt  83520
aaaatctgca aagcaaaaga tgcacaaggc aatgtccagg ggagatcagg catgagcttc  83580
cagctgttca ctcccagtgg agttatgcaa acagtgctca attctcccag caatggtgtg  83640
tgacaatgta cagtgtaccg ccaaccagag aagctcacct gagccttggt gtccagggtt  83700
tttattgggg ctcagttaca ttgacatgga gcacccatgt gactgacttt aactgctggg  83760
tctccagcac actccaagat caaactgata ccgtgtgtcc cagggcccca gctgaacaca  83820
aacaggcagt caccatagat cccattgtga gcataagcta ccaggcatgg cccaaagccc  83880
tagatataca gatattcttt ccaggagcca gccaagggcc agtccttcct ttggaatatg  83940
cagagtttga actccccaac cccaaggagt taactcttta ctacacagaa tataaatctc  84000
accaagtctt tcttcttgtc aagtcctctc aaggtgaccc attgctttta gcagtgtctt  84060
tgagaccctg cgtcatctgg ccttgaccca tatcacctgt gttatctctc cactctagct  84120
acattgaact tttctttttt gagatgtggt ctcactccat cacccaggct gaagtgcagt  84180
ggtacagtca cagctcactg cagcctcaaa ctcctgggct caagtgatcc tcccacctca  84240
gcctcctgag tagctgagcc cacaggtgca tgccattaca cccagctaat atttttattt  84300
ttagtaaaga tgggttctca ctatgtttcc caggttggtc tcaaactcct gggctcaagc  84360
agtcctccca tcttggcctc ccaaagtatt ggcattacag ggttagccca ccacatccag  84420
cccattgaac tttttaagga tcccctagca tcctatactt tctgtcactg gatagccttg  84480
gaattatttt tccttctttt tgaaatactc ttcttctttc caccctttgc tgtcaagtct  84540
cagaataggc attatttcct ccaaaaaccc tctcctgacc ctccaaatct ggatgaggac  84600
acttcctttg cccagagagc acctgtttta atcctctcag gtggctataa taaaatacct  84660
taaactgggt ggcttataca cctcagaaat ttattttcca cagttctgga ggctgggaag  84720
atcaaggcac tgacagattt ggtgtctgat gaggggccat ttcttgtttc gtagaagggg  84780
tcttcctact gcatctttcc atggtgaaaa gagttgaggc agctctctga aacctctttc  84840
atgagagcat gaatccctct gtcttcatga tctaatcacc tcccaaaggc cccacttcct  84900
aatatcttca cattggtgac taggtttcaa catatgaatt tgagaaagac acagacattc  84960
agaccatagc agtgctcttc caccaggttt tttatccccc tgtattataa ttgaggttta  85020
aattatctgc tttccttccc ttagattgta agctccatga gagcagggcc ctacccatcc  85080
agtcattgtc ctatccccca tgactacaac ttcctgggta cataattaat atttattata  85140
ttatgtagca aaggtatgct gccatactaa gagacccaaa aggccaccgg attaaaacct  85200
taaagaaaaa aaaataattt ctctcctata atagctgcaa ggttagccat gcaggttggc  85260
agggaagctc acttccacaa agtcactcag ggattcaggc tcctgttgcc ctcttctttt  85320
ctaccaccaa atgatcttca gcaccatttg cacaatcaaa acttaactgg tcttgaatag  85380
gcagaccttg aatttctgaa gtctcagacc caaaagtggc agctgtcact tccactgaca  85440
tatcactgat ggaaacttaa tcatgtgatc ataccaaact gctagggatg ctgggaaatg  85500
tagttttgtt gggaactcca tgacttggct aaaattccat tactgtagaa gatggtgggg  85560
gatgggggag tggtggacat ccagtggttg ctaccatatt tattgaatca aattgtcaaa  85620
caggacctat ctgataaggg gttcttttcc agaattaact gaagtattaa atcaggggca  85680
aaggcatgtc acctcatctt tctctcccta tattggcttt ctagggctgt tataacagag  85740
taacatgaac ttggcggctt aaaacaacag aaatttattt tctcttagtt ctggaggcta  85800
gaagcctaaa atcaaggtgt cagcagagcc accttgacaa ctgctctagg aaagaattct  85860
tccttgcctc ttctggtggc tcctggcaac ccttggtatt ctttgtctgg catccacttc  85920
aatctctgcc tccatcttca tttgcctttt ttctctgtgt gtctatgtcc tttcctcttc  85980
ttagaaggat accagtcatt gaatttaggg cttactctaa atccaggatg atctcacctc  86040
aagatcctta attagttaca tctgcaaaga gcttatttca aaacaagatt gcattctgag  86100
gtttcggtaa acacgaattt gggggaaata gtattcaact caattcactg ctttacttaa  86160
gaaaagagac catgaagtga gcctccttct gcttgagaga gagagcgagc ctttctgtgc  86220
aataggtcaa tgaatggatg cagctgaatt ccacataact ttataaaaat agatggccag  86280
```

```
cccatggggt ttgctgaccc ctgcccaaaa attccaaagt caacagcagt ctctttttta  86340
atcatttctc tatttttaa tttattttta tttttatgtt gagatagagt cccgctctgt  86400
cgcccaggct ggagtgtagt agtctcggct cactgcaacc tctaccttcc agatacaagt  86460
gattctcctg cctcagtctc ctgagtggct aggagtacag gtgtccgcca ccatacccag  86520
ctaattttg tatttttaat agaaacaggg tttcaccatg ttggccaggc tggtctcgaa  86580
ctcctgacct caagtggtcc acccacctcg gcctcccaaa gtgctgggat tacaggcatg  86640
agccaccatg cccggccagg attttcttca ttttaacagc attcttactt gtcccacatc  86700
cattctatcc tgggtctaat tagataacaa aatctacaga tcttgtttaa ctgacattgt  86760
cctgggggat actttttatc ttttgagaca aggtctcact ctgttaccca ggctggagtg  86820
cagtggcctg ataacagctc actgcagcct cgaccacctg ggttcaagcg atcctcccac  86880
ctcagcctcc agagtagctg gaaccacaga tgcatgccac cacacctggc taatttttaa  86940
atttcttgta gaggtggggt ctccctatgt taccaaaggc tggtctcaaa ctcctgggct  87000
caaaagagcc tcccacctta acctcccaaa gtgctgggat tacagatatg agccactgtt  87060
tccagccttg gaaatatagt ctaagaactg agtcaatagg cgatttttgtc attgtgtgga  87120
catcatgtag agaacttaac acaaacctag atggtataaa ctactgcaca cctcagttat  87180
ggggcatacc ctattgcacc taggctgcaa acctgcacag caggttactg tcttgaatac  87240
tgtaggcagt tgtaacacaa tggtaagtat ttgtgtatct aaacatatct aggccgggca  87300
cggtggctca cgcctgtaat tccagatcac ctgaggtcag gagttcgagc ccagcctggc  87360
caacatggcg aaactccttc tttactgaaa aatgcaaaaa ttagccaggt gtggtggcag  87420
gcacctgtaa tcccagctat tcgggaggct gaggcaggag aatcgcttga acctgggagg  87480
tggaggttgc agtgagctga gatcatgcca ctgcactcca gcctgggtga cagagcaaaa  87540
ctccatctca aaaaaataaa aaataaaaaa catatctaaa cagaaaaggt acagtaaaaa  87600
tacagttata accatatggg accaccattg tataggcagt ccgctgttga tcaaaacata  87660
tcaaaacatc gttatgtagc acatgactgt accataaacc acacggcttc aaacaaggga  87720
aatgtattct ctcactgttt tggaggccat aggtctgaaa tcgaggtgtc accagggtcc  87780
ctccaaagga tccgggggag gatccttcca ttggatttgg agttgcttca ctccagtctc  87840
tgcctcagtg gtgacagggc gttctcctct tccctctcaa agttccctct tctgctgtgt  87900
cataaggata catatgactg catttaggcc ccactcagaa aatccaggaa taaactcttg  87960
ccctcatatt cttaactaaa tcgtacctgc ataccttatt ttttctaaat aaggtagcat  88020
tccagggatt aggacatcaa cataacttct ggagggttca ctgttcaacc cactacagcc  88080
agaatgcgct ttgaattcag gttctgacat ctgggactgc ctcccacgta cacacaccac  88140
taccttgtac tgaatgcctg aagggttctg cccccacctc cactccccca aatatttgct  88200
gtggacctga gaaagctgac ttcatggaag cttcattcca ttgttctaag gacttttcat  88260
acattaacaa atgtcttctc tctatgggga aaaccacaga gaaatcaaga cagagtgggg  88320
ttaagtaact cacctgagga ggaacagtaa gtggcagagc caggattcaa accaacatgg  88380
ttttgcacag ttttgacatc atttgcaaca caaatattgt cacagatacc tttttgagca  88440
tctactgtgc taaccgccag gaaggaaaag aacatggggc cgggagagct cttgacaggg  88500
gacagggctg gccatggagg tctgtgtctt ggtggaagat gctatggttc tcttttttt  88560
ttttttttt tgagatggag tcttgctctg tcacccaggc tggagtgcag tagtgcaatc  88620
ttagctcaca gcaacctcca cctcccgggt tcaagcgatt ctcctgcctc agcctcccaa  88680
atatctggga ttataggcac acaccaccac gcccagctaa tttttgtatt tttagtagag  88740
atggggtttc accatgtggg ccaggctggt ctcgatctcc tgaccttgtt gtgatccacc  88800
cgcctcggtc tcccaaagtg ctgggattac aggcatgagc caccacactg ggcaactatg  88860
gttctctttt aactccttgt gctgaaatta ttgcagaagc ccaggccagt tcatccccag  88920
aaagtgaggc ataaacaggc agagctctac agaaacagag aatccacgac tggtttgatg  88980
gaggctgcct cactacctac agaatgggct ctgggtggat tgttctatct ggggagccag  89040
cccacccacc agtctcagcc cttggcgact ctttcctgct gtcacagcag ctggacattc  89100
agaaaccgaa acatgacagc cttccctccc tgttcctgcc cagtggagtg gaaacccctc  89160
gggacccaca taccgagcgt gcacagcagc acagagttgc acagttaaca cagcgcttct  89220
tctccagccc tccggatgca agctgacaga ttggcagctg gctgacttcc aaggtccagt  89280
gagttcttgg cagtcgcttt ctgacctgga cgagtggctg ccacctcctg gaacatcagg  89340
ctgcccccctt ggggagaggg tgacggtctc tctggaaaga ctgtgagctt tgaggtggtc  89400
atcaaaagcc attcttggaa acattctttg agctgtaccg tgcaattcgg tcaccaattg  89460
cacgtatttg gatattaata tccgtatgtg gatattaaat tggttttggg ttttgttttg  89520
ttttgattgt ggcaaaatat acacaacaat cctcctgcct cagcctccca agtagctaca  89580
ggcatgcacc accataccca gctaattttt ggatttttta aatttgtttg tttgtttttg  89640
ttttttgaga tggagtgtag cactgttgcc tgggctggag tgcagtggcg cgatctcagc  89700
tcactgccac ctccgcctcc tggattcaag tgattctctt gcctcagcct cctgagtagc  89760
tgggattaca ggcgcccgcc aacacgccca gctaattttt tgtattttta gtagagatga  89820
ggttttacca tgtcggccag gcttgtctcg aactcctgac cttgtgatcc acccgcctca  89880
gcctcccaaa gtgctgggat tacaggtgtg agccaccgcg cccggccgat ttttgtagtt  89940
ttagtagaga cagggtttca ccatgttggc taggctggtc ccgaattcct gatctcaggt  90000
gatccaccgc ctcggcctcc cgaagtgcta ggattacagg catgagccac cgcacacagc  90060
ctaaatgctg tgcctcacgc ctgtaatccc aacactttgg taagctgagg ccagaggatt  90120
gcttgagccc aggagtttga gaccagcctg ggcaacatag gaagacccca tctctataaa  90180
aaataaaaat aaattagcca ggcgtggtgg tgcaggcctg tggtcccagc tactcgggag  90240
gatgaggcag gaggatcgct tgagcccaag aggtcaaggc tgcagtgagc tgtgattgtg  90300
ccactgcact ccagcatggg tgaaagagca agaccttgtc tcaaaaaaaa ttaagcgaaa  90360
tttaaaattc tgtttctcac tcacacaggc tgcacttcaa gtgcttaatc atcccttgtg  90420
ggtggtggct atcatattgg acagcatgga tagagaatat ttttatcagc gtaggaagct  90480
tcatcagaga ggaccgctca gaggcctgtg gggaccagca cagtgcagta gaagacacag  90540
gccagctggt gagagactgg tcttctgatc ccagatctgt ccctcacttg ctaggtgacc  90600
ttggacagct ccctcagtcc ctctggagtt ttctcttcat tgttaaatca ggaaattggc  90660
ctcagtgaat tctgaggccc catctacttt tttttttttt tttttttttt tttttttaat  90720
tgagacagag tctcgctctg ttgaccaggc tggagtgcag tggcatgatc ttggctcact  90780
gtaacctccg cctcccaggt tcaagcaatt ctctgcctca tcctccccag tagctgggac  90840
tacaggcgtg caccaccatg cctgggtaat ttttgtgttt tcagtagaga ccgggttttg  90900
ccatgttggc caggctggtc tcaaactccc aaccttgagt gatcctcccg cctcggcctc  90960
ccaaagtgct gggattacag gtgtgagcca ccacgcctgg cctcatctag ttctaaatgt  91020
```

```
tatgacccac tcagctctga agacaaggga ggaacatcct ctcagtctag ctctgacatg  91080
cagaagcctc tcaccctgtc ccccaggtca taaaggcagg cgtgttgtga agagcacaga  91140
atgggctgag aaaaatatgc agggattgcg tctatctccc ttccttccgc acgtttcctt  91200
gtcggcacca cctgcctcta ttccgcgccg cacacacacc cgccttctct ctgtctcgga  91260
ggaagacagg atcttccatc ccccaaatcc tgccctgatt cctactctga agcctctgcc  91320
ctgactcctt taagctccct gggaatacag cccatctcct atgccctcct catcccagta  91380
gttcctacct tccccaaaat cgctttggga aagtccccca atgagtaacc agctgtccta  91440
catgggcatc tcagaacttc tcttctgttg ttgttgttgt ttgttttgct tttgttttga  91500
gacaggatct ctctttttca cccaggctcg agtgcagagg tgtgatctca gctcactgta  91560
gccttgacct cccaggctca ggcgatcctc ccccctcagc ctctggaata gctgggacta  91620
caggcacacg ccaccacacc cgggcaaatt ttttttagga cttttggtag aaatggagtt  91680
tcgccgtgtt gcccaggctg gtctctaact cctgggctca agcgatccgc ccactttggt  91740
ctctcaaagt gctgggacta cagacatgag ccaccacacc cggcagagct tctatttctt  91800
gagtgtgttc tcagccatgc taagacattt tctcttctca gcctgatgat gcttttggct  91860
tgtgtttctt tgtttttaat taccccttcc cagtcgctgt catgggatca tgagggtctt  91920
ctgtccatct agatgacacc tttcttgtgc cacgtgtctc caacattccc tggtttttaa  91980
acccttattg ctttcaagat actatccaag ctccttaatg tggcacattg tccttcgctg  92040
ctatctgcct gctttttttt tgagacagag cctcgctcta ttgcctaggc tggagtgcag  92100
tggcgcaatc acagcttact ctgcagcctc gacttcttgg gctcaagcaa tcctcctgcc  92160
tcagccttct gagtagctgg gaccacaggc atgcaccatc atgcttggct aatttatttt  92220
tatttatttt tatagagaag gagtctccct atgttgccca ggctggtctc aaactcccgg  92280
actcaaagtt cattgcagtt tcaatttttt ccttggctca aggatcctcc cacttcagcc  92340
tcctgagtag ctgggactac agacgggcac caacacacct ggctaatttt tgtatttttt  92400
gtagagatgg ggtcccacta tgttgcccag gcttctatct gcttttatct caccttccac  92460
tcttccatcc ttcctttctt ttcttttatt tcctttccct tcccttgcct tcctttcctt  92520
tctttctttc tttctttctt tctttctttc tttctttctt tctttttctt tctttctttc  92580
ttgacagagt ctggctctgt cacccagact gaagtgcaat ggcaagatct tagctcactg  92640
caacctccac ctcctgggtt caagcaattc tcctgtctca gcctcccgag tagctgagat  92700
tacaggtacc tggcaccaca cccggcaatt tttttttttt ttttagtaga gacggggttt  92760
cgctatgttg gccgggctgg tcttgaactc ctgacctcag gtgatcctcc cacctcagcc  92820
tcccaaagtg ttgggattaa caggtgtgag ccactgtgcc tggccttttt tttttttttt  92880
ttttttttta agacaggacc ttgctctgtc actcaggcca gagtgcagtg gcactataat  92940
cactttctgc agccgtgacc tcctgggctc aagggatcct cttgccttgg cctccctagt  93000
agctgggact acaggcatgt gccaccacac tggctaattt ttaaaacttt ttgtaggccg  93060
ggcacggtgg ctcacacctg taatcccagc actttgggag gccaaggcgg gcggatcacg  93120
aggtcaggag attgagacca tcctggctaa cacagtgaaa ccccatctct actgaaaata  93180
caaaaaatta gccaggtatg gtggcgggcg cctgtagtcc cagctactcg ggaggctgag  93240
gcaggagaat ggtgtgaacc tgggaggcgg agcttgcagt gagctgagat cacgccactg  93300
cactccagcc tgggcgacag agcgcgagac accatctaaa aaaaaaacaa aaaaaaaaaa  93360
caaaaaactt tttgtagaga tggattcttg ctaggttgcc caggctggtc tcaagcttct  93420
aggctcaagc agtcctcttg cctgtgcctc ccaaagcctt gggattacag gcgtgagccc  93480
ccacacctgg tcctaaccca ctttctgaac ttccaaccac accattttgt cctaatattt  93540
aagtcacacc ataacatgtc ccacttcaga aatgcctacc aaagtagtct tcaaatcttt  93600
ttaaatcagt ggaccctttc taccaaacaa atgttatttt ttaaatattt attttagagt  93660
aatttagact tttagaaagg ttgtagctgg gcgcagtggc taacgcctgt aatcccagca  93720
ctttgggagg ccgagacagg tagatcacct gaggttgggc gtttgagacc agcctgggca  93780
acatggtgaa accccgtctc tactgaaaat acgaaattag tcaggtatgg tggcacgcgc  93840
ctgtagtctc agctactcgg gaggctgagg caggagaatt gcttgaaccc aggaggcgga  93900
ggttgcagtg agctgagatc gcgccactgc actccagcct gggtgacaga gtgagactcc  93960
atctcaaaaa aaaaaaagaa aagaaaaaaa agaaaggtta taaatatatt ataaagagtt  94020
cccacatacc cttcacccag tttctcctgt tgtttgtatc ttatattatc accatatgct  94080
tgtcaatgct aaggaattgc tgggtgcaga gtggcacatg gctgcagtcc cagatactca  94140
ggaggccaag gcaggaggat atcgcttgag cccaggagtt caagtctagc ctgggcaaca  94200
cagtgagacc tcttttctgc aaaagaaaac aaataaaaca tctaaaaaag aatacactgg  94260
aggcggcgtg gaaacaagga tctcatttgg gagttgtctg caatgttctg agcaagcagt  94320
aacggaggcc tcaagtcagg gctgtggtca tggaggtggg gaggggtggt tggtttcact  94380
atctgtgttg acttaatttt agatttgcag actcaactga gtatgaactt taagagaaag  94440
agagaggcca ggcacggtgg gtcacacctg taatcccagc actttaggag gccaagtggg  94500
gaaggccgct tgagcccagg agtttgacac cagcctgggc aacatagtga gacccctgtc  94560
tctacaaaaa aaaattttta aattagccag gcagggtgat gtgtccctgt aatcccagct  94620
actcaggaca gtgaagcagg aggatcattt gagcccagaa agttgaggct gtagtgagct  94680
gtagttgcac cattgtgctt cagcctggga gacaaagtga gaccctgtct caaaaaggag  94740
aatggggaga gagagagaga gagagaagga gaaagagaga gaaagagaga gagggaagtc  94800
aaggagaacc ccacattttt tgacatggtg tattagtctc ttctcacact gctaataaag  94860
acatacctga gactgggtaa tttataaagg aaagaggttt aatgcactca cagttccaca  94920
tggctgggga ggcctcacaa ccatggcaga aggcaaagga gaagtaaagg catgtcttac  94980
atggcagcag gcaagagagc ttgtgccatt tataaaacca tcagatctca tgagacttat  95040
tcactaccac aagaacagta tgggggaaac tgcccccatg attcagttat ctccacctgg  95100
cgccgccctt gacacgtggg gattattaca attcaagttg agatttgggt gggaacacag  95160
ccaaacccta tcacatgggc aagtgaaagg atgggtttgc catcaaataa aatggggaag  95220
gagactgact aggtgggcag attaggaact cagctttcta tgaagtgcct actgatggat  95280
agagatattg tgttggccat ctattaggtt ggtgcaaaag taattgcggt tttgccatta  95340
aaagtaatgg caaaggaaat aacctttgca ccagcctaat aggaattgga gtctaaaatt  95400
caaaaaaggt aagtcagagc tggagatcca aaggcaggag tcagcctcct gtggaggcta  95460
tttaaggaac tgaataaggg catagatgca ggagagcacc caggactgag cccagggctt  95520
actctccatc attaaagagg ttggggaaga tgaggaggag ccagcagaga agactgaatt  95580
ggagcaaatc agaagaatgt gggtgctggc tgtcatgcaa ggaaagtgct aagccatttc  95640
aagtatgagg gaatgatcaa tgatgtccac tgatgctgat gtgttgactc aaatgaaaaa  95700
tgagaatcaa ccattggatg tagtggcatg gagatctttc gtgacctgag ccagagctgc  95760
```

```
ttaggtgaag aggtgaaggc aagaggctac tggaaggatt actactagct cttttaaaga  95820
gttctgctgt gaagggtaga ggaagagaga tggggcatgt gttagctggt gggggaagtg  95880
gatttcagag gtttgtttcc cttaaaaaaa aaaaaaaaaa gaaaaaagaa taaagaaaaa  95940
aaaaaggcca ggcacaatga ctcacacctg taatcccagc attttgggag gctgagacct  96000
cgggaatttg agactagcct ggacaacata gtgagacccc atctctacaa aaaaaatttt  96060
tttttaatta gctgggcatg gtggtgcatg cctgtggtcc tagctacttg ggaggctgag  96120
gtgagaggat ctcttgagcc tgggaggtcg aggctgcagt gagctatgat cacaccactg  96180
cactccaggc tggacaacag agcaagaccc tgtctcaaaa aaaaaagatg ggagacctaa  96240
cagcagattt tatgctgata ggaataacct attaggggag aaaaacatga ggatgctgga  96300
ggaagaagag tgtcaggagg acatctcttg gtggacgaga ggggatggca tttggtgtac  96360
aggtggaagg tttcacttta gatgacagca cacacagtta tctatagaaa caggagaaaa  96420
tgcactatat gggcatacat gctgggaggt agagagtaaa taatagtggt ggttgcttgt  96480
ggaaattctc ttctaatgtt tttatatttt tatggtttat caaggacaat ttatattttt  96540
acagtttact gcaaacaaca agttctaatt tattcaataa ttatttgtgg gtagaccgag  96600
tgcagtggtg catgcctgta atcctagcac tttgggaagc caaggtggga ggattgcttg  96660
aactcctgat tcacttctga gcttgaatca ggagttcgag atcagcctaa gcaacatggc  96720
aaaacactgt ctctacacaa aatacaaaaa ctagccaggt atagtggcat gcacgtagtc  96780
ccagctattc gggaggctaa aacgggagga tcatttgagc cctgaaggtg gaggttgcag  96840
tgagccaaga gcgagccact gcactccagc ctgggtgata gaataagacc ctgcctcaaa  96900
aagaaattct tattcttctt cttcttatta ttatttgagg agacatttac tttgtaccag  96960
gcgctgtgct agatgctgga gatacagaca tcaacaatga caaggctaag tgcctggcgt  97020
atttgtactt tgagtctaat aaaagacatc acacagacac acaacacaca cacacacaca  97080
cacaggattg tcaaaggatc aaccatttca catgtcaaga tcaggaatga tattggtcta  97140
ctactgcctt accatatctc ctaccatgac ctcatcttcc tcttgccaga ttttaagtct  97200
ttatacctca actcccagaa ctctcttcgc ctcacaccct atcacaatgt catccgtacc  97260
ccacggccaa tactccatca ttcgggaaag caaagttcca aagcgtcaag attgtatcaa  97320
tggacctgtc tctatggcaa cagtcctgaa tgagccaagc aaggtaaccc tggagatggc  97380
gtgaatgaga aagtggcctg ttgccacgga gacgtgctga atgggaaggc ccccacgagc  97440
caggctatgt cacgaagccg aaacagtcag catgaagtcg gtatgtctat tttcaactcg  97500
gaattacaaa aatacatttt aatagagctc atgacccatc tccttcctcg tccctgcctc  97560
ccaccccact cttcagcctt catcctacaa cacaatcgag cctcaccagg aaccccttcaa  97620
acccctcaag gacaccttac tgttccttca gtacacagtc cccttcctgg gctgaggtgg  97680
tattcctttg accaactact gtctcccctt tgggaccaac agtattctca aaagccatga  97740
gcttatggga agaacattaa ctacattctt tggggcaaga acagttgctc acctgtgaac  97800
cagctcagct tgcatctgtg agaatgattg caatgggtag accagttctc catcaaagaa  97860
tggccctagc accccacaca cagtggtata atctgatcat gctggtgtat tgaacatata  97920
atgttagtgc cacatgaaag gaatttgtaa aaggacttag tgcctagaaa ggtacctttg  97980
aagatcttgg aatctctgaa acttacccag gttccttata ccctgctcaa agtattcctc  98040
catttatttc ttcattcatt agttcttttg tttcaccaca tatatatttt tgaaacgggg  98100
tctcactctg ttgcccaggc tagagtgcag tggcaagatc gtggctcact gcagcctcaa  98160
cctccccatc tcaagcagtc ctcccacctc agcttcctga gtagctggga caccacaggt  98220
acaagccacc acgccaggct aattcttgta atttttgtag agacggggtt ttgccatgtt  98280
gcccagtgta ttcgtttgtt ctcacattgc tataaagaac tacctgagac tgagtagttt  98340
ataaagaaaa gaggtttaat tgactcacgg ctccacaggc tgtgcggaag gcatggctga  98400
ggaggccaca ggaaacttgc aatcatggcg gaaaatgaag gggaaacaag cacatcttca  98460
catggtggca ggagagagag agtgaggggg ggagtgctac aaaaccaggt ctcacgagaa  98520
ctcactcact gtcatgagaa aagcaagggg gaaatctgct cccaggatcc aatcacctcc  98580
taccaggtcc ctcccccaac attggggatt acaattcaac atgagatctg ggtggggaca  98640
cagagccaaa ccatatcacc caggctggtc tctaactcct gagctcaagc aatctgcctg  98700
ccttggcctc ccaaagtgct aggattacag acgtgaacca tatttattaa gcattgttac  98760
agcaaagaga agcattgttg cagcataaca attggaagac tccattgatg gacgtctcca  98820
tcaacaagaa ctgtcggata aactatggta cacccatccc ttagcgtgtt atgaagtcat  98880
tacaaaaaga agaagcagat ctctgagtgt caataagagc tagtacttat agggtgtcta  98940
ctgtatacaa gtgctgttag aaagtgagta ttaactcatt taattcttgt aacaagcctg  99000
tgaggtggat tctttcatat ccccatttta cagagaagga aataggaatc tctatatcca  99060
agatatgtta tcaggtgaca aaagcagttt ttgaatggtg ccgccatttt ctcgtaagag  99120
caaatctgga agattccatg agaaattaat aattgtgttt gcctctgtag cggcaccctg  99180
aaagatttgg aagtaggtgt ggaaaggaaa cttactttct tgtgtctttc tgaattttgt  99240
actgtctacg cgttttgtct ttcacaaaac caaacagaaa atgaccattt ggtgcatttt  99300
gtgtgtcagg cattcttcta gtctagagaa gcacaggaga gcaaaatatt ttactgacga  99360
gaaaaatgag gcatggagaa gttaagtgac ttgcccaggt agcagagctg ggattccaca  99420
tcatagggtt tatacaggaa acaggtaaac agagctgtgc ttgtgtgtgg gtatgtgtgt  99480
acacatgcat acatgtgtgc atgtgtgtgt gtgtttgtgt gtgtgtgaat gtgcttgtgt  99540
gttgggagag ggaaatggca agagaagaac ctacagaagg tcagcaggaa ccaacccatg  99600
ttttgaggag tttggacttt atcctgaagg cacaagggag ccatggaagg atttagacaa  99660
ggggtggttg tgcttagctt tttatttaga aggatgactc tggctgaagg gtgatggccc  99720
agaatacagg tatatgtgaa ggactcctcc tgccctagta ggaggatgcc cacccaccct  99780
ctctgcccag tgcagtatca aagggcaaat tgggtacaga gaattctcac caagctgggt  99840
agaatccact ctgatgctgg ggagtggaca ctgaatgcac cagcctctcc tcctgctcaa  99900
tccctgaatt gaagctgttc cactaatgtt agggatcaga ttcccttcat atatatatat  99960
atatatatat atatatatat atatatatat atataatttt ttttttgaga cagagtctcc  100020
ctctgtcacc caggctgaag cccattgtcg cgatcttggc tcactgcaac ctccacctcc  100080
caggttcaag caactcttgt tcctcagact cccaagtagc tgcgattaca ggcacccgcc  100140
accacacctg gctaattcta tatttttagt agagacaggg attcacctat gttggccagg  100200
ctggtcttga gctcctgggc tcaagtgatc agtctgcctc agcctcccaa agtgctagta  100260
ttacaggcat gagccaccat gcccgtcctt tttatattac cttttttttat agagatgtgg  100320
tttcactatg ttgaccaggc aggtcttaaa ctcctggcct caagcgatcc tccctcctca  100380
gcctcccaaa atgctaggat tacaggtgtg agccactgca tctgtccaga ctctgttctc  100440
cataaagctg gcatatggaa agagggaaga ccatccaggc aatatcgaag tcccattggt  100500
```

```
gctgatgtgg ctgctgagac cacatgaatg gatgcattct gactctgcca cctctcagct  100560
atgtgaccct gggccagtca gcaagtccct ctataactca gttttctcat ctgtaaaatg  100620
gcgtcaacag tagccaaccc cagcaaatac tgtgaaatat acagaacatc attataatgg  100680
tgaggatgat agagatgcta tgttatcaga atacctgggc ttgaaccagc tccccttctt  100740
gcaagctgtg tgacttggag ctgatgccca aacctctgtg ggcctcattt gtttcatctg  100800
ttcaatgggg ataataacac tcttacttca tacagttatg gaggatttat tgaaataatt  100860
gacatacagc tcttagaaca gtatccggct ccttgtaagc gctcaagaaa tattacagac  100920
tgttgataat aatgcaatac tactaccaat aatatggcca ggagcaatgg ctcacacctg  100980
taatcccagc actttaggag gcagaagcag gctgattgct tgagcacggg agttcgaggc  101040
cagcctgggt aacataggga gactctgtct ttacaaaaaa taaaaataaa aatacaaata  101100
attagccagg tatggtggtg catacctgta gttccagcta cttgggaggc tgaggtggga  101160
ggattgcttg agcccaggaa gttgaggcta cagtgagctg tgatcacacc actgcactcc  101220
agccagggca acagagtgag accctatctc aaaaataata ataatggccg ggcgcgctgg  101280
ctcatacctg taatcccagc actttgggag gccaaggcgg gcagatcact tgaggtcagg  101340
agtttgagac cagcctggcc aacatggtga aaccccatct actaaaaaca caaaaattag  101400
ccgggtgtgg tggcggggtg cctgtaatcc cagccactca ggaggctgag gcaggagaat  101460
cgcttgaacc cgggaggtgg aagttgcagt gagccgagat cacaccactg cactccagcc  101520
taggtgacac agtgagactc catctcaaat aataatatga gtaataataa taatatcatt  101580
tttatcatca ttcttactaa cagtctctca ctccttgccc tgcagttttg cctgttttct  101640
tggaataaca ctcttccaca cctttcccct cagggatggt tcacgtttag catcatgacc  101700
cacccctggg gattagttag ctcatttctg gaaagcactt tggagctgta ggtgctttgc  101760
aggctggaaa catcacggga cttgtaccat atttaagcaa tgccagatta ttctgcctgg  101820
caggggggagg acacagagga tacggccctg gtatcttttc tccctgccta cctcagcttt  101880
gctctgaacc attttctgtc ctgttcaggg cagcctgggc cacttgccac ttccagcttt  101940
ctcgggagag gatgccttcc tgatggcacg cctcttaaca cacacctggt gctgttgttg  102000
aaaaagcaac aattgactcc agcgccagca ctgagaggct tgtccttaaa attagcagga  102060
gctgttggaa ggtcgctgtt agctcttttg actggaacac actgttcccc aggtggcatg  102120
aggctgaata cagtgcaggg attggctctg ctctcaggtg gcctgctcca cgctcctgag  102180
ctccgggtgg aagctgtgac cattatttcc ttaacagaaa catatatagc agcattaact  102240
atgaacctta ttactgtgtg tgtgtgtgtg tatatgtgta tatatatata tgcacatatg  102300
tgcatatgtg tgcctatgaa cctgttctga gcactttaca aatgtcaatg tattttatcc  102360
tcccaacaac ccattttata aataagactt gaggcacaga gaggttacgt tactgcccca  102420
agatcacaca gctggagagt ggtgaggcca agatttgaac atatgtacca ttgtaccata  102480
tgtaccaact tttttttttct ttttgggatg cattcttgct ctgtcaccca ggctggagag  102540
cagtggcatg accacggctc attacaacct caacctccag gttcaagcta tcctcccacc  102600
tcagcctctc aagtagctag gaccacaggt gcataccacc atgcccagct aatttaaagt  102660
tttttttgt ttgtttgttt gtttgtttgc agagatgggg tctccttata ttacccaggc  102720
tggtctagaa ctcctaggtt caagcaatcc ccccacctcg gccttccaac atgctgggat  102780
tacaggcatg agccactgca cccaggtcct ccctccttat aaaggtcgcc aagcacaatc  102840
ttgtgagcct ggccctatcc acacccatac gcaacatggt gtgtattttt caaacaaaaa  102900
ctgaatgaac acctctggtt tgggttcccc tcacacttgt cccgggtttg ttgactctgt  102960
gttgtgggcc tagacaaagc agtgtctgga gctcctagac ccagggacca gacagtctgg  103020
gttcaaatcc tggctcttcc acttctgcct gagtgctctc tctgaacctg tctttcttta  103080
tctataaaat ggagataatt tttttaaact catcacttgg tcaaactgct ttgagcatgc  103140
aaatgagttc atatgtataa acctcttaga atgtcccagg caaagaacaa cacttcactc  103200
agatcaacat ttatttagca tctactgtgt acccatgact attctaggtg atgaggagac  103260
cctctggttc ttatgaggta gtgaggtggg ggagggtgag aaccctaaac attaacgatg  103320
gtgtgttcgc aggtgggaaa atcagtaaag tcgggtaaag ggaatttggg agtgctgtgc  103380
tcaagtcctg gccctgccac tttctggggt gcaagataca gcattgaata gggtggtcag  103440
ggtaggcctt attgggaaag tgatatttga gcagacgatc tagatgtcgg cacatattgc  103500
tactgtttga tggtactaat atgagtttga gtttcacttg caagtatata tatatatata  103560
tatatatata tatatatata tatatatgtg tgtgtgtgtg tgtatatata tatgtgtata  103620
tatatgtata tatatgtgtg tatatatgta tatatatatg tgtgtatata tgtatatata  103680
tgtatatata tgtatatata tgtgtgtata tatatgtgta tatatatgta tatatatata  103740
tgaaatttgg tccatttatt tatgctgatc aattaattga tgttgaaatt ataattgaat  103800
gttttattaa taaacagata cccacatact attttttcag aaattgttag gttttggggt  103860
tttctttaga ttttgattat ttttatttgc ttaattttct tttttctttt ttttaatttt  103920
atttttccat aagttattgg ggtacaggtg gtatttggtt gcatgagtaa gttcttcagt  103980
ggagatttgt gagaacctgg tgcacccatc acccgggcag tatacactgc accatatttg  104040
ttgtctgtta tccagtgctc acctcctact cttcccccca agtctctaaa gtccattgta  104100
ccattatttt actcacccac attctttggc ctgagatgct gagtggtcat gactcccaga  104160
tcccttcttg tttctgtatc aaagatcttt actaagatcc tggcctaggg aacctattcc  104220
ctttcctcat ccccaatggg agaaggggct tcttccccag cttatttgcc aactcatagg  104280
aaaggtatga aggagaggac tgtagttgtc ttgaagctgg tcagatgttg aagagatgat  104340
aatatttgct gatcaagaga gacaaagcaa tgctggaaga agaggctgtg ttagttaaca  104400
ccagctgcaa taaccaataa aaccaaaaat ctctggctta agagtatgca tgagtgagaa  104460
atcaacttct aaagtacaac tggtggccgg atgtggtggc ttatgcctgt aattctagca  104520
ctttgggagg ctgtggtggg agggtcgctt gaccccagta gtttaacgcc aacctgggca  104580
acacagtgag acaccatctc tactaaaaat aaaaaaataat aaagtgaaac tggtgagggg  104640
tgcaatgagg tggagtggtg ggtgactcaa atatggctcg actccatgca gtcactcagg  104700
gatccaggct gttggaggct ctccctgctt aaacatgtgg cttccaaggt tgttctaaga  104760
gcctacattg agacagcagc tggggaaaag ggaaagtgga gtgggaggta cttatgaggg  104820
ttcctggaag tggtgaacaa cacttctgcc tgcattctat tgggtggaat ttagtcatgt  104880
ggcccaggct agctgcatgg gaggctggga aatgtagtct ctgattaggc tgccatttcc  104940
cagtcccact tgtgaatctt tagtgggaag ctcaccatgt ttgcaccagg gattcagtct  105000
acctcccact catgcctcaa ctatgtatca ggcactgtcg taagtacttt acatatcagc  105060
ctacctaatg caaacaacta ctcagtgggt gctttattgg tcacatgtat tagtgagaac  105120
atggaaaccc agagccgtta aatatcttgc ccaaggtcac acagctagga agtggcagag  105180
ttggaatttg aatccaggaa atctggctgc agagccccac gcttagtata aattcattgt  105240
```

-continued

```
agtttagaaa gaggcagaag gaccctaaaa ttggcataat ccattttttg gtccctaagg  105300
aactgactga attgactact tgtaaaagtg agtcctggac aggcaacagt ggctcaggtc  105360
tgtaattcca ggactttggg aggctgaggc gggcagatca cctgaggtca ggatttcaag  105420
accagcctgg ccaacatggc aaaaccctgt ctctaaaaaa atagaaaaat tagctgggtg  105480
tggcggtggg tgcctgtaat tccagctact caggaggctg aggcaggaga atcgtttgaa  105540
cctgggaggt ggaggttgca gtgagcaaag atcacgccac tttactccaa cttgaatgac  105600
agagcaagac tctgcctcag gaccgccatg gccccctggg ttctaggtca gagtttctcc  105660
gccacagcac tgatgacttt gggggctgca ttattagctc caaaatggga gctatcctgt  105720
gcactgcctc aacttacttg atgccagtag cgcccgcgcc ccagttgtga gaaccaaaaa  105780
tgtctccaca cattgccaaa tgtcccctgg gaggtgaaat caccccctggt tgagagtcac  105840
tgttctagat tgttaaatat tatcttacac tctagcacaa gtccaaggca aactgactta  105900
gaaattacca accttgcaaa aaatagaaga tttcttaaag tcagtgagca tgatggtggc  105960
aagctgctga aatcacaccc ccagacatta gcagatggga tctggacagt attcatctag  106020
ttaaaaattg acaaggactg ggacactgca ggctcttcaa aagagaatca tttgaataac  106080
aaggggtcaa gacaggggta attggtgaaa gcccctgctc ataatttgaa aatataaata  106140
ggcatcatga aaattcatcc tgcaaaagtc aaaagtcgaa tgtgcagtgt tatacatgat  106200
cagttgattt gggaggggaa attgcatgca cacacatgag agcttgcaca cccacacaca  106260
cacacctgtt caagtgtgtg tgccagtgct cagtgaggac catctcccca acctgtctga  106320
tcatcttgct ttggggtgac cctatgggtg aggcagaaat tcttggatca tagttttcta  106380
atgaatatta taattgttaa cttctgatgg gtgctgactt tttcatcttt gcaacactgc  106440
gtaggtattt ttactctccc cattttacag atgagacaac tgaggctcag aaagattgat  106500
tagctctaca cgaagccagg atccaggctt agcctggctc caggaatcat gttttgagtt  106560
acgtagcttc cctgattctg agggacctcc ccacttctga aatcttctac tgttactccc  106620
catggccctt tcctattgac cggaggcacc ccagctcctc actcgtccct tatcttatga  106680
aacatgacca tgatgtctga attcaaagga gagcctgggc tttgtgggga aaacgaagca  106740
gaaaaagaaa ggtggaggtt ggtggttgtt tttggcatgg tgaggagcct gtcgttgctt  106800
gaggaaagca agaaaggaga ttgctggggc ttggatccat ctctgggtgc ctgtgggtct  106860
gtctgtaaaa atgagaactg gtcgtgctca ttagaggatt tgaccgttag gccttgggat  106920
agcgatttgg gaactttttt ctgctaagac aaagaataat atggttcagg ttcattttgc  106980
tcctgctttc ccaagcccta catctcttct gggctttttt ttttttcctt ttctctcctt  107040
cttcttcttc ttcttcttct tcttctcatt tttggatctg gacttctgct gactcatctc  107100
tctgagcaag gaaggaggga ggaagtcaga attgctcatt aaccgttttc tttagtgact  107160
cagctgtgat tcacatttta attaatggag gagaaaaacc tgatcagtcc taaggcatct  107220
gcccaatcac gcataactcc aggctggtga taataataat acttgaaaaa agtggggtgt  107280
cctgaattaa actatggctc attccccaca ttagtcttga ggactccacc aggccctcta  107340
agttccaggt ctcaatgggg ctccctgaac cagagcagct agtccaagcc ccgagcagca  107400
tttctgcaga gttagtctga ggtcaggaca agaaacagag gctcaagccc tcctgggatc  107460
gcaggaggat catgggaatg taatattgtt tcctgagctg gtctttggct ataatcccag  107520
gctcaagcct ggcctccctc ccctcggggc ctgaaatttg tcagagccta ttgcaggggc  107580
agcttctgtg ctttttgttt gcccagagaa tgagaaaagt ccagataatc atgaccgcta  107640
cttcctgagc acttactatg catcaggtgg tgtgctcagc acttctcatg aatgatcacg  107700
ttgaatcctc actctgtcca caaaaagaaa gagcttttat ataattctcc aacctcccta  107760
tgaggaaact gaggcttggc aattgcccaa tgtagacaat tagtaaataa tcaggcagga  107820
tataaaccca accctttccc acctgggagc cagagcttgc atctactata cttctctgct  107880
ttccagtcag ctgcaaagaa aaattggaag ctgatagctc attcaacaaa cacttattga  107940
acccttccac ctgctcagcc ctgttctaga caccagagat ccatcagtga accaaagagg  108000
caaatccatg gtctcatgaa actgacaatt tacctgccca agtgtattag ttactgttta  108060
taagttccta ttaagtgtat tagatatgct tgcagctgta acaaagaatc ccaacatgca  108120
taagggctca aaacaataaa aatttcgttc ttgcacagat aaagttcaaa aggtgtattc  108180
tttttttttt tttcttttgc gacggagttt tgctcttatc ctccaggcat gagtgcaatg  108240
gcccagtctc ggctcactgc aacctccacc tcctgggttc aagcattctc ctgactcagc  108300
ctccccagta gctggaatta caggtgcccg ccaccacacc tggctaattt tttgtatttt  108360
tagtataggt ggggtttcac catgttggtc aggctggtct taaactcctg acctcaggtg  108420
acccacctgc ctcggcctcc caaagtgctg ggattacagc cgtgagccac cgtgcctggc  108480
caaaaaaaaa atgtattctt aaacagcagg cacctctcct ctaagcagta agtcaggggc  108540
ccaggcttgt tccatattgt agctcctcat cttcaaccca tggcttccaa agtctccatg  108600
cttcttgata tcaagccaca gaagggaaaa gagcatgaga agggcacagg agaaatgttt  108660
ctgggacaga cccagaagta gtccatatga cttccatcta cctcccactg gctagagctt  108720
acatggcggc acccacttgc agagctggga aatggagtct aactgagcat ccaggaagga  108780
gagacagaca tgagtctttg cgtgggtcct cactgagaat caagctccac attttgatcg  108840
atgtcaccag agcgtacatg gcggcgccca cttgcagagc tgggaaacgg agtctaactg  108900
agcatccagg aaggagagac agacatcagt ctctgcgtgg gtcctcactg agaatcaagc  108960
ttcacatttt gatctgtgtc acctccttgc aagccctacc ttaggacaat tttaagggac  109020
attcctatct tcttccaccc ttaggacagt tttaagggac actcctgagt tcttccaccc  109080
acctcctctg tttcttgggc ttccagctct caggatttgc ctttgcctta caatggggtg  109140
aagcaagaat ctggaagaat gtctctcccc acaatttgaa gtcttatttg aaaaaaagca  109200
gtagagcatc cctccctctt gaggtaggga aatctagaat caaatcctgc ttctccagac  109260
tttgacctca gaaactgggg ggacttcaag gtcttcaggt gggcagcttt catgaaccat  109320
tcattcctcc cacctcatac caatcagggt cctaacagga aaaagaatta acttctagat  109380
ggttcaaaag aagaccatgc catgaagaga ctccttaaag agataggaac aggtgagaga  109440
aatagataac ggctgtttga ggtcctcaga gagaagccat cgcgagccct acatttcctg  109500
gaacccagtg gaggcagagc tgtgcagaag ggactactgt cagaaccagg gagggagcag  109560
ggaagcaata ttccaatctc tttccctccc ctcatcttct gccagcgctt cccctcagcc  109620
aaaccaaacc ggaaacggag caaagcattc tgggagttgt agtcttcaag ggtccgcctc  109680
gagggcacag agcccgctgg agcattgacc tagagggcac acagggaatg actagtttgc  109740
accatcatgt gacggactgc acgccctcga ttatgtaatc cactctataa ttcaactgca  109800
gagctgcatg gtacagcagg atagccacta gccacacgag gctatttaaa tataaatgta  109860
cattcattaa aatttaacca aatgaaaatt ttagccactg agccccattt caaatgctca  109920
ttagccacac gtggctcttg gctaccatat tggacagatc agaatagaac atttccatca  109980
```

```
tcccagaaag ttctaggggc cggcgcagct gtggtgtaac ctgagcccat gcatgttatg  110040
gaatggagaa gagagaaaac agcacaagag gcagttttga agggagacag agagctgtgg  110100
atcagtaggg aggagactct ctaggcaaag gagcagttga gaagcaagaa agttgagtga  110160
gctgctttgc tgcgatggag gcttccctca cggggaagag tagagtcaga aagctttagt  110220
tcaagttcag ctctgaaatg aaccaatgag tgttctgaca agacacctgg ccttccggaa  110280
ccttggtttt gtagtggcca agggcttgac cctctgaagg ttcactgaaa aaaatcaact  110340
cacaaggcat attaattgga gaaaaggcag gcagatttat ttaatgtgtt tgcacgagag  110400
ccttcagaat gaagacccaa agctgcaggg gaaattgtcc gttttttaag cttaggttca  110460
acaaagtatg gacagcggtg tagaaatatg attgaacaaa aagtgtacaa tgtaaatgct  110520
aatagactga gtggggaaac ccaaaaaggg ctgtcttgat tctccttggt ctctctgagc  110580
atgcatttct tccgggtatg ggacaagacc ctctctggaa tggagggggg gctctcttgg  110640
ttctccttgg tctctctcag catgcattcc ttccgggtat ggggcaggac cctctctgga  110700
ataagggggc tgtcttgatt cttcttggtc tctcagagca tgcattcctt ctgggtatgg  110760
ggcaggaccc tctctggaat gggatcctta taacctacgg tcaaataacg taagttagat  110820
aatttctttt tttttttttt cttttttttg agacagagtc tgattctgtt gcccaggcta  110880
gagtacagtg gcacaatctc ggctcactgc agcctctgcc ttctgggttc aaatgattct  110940
cctgcctcag cctcccaagt agctgggact acaggtaagc accaccatgc ccagctaatt  111000
tttgtatttt ttagtagaga cagggtttca ccatgttggc caggctggtc tcaaactgct  111060
gacctcaagt gatccaccac ctgggcctcc caaagtcctg ggatttgtaa tcccagcatg  111120
agccactgtg cccagccaga tcatttcttt ttctttttct ttttcttttc tttttttttt  111180
ttttttgag atggagtctc actctgttgc ccaggctgga gtgctgtggt gcaaactcag  111240
ctcactgcag cctctgcctc ctgggttcaa gcaattctcc tgcctcagcc ttccaagtag  111300
ctgggactag aggtgcgcgc caccatgccc agctaatttt tgtattttta gtagagacag  111360
tgttttgcca tgttggccag gctggtctta aactcctgac ctcaagtgat ccacccacgt  111420
cggcctccca aagtcccggg atttgtaatc ccagcatgag ctaccacagc tggccagata  111480
atttttttat aactagtttt tacaaagaaa ggtggaggga aagttagagt aacattttta  111540
ggtgttaggg ctgactttgg ggaaaagagg tctggtttct acgacccgcc ttagggaaga  111600
gggattctag tttttgtggc tagccccagg ggagaatggg actaagagat agaagggcag  111660
gagaaggtca gagaaaaact tttgcttctg tggctgcttc ggagaacttc attttggggt  111720
attgttttct gagccccaac agtttgctta tcagtgaagt gggtataggc gcccacctcc  111780
cacagtgacg atgctgtgaa cagggctttg gaagagtaga actatgaaat atttgttgtt  111840
gccttgtggg gaaatggtcg ttaaagccaa aattgttcaa gagaagaagc aggaagagtt  111900
cctttctttc ctgcaggtat cctcttaagc tgagtcttca gaatcccctg acaacgttta  111960
atcaacactt tattaaattc accccaaccc tgcttcaaac cttcacctgg tcctcgagat  112020
cttccaactg tttcttgatg aagttagcag gcaattgtat ggcgggatca tcatctcatg  112080
ttttgttttg ttttttcct ttttaccctc tgactttgag aaatccttgt ccttttactt  112140
ttccaaacct gagagcattg cagagaagtt agaattgagc aggacatggg cttaagaccc  112200
agcccagcca tgtgctagct gtgtgaactc gaagcagtga ccccacctct ctgacctgga  112260
aagtagaggg aatgatagga cccaccaccg ccacacttgt agggtcatca tggggattga  112320
ataaaataat gcataagact tggcccacag caagcactca agaaatgtta gctacttcct  112380
aaatatattt ttaacctttt attgaatata acatacatac agaaaagcac atgtatcata  112440
caagtagagc ttgagtgatt ttcaaaaact gagcccagtc atgtaaccag cgcctagttc  112500
aagaaacaga acatagccga gtgaggctga ggcaggagaa tcacttgaat ctgggaggca  112560
gaggttgcag tgagcagaga tcatgctatc gctccccagc gtgggcaatg ggggcggagg  112620
ggaagagaga gagagagaga gagagagaga ggaaggaggg agggaaggaa ggaaggaagg  112680
agggagggag ggagggaagg gaaggaaggg gagagagaga aaaggaaaga aaagaggaag  112740
acagaaagag agagagaaag gtaaagaaag aaaaggaaag aaagagaaag aaagaaaaga  112800
ggaagacaga gaaagaaaga gaaagctaaa gaaagaaaaa aaggaaggaa ggaaaatagg  112860
gagggaagag gaggaggaag aagaagaaga agggggggag ggagggaaca gctgcagctt  112920
cgaggaagga aggagggagg gaaggaagga aggaaaggaa ggaaggaaaa aaaaacagca  112980
ccaacgttta gaaacccccct tgtgcctctg aggtcaccag taactccatc ctgacttcaa  113040
acagtctaga ttagttttgc ttgtttttga actttaagca catggggtca tacagcatgc  113100
atgcattgac ttctttccct tgacgttgta tgtgtgagat tcatctgtgc tgttgctgtt  113160
catttgttct catcgctgtg tgtgctgaac cacctgttca tttactctac taatggtggg  113220
cagtttggtg ctttctactt tggggctatt ccagagaaag ctactttgaa cacactcaga  113280
tatgtctgtg ggtgaccact cttcatattt ctatgggaga tattcctagg accggaacat  113340
ctgagtcaga gggaggaatt ggtttagctt tggtaggaac tgcctaacaa ttggccgggc  113400
acagtggctc atgcctgtaa tcccagcact ttgggaggct gagggggggca aatcacttga  113460
gctcaggagt tcgagaccag cctggccaat gtggcaaaac ccctggccaa catggcaaaa  113520
ccccgtctcc gcaaaaaaat acaaagatta gccgagcatg gtggcgtgtg cctgtaatct  113580
cagctactca ggaaactgag gcaggagaat tgcttgaacc tgggaggcag aggttgcagt  113640
gagcagagat tgcactactg tactccagcc tgggtggcag aatacatgaa actccatctc  113700
aaaaagaaga aaggaaggaa ggaagggaag gaaggaaagg aaactgccca acagttttcc  113760
caagtgtttg ggatggaagg aaggaaggaa ggaaggaaaa gaaactgcct aacagttttc  113820
ccaagtggtt ggaccagtta aaactcccac cacctgtgaa tgagagtttg tttttatttt  113880
gctcctggag tgcctctcct gtagcaggtt cccactgaat gtctgggaat tcaaatgtaa  113940
tgcacttgtt catttcctca agagcttcac tccatcaatt ggattcatcc attggctctc  114000
ccatctccac tgacactatg ttctcacctc tatttggaag acatcctgcc tccacctgcc  114060
caagtcacat tatcttctca ttccagcctc tcaaggagag ttttctcttt caccacctcc  114120
tctagccctg gtgattggca aggtctcgca acagtaccct tcaaaacact catgactgtg  114180
aatgcactgg ccttcactaa gtttcccatt cttctctttc tttctttttt cttttctttt  114240
cttttttttt gaacagagtt tcactcttgt tgaccaggct cgagtgcagt ggcacaaaca  114300
cagctcactg tagcctcaac ctcctgagct caaggtatcg tcctgcctca gcctccttag  114360
tagctgggac cacagacatg caacgttgtg cccagctgat tttctttttt ttcttttttt  114420
tttttttttt gagacatggt ctcaccctgt caaccaagtg cagtagcatg atcacagctc  114480
actgcagcct tgacctcccg ggctcatgcg attctcccac ctcagcctcc cgagtagctg  114540
gggctacagg cacaagccac catgcctggc taatttttgt acttcttgta gagaccaggt  114600
ttcaccatgt tgcccaggct ggtcttgaac tcttgggctc aagcagtcct cctgcctcag  114660
cctcccaaaa tgctgggatt acaggtgtga gccagcacgc ccggccatgg ctaatttctt  114720
```

```
cattttttggt aaagacaggt ctcactttgt tgcctaggct ggtcttgaac tcctggactc  114780
aagcaatcct cctgtctcag cctcccaaag tgctaggact accgatgtga gccaccgcac  114840
ccggcaattt ccccttcttg acttctccag agctctcatc cctctcgagc tcctgtctct  114900
tctagaatca cttacctcac caccttatgg ggtttttgcc tctgttccta ctcctcttta  114960
tttaagaaaa cactgtactt taagagggct tcagaaacca cccgaaatag aaacatgtcc  115020
ttttgttcaa tcctttactt taaaagacaa ataaaatgaa gaattgctct ccatgtagaa  115080
ggttaaggag cttgggagga ccttctgtga gtggggagaa ctttacatta aaggaaaaaa  115140
aatgctggag aatagctgtg aacccaggaa gggagaagga cttcctccac tgaacttgta  115200
aagcacaaac tctaaggcaa aaaaagacat gattacatga aaactaagat atttgttcaa  115260
ataaagatgc aattggggcc aggtgcggtg gctcacgcct gtaatcccag cactttggga  115320
ggccgaggca ggcgaatcac gaggtcagga gatcgagacc atcttggtca acatggtgaa  115380
accccatctc tactaaaata caaaaaatta gccaggaatg gtgtcacgtg cctgtaatcc  115440
cagctacttg ggaggcttag gcaggggaat tgcttgaacc agggaggtgg aggttgcagt  115500
gagctgaaat cacgccactg cactccagtc tagcgacaaa gcaagactcc gtccaaaaaa  115560
aaaagatgca atagcaggtg gttcgggaac caaaccttac atccagatgc tggttgtccc  115620
atttcctgtg aatccttggg tgagttatca acctctctga gcctcagttt cctcgtcaat  115680
aaaatggaga aaatagtatc tacctatgga attgttgtga gttttgaatg agttaatatt  115740
tataaatcat ttagaatagg aattagcaca tggtaaatag tggatagaat cataaaaaaa  115800
aaattgatca ggggttaact tctaactgct gtttgttata gaggtcccta gcactgtgtg  115860
gtcattttaa atttagatga tttagaatta aatgaaattt aaaactcagt tcttcattca  115920
cactagccac attttaagtg ctcaaaaccc acaggtgact agtggctacc atatttggca  115980
gcacagattg agaacagatt tatcatccag aaagttctgt cagacagtgt tgatcaaggc  116040
tacatgaggg tctgggtgca gtggctcaca cctgtaatcc cagtgctttg gaaggccaag  116100
gtgggaggat cactggaggc caggggtttg agaccagcct gggaaacaga gagacctcat  116160
ctctaccaac attttaagaa ttagccaggc aaagtgttgc atgcctgtag tcccagctac  116220
tcaggaggct gagacaggat tgcttgagcc caggaatttg aggctgcagt gaactatgag  116280
cgcaccgctg cactccagtc tgggtgacag agtgagacct gtctctaaac ataaaaaata  116340
aaaatgtagg tggggcatag tggctcccgc ctgtaatccc agcactttgg gaagccgaga  116400
tgggcagatt gtgaggtcag gagatcgaga ccaccctggc taacatggta aaaccgcgtc  116460
cgtactaaaa ataaaaaaaa attagccagg catggtggcg catgcctgta gtcccagcta  116520
ctcgagaggc tgaggcagga gaattgcttg aacctgggaa gcagaggttg cagtgagctg  116580
agattgcgcc actgcactcc ggcctgggcg acagagcgag actctgtctc aaaataaata  116640
aataaataaa taataataaa gtaaaaataa aaatgcaaag actacctgag ggaatgtctg  116700
caagtcaacc agaataacac agcaacccca ataggaaaac aggccgaaaa tgtgaacagg  116760
cggatcaggg aagtgaagtc tgaaaagcta atcagcctat gacatggtac tcaaagtcat  116820
ttgtaaccag aaagatggaa atgaaagcag tatctctgta cacctttaat attggggaaa  116880
aaatatgtga ataagccaag ggtttccagc gatgcgggca cagaggaaag tcttgcacca  116940
ctcaaagggg tgtggcccag ggaggccact ctggagacat atcggtagta ctcagtccag  117000
tgaggtccag caccatcagc gcttatgtcc ccaggcatcc atcccaggga cattcttacc  117060
aggtctgtta ggggcaggta cgagaatgct tactccagca ccatctatat aaggggagct  117120
gaaggccacc tggtgtccct cctggagacc aggaggcggc atgtgacagc ggcacccatg  117180
gagcaccaga atgagtgaga gctccagacc gcatatccga cagatactac gggatggggc  117240
ttttagaaat atggttgttg ccgggcacgg tggctcatgc gtgtcatccc agcactctgg  117300
caggccaagg cgggtggatc acctgaggtc aggagttcga gaccagcctg gccaacatgg  117360
tgaaaccctg tctctattaa agatacaaaa attagctgga cgtggtggcg ggtgcctgta  117420
atcccaacta ctcgggaggc tgaggcaaga gaatcgcttg aacccaggag gcagaggttg  117480
cagtgagccg acatcgtgcc actgcactcc agcctgggtg acaagagcaa aactctgtct  117540
caaaaaaattt aaaaaacaaa aaataaaaat atggttctgg gtgaaaacag gaaacaacag  117600
aatgtgtcta acttcatcct gcttatgtca gttaaaaata gacacactca aaatatcgca  117660
cgtgtttttg cgagaatgca ctcctataag gccaaattaa acattctctc agttgtctct  117720
gggagggaga agaatgaaag tagggtatag agagatatag gggaattaat gcatgaatga  117780
atgaaggtat aaacaagaga caggcgtcat acagaccaaa ggtaaagata tcccgtaacc  117840
tgaggagagc aaagaacttg actctgcatt tgaagattca gaaaatgaat ttcagaaata  117900
gttttctcgc caggggtgg ctcacgcctg taaccccacc actttgcgag ggcgaggcag  117960
gtggatcact taaggtcagg agttcgagac cagcctggcc aacatgatga aaccctgtct  118020
ctactaaaaa tacaaaaatt agccaggcat ggtggcatgt gcctgtaatc ccagctactc  118080
aggaggctga ggcaggaaaa tcacttgaac ccgggaggca gaggttgcat tgagctgaga  118140
tcacaccatt gcactccagc ctgggtgaca gagcaagact ttgtctcaaa aaaaaaaaaa  118200
aaaaaaaaaa aaaaagaaga ggaagaaatc gttttttcaa gaaggggaaa gctgggtgat  118260
ttaagaatga acttgaagag gatcactcag tcctcaacct aggagtggca agaatataga  118320
ctgtatggga agtggttctg ctccttggta cccatcttag aaatatttgg cctgagtctg  118380
taagaggcag gtactttatc taacctgagg ttagggggcc actacatccc catcccctcc  118440
cctgctttct aaccatgcta acatcttctc actctcctgt ctcctctcct tctcactccc  118500
ctaatctgcc tattcacatt ttgggcctgt tttcctattg gggttgctgt gttattctca  118560
ctgatttgca gacattcctc tgtgtcatct ttttaatttt gttttaattt ttagaggcag  118620
gatgtcattc tgttgcactg gctgtagtga cgtagctcac tgcagcctca aactcttggg  118680
ctcaaactcc tgtcctctgc ctccacttct caactggtaa cctcacttct cttcatgagg  118740
tctctccagc cccagggcct ttgcacatgt tcccctctct tctgagtggc atatggtagt  118800
tgctcctctg taaatattta ttgacatcct gacttccaac cagcagagaa ttgacctcct  118860
tcccatgctc aggctagtga aggcatgagt ttggctgagg tcccagtggg gaaggtgagt  118920
ggggtggcag agttaaccag gagcagcatg gtagaatggg taaaaccaga cgtagcacgc  118980
aggcaccaca tgttagctgg acaagtagtt taaccccatg ggtctcaatt tccccatcaa  119040
tgaaagggag aatagaacaa gtccctggta agcagcataa aatgagctct cagaatgtaa  119100
agtaacaagc acacaacctg gaagagaata catttagtga atattggctc ctttaatcag  119160
caggttctga tatgacttag ctacaattaa gaaaataaaa atggaggccg ggcgcagtgg  119220
ctcatgcctg taatcccagc actttgggag gccaagacgg gtggggtgga tcacctgagg  119280
tcaggagttt gagaacaggc tggccaacat ggtgaacccc atctctacta aaaatacaaa  119340
aattagccag gcgtggtggc gcacgcctgt agtcccagct actcgggagg ctgaggcagg  119400
agaaacattt gaacccagga ggtggaagtt gcagtgagcc cagattgcac cactgaactc  119460
```

```
cagcctgggc gacagagtga gatttgtctc aaaaacaaaa gaagtctgga ggccaggagg  119520
ttggttgcag ggttggttcc ttggctcaac aatgtctcca aagagtcctt ccatctttcc  119580
actctaacat cgtcactgta aggacttttt ttaacattta ccactcacag ccccaagacg  119640
actgcgtcag ttctttcttt ttttccttca gacagagtcc cgctctgtcg cccaggctgg  119700
agtgcagtgg catgatctcg gctcactgca acctctgcct cctgggttca agcgattctc  119760
ctgtctcagc ctcccgagta gctgggatta caggtgcctg ccactgcatc cggctaattt  119820
tttgtatttt ttttagtaga gatagggttt caccatattg gtcaggctgg tctcaaactc  119880
ctgacctcag gtgatgcacc tgcctcggcc tcccaaaggg ctgggattac aggcgtgagc  119940
cactgtgccc ggccgatgac tgcctcagtt ctaaggtact tacccagcca tccacgtaga  120000
cagacacaaa agcatccggc caaagaagag ggagaggaag ggctgtctct taccatgtga  120060
ctcatctcac ggggaaaaaa tccttttcca gaagcaccca gcagattttt cacccagatc  120120
ctgttaggcc tacgaatggg tcatgtgaca agtgctctta ttgcaaggaa tcttgggaaa  120180
aagagactat taggcatttt ctgcctcttt gatgggaggt gggctctgcc agtaaggcgg  120240
gtagtggtgg tggctcttgg atggacaact gtgtcttcca ttcttcttct tctttttttt  120300
tttttttaa gagacaaggt ctcactctgt tgcccaggca gaaatgcagt ggcacaatca  120360
cagctcactg ctgcctcgac ctgccaggct caggtgatcc gcccacctta gcctcacgag  120420
cagctggagg agtgtaccac catggccggc taatttttat attttttgta gagatggggt  120480
ctctttatgt tgcccaggct ggtcttgaac tcctgagctc aaacaatcct cctgcctcag  120540
cctcccaaag tgctgggatt acaggcataa gccaccacgc ctggactctc ttctttaaat  120600
actgagcctt ccacctcttc tagaatatac tctgttaatt atcaaccaca cttttctaca  120660
tttttgcttc attattcatt cagtaaacat ttattgagtg cctactgtat gccaggcaca  120720
gctttaggtg ctggagatgc tatgaacaaa acagatgaaa atttctaaaa aataaaataa  120780
aaaataaaaa taaattttgc aaagccaggc acagtggctt aggcctatag ttccacctac  120840
tcaggagtcc aaggcagtag gatctcatga gactgggagt ttgagtccag cctgggcagc  120900
atactaggac tctgtctcta aaaaagaaaa gaaggccggg cgcagtggct cacgcctgta  120960
atcccagcac tttgggaggc cgaggcaggt gaatcgcaag gtcaggagtt tgagatcagc  121020
ctgaccaaca tggtgaaacc ccgtctctac taaaaatgta aaaattagcc aggcatggtg  121080
gcaagtgcct gtaatcccag ctacttggga ggctgaggca ggagaatcgc ttgaacctgg  121140
gaagcggagg atgcaataag ccgagatcgt gccactgcac tccagcctgg gcaacagaat  121200
gagaccctgt ctcaaaaaaa aaaaaaaaaa gaaagaaaga atagaaaata tctgccctac  121260
ggggatggac atgctagaac atcaaagtcc aatggaactt tctgcactga tgaagtatgt  121320
atgtatgcac cagccacatg tggcttggga gcacttaaaa cgtgactggt acaagcgaat  121380
ttttcattta atttaaatga atttaaatct gtatttaaat agccatgtgt ggctagtggt  121440
tactttattg ggcggtgcag ctctctaaag gccaagagat acatcatcaa cttctctccc  121500
ttgacccata ttcagttctc tcccaccctg aaaatctcct ctcctaccca ggctcacatt  121560
tccagttctt ctcctcttgt tctccctcaa ccatcagccc ccgcaagact gacgtgaccc  121620
tgatgccgta tgaaatgcat tcttcatcct ttactcttac tcacctctgt gcggccctgg  121680
agaccagtga cctctccttt ctcaaaatac tttatttctg tgtgtttttg ttgttgctat  121740
tgtttttggg gggttttctt gagatggagt ttcactctca tcacctaggc tggagtgcag  121800
tggtgcgatc tcagcttact gcaacctctg cctcccaggt tcaagcgatt ctcctgcctc  121860
agcctcccaa gtagctggga ttacaggctc ccgccaccac ggctggctaa ttttcttgta  121920
tttttggtag agacggagtt ttgccatgtt ggccaggctg atctcgaact cctaacctca  121980
ggggatccac ctgcctcggc ctttcaaagt gctgagatta caggcatgag ccaccgcacc  122040
cagcctcaaa atgcttttga acttgactgt caggtatgcc attctccaca ccagtctcct  122100
cccatgtctg tgtcttctcc ctctccactg gggacccttg gcttttttcca cttcactcat  122160
ctaccctggg ttatctggtc ttccataacc ctgtcctctg ccacacctca cttattcacc  122220
caccacaata tttattgagt actcactagg ccatgaaaga tgctatacaa aaaaagcccc  122280
tgtcctcgtg gagctgacat tctagaagaa agcatgaata ataaatacga cttaataaac  122340
agtacggcca ggcatggtgg ctcacgccta tcatccaaac actaagagac caagatgaga  122400
ggatcacttg aatccaggag tttgagacca ccttgggaaa cgtactggga ccctgtctct  122460
acaaaaaaaa tattaaaaat tagctggata gggtaatgca tgcctgtagt tccagctact  122520
tgggaggaca aggtggaagg attgcttgag cctgagaggt caagtccgca gtgagctgtg  122580
actgtgcact gcacgccagc ctgggtgaca gagtgagatc ctgtcttaaa aataaataaa  122640
taaacaaaca aacaaacaat ataattccag agagtgaaga ggcaggatct ctttagctag  122700
gaagttgagg gatgttctct ctgagaaggc agaatctgag tttcaacctg aagaattcga  122760
agaggccagc taggcaaaag atgagagttg aaggaatggg gacggcagag gagacagcca  122820
atatagtaat tctcaataaa gcagaaagtg agcttttcct gctggcagaa cagaaaggaa  122880
gtcggagtgg ccagggtgtt gtgggacaag gtggtcagca ggagtcacat cacgcaaggt  122940
catgtggtca tggtagactt taaattttac tccaagcctg atggaagcca ttggaagatt  123000
ttaactaagg agtgacggaa aactggcatc tcaaactcaa catgtctaca acccagttct  123060
tgatctttga aaccttcttc ctccatcttc cccatctcca ttgacagcaa cttcatcctt  123120
cagttagctc aggccaaaac cctggagtca cccttgatac ctctctcctg ctccacactc  123180
agtctttcca ttggaagccc taggggctgc catattgttc tccatagcac ttcacaccgt  123240
ctgacatact atatcttttc ccactattgc tttgtccttg gtagcatctt taggcactct  123300
ctgaatatct ggcacatagt acgtgctcac taaatccttg ttgaataaat gaatgaacat  123360
cactccgtgg tcctttcaga accagagcca ttcttctctt tcttcaccac cgttgcccct  123420
caccccgccc aactagtcac aggagttgaa ggatgacaca gtagagaact gggattctgg  123480
agtcctgtgg ctggtctggg gttcgagttc ttactcagtg gtaggaacct ccatgtggga  123540
ttaacttatc tggtctttag tttcctcctc tgtaaaatgg gcctcaaact gccaaccgct  123600
gggatgcagg gaggatttga tgagcccagg caggctccct ggagcacagc aatcaatggc  123660
agctatatat aaaccggggc ctcttttgta ctcccactgc ctttgtccta gttccagccc  123720
tcattacacc agcctgctct tgcggctccc tcctaacttc tgctccatca ccaccaatct  123780
gtcctttcag ctgtcaggct tgtcttctga acgccaaccc taatcacatc ccttcctgct  123840
ccaaaacctt acatgactct cactgtccac aggacaagac ccagcctcta gttgacagcc  123900
tccactgtcc agcttaccca acctctcccc taccacatac cctgagtgga gccttctgcc  123960
tccatagggc tttcttagcc agagaagcct cccttatctt cctgttctcc tcctaattcc  124020
ttcttatcct tccagggagg aggctgtgag gtaatgcatc ttgggagcca gctgggattg  124080
cacagggtgg tgagattatc tgcatttccg aggcttgaac aagttaaggc aatgggaaag  124140
gtcacacaat gagaaaatgc agggccagga tttaacccgt ctgagatgtt ctgactgtgc  124200
```

```
tatgctgcct ccccggacat gagctctgcg ataatgctgt ccccaggctg taatcattcc  124260
ctctttcatc cctgcctcct ctatccctgg ggtcagaggg acttgtagtt gaatctctca  124320
ctcactcatt ggtgtggtct ctccctaaag cagggtggag tttgtcttag cgttatcact  124380
gcatccagca caacctccct ggtccaggct tatcagcgtt caactgcgtc aatgcagttg  124440
cctcctcctc aatctcccag cttccggcct tgccccctag agagatcata ttttaataca  124500
agtcagatta catccctcct cccctcagaa ccctccatgg ctcacacctt actcagagaa  124560
aaagccaaag tcctctccac aacccacaaa gccctgcacc atccatcacc tcactgcctt  124620
cgtcccctca caccctcccc cttgctcgct ctgcttcagc cacaccaact catctctgtt  124680
tctcaaatac accaggcatg gcctagctat taaatgcacg gtccagcctg gtgcatttga  124740
agaacacgga tgaattggtg tggctggaac agagtgagtg agggggagag cgggaggagg  124800
acctttgcac cagctggacc tttgcaccgg ctgttccatt tgcctagagt tttccctgac  124860
atattcatat ggctcactct cttgcttccc ttgctttctc ccagtcttta ttcaaatgtc  124920
tatttctctg cacttgtgct gtttgataca gtcaccgctg gccacatgtg gcctttgagc  124980
acttcagttg aaacacatga aagtgtagaa tattgaccag attccaagga aaaccatgtg  125040
caaaatatct tttatctctt aagatacagg gtctcgctct gtcttccagc ctggaatgca  125100
gtggcacgat cacagctcac tgcagcctca aaatcccaaa ctcaagtggt cctcccacca  125160
acagcctccc gagtagctgg gattacaggc acacaccaca atgccccgcc cattttttta  125220
attgttatta ttttttttaa tagcgacaag gtcttgccat gttgctcagg ctggtctgga  125280
actcctggcc tcaagcgatc ctcctgcctc agcctcccga gtagctgaga ttacaggcag  125340
gagcttttgt gcccagcagg tctacgatct tcttagaatg cttcaggctg ggcatagtgg  125400
ctcatgcctc aaataccagc actttgggag gccaaagcag gcagattgct tgagctcagg  125460
agttcgagac cagcctgggc aatatggtaa aaccctgtct ctccaaaaaa aatacaaaaa  125520
ttagctgggc ttggtggctc ccacctgtag tcccagctac ttaggaggct gaggaaggaa  125580
gatcacctga gcccaggagg cggaggttgc agtgagccaa gattgagcca ctgcactcca  125640
gcctagacaa cagggagacc ctgtctcaaa ataaataaat aaataaataa ataaataaat  125700
aaataaataa acaaacaaac aaacaaacca ataaatgaat tttacctgtt tctttttact  125760
tttttaatgt ggctactagc aaattttaat tttttttttt tttttttttt tttttgagac  125820
agagtcacgc tctgtcaccc aggctggagt gcagtggtgt gatcttggct cactgcaacc  125880
tccacctcat gggttcaagc agttcgcctg cctctgcctc tgagtagctg ggattacaga  125940
tgcccaccgc cacgcccagc taattttttg catttttagt agagatggag tttcgccatg  126000
ttggccaggc tggtctcgaa ctcctggcct caagtgatct gcctgcgtcg gcctcccaaa  126060
gtgctgggat tacaggcatg agccaccgcg cctggctata aaatttcata agtagctctt  126120
aatagatttc tcctgggcag tgctggtcta aacacttttt tttttttttt ttttttttga  126180
gacggcatct tgctctgtca ccaggctgga gtgcagtggc gcgatctctg ctcactgcat  126240
cctctgtcac ccgggttcaa gctattctcc tgccttagcc tcccaagtag ctgggactac  126300
agacacccgc caccacgccc agctaatttt tgtattttta gtagagacgg gttttcacca  126360
tattggccag gctggtctcg aactcctgac cttgtgatcc gccagccttg gcctcccaaa  126420
gtgctgggat tacaggcatg agccaccgca cctggctata aaatttcata agtagctctt  126480
aatagatttc tcctgggcag tgctggtcta aacacttttt tttttttttt ttttttttga  126540
gacggcatct tgctctgtca ccaggctgga gtgcagtggc gcgatctctg ctcactgcat  126600
cctctgtcac ccgggttcaa gctattctcc tgccttagcc tcccaagtag ctgggactac  126660
agacacccgc caccacgccc agctaatttt tgtattttta gtagagacgg gttttcacca  126720
tattggccag gctggtctcg aactcctgac cttgtgatcc gccagccttg gcctcccaaa  126780
gtgttgggat tacaggtgtg agccaccgcg cccggccctg taacactttt aacactgaac  126840
tgtttgcctt ccaggtggta aagagcaggt gcctttactg atagaaatgt caccactccc  126900
ttcatcccgc cagccccatg tcactgacgc gtcctttccc cttgctctgt ggtaactttc  126960
tcctaagcac tcatcgccct aacatctgtc atacaggtat acctcagaga cactgctggt  127020
ttggttccag gtcgccataa caaagcgaat attgcaataa agggagtcgt gcctttttttg  127080
gtttcccagt gcacataaaa gttatgctta cactatagtc tgttaagtgc atgatagcat  127140
tatgtctaaa aaaaaatgta cataccttaa ttttaaaatc catcaaggct gagcacagtg  127200
gcttgtaatc ccaacacttt gggaggccaa ggcaggagga ttgcttgagc ccagggattt  127260
gaaaccaggc aacaaagtga gaccccgttt ctacaaaaaa attcttttta aaaatagctg  127320
ggtatggtga cgcatgcctg tggtcccagc tacatgagag gctgaggtgg gaggctcact  127380
tgagcctgag agattgagac tgcagtgagc tgtgatcaca ccactgcact ctagcctggg  127440
ggacagagtg agaccgtatc tctcaacaaa aattaaaaaa aaaaaaaaaa aaggctgggc  127500
acagtggctc atgcctgtaa tcccaacagt ttgtgaggcc aaggtgggtg gatcacttga  127560
ggtcaggagt tcaaaaccag cccagccaac atggtgaaac cccgtctcta tgaaaaatac  127620
aaaaaaatag ccgggtgtgg tggtgcacac ctataagccc agctactcgg gaggctgagg  127680
cacgagaatt gcttgaacct gggaggcggg ggggagattg cagtgagccg agattgcact  127740
gctgcactcc agcctgggtg acagactgag actctgtctc aaaaaaataaa taaataaata  127800
aataaataaa taaatgtttt attactaaaa aagttaacaa tcatctgagc cttcagtgag  127860
tcctcatctt gctggtgaag ggtcactggc tcagtgttga tgggtgctga ctgatcgtgg  127920
gggtggttgc tgaagattgg ggtgcctgtg acattttctt aaaataagac aagaaagttt  127980
tccgcatcca tcgactcttc ctttcacgaa agatttctct agcatgagat gcttgttgac  128040
agcaatttta cccacagtag aacttttttc aaaattggag tcagttcttt caaaccctgc  128100
cactgctttg tcaactaagt ttatgtcata ttctaaatct catgttgtca ttttaacagt  128160
gttcacagaa ttttcaccag gagtagaatc catctcaaga aatcactttc tttgctcttc  128220
cataacaagt aacgcctcat gcattgaagt ttgatcatga ggctgcagca attcagtcac  128280
atcttcaggc tccacttcta actctagttc tcttgctagt tccatcactt ctgcagtgtc  128340
ttcctccagt gaagtcttga actcctcaaa gtcatccatg aggatcggaa ttgacttcct  128400
caaaattcct attaatgttg atattttgac ctgttcccac gaatcacaaa tgttcttttt  128460
gttgtttgtt tgttgtggat tgttttttta tttttaattg agttgaggtc tcactatgtt  128520
gcccagactg gtcttgaact cttggcctca agtgatcctc ctgccttgat ctccctaagt  128580
gctgggatta caggcatgag ccactggaac agccacaaat gttcctaatg gtatctagaa  128640
tggtgaatgc ttttcagaaa gttttcaatt tcctttgccc agatgcatca aaggaattta  128700
tctatggcag ctatagcctt atgaaatgta tcccttaaat cataagactt gaaatagaga  128760
attacttctt gatccatggg ctacagaatg aatgttgtgg ctgggcatgg tggctcacac  128820
ctgtaatccc agcactttgg gaggctgagg caggtgggta acttgaggtc aggagttcaa  128880
gaccagcctg gtcaatatgg tgaaacccca tcactactaa aaatacaaaa attagctggg  128940
```

```
catggtggcg tatgactgta atcccagcca cttgggaggc tgaggcagga gaattgcttg  129000
aaccctcttg aagacagagg ttgcagtgag ccaagatcac accactgcag cgacagagtg  129060
agactctgtc tcaaaaaaaa aaaaaaatgt tgtgttagaa gtcataaaaa caacattcat  129120
cttcttgtac atgcccatta gaggtcctgg ataaccagtg cattgtcagc agtaatattt  129180
tgaaagaaat ctttttctg gctgggtaca gtggctcgca cctgtaatcc caccactttg  129240
ggaggccgag gcgtgtggat cacctgaggt cgggagttca agaccagcct ggccaacatg  129300
gtgaaacccc aactctacta aaaatacaaa aaaattagcc aggcatggta gcaggtgcct  129360
gtaatcccag ctaccctgga ggctgaggca ggagaatcgc ttgaacctgg gagtcagagg  129420
ttgcagtgag ctgaggtcgt gccattgcac tccagcctgg gcaacaagag tgcgacttca  129480
tctaaaatac atatatatat ataacatgtt atatgtaata taaattatat atataacata  129540
tatgtaatat aaattatata tcacatataa catatatcat gtgttatata tatcacatat  129600
aacatatgtg ttatatatca catataacat gtgttatata tcacacataa catatattat  129660
gtgtatatat gtcacatata ttatgtgtta tatatgtcac atataacata ttgtgttata  129720
tatatcatat ataacatata ttatgtgtag tgtatcatat gtaacatata ttatgtgtag  129780
tgtatcatat ataacatata ttatgtgtag tgtatcatat ataacatatg tgtagtgtgt  129840
tatatataac atatattatg tgttatatat ctcatatgtt atatataaca tatattatgt  129900
gttatatatt atatatatat ttttttctga gtagatctca acagtgggct taaaatatca  129960
gttatccatg ctataaacag acgggctgtc attcagtctt cattgttcca tttatagagc  130020
acaggcagag tagattcagc ataattctta agaccttagg actttaggaa tggtaagtga  130080
gcattggttt caacttaaag tcaccaggag cactagctcc taacaagaga gtcagcctgt  130140
cctttgaagc tttgaagcca ggcattgact tctcctctct agctatgaaa gtcctagatg  130200
gcaacttctt ccaatagggc atttcatcta cattaaaaat ctattattca gtgttgccag  130260
cttcattaat aatctcagct agatcttctg gataacttac tgcagcttct ccatcagcac  130320
ttatcacttc accttgcact tttatattat ggggacacct tctttcctta aacctcatga  130380
accaagatct tctagcttca gatttttctt ctgcacttcc ccacctctct cagtcttgct  130440
gtgggcttgc tgtggattag gctttggctt aagggaatgt tgtggctggt ttgatcttct  130500
atccagacca ctaaaacttt ctccatgtca gcaagaagcc tgtcttactt tcttatcatt  130560
catgtgttta ctagagtagc ccttttaatt tccttcagta atttttcctt tgcattcaca  130620
acttggctaa cctctagctt atggcctttt gtttgtttgt ttgttttgtt tttgagacag  130680
ggtctcactc cgttgcccag gctggagtgc agtggtgcaa tcaccgctca ctgcagcctt  130740
gacttcctgg gaccaagtga tcctcccacc tcagcctcct aagtagctga gaccacaggt  130800
gtgcaccacc acacccagct aatttttta ttttctgtag agatagggtc tccctatttt  130860
gcccaagcta gtctcaaact cctaggctca agccatcctc tcacctcagc ctcccaaaat  130920
gctcggatta caggcatgag ccaccatccc tggccctatc tcagcttttg acacgccttc  130980
ctcactgtgt ttaatcattt ctagctttta atttaaagtg agagacgtgc aactcttctt  131040
ttcacttgag cacttaaagg ccattgtaca gttatacact gacctaattt caatattgtt  131100
atgtctcggg gaataggaag gcccaaggaa agcgggagag atggggaaat ggccagttgg  131160
tagagcagtc agaacacaca caatatttat cgatcaagtt tgccatcttc tatggatgtg  131220
gttcgtggca cccccaaaca atgactatag tcacatcaaa gatcactgat cacagaccac  131280
cataacagat gtaataatta tgtaaaagtt tgaaataccg taagaattac cagagtgtga  131340
cacagagacg caaagtgagc acacgctgtt ggaaaaaaaa tggccctgat agacctcctt  131400
gacacagggt tgccacaaat cttcaatttg taagaaacac aatatctaca aattgcaata  131460
aagcaaagca caatgaaatg aagtcttcct cggccggtgt ggtggctcac gtccataatc  131520
ccagcacttt gggaggccaa ggcaagagga tcccttgagc ccaggagttg gaggccagcc  131580
tgggcaacac agggagactc catctctaga acaaaacaaa acaaagcctg cttatattta  131640
ttgggtttac tctcagtctc ccccacacag agatagggcc tggcttgtta ttagtgctca  131700
gttgatgttt gtgaagtgaa atactaagga cttaaccact gcctgttctt tgctgttcat  131760
gccctgacag cttttatgtg ccagcacaga agaaaacaag gtgcaagaag agaatagtga  131820
tctctaagtc agaatttgag gaacccaaat tagtaccaga aagctgggag gagaagagaa  131880
aaataaagta aatcaaatta aaagttgaat gggccaagtg cagtagctca tacctataat  131940
cccagcactt tgggaggctg aggtgagagg atcacttgag gccaggagtt ctagaccagc  132000
ctgggcaata tagcaagacc ccatctctac aaaaaaaatt ttttaatttt ctgaatatgt  132060
tgttgtacac ctgtagtccc agctgcttag gaggcagagg tgggaggatc gcttgagccc  132120
aggaggttga ggctgcagtg agctgttgtt gcaccactat actcaagcct gggtgacaga  132180
ataagtccct gtctccaaaa ataaaaataa ataaattcat tttttgtaaa gttgtatgtc  132240
atggcccctg cctactctgg cttcatgact tgctgcttga acctcaccat ccaaatccca  132300
gtggtgacac catgtcattt cttgaatttg ccaagccctc tttcagtccc aagctctctg  132360
tcatggccac tctcagcctg gaaagttctt tccccactgg ccagatttct ccccctcatc  132420
tatggggaact tgacttgaag taggggtat cccaggccct ggactagtta acacgacctg  132480
ctgtgtgccc ctcaaagcca ttgtcttcct agctgagaag gcatcacacc tgcaacagat  132540
tcactcattg tgtgcatgtt tttcttaacc acttctcttc tgcatcagct ccatggggca  132600
gggatagtct catatgtcac tctacccagc acataggata cgctcagacg cccacttgtg  132660
gatggtggaa aaggtcagcc caacctaata tgcccatctc tcctctaggg gtaatcttga  132720
gaaaaaaagt tgggaacttg ctttgtgtta gtttaggatg acccagaata gatcctgaaa  132780
caagaattta gggcaatcct tgtgcaagta gttcatctga gaggtgaccc cagaagggtt  132840
ggagaaggag aggggaggtg gggcaaggaa gggtgagttg tcctgtaggc aactgagctc  132900
cgtcctactg ggagcccacg tggaactcac ctcttaagtg atccagaatg aagggtgagg  132960
gagctgcggt attgatccac caactcccag caatctttgg ttgagggctg ctcccttaaa  133020
gttcattccc tgggcctgcc ccagatttgg agacagccct aaggcaagag gtacagatac  133080
cagttggcca cagactgaag tgttaagacc caagcccctg gataaaactg aaaaatcaag  133140
ccagatgtgg tggttcccac ctgtaatccc agctactcag taggctaagg caggaggatt  133200
gcttgagccc aggagttcaa tgctgtagcg agctatgatt gcaccactgc attccagcct  133260
gggcatcaga gcaagacccc atgtctaaaa taaaaataaa ctgaaaaatc cccaagttat  133320
ttgctgtgac caaccttcca ttaaccacag accctctggt attcagcatt tcttgtccat  133380
tatatgaagt tctgatgaca gtctctttta ttgtattgtg ccttgaccac gcactgtaca  133440
tcacttagct ctgaaatgga catgttcagg aaacagggcc aggtgggacc ctgtgtttca  133500
acagcaatac ttttacaaat gaggtctcat gacagggtct tgctcggagg gtttctatgg  133560
aagcctcatc ccacctactg ctatcatcct tactaacttg catttacaaa agggactctt  133620
tttgaccaga ggcttggggt ctgtagctgc cttctagcca gctgatgctg gctggtccac  133680
```

-continued

```
acaagcagga tcacacccat tttttgttt tcttatttat ttctgaatag gttagcatac  133740
cggtaacctg tgtgcctggc attgtgctga ccacttttttg tcaacttact gaatcctcac  133800
aacccttgga ggtattgata ctattgttat ccaggttata caaaaggggg aaactgaggc  133860
acagagcagg gatgtccctt gcccaaggtt acccaactgg aaagtggcag atctgggatc  133920
tgaacccatg caggctgggc tcttaacact gaactacttt cctgccattt gttaaagagc  133980
cacaaaccag gccaggcacc atggctcacg cctgtaatcc cagcactttg ggaggccgag  134040
gcgggtggat cacctgaggt caggagttca agaccagcct ggccaacatg gtgaaaccct  134100
gtctctacaa aaatacaaaa aaaagtaccc gggcatgatg gcgggtgcgt agtaatccca  134160
gctactcggg aggctgaggc aggagaatcc cttgaacccg ggaggcagag gttgcagtga  134220
gctgagatca caccattgga gatcgcactc cagcctgggc aacagagtga gactctgtct  134280
caaaaaaata aaataaaata aaataaagag ccacaaaccc cgaaaggtct gccattcccc  134340
cagggcccca ggccacccca caatctattg tcattgtagg ttgtgaaata tactgaatgt  134400
caccccaacc ttgagccatg gggaagattc catttctctc attgcaacat ttgtgcaaca  134460
tgaaccatct gttgggggtc ttcgtaaatc accttttatc ccgtgaggca ggtactgtta  134520
agaccatttt acaggtgaca aaactgaggc cagtggtgtc gagtcacctg cctgtggtca  134580
cccaaccaat acaggacagc ttggaatccc aagcaccccc gccctgctgt ctgaccccca  134640
aaacccaccc tctgttctcc attctggctt ctttctttca gcatcttggc gacagttggg  134700
acggagtttg acctacggac gctgagggca gttcgagtgc tgcggccgct caagctggtg  134760
tctggaatcc caagtgcgtg agtttccgac cctgacaagg ggtttgctca cgggccccag  134820
gagccctcag tttcccctat gcagagcatc tcaggaggcc acatcctgcc accagcctgt  134880
gtgagggcag tctcttcttt gggactccct atagggaacc ccctaggaat atgactgtag  134940
ctccccatga gctcctgaaa gcaaactagg agccacaccc atttattgag cacctactgt  135000
ctatcgggag ccatgctaag caccacgtgt gatctcattc agtactcaca gccctatgaa  135060
gttgatagga ctgatgtctc tattttatgg agggggaaac tgaggctcag agtggctgaa  135120
acattggagc agggttttgt ggctgagaag tggcagaact aggagtgagc aagtgtgact  135180
ccaagcctgg gccgtaccac tggtggcaat gaccattccc atttaatgag tgcctgctgc  135240
gtgcagggca ctacagaagg actttacatg aattacctta tttcatcctc acagtcaccc  135300
agcgaacacc cattttacag atgagacggt tgaggcttaa ggaggttaaa ttactcacct  135360
gaattcttag agtggacagt aatgagctct aaaattcata ctcattcctt gctgctttct  135420
cattctccac agatacatct agtccccgtt taagggtggc tgccatatgc agggtcaaga  135480
ttaagtgtag gttgagccaa aaaaaaatgt aaaaagcaaa aataaaacag ggctgtcctt  135540
tttctatctt cttgtcttgg ttaataataa taatttagcc aggcatggtg gctcatgcct  135600
gtaattccag cactttggga ggatcacttg aggccacaag ttcgagacca gcctgggcaa  135660
cattgtgagg aacaccaccc ccaccccccc gccaatatct acaaattttt tttttttttt  135720
tagaaattag ccaggttgac tgggcacagt ggctcacacc tggaatccca gcactttggg  135780
agaccgaagc gggcagatag agcgagctca ggagttttaa gaccagcctg ggcaacatgg  135840
cgaaaccctg tctcaaaaaa aaaaaaaaat tagcaggcat gatggtgcac acctgtagtc  135900
ccagctactt aaaaggctga ggcaggagga tctgagccca ggaggtcaag gctgcagtga  135960
gctgtgatag caccactgca ctccagcctg gacaacagag tgagaccttg tctcaaaaaa  136020
acagacaaca aaaagtttaa aaacaaacaa tttataggct gggtgcagtg gctcatgcct  136080
ataatcctag cactttggga ggccaaggtg gatgggtgga tcacctgagg tcaggagttc  136140
gagacctgcc tggccaaaat ggggaaaccc cgtctctact aaaaatacaa aacttagccg  136200
ggcgtggtgg cgggcatcta taatcccagc tactcgggag gctgaggcag gagaatcact  136260
tgaacccggg gggcggaggt tgcagtgagc tgaaatcacg ccactgcact ccagcctgga  136320
tgaaagagtg aaactccgtc tcaaaaaaag aaaaaaaaaa attaaaaagc acttactatg  136380
tgccagacat tattctaagt atttccattt ttttaaagtc ctttatcctc ccaacaagcc  136440
tgtgaagtag tctcttttat tatcaccatt ttacatttta ttggcttcgt tcttccggtt  136500
cattgctacc caggtttaaa gagtaagatt tcccagagga tcaccagcag gatctttttg  136560
tagaaagaag acacttctat ccaaggtctc tgcaagatcc cagcagatgc ctgcatcata  136620
ttaaattaag ggccatccca aatctaatag tcaaaagagc caggtgcagt ggctcacacc  136680
tgtaatccca gcactttggg aggccaaggc aggacgattg cctgaggcta ggagttcaac  136740
accagcctgg gcaacaaagt gtgaccctgt ctcaaaaaat atatgtatat tataatagca  136800
gtagtaacaa gagtctctgt ttaatgacca cctatgactt accaggtact tcactgtgtg  136860
tgaactctct catctaatcg tatgagggag gtactattgc agtcccccatt tacagatgga  136920
gaagctgagg tttggaattc actagtaagt ggatgactag gtcaggttcc cttgaagcgg  136980
atacttaggt gggtgttcag atgcacctgc tttattgggg gacggctctt gggagagaca  137040
gcaggagatc agcagggtgg ggctggggaa tggatagagc agggacgcaa tttcagctgg  137100
agtgtgtgtg acaccagagt tgtcctccaa tgcatggcaa ggatgccggc cttttgtact  137160
tctatagtca gtcactgtgg atgggaggta gagacgcagt agctcccagg tgagatagct  137220
tttgatcacc aagggcaatt ctactaagaa gagaggcagc tgggaggcat tagcaaccaa  137280
catccatagc agctggaggg cgggtacacc agaaagaaaa tgggatcttg gccagacacc  137340
aagagtatcc agcaccttaa ccactgcacc acactgcatc tgttagcacc cacattacat  137400
tttttttttt tttttttttt tttgagacgg agtctcgctc tgtcgcccag gctggagtgc  137460
agtggcgaga tctcggctca ctgcaagctc cgcctcccgg gttcacgcca ttctcctgcc  137520
tcagcctccc gagtagctgg gactacaggc gcccgctacc acgcccggct aatttttttgt  137580
atttttagta gagacggggt ttcaccgtgt tagccaggat ggtctcgatc tcctgacctc  137640
gtgatccgcc cgcctcggcc tcccaaagtg ctgggattac aggcgtgagc caccgcgccc  137700
ggccagcacc cacattacat ttttaagccc ttggagtggc atggccccctc gagctatcct  137760
gacagcttcc ctcttcttact gtggtctcca cccatcaaga gccatgggaa gttcctgcaa  137820
tcaagaagca aagcctcagg ctatatgttt gaaccttcat tttgatcata gactttccta  137880
gtagatacca tagtggttac aaacatagga tgttgtcatc gttcagacct gagttaatag  137940
cctcaagaaa aaaatggtag tggaaccagg tatggtgaag tgtgcctgta gtcccaccta  138000
ctcgggaggc tgaggcagga ggctcgcttg tgcccaggag gtcaaggctg cagtgagccg  138060
tgatcatgcc actgtattcc agcctgggtg acagagcaag cccatctcaa aaaaaaaaaa  138120
aagccaatga taggcagaga aatactaact aaggctcttg ctctgtcgcc aggctggagt  138180
gcagtggtgc aatcacagct cagtacagcc tcaacctccc cagactcaag caatcctacc  138240
atctcagcct cccaaatagc tgggactcca ggcacacagc accatgccca gttaattttt  138300
ttgtattttg tagagacagg gtttcaccac gctgctcagg ctggtctcaa actcctgagt  138360
tcaagtgatc cacccgcctc agcctcccaa agtgctggga ttacaggtgt gagccaccac  138420
```

-continued

```
gcttggccag ctattattat tattaacatt cttcgagtct tacaacagtg gaacttttag  138480
tgcaggatgc gaatttcagt attaacccct tcctctccca aaaggatttg aagcccagag  138540
taattcagcc gccatgaatg aaccatttgt tagatgagag gctactggag gctgagcttg  138600
gtaggataag agcttgcatg gggtccctga ttgatgacaa tacccccaga tttaggtctt  138660
cagatgccca gttgggtgtg tcttctgttc cactgtgtcc cttcggggac tgttccctgc  138720
cttctttctt tttgagatgg aatctcgcac tttcacccag gctggagtgc aatggcgtga  138780
tctcagctca ctgcaagctc cacctcccgg gttcacacca ttctcctgcc tcagcctccc  138840
gagtagccag gactacaggt gcccgccacc acgcccagct aatttttttg tatttttagt  138900
agagacgggg tttcaccata ttagccagga tggtctcgat ctcctgacct cgtgatctgc  138960
ccgcctcggc ctcccaaagt gctgggatta caggcgtgag ccaccacacc tggccccctg  139020
ccttcttatt caccaccatc tttctgaatt gggttgctca gaacagagaa agcaacatca  139080
gcacatgggc aaacatgggg cttcatttca gatggacctg ggttcaaatc ctagttctgc  139140
ctttttttttt ttttttttt tttttgaga cagagtcttg ctctgtcacc cagactggag  139200
tacagtggcg tcatcttggc tcactgcaac ctctgcctcc caagttcaag caattctcct  139260
tcctcagcct cccaagtagc tgggattaca ggcgctggcc accatgccca gataattttt  139320
tgtattttta gtagagatgg ggtttcacca tgttggccag acttgtcttg aactcctgac  139380
ctcgttaatc cgctggcctc ggcttcccaa agtgctggga ttagaggcgt gaaccgccgc  139440
cgcgccctgc ctagttctgc catttctcat gcattctctg ggtgaatcac agcatctctg  139500
ttagccttgc ttcccacttc tgtaaaatga gagtgacttt acatgtatgg ccacctcagg  139560
ggcttgtcac tagaagccag tgaaataatg ttgagtctgg ttccttgggg ttgaaattgg  139620
gaccgccaac cgctttccta cccagagcag caactagcct atatggcggc cttttatgaa  139680
tgaggaaaag acaccgcctc ttggcagaaa aaaaaaatta agaaaatggc tccctcttct  139740
gggtgcaagt tgcccaacac ccaggaatat ggctccaaaa gcaatggact cccacccctt  139800
tcttgcccaa aagatcatca aatggaacag catgtcaaat acctttatta agtactttaa  139860
agttggctgg gctctgtggc tcatgcctgt aatcccagaa ctttgggagg cagaggctgg  139920
aagatcgctt gaggtcagga gttcgagacc agcctggata acatagtgag accctgtctc  139980
tataaaatat atatatagat ttatttgaga cagcgtcttg ctctgccact caggctgggg  140040
cgcagtggca caatcatagc tcactgcagc cttaacgatc ctcctgcctc agtccctaga  140100
gtagctagga ctacaggcat gcaccatcat gcctggctaa ttaaaataaa taaataaata  140160
aatactttaa agttaaaagt gctttttaaa aaataataag gccaggcgtg gagactcacg  140220
tctgtaatcc cagaactttg gaagaccgag gcgggtggat cacgaggtca ggagatcgag  140280
accatcctgg ctaacacggt gaaaccctgt ctccactaaa aatatgaaaa attagctggg  140340
cctactcggg aggctgaggc aggagaatgg cgtaaacctg ggaggcggag cttgcagtga  140400
gccgagatgg caccactgca ctccagcctg ggcgatataa caagactctg tctcaaaaaa  140460
aataaataaa ataaataata ataataatag gggccaggta tggtggctca cacctataat  140520
cctagcactt taggaggctg aggagtttga gtccttggag accaggggtt tcaggccagc  140580
ctgggcaaca tagcaagacc ccatctctac aaacaagttt taaaacttag ccaggcatgg  140640
tggtgcatgc ctgtagtcct agctattgca gggactgagg caggaggatc acctgagccc  140700
aggaggttga ggctgcagtg agctgtgatt gtgccactgc actccagcct gggcagcagt  140760
gcaaaaccct gtctcaaagg aaaaaaaaaa cctaggaagt gttgttccca tgataaggat  140820
cagcctccgt gtggtgcttc cttcaccatt gcccaatccc caggctcctg ggtgcttaat  140880
attccctcag gaacacacct gctttgtctg ggagagacct gggcgtcttg gtggcggggt  140940
ttgggggtac ttgctcatgg gcttatgggg cctctctctg tgtcccccca ggtttacaag  141000
tcgtcctgaa gtcgatcatg aaggcgatga tccctttgct gcagatcggc ctcctcctat  141060
tttttgcaat ccttattttt gcaatcatag ggttagaatt ttatatggga aaatttcata  141120
ccacctgctt tgaagagggg acaggtaggt ccacggagca tgatgcatct ttccagtttt  141180
ctccttcagg gacaagctct tgggaggatt aggcaggggt gtgcttcttt ctcctggcag  141240
ctgggaggac cgtctccttc agagagcact acaggagagg cagtgagtga aatagcctct  141300
gagatcttag ctgttgaaag gggtggggtt ccacagaagg tgacccagca gagaaagagt  141360
ttatttggga atgatcccag gaagcaccat cgggggaatg aggaagtgag cagagaaaga  141420
agggatcttt taaagagtgt gctatcaagc gggttaccac ttaaaactgg gactggatcc  141480
ccctgggcac ctctgggaga cagcaaagaa cacacaactc agctggtcac ggtggctcac  141540
gcctgtaatc ccagcacttt ggggggccaa ggcgggtgga tcacctgaga tcaggagtca  141600
gagaccatcc tggccaacat ggtgaaaccc catctgtact aaaaaataca aaaattagct  141660
gggtgtggtg gcaggcacct gtagtcccaa ttactcagga ggctgaggca ggagaatcac  141720
ttgaacccgg gaggcagaag ttgcagtgag ccaagatcac accactgcac tccagcctgg  141780
cgaaagagtg agactccatc tcaaataaat aaataaataa aaatataaat aaaaaaagaa  141840
cacacacctc agagccgtcc cagccaaggg gcaagggagc tggggtattt atacactggc  141900
ttctttttga cattggtgag gactgctcct agagtgggaa ttaatgcctg gcacatctgg  141960
ctgagtggaa caggtattct gggtgctttc agacctcgac cagtcctgac ttctaaagca  142020
agcaagaagt ggggagagtt gggccagaaa agggttattg cctcaatgca ttgtgagtgg  142080
taccttgtgg aaggtgagag acagagaaga ttccaggcac aggtgccatg ctaaacgata  142140
gttctcattt attataggaa cccatggatt tattttgttc tctgccctga gtgctgggtg  142200
agagtactgg atgagtcctc ctggtctccc ccaaccccca ggatgtacca gagatacccc  142260
aattgggagt cctggcacca accaatcaga acctagcact cagcagcatt ctgcccctcc  142320
ctgactatgc ccacattaac ccttcagtgg ctgggtctgg gggtagggtg agccccggaa  142380
aagccaggca gcgcagagac actctcccag ggctcagctc tgaaccagca gtgtggaagc  142440
agtgtgtcca ccacgatcca cactcaggaa ccaaatagcc cttggatacg ttttcagtta  142500
aatctttgcc atccaaactc tagctgcttg ctctctaaag ctccagaatg aaatggaatc  142560
aagtaggaag ggatgccttc agtatttcag tatttggacc actggccatc tgggtgcaga  142620
cagactgaat agcagttctg gttctgatga tttgggtcaa gggagctgtg aattgaagga  142680
gtggatagaa ggaatcaaga agcccaaagg ggaacccagg tgggcagaga aagaggtttc  142740
aggcccctta tttgggaaag gcagccacag aagaagattc tgtctgggag tggatttcca  142800
cccaccctct ccacccagtg acccccaagt ggatccgcag aggcagcccc tgagccctcc  142860
ctccccactc ctccccacgg ggagggaaaa cccactgggg aaggtttatt tgcaatggtt  142920
ggaggtttgg gttttttttgt gggttttggt ttgttggttt ttttttcct cttttctct  142980
tgctcctcct gtctctttct ctcctgggct tgtgaagttt gctcaatatg gaatgtccta  143040
attatttctt tccccgatga agaaggtgtt aattgaggca gagctatttc tgctcctggc  143100
ctcgtcaccc aggcggaaat gcgagagaga gagagagaga gagagagaat gaatatgggg  143160
```

```
cagggcctct tggaaaaatc agccgtgagc agagaaacca ggactcctgg atcctaggtt  143220
tctgtgaagt tttattttat gtttttctac cctagactag ctaaaggaga agaggccatg  143280
gggttggctt gggtccgagt ggggttttga ggggacagat gtgggtggtg ccaccagagg  143340
ggaggaagcc tcgatttagg agaaagactg aaaagctagc tcacgattaa aaatataaga  143400
cgtgtgagta agagacagat atatacagac acccaggcag tgggttaatt ttaaaatgta  143460
tttataaccg aattcctcag acactctgga cgcttgtttt tctagaagca acgctcagag  143520
tgtttcgtgt cggtggttgg ggggttgagg gggattgcaa agctgctaaa gatagacccg  143580
ttttcagtag cattcctcag tgtcgggagc ccagttcctg tgtgcccagc accgtgccaa  143640
tcgcttagaa ggaagcaaag ataaagtgga aggcttcctg ctttctaaga gcttccaaaa  143700
tagttagagg aaacaagacc cctcatttgc agccattttt aacagtgaag gctaatgtgt  143760
gattataccc acgcccccct aaatatgaaa attcagtagc tattgtatgc ctgaaagggg  143820
ccaggtgcag tggctcacac ctgtaatccc agcactttga gaggctgagg tgggagtatc  143880
ccttgaggcc gttagtttga gaccagccta ggcaacatag ccagaccctg tctctgctaa  143940
aataaaaatt taaaaattgg ccgggtgcag tggctcacgc ctgtaatccc agcactttgg  144000
gaggccgagg caggcggatc aaaaggtcag gagttcaaga ccagcctggc caacatagtg  144060
aaaccccgtc tctactaaaa atacaaaaaa aataaattag ccgggcatgg tggcgtgtgc  144120
ctgtagtacc acatacttga gaggctgagg caggagaatc acttgaacct gggacataga  144180
ggttacagtg agccgagatc acgctactgc actccagctt gggcaacaga gtgagatttt  144240
gtctcaaaat aaaaaaattt aaaaattagc catgagtggt ggtacatgcc tatagtccta  144300
gctactcagg aggctgagga agaaggatca cttgagccca ggaattggag gctgcaaggc  144360
tgcagtaagc tatgatggtg cccgcactcc agcctgggtg acaaagtgag accctgtctc  144420
aaaaaaaaaa aaaaaaagag agagaggaag gaaagaagga aggaagggag ggagggaggg  144480
actggggctg tgttaactgg gctacacaaa gaggctacat ggagggtggg aattgagcca  144540
gacttggaca tggcgtggag acagagaaga ttccaggcac aggtgccatg ctaaacgata  144600
gttctcattt attataggaa cccatggatt tattttgttc tctgccctga gccttatgtt  144660
taaaagattt ttgccttcca acctgtattt atcaaataat agttcatgta ccaagtccag  144720
cataagtgag gaaggcgttt ccaacaactt aagttcatgg cgaggctaga cttggagttt  144780
ctattcagcc agagcttgaa aggccaacaa gattcattca ttcagcattg gtttatttcc  144840
ctctgctgtg tgctcagtca agggagcaga gaattggtgc tgcgaagtct gtagcacata  144900
cattgagaga tatttttgtt gagtaggaag cttgagttta cacacactca gctgtttgtt  144960
ttcttgtccg acaatgccac ggtcgtcttt gaaaaccttc aaaagcatcg ctcacagaat  145020
aaggtcctct cagacccgct gtgctggtaa aatgaggaca ctcccagatg tgagctttcc  145080
tgcctcccta ccccatcaat accttaagat ttggactgac ctttagcgtt cagcctgact  145140
gccacctccc caggaagctg tctttggttt ccagcaaaag gggtgtctgt tggcacgttt  145200
ctctctcctt gtggcatttt cacagcctgc ctcctgctat ttggggagaa agctcagctc  145260
ctgttcctta cccttaggca agggtaggaa ctgtgtgtac tggtgtccct cacccccaga  145320
acagctccct gagcccagta catcccaaga agaaaaaaat cagcaaggct tataggagaa  145380
taacacaatg cgcttgacaa atttgtccta atggatgtcg gaagaaggct gcacttacca  145440
gctacaccat gcacacggca catttactaa aactgactat attatggacc ataaagtttg  145500
tctcaacaga ggtcaaaaag ctgaaaaaaa tacaaataca aaacatattt tctgaccgta  145560
atgcaattaa gctggaaatc agtaacaaaa agagaactct aaaagtgttt gcagattaac  145620
agacatgcct ctcatttatg gatgaaatga tatgatgtct gagctttgct ttaaaaatat  145680
tctaggctgg gtgcagtggc tcacgcctgt aatcccagca ctttggaggc cgaggcgggc  145740
ggatcacttg aggtcaggag ttcgagacca gcctggccaa catggtgaaa ccccatctcc  145800
actaaaaata caaagattat ccaggtgtgg tggtggccac ctataatccc agctacttgg  145860
gagcctgagg caggagaatc ccttgaacct gggagtcgga gattgtagtg aggtgagatc  145920
atgccattgc actccagcct gggtgacaga atgagactcc gtctcaaaaa aaaaaaaaaa  145980
aaaaaattct agtggcaagg caaagtgttt ggaggggata cagaggaata gatgaaacaa  146040
aatttgccag aagtaaatag gtaagtgtct aaattggtga taggtacatg gtgaatcatt  146100
atattgtttt atacttctct ctcgctctct ctctcccccc gttctctccc tgtcttcctc  146160
tcccctctgt cttcatatat atatatatat atatacacac acacacacac agacacctaa  146220
taagtttttt taaaaaacaa atacatctaa attacccata ggtcaaagaa gaaataataa  146280
tggaaattag aaaatatttt acttgaacaa taatgataat gcatgacaaa atgttgagat  146340
gcaggtaaag ccacacttaa aggcaattta tagccttaaa ggcagttaat ccatccatct  146400
caaaagttta ggaaaagaat agaaaaaaaa aaaaaactca tggaaaacat aaagagaaaa  146460
gtagtaaagc tcagagaaga aattaatcaa tagaaaacca ataatagacc cccaaagcca  146520
aacattgatc tctttgaaga ctgatcacgt ttgtcccaaa agttattcgt tccaacagca  146580
ttatagagtc actggtccct atttctcaga gctggttttc cctgctcctt cccctgactt  146640
ttctcccctt cccttttgta gatgacattc agggtgagtc tccggctcca tgtgggacag  146700
aagagcccgc ccgcacctgc cccaatggga ccaaatgtca gccctactgg gaagggccca  146760
acaacgggat cactcagttc gacaacatcc tgtttgcagt gctgactgtt ttccagtgca  146820
taaccatgga agggtggact gatctcctct acaatgtaag tgatgctggg acagtgtgtg  146880
tggacaatca gagtctcagg gaggtggcct cctgggacca gtgagactcc aaggctgcaa  146940
tggagggacc ctgagctggg aaaggcagcc caaggacaac acagccccac tgaagctggc  147000
ctgaggctca ggcttttgaa gattacaggg gctcatgagc agaactctaa ctatagggca  147060
tagaagtctg gagggccccc agatgcaaca tcatttttca ttgtgcaagt gtttagatat  147120
aattttagat ttttgaatac ggaaaggtta tgtgatccaa aaaccaacac agataaaaga  147180
tagagtaata tctttggacg taggcgaggg gtccctgccc tgaggctcac ccagtccttc  147240
tccagccata ccactccccg tgggatgaga agttcctgga gccaagggga tgtgtctacc  147300
aagagcttgt gccccacttt gtaggccatg ttttaagtta ccaggatcct ggaattccct  147360
gcccatggcc agattccatg aacttgcgtg caattctcat atggatctgt tcgtaaccca  147420
actgagggcc aaggacatcc gaggggtggc tgttaacaca aatgtggcca gagcttggat  147480
gtacaagctg gaatgcccac acatatgtgt ggagcccctc tggcaggaca gagccatgac  147540
taagaagaga aagggacagg acagggctgg ctctccccac accttgaccc agtgcagata  147600
tccggattct aaattccacc ctgaccttcc aaagtgtaaa ggaaggtata tttgcaaagt  147660
agaagcacac agcatgtttt atttagttac cttttcaata tttccccgta gtatgtggtc  147720
tgcttttgta ctcttgccct agatcttaaa aatgttaggg atgtttctgg aaagatgtat  147780
ccctgccccc acttgcatgc tacttcctct tcccacaata tgcaacccct ttagttcctc  147840
agaatatcct tccaatgttt atttatgcaa ttataattat aagcataatc gaatctatgt  147900
```

```
cctcccccct ctttcttatc ccaaggagta gcattctata catgctgttc aattctgtga  147960
tttttgtttt ctcataacca cacgttctag agatctttcc actgcaggac atggacagtc  148020
tcttcacggg tgcacactag tatgcccagc taatttttgt agagacaggg ttcttccgtg  148080
ttgcccaggc aggtctggaa ctcctgggct caagcaatcc tcccgcctct gcctcccaaa  148140
gtgctgggat tacaggcgtg agccaccacg cctggccttc tttattcttt tgcacagctg  148200
catagcattc tattgtgtgg ctgcccatag ttttatttgt ttgccattaa gagaaatgct  148260
tgactggctt cctgtccact gacatggaac atgatgctgc tctgccagga gcatgttgca  148320
cgtacctctt catactttg cagatatagc taggggggttg gagggtctcc attcccagaa  148380
gtgggattgc aggatcaaag actaaatgca tttataattt tatttttggg gaagattttt  148440
gttttgtttt tttggagaca aggtctccct ctgtcgtcca ggctggagcg cagtggtgta  148500
atcatagctc actgcagcct taaactcctg ggctcaggtg atcctcccac cccagcctcc  148560
tgagtagctg ggaccacagg cacacaccac catacctagc taattttttaa gaacaatttt  148620
atagagatgg ggtctcacta tgtttcccag gctgctctca gactcctggc ctcaagcaat  148680
cctcctgcct cagcctccca aagtgctagg attacaggtg tgagccactg cacccagcct  148740
aaatgcattt ataattttga tagatattta ggtgtgcaag ttttaaaccc cactctgtcc  148800
tcaccacagt tcaccttccc tcacctacta tgcaggtaag cagtccccag gcaggtcact  148860
tgtcagcagc tggagtgggg cagagccaag gattcaggat caaacacaag gatgccacaa  148920
ctgtagtgac cccatagagc accctggggc tgctccatac acacagctct gttgaccagt  148980
ggaggtctcc tcttcacctg ccctaagggc tgaaattacc attgaagttt aggccagcgg  149040
ttggcctgac ccgggagcaa tacctggctt cctcctcctg tacatagaga agctgaactt  149100
tcctcttggt cctagtgtat gttccttaac aacccattta tgcctagtgt tccattattg  149160
gaatgctaat cctgtgggag ttatttacat cctgctgctc aaggtcatca ctaaggtcgg  149220
atttttcaca cacacaaaaa ttgcaacctc cggcataaat gggttaagga atttccccac  149280
ttgtgggtgg agggagattt gcaaaaactc atccttgtaa tcctgatcaa caaaggcccg  149340
ttttagttgg gagtaggcag caaaaggagc cacatgaaca gttgcgcctg tcacgcactg  149400
cacaagaatg tcattcatat catagacaac atacgatttc tactgttatc ctgataattt  149460
attgacagaa aaaaggatgt ggggaaggga catggtgttc taatttgcat gaaaacctcg  149520
tctgagtgta gcatctctgg gaacatgcag cagatccgag ctcaggccct ctcttggccg  149580
tcacctgcaa acagcttgga caaagggtca gcccaattgg ccaaaactca ctggggaatt  149640
tttgtgggtt ctaggttttt actttgcaag gctggtgtga gaggaggttc cagcaggaaa  149700
tgaaccctcc tgagagggaa agagactggg aaatggagaa ggctgggaac tcagggagag  149760
aatgggagtg gggaatggga gctgaaaaaa attgtgagca taaaaaaggg atatgtcaca  149820
gggttggatg accagagaaa gcgtctgggg gttcagatta agatgctggg ggcgtgccca  149880
gtggtgggac aggaagcatg aatttccaga gggctcggtt ataaacatca ttgtccaatg  149940
ggtgtttccc ttggaagcct ctaagcttag agctaagcca cctctgggga cacaaactga  150000
gtggttaaga gcagagactc aggtgtcagc ctgtctgggt tccttccgac tcttccactt  150060
ccttgctgtg cagccttcgg caaggtgctt ggcctctctg tgccactatt tccacatgtg  150120
caaaacgaag agaagcatag tcccacctca caaggcacga ggactaagta aggtggattc  150180
gcatgaagtg tttagaactg atcctggccc ggggtgacct ccgtgtaagt caaattcccc  150240
accctgcatg gtgttccttt tagaaatgtg catgaatttt tcattagaac agctccagca  150300
gtgcctgagg aagtggagtg aggtgtgaga ggtcttactt tattcccctc gctggccctg  150360
ctattaacca ctaactcaga gtagctttct agcactttcc acacatttac atcccaccct  150420
cgtcctttgg ttagcagccc atgcaatgat ttggccttaa tgtgaaccta gaacacagct  150480
tctcgcccag ggatgatttc tgcccccagg ggacacttgg cagtggctgc agacattttt  150540
ggttgtcaca actggatggg aagaaggagg atgctattgg catcaagtgg gtaaaggcca  150600
cggatgctac tcaacattct acaatgcaca gcatccccca cctctgcccc accatagaga  150660
atgatccagg cccaaatgtc agtaaggttt ctgtcaggaa accctgggtc agaagaccaa  150720
ggttccttga ggacggggat gccttatact gcaatcagct gtcactctct gcctctctct  150780
ggggctgctg tgatcacctg gcctgcatgg acaaccccta ggagcagccc ccatccagtg  150840
cctggagaag tcagtggata aataccccag ctccctccct gtcgggcgtt ttgctctgcc  150900
ctgcatctct ccagtgggat caggctctgg ttgcccgcag ggttaacctg gtcacgtaca  150960
caccccttcac ttgccacctt cccttccctg tctggtattt cctgggatga acttttagat  151020
ttatttcctg gggctgctat aatgaagcac cacagactga gtagcttaaa acaacaggaa  151080
tttatggtct gacagttctg gaagccagaa gtccaacccc aagatgttag cagagctgac  151140
aacacgcccc tcaaaagcct ccgggggagg atccttcttt gcttcttcct ggcttttgct  151200
ggtttcccac aatctttggg attccttggc ttctagagcc ttcattctcc attccagtct  151260
tctgtcatct aatagcatcc tcccagcccg ggcacagtgg ctcacgcctg taatcccagc  151320
actttgggag gccgaggcag gcagatcact tgaggtcagg agtttgagac cagcctggcc  151380
aacatggtga aaccccatct ctactaaaga tacaaaaatt agccaggcgt ggtgggcggg  151440
tgcctgtaat cccagccact tgggaggctg aggcaggaga atcacttgaa cccgggagat  151500
ggaggttgca gtgagccaag atcatgccac tgcactccag cctgggtgac agaatgagac  151560
tccgtctcaa aaaaaaaaaa aaaaaaaaaa agaaaaagaa aagcatcctc ccttcgtgtg  151620
tctgtgtgtg ttctcctctt cttagaagga catcagttgt attggatcag aacctaccct  151680
actccagtcc aacctaattt taactaatta cgtctgcaat taccctattt ccaaataaga  151740
tcacattctg aggtaccagg gggttaggac ttaaacattt ttgtgtgtgt agcaggagga  151800
cgtaattcca tttataactc ctcctaaata aaacgacttg catgtgaact cttgtctggg  151860
gcttcccaaa gtgagataac ccctctctct accccctaaaa caacgagtag cgtctgtcaa  151920
tgccagggtg caggggctaa ggtgcccatc tttgagtttc tgctgaggag gacacagctg  151980
ctacgttgga gcactcttgg gttctgcctt cgtgcccagc catctccctt gggctagccc  152040
tgccctgggt ctatcctaga atgagcctcg atctgtttgg ccataggcaa gcagagtgtc  152100
tggaaatctt tgtcctccat gactggtgct ggagccgaag ccagtgggtg tggccttgcc  152160
agccaactcc atttacccag ctctgaacaa gctagtagtt gagatcaacg gagagtccag  152220
acagtcgctc caagcatctt ggaatccatg gacacaggtg taccgcagag gcttcccacc  152280
tgggtaggca gccctttgta agatcctggc accacattta ttctcttaac atcctttcag  152340
ttatccagta atcatttatt gagcacctac tgtgtgccag gcaatgatta ggtgattgga  152400
gacactgcaa cgaagaagac agactaaaat ctccaccctg gtaggagaga cagatgcaaa  152460
tggtaaacat gataaataat caatcaccca gaaagcagga gacactaagc aaatgtgtat  152520
gtactatggg aagcccaata ggaacgaaag ctacacaaga gaacaagtga tgggtggttc  152580
cttagtctag gtcaggcaat cagggagggc ttctcagagg aggtgatgtt tgagcagaga  152640
```

```
aggagggagc caggcagatg ttttggaaac agcattctca gcatggagaa cagtggcagc  152700
tcacctacag gatgtgtttg attcccttcc agattttgta ttcgtttctt gtttttctcc  152760
cttggcttcc tggtttaaat gccttttgaa gaaatctaag ctcaactaat cagcgatgct  152820
gttgaaggtt tatatcagga tatgcatccc agagttattt acaaaattag aacaaaactg  152880
gaagcaattg aaagcctgac aataggagat cagttaaata ccgtatggtc cttccgtatg  152940
atggcatatt atgtcatcat taaaaatcgt ctgctgggag aatattaagg atacagggga  153000
aaggctcacc atataatgat gagtgggggt gctgggcgca gtggttcatg cctgtaattc  153060
cagcaatttg ggagtctgag atgggtggat cacttgagcc caagagtttg aggccagcct  153120
gggcaacaca gtgaaaccca atctctacaa aaaaaaaaaa acaaaaatac aaaaatcagc  153180
caggcatagt ggcgtacatc tgtagtccca gctactcagg aggctgagac aggaggatag  153240
gatcacttga gccctggagt cagaggtggc aataagccgt gatcacgcca ctgcactcca  153300
gcctgggcaa cagagtgaaa ccctgtcaaa aaacaaaaca aaaaaaatga tgagtgggag  153360
aaacaagttt ttaaacaggg atcaaggagg ccaggcatgg tggctcacac ctataatccc  153420
agcactttgg gaggccaagg caggcagatc acctgaggtc aggagtttga gaccagcctg  153480
gccaacatgg cgaaacctca tctctactaa aaatacaaaa attagccagg catggtggcg  153540
ggcgcctgta atcccagcta cttgggaggc tgaggcagga aaatcgattg agcccaggag  153600
gtggaggttg cagtgagctg tgatcatgcc actgcactcc agcctgggca acagagcgaa  153660
agctgcacga gagaagaagt gatgcatggt tccctagtct aggtcagcca atcagggagg  153720
gttcctaaga ggaggtgatg tttgagcaga gaaggaggaa gccaggcaga tgttttggaa  153780
acagcattcc cagcatggag aacagtggca gctcaccctg tctagaaaag aagaaatgat  153840
aagaggggaa aatgagtttt taaaaaggaa tcaaggggag gtaaacctta tgatctcaaa  153900
ggtacaaata tgaaaatata agtaaagaaa aactggagga cactgtacca agctgacctt  153960
cgggtggtgg gatttgggaa tcttgatatt ctcaatactt ctttgtatct tcaaatttct  154020
ctatgatgat cacagtttac tttttttttt ttttttgag atggagtctc actctgttgc  154080
ccaggctgga gtgcagtggt gcgatcttgg ctcacttggc tcacctctgg ggttcaagca  154140
attctcctac ctcttcctcc caagtagctg ggactatagg catgcaccag catggtcagc  154200
taattttttg tatttttagt aaaaatgggg tttcatcatg ttggccaggc tggtctcgaa  154260
ctcgtaagtt caagtgatcc accaacctca gcctcccaaa ttggcttgag ccaattaaac  154320
ttgtcttgct aaatggttag cggggagaaa gaagaaggtc tcgggtcatt cctagaccag  154380
gaggcaggga gaaagggagg agaatgaacc tttcttaggc aaacagtgtc ctaggtgtcc  154440
ttatcttaca taatctgtcg agagagtcac actaaaataa atcattgatt gattgattga  154500
tacatcaata ataaatggcc agccttggtg gctcacatct gtaatcccag ctacttagga  154560
agctgaggtg ggaggattgt ttgagacaag gagttcaaga ccagcctggg aaacacagca  154620
agactcatct taaaaaaatt ttttttttta attagccaga tgcggtggct cacgcctgta  154680
atcccagcac tttgggaggc cgaggcgggt ggatcacgag gtcaggaatt cgagaccagc  154740
ctggccaaca gggtgaaacc ccgtctctac taaaaataca aaaattagcc aggcgtggtg  154800
gcacacgcct gtagtcccag ctacgcagga ggctgaggca gaagaatcat atgaacctgg  154860
gaaacagagg ttgcagtgag ctgagatcac gccattacac tccagcctgg gcaacaagag  154920
caaaactaca tctcaaaaaa aatgtttttt aattagccgg gtgtggtggt ccatgtctgt  154980
agttccagct acttgggagg ctgaggcagg aggattgctt gagcccagca gttcaaggct  155040
gcagtgagct atgatcccgc cactgcactc cagcctgggc aacagcaaga ccccatctct  155100
taaataaaca cataagtaaa taaatgatca tttttatttt attattaaat acacaagata  155160
aatgaaaaac aggcaaatct ttcttacaaa agaattccat ttaaagtatg taaacttcac  155220
tccccactgc cccaggaggt ggagactaat ctcccctact ttgagagtgg gctggattta  155280
gtgactcatt tccgaagaat agagtaggta aaggggaaaa tagaagtttt atagcggagg  155340
aacagataga taccacttta accaaatgat gaagattagt atcccccagg gatgtggata  155400
ttatgtaacc cttgatttta tgcctatata gcgttcttcc caaaaactcc taatcccagt  155460
tttttggggt tttgctctgt cttctaagct ggagtgcgat gatgcaatca tagctcactg  155520
cagctcaaac tcctggtctc aagcgatcct cccacctcaa cctcctgaat agctagggct  155580
gtaagcacat accatcatgc ccagctaatt gtattttttt ggtagagaca tgttctcaca  155640
cattgcccac gctgtcctcg agctactggc ctctagtgat cctcccaccc cagcctccag  155700
agtcactggg attataggca tgagccactg tgaccagccc agaatttttt tttaaggagt  155760
tgtgatgtcg tttaagagat gtgattcttc ataacacatc aacaacaagt cccagcgatg  155820
ggttggataa gtcttgggat ttcatgggag tattaagctt aaaagacttt gcatgatatc  155880
tgtgaactat atgtgatttc tgttggtaat gggggtcact gattctgcgg tttgccacct  155940
ccaatcatca tggaagaaaa tgttccactt ccagtgaaag taagaggaag taaaggggta  156000
attattttct atctaaattc acgaactcct tgaattctgt ccacagaccc ctaagtgttt  156060
cctccccaag gtgaaactga gagaatcttg ccagtgcctt ccgcagtcac tgtggctaga  156120
aaacccctca gaagaggtga tagtttagca ggtaactgga gttctcacca tccgtgtctg  156180
gctcagcccc catcacaacc agttacccag cccaaaatgt cagtagtact gaggttgaga  156240
ggctctgctc taggaggcca ggcctctcag aggaaggagg attggggtac tggctgggcc  156300
tcaagatgaa cctacccccct aagagctttg ggatggcgtg agtttctgtc catacccaag  156360
gactacaaat gcaggtttac tggaaattct gtgccaaaag tgaggtccaa ctcacttcta  156420
actgctacaa aacaaacctc catcaacata gcccatctct gttcttgacc tggaagctcc  156480
aaggtatcca catggctccc atgcccacta gacgggcctc ttccctggac cttcctgggc  156540
cagagaaggc tctgggtagc cttgtggaat caagatgggt gatcagccac ttcctctgtg  156600
ccaccctgtt ttggctactt ccctaggcat cagcctggga ttccttgatg gtaaaaatat  156660
aaaactctct gagctagggc ctttaatatc cccattttac agatgaagaa actgagtccc  156720
agagctgtgc acagcgattg agagtcagaa ttcagctctg tctcactcag tgtcaacatc  156780
ctcagattct gccatttata gcctcccaca gcaaatagga ttgagggctg cttctctgag  156840
ctcaagggga tagaatgggg aaccccatga gtactgcaac aaaactgttt gctggagaca  156900
agagctggtg gctctgtgtt gttctagtga caggtggcct catttcacag ggaccccctc  156960
accctatgtg ccccatgtgg ctcagaaaag ccagaaattg tctccactct cacaggggaa  157020
ggtccctgac cccctctttg ccagctgggc caaggcaaat tggggtcact tcatggggta  157080
caggacctac cctctcttgg ttgcccccaa ggaggggatg tggaggggct ggggacctgg  157140
caggaccagg gtgtcttgag ttaatttggg gctgccttta gccgagggct tctgtgtgcc  157200
tggcatcagc tttacattgt gtcttgatcc gtaaaacagc cctgtgagga aagatatttt  157260
taaccccatc ttccagatga ggaaacggag gcccacaggg tgacgtgacc tgccaaggtc  157320
ccctagccaa gagtgacaaa gccagggttc acacacagct ctggacacaa ttcatcaccc  157380
```

-continued

```
ttcatccgtc tctctctgac tctttctttt tccctctctc tctttgtctc tctttttttt  157440
tttttttttt tttgagacag cgtctcactc tgtcacccag gctagagtgc agtggcgcaa  157500
tctcggctca ctacaacctc catctcctgg gttcaagcga ttcttgtgcc tcaacctccc  157560
aagtagctgg gattacaggt gcgtgccacc acacccagct aattttgggg ggttttgttt  157620
tgttttgaga tggagtcttg ctctgtcgcc aggctggagt acagtggcgt gatctcggct  157680
cactgcagcc tctgactccc aggttcaagt gattcccctg cctcagcctc ctgagtagct  157740
gggactacag gcatgcacca acacgcccag ctaatttttt gtattttagt aaagacgggg  157800
tttcaccatg ttggccagga tggtctcgat ctcctgagct catgattcgc ccgccttggc  157860
ctcccaaagt gccgggatta caggcgtgag ccactgtgcc tgccaatttt ttgtattttt  157920
aacagagact gggtttcaac atgttggccg ggctggtctc gagctcctga cctcaagtga  157980
tctgcctgcc ttggcctccc aaagtgctgg tattacaggc atgagccacc atgcccagcc  158040
tttgtctctt ttattcttgt gttctctctc tctcttcctt ctctttctcc acctccttct  158100
ccttctctcc cttctcctca cccttctttg tgcttttctc tgtgagtttc tcttcttctc  158160
tatttctctc ctttggtgaa tgtcaattag aaaagcagaa aaactgcgtt taatttgtga  158220
tcataaatgc atgtccctgg ccaggcgtgg tggctcacgc ctggaatccc agccctttga  158280
gaagctgagg caggaagatt gcttgagacc gggagttcaa aaccagcctg gtcaaaaagc  158340
aagaccccat ctttaaaaaa gaaaaataat taattagctg ggcatggtgg tgtgtacctg  158400
tagtcccagc tactcgggag gctgaggaag gaggattgcc tgagcccaag ggtttgaagc  158460
tgcaccgagc tgtgattaca cccctgcact ccagcctggg tgacagaacc agaccctgtc  158520
tcaaaaaaaa cctaataatt aaaaataaat aaataaataa atgcgtgtcc cctggccagt  158580
ggttgctaat gtttggaatc acctttgacc catgcccttt ttcattcata gatgtttgtc  158640
ttgaccaaaa tcaaagcatt agactttgga ctataaatca ctggttcatt caacaaccat  158700
cattgaatgc ctactgtatg cagacactct tctggacaca gaggagttga cgtgttggtg  158760
gggaaagcca gtgatcagtt gggataaaaa gggcagacag cagacattaa atagtttagg  158820
ctttgtgggc cagatggtct ccatcgcaac gactcaatct gctcctgtag cgtgaaagta  158880
acgacagata aagcgcgtaa gtgaatgagc atggctgtgg gccaattaaa cgttaaccta  158940
taaaaacagg tggctggccc gcgggctgta gtttgtggat cactgcctta gagatagtgt  159000
tagagggtgg tgagaggtcc gggatagaat aaaacagtag agagtttgtg cattgtcaag  159060
atgagaggtt gcagttcttc ttatacaccc cgaatggccg ggcaccgtgg ccattatgat  159120
ctataattct aacactttgg gaggctgagg caggaggatc ccttgagccc tagagtttaa  159180
gaccagccta ggcacatagt gagaccccat ctctacaaaa aaaaaaattt aaaaattagc  159240
tggacatggt ggagcatgcc tgtaggccca gctacttgag aggctgagat gggaggactg  159300
cttgagcctg ggaggttggg gctgcagtga gccgatcatg ccactgcact ccagcccgga  159360
tgacagagca agaactgtct caaaaaaaaa aaacaaaaaa acaaaaaaaa cagacctgaa  159420
ggaacaaatc atatgaatgc attaaagtat cacatgtatc caaaaaatat atacatctat  159480
cagcctggca cggtggctca tgcctgtaat cctagcacat tgggaggcca aggcaggcag  159540
attgcctgag ctcaggagtg caagaccacc ctaggctaca tggtgaaacc ccgtctctac  159600
taaaatacaa aaaattagct gggcatggtg gcaggcgcct gtagtcccag ctacttggga  159660
ggctgaggca caagaattgc ttgaacccag gagacagagg ttacagttag ccgagatcgt  159720
gccactgcac tccagcctgg acaacagagc aagactctgt ctcaaaaaaa aaaaaaaaaa  159780
aaaaaaaaaa aaaatatata tatatatata tatatatata tatatatata tatatatata  159840
tataatcaat taaaaatttt ccttaataaa taaacatttc tctccttctc tcccttggtg  159900
aatgtcaatt aataaagcaa caaaactatg tttagttagt gatcattaat gtatgtccct  159960
ggctgggtgt gatggctcac acttgtaatc ccagcacttt gggaggctga ggcaggagag  160020
gatagtttga ggccagcaat tgcttgaggc tttttgaaag acatgaagga gatgaaggga  160080
gccatggaga tatctcaggg aacagcagcc gaggtagatg gaacagccag tgcaaaggtc  160140
ctgaggcagg atgttcctgg catttgtgag gacatgtagc tgcccagatg tccagtgggg  160200
agtgagtgag gatgaaggaa ggagctgatg aaggaagatg ataaaatact tcatggatca  160260
gccaggcatg gtggctcccg cctgtaatcc cagcactttg ggaggccaag gcgggtggat  160320
cacaaggtca agagttccag accagcctgg ccaacatggc gaaaccccgt ctctactaaa  160380
aaatacaaaa aagttagcca ggcgtggtca tgcacgcgtg tactctcagc tacttgggag  160440
actgagactc gagaatcgct tgaacccagg agatggaggt tgcagtgagt tgagatcacc  160500
ccactgcact ccagcctagg tgacagagcg agactctgtc tcaaaaaaaa aaaaaaaaaa  160560
aaaaagactt cgtgaacaga cagcctatat aatttatgat ccaaaccagg acagttttga  160620
gagtgaaagg ggaaaaagag cactgaaaaa ataattagca ggcctggcat gatctataac  160680
gggtataaag tgggacacac agcctctctc acggtcactg tcagacttca gctttttcac  160740
actcaaatcc acccccatgt ttatcccata tactggagaa acgggtgttc tcctgagctg  160800
agttttgggg ttttttcctt ttgttttgtt ttgtttttgt ttttttaaca tcctgtatac  160860
tttttctcaa tgaaccatgc tcaaaaaaat tagaggaaaa taaaccataa aacagaaggc  160920
actgaaggat tttgctggga ctcagccatt agtttgtttg atgagtattt atggagcgct  160980
ttctaagcac caggcaccac cagcgatact gggatgaatc agtaacatcc ctcacccttg  161040
aagctctctt gggcccattg ttatttactt aaaatactat gcaagtacgg agaaggggtg  161100
aagtgggaaa aaatcagttg gttgtaaagg ccagaatgac gggtctagtc ccacccatgc  161160
catctgcacc ctgtgtgatc caggcacatc atgttgcctc tctcagcttc agtttctcca  161220
tccaccaggc acagagatgg cgggaatcga ggaagatgtg gggagtattt catcagccca  161280
aaaagacttg gctaatgcga ccataattct gccttctgcc tctcctttcc cagaaaaata  161340
gcttaatcat ttggatttgg gataaacaca tttcctgtgt ttattattta aatgatccac  161400
caagctgggc atggtggctc acccctgtaa tcccaactct ttgggaggct gaggagggcg  161460
gattgcttga gcccaggagt tcaagaccag cctggccaac atggcgaaac cccatcttta  161520
ctaaaaaaat acaaaaaaat tagctgagcg tggtggtgcg tgcctgtaat cccagctact  161580
tgggaggccg aggcacaaga atcacttgaa cctgggaggc agaggttgca gtgagcctag  161640
atcgtgccat cacactccag tctgggcgac agagtgagat tctgtcccta aataaataaa  161700
taaataaata aataaataaa taaaataaat gatccaccaa caggaacccc aggaacattt  161760
gtattgacta tgcaactaat gcttagtgag cacctactat gtccctggtg ctgatctgga  161820
cactgggatt tagacaggaa aaatctctac cctggaggag ctgatgatca agatgacaat  161880
cttgaaatgc ataagttgac aagatgattc agacagtgga acgtgctggg aagagaatga  161940
gatgtctggc tgagctgcag gaaggggcaa gtccttttga ttgagaggtc caagaaggct  162000
tctctgatgg gggcacaatg gatctaaggt tgagtgataa gaagaaattg gccaagccaa  162060
gacctaaagg cagagttgct ccaggcatag gttcagagaa tggaaataat tggctgattg  162120
```

```
tgatcttgaa cttgaccttt cttttcttct gctaactttg ggtttggttt gttcttgctt  162180
ttctggctcc ttgaggtacg tgttgggttc ttaatttgta attttttttt ttttttttttg  162240
ctttttttgag acagagtctc actgtggtgc ccaggctgga gtacagcagc atgatcttga  162300
ctcactgcaa cctctgcctc ctaggctcaa gtgaacctcc cacttcagca tccccagtag  162360
ctgggactac tggtgcacag caccacaccc agctaatttt tttattttta tttttttagag  162420
atggggtctc actgtgttgc ccaggctggt ctcaaacccc tagctcaagc gatcctcctg  162480
ccttagcccc ccaaagtgct gggatgagag gcgtgagcca ccacatctgg cctctgtttt  162540
ttgtgatgta ggtatttgat gctataaact tccctcttag ttgcttcttg gcccttttagc  162600
taaggtcaag tgtaaacttc cctcagcact gcttctgctg catctcacag gtgttggtgt  162660
gttgtgtctc tattttcatt catttccaaa attttttaag tctccatctt aatttctgca  162720
ttgacccaat ggttgttcag gagcatgttg cgtaatatcc atatatttgc atcatttctg  162780
aaattcttct tggtattgat ttctagtttt atcccacggt agtctgagaa gatgcttgac  162840
agaattccag tattttaaaa tttgttgaga gttgttttgt ggcctaacat gtggtctgtc  162900
ttggagaatg tccatgtgct gatgagaaga atgtatgttc tccatcagac atgcaagaga  162960
cagacacttt ctcacctgcc tcatgggatc cataaaagag tcaatcagaa gttggcattt  163020
aagaaagacc agaaggaggc tgggtgcagt ggctcatgcc tgtaatccca gcactttggg  163080
aggctgaagt gggtggatca cctgaggtca ggagttcaag accagcctga ccaacaaggt  163140
gaaatcttgt ctctatttta aaaaatacaa aaattagcta ggtgtggtgg cgggcacctg  163200
taatcccagc tactctggag gctgaggcag agaatcactt ggacccagga ggtggaggtt  163260
gcagtgagct gagatcacac cattgcactc cagcctgggc aacagagcaa gaccccatct  163320
caaaaaaaaa aagaaagaaa aaaaagaaag aaagaccaga aagaggtgaa ggagcaagct  163380
acagagatat caaactgtat caatctggct gggcgtggtg gctcatgcct gaaatcccag  163440
cactttggga ggctgaagca ggaggatcac ttgagcccag gagttcgaga ccagcctggg  163500
caacagagac cccctctcta caaaatataa aaatttaatt aaaaagatgt attggtcagg  163560
gcagccaagt tatgctgcag taacaaacat ccccaaagcc tccatgactt ttgacaacag  163620
atgtatttcc tgctcatgct acatgtccag tgcaggttgg cagtggggaa gaagggggct  163680
ctgttcagtg cagtcacttg agacctagct aatcacctag aacattgcca cttgctattc  163740
cagaaggaaa aaaggaatgc tagaaggtcc cacactgaaa gttcaatgct ctggctccaa  163800
aatgacagct atttccactc actcctcatt ggccagcact tagcatgtgg tcctcagcca  163860
accccaaagg gactcaggaa ggaccatccc accatattgc tggaaatatt tgatggcagc  163920
attaatgggg aacagtgttc caggcagtgg aagtctttga gcccttggaa gaaagacaag  163980
gcgatctcta gagcacatcc ttcccaatat taatgaattt aacaaatgag caagccatcc  164040
tcccccactc tccttcccga attcagactt gtgcatatcc ctcccttaac ttgaactgcc  164100
aaagaagaga tgagaaccag gagaagagat ctgtgacccc atctttgctg atgaactacc  164160
acagaacagc catggcatct ccagtccttg tgcttgtaaa atgtactttt cattttgctc  164220
ctgaacgaaa tccacccacc cccaccccca aaccagggaa agctcatctc ctaatccaaa  164280
actgcaccca gccttccacc accttcttcc ctgggaattg ttgattccag agtatggaat  164340
tgaataattg gatgagtttg gaagagaaaa agtgtctcta aaatcaggca gcagaagccc  164400
actccccaga gaggatggtg cagatgagag ttcaggaggg agcttggctt ggggttgacg  164460
atctgagcta tgcagggaac ttggacacac ctctcaatca gtcattcaac agacaccact  164520
tattgagcac cgactgtgtg ccagatgttg tcctaggggg ctgggaatac aggaatacag  164580
cagggaacaa aaaggacaaa gcccctccct cttgtcgaat ggacattcca gccaggaaga  164640
cgagagaaca agagaaataa gtaaagtata taggcggtga aatgcaaatg ggaaaaaaga  164700
aacaatgggg accagaaatg aggggtgcaa ttgtaaaggg ccatcagggg aggcctccct  164760
cagaaggtgg catttgagta aaaaacctga aggaggtgag gggaaaccat gtagcaatct  164820
caggaaagag cattccaggc agggagggac agcctgtgca agggccgagg taggactgtg  164880
cttggcgtgg ttgagaaact gcaaggaagc caggtggctg gaaccgaatg agcgagggaa  164940
aaggggagga gataaaagca aggagatggg agggttggag gccccctctg ccattcagta  165000
actgagtaac ttcatttatt tcctgtagct tgaaccacaa agaaccacaa atagagtagc  165060
tgaaaacaac agaaatttat ttattctctc gcagttcagg aggccaggag tccacagacc  165120
atcaaggtca gctgggccac agaccatcaa gatgtcagct gggccatggt gcctcctgag  165180
acttggtctg aaatcccttc ttgcctccct cctagcttct ggtggtttgc caacagtgct  165240
tggtggtcct tgtcttgtag acgtatcacc ctgatcccgc cttcatctcc atttcacatg  165300
gccttctccc tctgtgcaag gttgtctctg tgcccaggtt tctccttttc ttattattta  165360
cttatttgtt tgtttgtttc tttattttag acacagggtc ttgctctgtc tcccaggctg  165420
gagtgcagtg gtgcgatcat agctcactac agcctcaaac tcctggcctc aagcaatcct  165480
cctacctcag cctcctgagt agctgggact gcagatgtga gccactgtgc tctgcccaga  165540
tgtcctcttt ttataaggaa acccgtcatt taggatgagg ttccacccta atgacctgat  165600
cttaacttga ttccatctgc aaagacccta tttccaattc ataggtacca gggattagga  165660
cttcttcaat gcatcttttt ggagagaccc actgcaaccc acaacagaac tgtgggcatg  165720
taacttgacc tctcggccag gcgtgatggc tcacacctgt aatcccagca ctttgggagg  165780
ccgaggtgag tggatcgcct gaggtcggga gttcgagacc agcctggcca acatggtcaa  165840
accccgcctc tactaaaaat agaaaaatta gctgggcatg gtagcaagca cctgtaatcc  165900
caactacttg ggagggtgag gcaggagaat tgcttgaacc caggatgtag aggttgcagt  165960
gagccaagat agtgccattg cactccagcc tgggtgacag agtgagactc catctcaaaa  166020
aaaaaaaaaa aaaaaataga cctctctgtg cctcagcttt ctcacccggg aggatgggga  166080
taattatata cccactcctg gggttcatga gaggattaaa tgagctcaaa cagtccaagc  166140
ctccacgtgt gtctgttgtg gtgctgggta gcatgtcctg tggccagagg ttcccaagct  166200
tgtcgaggac ccaggcaagg gcagattcgg gtcttgttgg cagcacctga gatggacggg  166260
ctgccttggt atggaagggc ctcggctgtt tttccctttc agtcctgtcc ctctccccca  166320
tcctccaccc tgtccctgtc atctgagcct gctcctcgtg atggctcaga gtctccctac  166380
tggcggccgg tgcagagttt cgttccctgg gctatattta gccctgagaa atgggaacga  166440
gaaccctcag ccgccaaagt gatggagaga ggagcacaaa gccagtgctg ccttctgtcc  166500
agcaatgttc cgctgactcg gttctttctt ccagaacctt ccagaagcaa agcattggca  166560
tttctgagct cgttaaaaca aggatgtggg ctggtggctg gcacattcat tgtccccaga  166620
acctgtctgt gtccatgatt aaagctgact ttgttagttt tattttcagt gcttttttttt  166680
ttttttaatc catggcaaaa cacacatgac ataaaattta ccatcctaat atttttttta  166740
actttgtaac attttttaat tgacaagtaa ttgtacttat tcatggggta catagtgacg  166800
tttcaatgca tataatgcgt agtgctcaga tcagggtaat tagcatatcc atcttctcag  166860
```

-continued

```
acctttattg tttctttctg ttaggaacat tcaagctcct ccttctagct atttgaaacc  166920
attaatatat tgttgtcatc ctaaccattt ttaaggatac agtttcgtga aattaagtat  166980
aatacattca cattgttgtg caactgtcac caccatccat ctcccaaact tttccatctt  167040
ccaaatgtaa ctctgtcccc actaaacgcg aactccctgt tccccctccc ccagcccttg  167100
gcacccacca tgctactttc tgtttttata aatctgacga ctctagggac ctcctataaa  167160
tggaatcata caggattttc ccttttatga ctggtttatt tcacatagca taatgccctc  167220
aaggttcacc catgttgcag cacgtatcag cattttcttt ctttttaagg taaagttgac  167280
tattaaaaaa aaacttctgc cgggctcagt ggctcacgcc tgtaattaca gcactttggg  167340
aggccaaggc aggcagatca ggaggtgagg agttcaagac cagcctgacc aacatggtga  167400
aaccccatct ctactaaaaa tacaaaaatt agccaggcat ggtggcgggc gcctgtaatc  167460
ccaactactc aggaggctga ggcaagagaa ttgcttgaac ccgggaggca gaggttgcag  167520
tgagctgaga tcatgccact gcactccagc ctcggcaaca gagtaagact ccgtctcaaa  167580
aaaaaacaac tttttaagaa ttgaagtaga ataaacatac agaaaaatcc gcggattata  167640
agtgaagagc ttgattaatt gtcacaaact aaacacatcc atgtaaccag cacacaaatg  167700
aggaaacaga aacttctcag ccccagaagc cccccctcata tcctgttcct agtcactacc  167760
tccccgcaag ggtaccccta ccaggacttt gagcatcatt caccagttta gcctgttttg  167820
tattttgcat aaatgaagtc tggcttcttt tgcttgacgt taacttttta agatctcatg  167880
tgacctgtgg cattgttcat tgcatgtatc ctctctctcc tattgataac agtgtggatt  167940
gtttgcaatt tggagctatg atgaatacca ttgctatgaa tgttcttgtg tgtgctttct  168000
gttgtgtaat tattcagaat tactatttcg gaattactat ctaattgtag tgatcttgga  168060
tcagtaacta tccaagaatt actgggtgtt ggcaaaggta catacagtta tacactgcac  168120
aatggcattt tggtcaacaa cagatcaaat atgtaacagt ggtcccataa tggaccgaat  168180
acataacagt gattatcata cagtattttt actatagctt ttctgttttt agattctttt  168240
tttttgagaa cgaagtctcg ctctgttgcc caggctggag tgcagtggtg tgatctccgc  168300
tcactgcaag ctccgccttc tgggttcacg ccattctcct gcctcagcct cccaggtagc  168360
tacaggcgcc cgtcaccagg cccggctaat tttttttgta tttttagtag agacggggtt  168420
tcaccatgtt agccaggatg gcctcgatct cctgacctca tgatctgccc gcctcggcct  168480
cccaaagtgc tgggattgca ggcgtgagcc accgcacccg gcctgttttt agatattttt  168540
agatacacta tagagttaca attgcctaca gtattccata gaataacatg ctgtatgggt  168600
ttgtagccta ggagcaatag gcgagaccat gcagcctagg tgtgtagtag gctataccat  168660
ctaggtttgt gtaagtacac tccatgatgt ttgcacaaca aaatgaccta gtgacacatt  168720
tttcagaatg tatgcccatt gttaagcatg acttaatttt agcatagaaa ctctcaacca  168780
atttttcaag tagttgtacc atgtgttatg ggttttattg tctcacccca aaattcatat  168840
gttgaagtcc taaccccccag tacctcagaa tgtgacctta tttggaaata gattcattgc  168900
acatgtaaag gttttgccat tggcaaaact gccgttattt ttgcaccaac catagcagtt  168960
aagatgagat cattagggtg ggtcctaatc taatacgatg gtgtccatat aaaaagggga  169020
gattttggca cagagacagg cacactcaca ggaagaatgc catgtttaaa caaaggcaga  169080
gctcaggatg atgcctctac aagccaagaa tcagcaaaga ttgccagcaa accgccagaa  169140
gctaggagag aggcataaaa cagattctgt ctcacagctc tcagaaggaa ccagcccttc  169200
tgacaccttg agcttggatt tttggcctct ataactgtaa gacaataaat ctttgttgtt  169260
taagccacct aggttgtggt tccttgttac agcagccaca ggagatgaat acagcatggt  169320
gccctcccat tggcagatta tgagggttcc agttgctcca cagcttcaca gacacctggt  169380
agtaatgacc tcatcttaac ttctttctca ttttagcctt tcttccaggc agcagcagtg  169440
tcatacatgc ttttaaaggt gggcttttaa agccacactt gagagccctg cattctgcag  169500
gtgtcacagg gtgatcaact attcaaaggc taccccctgcc ctgacagctg gaggcaaggc  169560
ttcccagcac agaggttaag cccatggact ctggggccag gtggttagtg caaatcccat  169620
gtccactagt gaataactct gtgatcttgg gctgatgatt ttgtctttct aagcctcagt  169680
ttcctcaata gtaacatggg cattataaca tagaggcatc atgaggatta aatgactaag  169740
tgagctaaca tacataatgt gcttaggaag gtgccagcac accataaata ctctgtaagt  169800
gctggctttt atcattcttt tctctctctc tctctctctc tctctctctc tctctctctc  169860
tctctccctc tctctctctg tctctctttc tctctccacc ccccaacctc ctctccttga  169920
ttttcttccc ctcatcttac ttccttcttg ctatagtgtt ctattttctg tttcagagag  169980
tattctattt gtggactttt ttcctcttga aaattgagct gaaacttctg agaatttttt  170040
gtgattggca ttaaggctgc agggaatgga gcagggagac acttgaggaa agggctcatg  170100
gaccatctgt ctggcttggt gatttcacca ggccatcaga ctctgtggtc atgcatctcc  170160
tctaagggga gtctatgact gtgttgggag aagagaagga accagggatt aattaatcca  170220
tttcaatagg ttttgtgttt tgtttggttt actttttcct tctccttctg gactgtggtc  170280
tgggaagtcc tcttgtgttt cttactccat tcccaggtca attatgttat gtgaggagaa  170340
cataattaag agagagcttt accctttgga tgttttcttc agaaaacgtt cctccatttc  170400
cccctctggg atgccagagc cccagaactc cacaagccaa gaacatttaa gacagagcca  170460
caagagaacc gagcttcccc ttccctcacc tgtcaggttc tatctgagtc ccagtcaact  170520
ctcacctgct ttccctcctc acaccctaca gagcaacgat gcctcaggga acacttggaa  170580
ctggttgtac ttcatccccc tcatcatcat cggctccttt tttatgctga accttgtgct  170640
gggtgtgctg tcagggtaag tttctgctac tccccacccc atcccactca ctcctctttg  170700
ctaacttctt tccaagtaga ggccattgaa gctttgtttt cattcactag acagagaaaa  170760
ggcttcttcc cttgtttggg ttaccagact gttattagca agccatgcac aggtgcagag  170820
gttgtgtact gctaggggta cccagtgaga gggttcatat gggctttact ttctttacat  170880
ttttttttaaa aaccaatagt ttgggtttac ttctccccca ttttccaaat ataaaatcat  170940
agcatatgct ctaacggtgt attttcctga cccatattgt cctctatccc caagattttt  171000
ttggcttaat cataaatggg cttcattttt cttaccataa gaagtctggg cacttgtatg  171060
gtggctctat ggcaccatca gcaaccccag attcttccag ctttccattc tgacatcttt  171120
accagaggct tccaatctcg tggatacctc atggtcttaa gatggctgcc tcacgccctc  171180
cggatggcca cttcatgttc caaacaggaa aaggaagaag ggaaacagga agaggtggga  171240
cctatggcag agaagccaac ctgctgcaga aatctttcat tcatggctta ttggtctaac  171300
ttaaaagagg gctgaaataa ttattagcca aaagtatgaa gagaatgaga atgaggtatg  171360
cagccagtgg tggttggcat ggcatggttt tatcctttcg gttttttttct tttttattgt  171420
ttttttttga gacggtgtct agctttatta cccagactgg agtgtagggg gcgatcatag  171480
ctcactgtaa cctagaactc ctaggcacaa gcgatcctcc tgcctcagcc tcctgagtag  171540
ctaaggcaac aagtgtatgc caccatgccc agctacattt tttatttttc atagagatgg  171600
```

```
ggcccactgt gttgtccagg ctggtctcaa attcctggcc ttaaatgata ctcccatctc  171660
agcctcacaa agtgctggga ttacagacat gagccactgt gcctggcctt tttctttacc  171720
taggcacagt tgtcgggaaa tgtgtgaagc tggcagaagc acccatcact ataatatccc  171780
agtcttttcc cagaagtcct gactcctcct gttgaaaact cctgacctcc agggacttct  171840
gaatccccaa acacacacac acacacaaac acacacacac acacacacac acacacacaa  171900
acacacacac aaacgtttcc taacattttc aaaacagcca tactctggct tttctatgct  171960
tctccaggga gtttgccaaa gaaagggaac gggtggagaa ccggcgggct tttctgaagc  172020
tgaggcggca acaacagatt gaacgtgagc tcaatgggta catggagtgg atctcaaaag  172080
caggtgaggc cctttcatcc tggggcccag ggatggagat cccaggccac ggagtacaaa  172140
gagagtcatg cagtttggag aaggctaagc tgggagggtt atgatgggag gagaaagaga  172200
acctgaattg gtagtcccaa attttatcaa caagaatcca gagtctgata tgaagaagtc  172260
taagatgaag ccaggatctg acatcacgta acttgaattc tgaaatcaga cgctggttta  172320
catcccggcc ctgccacttt ttacccatgc accacacatc cctgtacctc cgtttcctca  172380
gctgttacat ggaggcgatg gtagtgccta agtcatagta ctattggagt atttagtaaa  172440
ataatctcag ctgagtcact tggggagaga agtgcctgat acacggtagg cacatattta  172500
tttgttcagc catttaacaa acatttaggg agcacctgct gtgtgccagg cactgatcta  172560
agcactgagg atatgggagt aaacaataca caccaaatcc ctgccctcag agctctgata  172620
ttctaatgag agagataaag caaacaaata catgtcatgt tgggaactcc caaattcaga  172680
gaaggaagat aaaacagact aggaagataa aacagagtag gaagttggcc gggcgcggtg  172740
gctcacgcct gtaatcccag cactttggga ggctaaggcg ggcagatttc ctgaggtcag  172800
gcattcgaga ccagcctggc caacatggtg aaaccctgtc tctactaaaa atacaaaaat  172860
tagccaggca tggtggcgca cgcctgtaat cccagctact cgggaggctg aggcaggaga  172920
attgcttgaa cccaggaggc agaggttaca gtgagctgag gtcgcaccac tgcactccag  172980
cctgggcaac agagtgagac tctgtgtcag agaaaaaaaa aagagtagga agttagaggc  173040
agggtggtca gggaaggctt ctctaaggaa gtaccctctg agcagagaga cctgaaggac  173100
gtgaagaagg aagctgtggg gatgtcaagg gaaggggcat tccaggcaga gacagcaagt  173160
gcaaaggccc tgagctagga acgtatttga gacacagcaa ggaagccagt gcagctgaaa  173220
cagagtgaga ggtggggaca gctggaggag aggaagacag gaaggtgatg gagatcagat  173280
caagcagggg cttataggct gtggtgtgga cattggtttt tattttgcgc gaggtgggga  173340
gaatgttggc tattgctact gttgcggagg tggggcttga agtcacaaac cacccagcag  173400
catgtttttt ggtcggttga gctgtcacca tcagtcagca gagaatgggg gtggccgggc  173460
agacccttct tcctggtcca agggagaact catcctccaa atgcaggagc ttaactctgt  173520
gctcttcctc ttcagaagag gtgatcctcg ccgaggatga aactgacggg gagcagaggc  173580
atccctttga tggtaactgc tctaaaccca cctcaggggt gggtcccagg ggagaaggga  173640
gaagctgtgg tggggagtcg ggggagagca ggtgactggt tctaaggatc ttgcagaggg  173700
tagacgttcc tcttggagga attttaggac ttccatgcag agtttcccta ttctggcctc  173760
cacttttttg ttttaaccat ggacctggtt ttttctgctt tgtgccttgg tttttctcat  173820
ctgcaaaatg ggtatgatat aaacaatacc ctagctcacg agattgtttc tcagaatgat  173880
attcgttatg gcaaatagaa cacctgggat agtgcctggc atggggtcag cacgtttctg  173940
tttgctaaat aagtaataat tccaccaata atccagttta ctgtgaacgg ctgctgtctc  174000
ccatgttaga aacttaacga gacagaacca tgactttctt tcttttcttt tttttttaat  174060
tgagacagag tctcgctctg tcacccaggc tggagtgcag tcacacgatc tcacctcact  174120
gcaacctctg gctcccaggt tcaagcaatt ctctgcctca gcctcatgag aagctgagat  174180
tacaagcatg agccaccatg cctggctaat ttttatattg ttgatagaga tggggtttcg  174240
ccatgttggc cgggctggtc ttgaactcct tgcctcaaat gatctgcaca ccttggcctc  174300
ccaaaatgct gggagtgtag atgtcaattc atggtcccct ggaaacctga atatgaaagg  174360
agggaccatt aaaaaggtgt ccaaaagccc aacctcccca gcatagctgg gagtcagggg  174420
acagactgta agagtcactg tgtatccaac ctgaggcttc atgaaagtaa agtttcctag  174480
aatttagaga tagggttgga tgcggtctgt ctgtggctca catctgtaat cccaacactt  174540
tgggaggcca agacaggagg aacacttgag cctgggagtt caagaccagc ctgggcaaca  174600
taatgaggtt ccgtctctac aaaaaaataa cttagccaga tgtgggggca cacgcaccta  174660
tggtcccagc tactcaggag gctgaggtgg gaggatcact tgagcccaag aggtcgaggt  174720
tgcagtgggc accactccac tccagcctgg gtgacagagt gagaccctgt ttcaaaagaa  174780
aaaaaaagaa tttagagata ggccagaata atatgtctgc aatataataa taacagcaat  174840
aagaaaaata atagtactcc ctgaaaaatg caacttcttg cttgagattt atcttctcat  174900
actttagaaa actggttaga caggggctgg gcgtggtggc tcatgcctgt aatcccagca  174960
ctttgggagg ccaaggcggg tggatcactt gaggccagga gttcaagacc ggcctggcca  175020
tcatggcgaa accccatctc tactaaaaat acaaaaatta gctaggtgtc atggcacacg  175080
cctgtaatcc cagctactca ggaggctaaa ctacgagaat tgcttgaacc tgggagacgg  175140
aagttgcggt gagccgagat cacaccactg cactccagcc taggcgacag agcaagactc  175200
tgtctcaaaa aaaagaaaga aagctggtta gacagggtga tgacttttga ttaaaaatct  175260
gagagatttg agggaaataa aagaactggc actgcgtccc agaaggttat aaaatgaatt  175320
ttattatctt agttggggag gggagattac ctaactcccc taaatgagtt aggtaatcta  175380
actcatttag ggtacctaaa tctttttatt ggaagtctac acctgaactt gtctgctgtg  175440
gagcccctgg ggtgtatagc ttgaatatgg gggcagaatc ccaaaattgc agcctgccta  175500
gcgagtatgc tacaggtcaa ggggtggact gttttcataa gaaagtgagg tttcttagaa  175560
tttaaaaata gaggctgagt ggggcggctc acgcctgtaa tcctagcact tttggaggcc  175620
aaggcaggca aatcacttga ggtcaagagt ttgaccagcc tggccaacat ggcaaaaccc  175680
catctctact aataatacaa aaattagcca ggcgtggtgg tgcatgcctg tagtctcagc  175740
tactcaggag gctgagggag gagaatcgct tgaactcagg aggcagaggt tgcagtaagc  175800
caagatcaca ccactctctg ggtgacagag caagattctg tctcaaaata aataaacaaa  175860
taaataaata aaccagaagg aaaatagtgg ctgagggccc agacctggag tcggactgaa  175920
cccgacttga ttcttgtctt taccccttta agcaaagtga tagtgccacc ttgaacctca  175980
gtttacacat ctgaaaaatg ggtatactat tagttcccgt gagaacagtt gccgtgagag  176040
ttaaatccaa ggacacactg tgtccatatg gtctgtgttg caaaaagggt aacgtctttt  176100
tctcttgcca tgtttccatt gttggagctc tgcggagaac caccataaag aaaagcaaga  176160
cagatttgct caaccccgaa gaggctgagg atcagctggc tgatatagcc tctgtgggtg  176220
agtcccttcc tctgccacct atcagttgtt catcacctat cgcccaagag acatggtggg  176280
gtgggggcag agggcttgca aaccgtgctg cctggatttg ggtctcagct ccacccttc  176340
```

```
ccacctgtgc gtgtgtcctg ggcagattac atcattatgg gaataacatc cgtgcctagc  176400
ttctcattat tttgtgggaa ttcaactaaa tgatccccat gaagcatggc aaaccagcac  176460
ctggcaggga cgaagctccc agtcaagttg gtgaatgttt gtgactcatt cgggaagtat  176520
tcatggggga cctgcttata ttaggtgctt ggttgcaaac aagacaaggc agtcacgagg  176580
ctgagctggg aggatcactt gagcctggga agtggaggct gcaataagcc attattgtgt  176640
tactgcactc cagcctgggc acagaaaaaa aaaaaaagac acaaactgag ccaggcacag  176700
tggctcacgc ctgtaatccc aacactttgg gaagctgaga tgagcggatc acctgatgtc  176760
gggagttcga gaccagcctg gccaacatgg tgaaaccctg gctctactaa aaatacgaaa  176820
aaaattagcc tgtagttcca gctactctgg aggctgaggc gggagcatca cttgaacctg  176880
ggaagcagag gttgcagtga gctgagatct catcactgcc ctccagcctg ggcaacagag  176940
caagatcctg tctcaaaaaa aaaaaaaaaa aaaagacaca aaccaaatcc ctacctacat  177000
ggagctcaca gtccagtgca ggaaatagaa attaaacaga gaattacaca aataaacctg  177060
taatggtaat ggcacttcag ggagaggctc tgggcttagc ttgctctaga aggatgggga  177120
gcagtcaggg aaggctacct ggaggaagtg acggttaagc tgggaactga aggatgggta  177180
ggagatcact gtggtggtga tagcagaagg aacagtgtga gaggcagggc tcagaccttt  177240
gccaccacaa gggccagagt tcgagggagg agggaacatt tattctttcc cttctcactc  177300
ctctgtccta ttgattcatt ggctgtgatg atgttgattt tgaccttcta aagtgagaat  177360
gtattgttat tgttgttgtt gttctttaat gggtttttgt ttttaatgga aggaagagca  177420
tccaggcaga ggaaataaga ctggaataag attgagggga gaaggaattt aggctgcttg  177480
ggaaactgtg tggccgcagt ttagaggaag aaaggatggc aagagaaaga ggaagggagg  177540
aagagaagga gggagagaag tgaaggaagg agggaagtta gtacatccat gtgtttctga  177600
tccatagttt ctgatccact atttcgtatt cccctttat cgctcgcccc tagtttataa  177660
ccttattgct gagtttaggc ataatttcca ttgcgatcac atatctcgta gggtggatac  177720
actatggttt gtttagccat agctctatta tagggtgttt gagttgtttc caataatttc  177780
tcttacgaag aacactgctg tgcacattta cgtacaatga ctccccccac cctttgggcg  177840
tatttccttg gggataatta taggatcaaa gatattaaca gcttttcaac tcattattca  177900
aagagccatt ctgagtttca aaaacatgga acccatttat aaacctgcca agtatgcata  177960
tgttcatgga ttccccaccc aggccatcga atattaccaa tttaatttcc tttcccagtt  178020
aagtgggttt gtaatgaaac cttaaagctt gttttcattt gcatttttaa tttccagcca  178080
aaacacgctt ttctttgtaa tggagaactc attctgcttc cactcgtgtg tgcatctgtt  178140
taatttcctg taagcaaatg tcaagaattg gagcgctcag taggtgtctt gagtatttga  178200
tcaattatgt ctgtctcacg tgttacgtta cctccattgt ttaaaatctg ttttatgacg  178260
aggtacagtg gttcacgcct gtaatcccac tgctttggga ggccagtgca ggaggatctc  178320
ctaagatcag ccgttcaaga ccagcctggg caacataaca aggctccatc tctgaaaaac  178380
aaaatgttga aaaacttagc caggcattat ggcacacacc tatagtccca tctatttagg  178440
aagctaaggc aggaggattt cttgaaccca ggaattcaag gttgcagtga gctatgattg  178500
tgccactgca ctgcaacgtg ggcaacagag tgagaacctg tctcttaaaa aaataaaata  178560
acatacattc ttaaaaatct actttgctgg ccgggcgcgg tggctcacgc ctgtaatccc  178620
agcactttgg gaggctgagg cgggtagatc gcttaaggtc aggagtagga gaccagcctg  178680
gccaacatgg tgaaaccgtg tctgtactaa aaattcaaca attagctggg tgtggtggcg  178740
tgagcctgta atcccagcta ctcaggaggc tgaggcacaa aatcacttga acccgggagg  178800
cggaggctgc agtgagctga gatggcgcca ttgccctcca gcctgggcat caagagtgaa  178860
actccatcaa aaaaataaaa aatctgcata tacatatata tgtatatata tttttaattt  178920
ttttaatttt tttttttttt tctgagatgg agtcttgctc tagcacccag gctggagagc  178980
aatggtgcca tctcggctca ctgcagcctc cgcctctgtt aacaaggcag gtgacattgc  179040
agctttctaa acagacccaa aacccaggcc agtggcttgt tctttcatag ccacgtttgc  179100
tacaggcaaa tccaccaaaa cccacctcat cagcctgatt actcaaaaag acaaagaaag  179160
gagcccccaa tctagccagt ggttttctag accaccccaa aagagatctc tggaattcca  179220
ggattctggc aaggaatcac atttagcttt atttatttat gtaaagaatg caacaataca  179280
ggctgggtgt ggtggctcac gcctgtaatc ccaacatttt gggaagctga ggtgggagga  179340
tcgtttgagg tcaggagttt cagaccagcc taggcaacat agtgagaccc tgtctctatc  179400
aaatattagc tgggcattgt ggcacacgcc agtagtccca gctactcgtg aggctgaggt  179460
ggatcacctg agcccaggag gtcaaggctg cggtgagcca cagcatgccc ctgcactcca  179520
gcctgcgtga cagagacttc atctcaaaaa aaaaaacaaa aaaaagtaat aatacagtaa  179580
tgcatatttc aaagtaaggt gggagctatg tggtatttgc gttcacgttc acattatacc  179640
acagtatgca cagtcctttt tttttttttt ttgagacagt gtcttgctct gatgttcagg  179700
ctggagtgca gtggtgcagg catagctcac tgcagcctca aacccctgga ctcaagtgat  179760
cctcccacct cagcctccca agtagctggg actataggtg tacactgcta cactcagcta  179820
agttttttat atttttact agagatggga tctcaatatg ttgcctaggc tggtctcaaa  179880
ctcctggcct caaacaatcc tcctacctcc acctcccaaa gcagtgggat tacaggcgtg  179940
agccaccaca cctggcccac atgcagtctt atataattgg tgattctact gcgctgttga  180000
atcagttgat aaacgcacta taaagcaggt tcattcctaa ttgatgaact tactgctgaa  180060
ataaggaact tgaatcattt acatgaaaag ttgagccatg ttgctgaaag gatatcaatt  180120
tttttttctt ttttttcttt tttttgaga tggagtctta ctctgtcgcc caggtgggag  180180
tgcagtggtg cgatctcggc tcactgcaac ctccaccttc caggttcaag cgattctccc  180240
acctcagcct ccaagtagct gggactacag gtgcacacca ccacgccctg ccaatttttg  180300
tactgttagt agagatgggg tttcaccatg ttggccaggc tggtctcaaa ctcctgacct  180360
caagtgatct gcccacctca gcctccgaaa gtgctgggat tacaggtgtt agccaccgcg  180420
cctgacagga tatcaaattt catttagact gcaggaatac gttcaagaga tctattttgt  180480
acagcctggc gactgtatta ataacaatgt attatatact tgaaaattgc tcagagagta  180540
ggttttaagc attctcaccg tgagaaaagt gataagcata tgtaataatg catatgttaa  180600
ctagctcaac tgagccactc catagtgtat acatatggtc aaaatatcat gttatgcact  180660
ataaatagat acagcctgta tctgtcaatt taaaataaat gaataataac tttaaaaaga  180720
aaaataacag tatggctggg cacggtggct cacacctgta atcccagcac tttgggatgc  180780
caagacaggc ttgaggccag gagtttgaga ccagcctggc caacatggcg aaactttgtc  180840
tctaataaat atacaaaaat cggctgggca tggaggcggg cgcctgtaat cccaactact  180900
tgggaggcag aggcatcact taacctggga gatggaggtt gcagtgagcc aagatctgca  180960
ctccagcctg ggtgatagag tgagccttta tttatttctg taaagaatgc aataatacag  181020
gcctggtgcg gtggctcatg cctataatcc caatgttttg gaaggccaag gtgagaggat  181080
```

-continued

```
catttgaggc tacaggcgca tgccacagtg cccagctaat acttgataga gacacggtct  181140
cgctatgttg cccaggctgg tctcaaaacc ctggcttcaa atgagcctcc caccttggcc  181200
tcccagagtg ttgtgattac aggtgtgaga cactgtacct ggcctgtatt aaaaaaaaaa  181260
aaaagaagaa gaagaagaag aggaggaaag aagaagaagg aagaaggaag aagaagaaga  181320
ggaggaggag gaggaatggg aaggggaagg ggaagaagaa gaggaggaag gggaagggga  181380
agaagaagag gaggaggaag gggaagggga agaggaagaa gaagaggaag aagaagacga  181440
agaagaagca caatgataaa taagtaaaat gtggagcata tgaaaacaaa acaaaaaaaa  181500
gttgatccat tatgaatgga agctgccatt gtaactctgc ttttttagga aaaccagacc  181560
ccatttagat gattttattt gtttttaaag gcaggttctt gctctgtcac tcaggctgga  181620
gtgcagtgat atgatcatag ctctctgcag cctggagctc ctgggctcag gcgatcctcc  181680
cagcttagcc tcccaagtag ctgggactac aggcaccacc acacccagct aatttgttgt  181740
tgttgttgat gttgttgttg agatggggtc tggctatgtt gcccaggctg gtctcaaact  181800
cctggcctca agtgatcctc ctgccctggc ttcccaaagt tctgggatta caggcatgat  181860
tttttattaa tttatttgca gctgacaaat ggtaattgtg tatgtttatg gagtgcagtg  181920
tgatgtttta atctatgtat acatcataga atgattcagt catgctaatt aacacatcca  181980
tcgcctcacc acctcaccgt tttttgtgtg tggggaaggc attaaaaatc tcttagcaat  182040
tttgaaatat gcaacacatt actatttatt aataatgcaa tataaataca caataatgta  182100
ttaatgcatc actaaatgcg atgcaatgca atgcaatgca atagatcact aaaacttact  182160
cctccagtct aactgcaact tataccettt gatcaacatc ttctccttct caatccctcc  182220
tcctcccctg cagcctccag gaaccacctt cctgctcttt ctatgagatc aattttttt  182280
agttttaagc tcccacatgt gagatcatac tgtaattgtc tttctgtgcc agcttatttt  182340
actcagtata atgtcctcca gttctgtccc tgttgtcaca cattacagaa tttctttctt  182400
ttagggctgt atagtattct atttgtatac ataccacatt ttctttatcc attcatccat  182460
tgtgggacac ttagtttgct tccatatttt ggctattgtg aataatgctg aagtgaacgt  182520
gggagtgcag atgttctgaa aagacttaaa tgtcagacct gaaatggtaa agatgctcca  182580
agaaaacata aggagaaagc tccatggcat tggtctcggg aatgattttt tggacaggac  182640
ctcaaaagca caggcaacag aagccaaaat ggacaaatgg gatcgtatca aactaaaaaa  182700
tttgtgcaca gcaaaggaag cgttcagcag aggaaagaga caacctaagg aatgtgagaa  182760
aacgtttgca aacaatacat ctgataagga gctaatatcc aaaatatata aggaactcaa  182820
acaactcaac agcaagaaaa caacccaatt aaaaatgggc aaagacagct actcgggagg  182880
ctaagatgtg acgatccctt gagcccggga ggaggaggtt gcagtgagct gacattgcat  182940
cactgcactc caccctgggc gacagaagga gaccgagacc ctgtctcaaa ataaaaaata  183000
aaaatgtgca aaggatctga acatacatat cccaaaagaa aagacataca agtggccaac  183060
aggtatatga ataaaatgct gaacatcact catcatcagg gaaatgcaaa tcaaaaccac  183120
cattagctat cacctcacac ctgttagagt agctattatc tttttgtttg tttgtttgtt  183180
ttttgttttt tgttttgttt ttgagaggga gtctcactct gtcacccaag ctggagcgca  183240
gtgttgtgat ctcagctcac tgcaacctct gcctcctggg ttcaagggat tctcctgcct  183300
cagcctcccg agtaactgaa attacaggca cacgccacca tgcccagcta actttgtat  183360
ttagtttcac tatgttggtc aggctggtct tgaattcctg acctcaaatg atctgccctc  183420
cttggcctcc caaagtgctg ggattacagg tgtgagacac tgtgcccagc ctagagtagc  183480
tattatcaaa aagacaaatg aggtttgttg aagttctaac ccctggtacc tgcaaatgtg  183540
gccttacatg aaaatagggt ctttgcaggt ggtaatcaag ttaagatgag atcaaactta  183600
attagggtgg gtcctaaatc caatgactgc tgtctttata agaggagaag caggctgacc  183660
aacatggtga aaccccatct ctactaaaaa tacaaaaatt agctgggtgc agtagtgcac  183720
acctgtagtc ccagctactc aggaggctga ggcaggagaa ttgcttaaac ccaggaggtg  183780
gaggttgcag tgagcagacg tcatgccact gcactccagc ctgggtgaca gagtgagact  183840
ccatcttaca agaaaaaaaa aaaagacaaa tcataacaag tgctggcaag gatgtgggga  183900
aacggggatc catttacatc attttaataa cacaggctct atatgggtgg tattgagttc  183960
ccagagttgc cattacaaaa tgtcacaaac ccagtggctt aaaacaacag aaatttcttc  184020
tctcacagtt ctagaggcca gaagtccaaa ctgaaatcaa ggtgtcagca gagccaccac  184080
gttccctcag aaggttttag gggagaatct gttccatggt attttcttag tttctggtgc  184140
tgccagcgat acttggtgtt cctcagttca tagatgcata attccagtct ctgcctctgt  184200
tgtcatatgg tcttctttct gtgtttctgt atgcgatttc ttttttttt ttttttttct  184260
gagacaagtc tcactccatc acccaggctg gagtgcaatg gcacgatcac agctcactac  184320
aaccccaacc tcacaggctc atgccgtcct cccacctcag cctcccgagt agctgggatt  184380
acaggcgtgt gccaccatgc ccggctaatt tttgtatttt tagtagatac ggggtttcac  184440
catgttggcc aggctggtct cgaactcctg accttacgat ctgcccatct cggcctccca  184500
aagtgttggg attacgggca cgagcccacc gcacctggcc ctaattactt tatttttttg  184560
taaatttttt tttgtaaatt tcatgtagcc tgagcataca gtgtttataa tatatacagg  184620
agtgtacaat aatatcctag gccttcacat tcactcacca ctcaactcac tccctcacca  184680
agagcaactt ccagtcctgc aagctccatt catgccaagt accctatgca gctgaaccac  184740
cttttctctt ttatactgtg tttttactgt accttttcta tgtttagata tgttcagaca  184800
cacaaatact atgatgttac agttgcctac agtattaagt acagtaacat gctgggcagg  184860
tttgtagccg aggagctaca aaccacgtag cctgggtgtg gagtaggcta caacatctag  184920
gtttatgtaa gttcacttta agatgctcac acaaggacaa aattgcctaa caatgcattt  184980
ctcagaacac gtctccctca ttaagccaca catggctgta ttacaattta catataattt  185040
taagcgtata taaattgcca gaaatcacca gatgaatcct tggcggtgac ataccccttc  185100
ccccaccata gaacattgca gactggcccg gacgcccagt atctcatgcc tgtaatgcca  185160
gcactttggg aggctgcagc gggcagatca cttgaggtta ggagttcgag accagcctga  185220
ccaacatggc aaaacaccat ctttactaaa aatacaaaaa ttattcggac gtggtagtgg  185280
gcacctgtag ttccagctac ttgggaggct gaggcaggag agtcacttga acttgggagg  185340
cagaggttgc aatgagccaa gatcgtgcca ctgcactcca gcccgggtga cagaatgaga  185400
ctctatctca aaaaaaaaag aaaaaaaaaa aaaaaggaaa agaacatttc agactggtac  185460
cagttacacc ggctcttgat cccttgaatg tggctgaccc tgaactagga tgtacttcat  185520
aataacacgt ccggctggga atacttagta caaaagaaag agtataaaat atcttttgaa  185580
tccaccttga tattgattcc atgttgaaat ggtaatattt tggatgtatt gggttgaata  185640
aaacatctca tgaaagtgat ttttaaaaat ctagaaattg tctgcaatta taattccaga  185700
ccacagagaa aaacgagaga caggaatgta tagaaaaagg gaacgtggga caaagtgagt  185760
atgaaattca actaacagaa gtgacagtgc ctagcatggg gtccagcact tagtaggtgt  185820
```

```
tcaattaata ttcatttccc tctcccttac cagtgaaggg tatgcctgtc gtggggaatg  185880
tgtcttcagg ctgagtgatc aggaaggact ttctcaatgg ctggcacgtg aacctagtca  185940
tgatttcagc tcttgaggtt gtactagaag atttatatcc aataatcgta aggtaccact  186000
tagcatcacg ctaagatgta ttaattcatt tatgcctttg gatggcccct tgaggtagga  186060
agtgtggttg tctccagttt accaaggtgg cttgcccaag gtcatctgct ggttggtgat  186120
taagccaggt tttcagtgtg gctccagcag gagtgggggc tggggacctt ctacctgctg  186180
tggtttctct ctctctctct ctctctctct ctctctctct ctcgatctgt ggaacatccc  186240
ccctgtcccc caaggtccca agggtcttat ttcttttggc caagcccttt ggagacctgc  186300
agatctggac acatctttga gagtttcagg aactagggcc agaaatgctg ggcagggtca  186360
tgaggagctg ccactggggt tgagaaggtg atggacatga ggggaagggt ctttgcagaa  186420
aggagaggcg tccctgtaag caggtcacag ccactgggcc tggccaactg cagccgagtg  186480
gaatgtgccc ctgccccatg accatatgcc ccaggtgtgc aatgtggcgg cccagagcac  186540
acactctgaa ccatcttgac acatcttcac tggttactag accccccctca gcctgtttcc  186600
ttggctgtaa aatggggatg acgctggtcc ctacttccta gggctctgag caggagtaag  186660
tagcttgtcg tataaaacat gttccctgca gtgcctggtg cctgctaaat gttccataaa  186720
cgtcagctgt tattttcatt caggggaagc tgaaatccat attttcatgg aaaatctccc  186780
agtttttaaa tgtggaccaa taatttcagc tttcacaaac ccagtatgag tcggtatggc  186840
ccctagggtg ccaactcaaa atctctgttg agaattttgc tgataggaag tggcctcctt  186900
ggaggtgttt gctgtgtcct gtgtctggca agtggggtgg ttttgataaa cgtgctggat  186960
ggatgtatgg gtgaatggat aaatggagga atgaatggag aaacaaatga gcaaatgaat  187020
aatgaatgga tggatgaatg gatgagcgaa tggatggatg aatggatgag caaatgaatg  187080
atgtacacac aaaggaatgg ataaatgatg aatgtgctaa tgaatttaag aatgatgaaa  187140
gaatgaatga ataaatgaac aaatggatgg atgaaagaat gaatgaatgt actaatgaat  187200
gaatcaatca atgaagaacc atttaaaaat gaatgcaact gagggtttat aagaaaaggt  187260
atcttaagcc tgggcatggt aattcatgct ggaatcccaa tgcttaggga cgctgaggcg  187320
ggaggatcgc ttgaacccag gagttcaaga ccagcctggg caacacaggg agacctcatt  187380
gctaccaaaa acaaaattgt tttaattaag cgggcatggt ggtacgtgcc tgtagtcata  187440
gctacttggg aggctgaggt gggaggatcg cttgaaccca ggagttcaag gctgcagtga  187500
gctaggatca agccactgca ttccagcctg ggcaacaaag caagatcctg tctcaaaaaa  187560
aaaaaaaaaa gatgtatttt agaaggtaaa ttcaatctgt ccaaaactga gctctgacct  187620
tcccctaaac ctgtgcccat tcagtggatg agagctccat cccttaaggg gttcaccaat  187680
tcatccattc ctttgtatgt acatcattca ttcaccttgg ctcatccctc tctcttacat  187740
ccacaccgtt ccatcagcaa atgttgaatc tgtcttaaat gattcatccc aaatcctccc  187800
cgcttaacta ccacccaact ccagccccca tccatcatca tcatcacttg cctggatggg  187860
ttcagtcacc tccagcctgg tctcccagct cccgtcctca cctctcactg tctactctcc  187920
cactcggcag ccagagggtg cctgtgaaca cccaaatcag gttccatccc tcctctactc  187980
agaaccctcc acggctcccc cctcactcag ggtaaaagcc aaagtcctcc ttgtggtcca  188040
ccaggccatg catgatctgc ctgtcacctc cctgccttca ccaccttcct cttttcccct  188100
caaccactcc actccagcca cactgacttc cttgtgctct tccccaaaaa tgtcgggcag  188160
acacattcat gcttcaggac cttaaatttg ctgtttcctc tacctaagat actaaagtga  188220
caagtcaaca cactcacctt gaccatgcaa tttaatgttg cagcctaccc tgtggactct  188280
ccaagggctc ccagtccctc tgtgatgctt tactttttct cttaaaaaaa aaattgttat  188340
ttaaaagaac ttgtctcgct gtgttgccca ggctggtgtc aaactcctgg cctcatacag  188400
tcctcccatt ccagcttccc aaagtactgg gattagaggc atgtgccact gcacccatcc  188460
caactttttt tttcccatag cacttttcat tttccatccc actgttaatt tacttattac  188520
gtccactgtc tgtctcctcc ccttagaggg tcagaccccg gaagtccagg ctctgttgcc  188580
taatgtatcc tgagcccctg gaacagagcc tggcacaaaa taggtactca ataaatgcat  188640
aagagcaaaa ctatatgtag gcagaggaca cacccagctt attcctcagt gatcacttct  188700
aaagttaaat gtccatggaa aacagtctca tccacatctc tttctggagg ccttccaagc  188760
gtgctccatg cagctctgtt gcctgcccct gcatcaggga atggaggctc tgctttatcc  188820
tgccctgtgg tgtgactccc agaggcatca gatgtggctg ggagtgggag acatggaaaa  188880
ttggctcctg caacagagaa ctatcagcct tcccatcaat tggttacttc taattctgtt  188940
atttttcagg ggcactgtct tctcataagc tccatctatg caaaactaag cccatgggtc  189000
atgatggttc cctcaggcca gaggcttgct ggagagacta atggatcccc tggctaaaat  189060
ctgtgcttgg gctgcacatt ggttaatttc ttctgaagga acagcctgag cctgacattc  189120
tccatctttt ccctggcagg ttctcccttc gcccgagcca gcattaaaag tgccaagctg  189180
gagaactcga cctttttttca caaaaaggag aggaggatgc gtttctacat ccgccgcatg  189240
gtcaaaactc aggccttcta ctggactgta ctcagtttgg tagctctcaa cacgctgtgt  189300
gttgctattg ttcactacaa ccagcccgag tggctctccg acttcctttg tgagtatcac  189360
ccagccccac ccctgccaac tccctgatcc ctccctcaca ccctttttcc acttctcttt  189420
ctctggtagt atgtgtatct tctttggtcc tcattgaatc tgccctttcc tttagccatt  189480
tctataactg tcactggggc caatgttact gttgctatga caatggaacc catctccctt  189540
agacctgaga gctggaagct ggaattcaga ccaacaaatg ctcctgtgat tcctttctaa  189600
gagagaggga cagaggggtg ctggtgaagg ggatgttgga agagagacag agaaagacgg  189660
agctcataag atagacagat agaaacagaa acatacatgt attaataatt tttatgtaca  189720
tctctggaaa tgttcataac ttatggttaa gagaggatgc cttagaaata aggagtggct  189780
tatatgttgc cctcattttc tctacttatt tctgactcta cttctctctt ctttcaaacc  189840
ttctgcttct ttcctgttag gttggtgcaa aattaattgc gttttttgcc tttttttttt  189900
tttttttaa ccacagttac ttttgcacca acctaatact tcctcccctg ccctttttgg  189960
cttccttatt cattcataga acatcccctc cagtatctgc gagagcgttt tgctccctca  190020
aggtacaagg cccactaagg ctttgccctc tgggcctatt cccagattct atgtgagtta  190080
gcatgagata gtatcaaaat tgagggccaa gtgagggtga ggaaaagcag caaaagatgg  190140
ggagatgtct gagcaggatt taaaaagtaa agagctcgag gaatcaacaa gagcagcgac  190200
tggggccagg catggtggct cacacctgta atcccagcat tttgggaggc tgaggtgggt  190260
ggatcacttg aggccaggag ttcaagacca gcctggccaa tatggtgaaa ccctgtcttt  190320
acaaaaaata caaaaattag ccagatgtga tggtgcacac ctgtaatccc agctactcag  190380
gaggctgagg cactagaact gcttgaatcc aggaggcaga ggttgcagtg agccaagatc  190440
atgccactgc actccagcct gagcaacaga gagagtgtct gtctcaaaaa ataaagtaaa  190500
ataaaataaa ataaaataaa gagtagtgat tgggcagtga ggggggcagg tggatgccct  190560
```

ggctttggct cacaggcccc aagtaaggac ttctcaaaac gtcttttgcc tactggctgt 190620
ctaatttatt cactgacctt ctgacctggt tcagaattga cttaggacag caagaagaga 190680
cagtctagtc tttgacctag aaaggcccgt gagcctagtc caggccattg tcttcttata 190740
accctccttg ttcccagtca cgttggctga ccccccagga cacccctcag gaaccagttc 190800
tccttcccag ggccctgacc tagtttcaaa cttagtaatt gtttttagtc cctctggagt 190860
ctcttataaa tgaggactct acttcgtgtt ttaacttcct ctaatactct atttttaatc 190920
tcctatattc tctctactaa tcatcttgta cagtctgtcc tggttcagga acaagggact 190980
gagacttcct gcctgggtcc tcagtgtcta taaaggtcct ttactcattc ccactttccc 191040
tttgagaaaa ctgagacaca gagaggttaa gtagattgcc caggatcaca cattagcttg 191100
gcatgatggc gggcgcctgt aatcccagct acttgggagg ctgaggcagg agaatcgctt 191160
gaacctggga ggcagaggtt gcagtgagcc cagatcatgc cactgcactc tagcctgggc 191220
aacagagcta gacgccatct caaaaaaaaa aaaaaaaaaa aaaagataca cattaatttc 191280
agagatgtca aaatataaac aaaaatgtat atcttggcat cagtgaagtg tagttgtttc 191340
tctggatctc agactccaca tctatgtggt agaaaccgga tttgatggtc ctgaaagttc 191400
ttccagatgc aacaatgcta aggataagta attctttcaa gtcttgtgca tcacctgcta 191460
tcatgtttcc atggtaactg aggaacaaga tctcagaaac tcttcagtcc tcccagagtt 191520
acttctggtg ggtctaggaa tgtgtcagat gttacaaaca gacttcctct gctgatattt 191580
tggtcctagg aaccctagag ttcccctcag acactaagat ctccttagcg tcctataaat 191640
aaggagaaat tttggtgata aatactgtga aggactttga cggtcagttc aaaacacctc 191700
ttaaaagcat gacatagcaa acacccttgg caaatatctt agttcatttg tactgctata 191760
acaaattacc cgagactggg taatttgata agaacagaaa tttattttct cacagttctg 191820
gaggctggga agcccaagat caaggcattg gcaggtttcc ctgtctggcg aaagctactc 191880
tctgcttcca agattgcacc ttgaacactg tatcctctgg aagggaggaa cactgggtcc 191940
ttacatggca gaaggtggag gagcaagagg gacaaacttc ctctgtcaac ctcttttata 192000
agggcaccta atcccattca tgagagctct accgtaatga cttaatcacc tcctgaaggc 192060
cccacctctt aatactgtta cattggcaat taagtttcaa cgtgaatttt ggaggggaca 192120
caaacattta aaccatcaca accaccaaac acaattagct ttgtggcctt aattagctat 192180
atgaaattca tggaagttag tttcagtcct ctgtctcttt cctttctgta tgctttctgc 192240
tcctcagaaa ccctcctcat ctctcctttc tatccattaa gtacccacgc ccttcctaac 192300
tcctcatctt cctaccctac caagaaagcc ctctcagaaa aggatctgat gtcagccatt 192360
tatttgctgg agcaaatgca tatccatgtt ttaccccctcc ctgaggcatt tgcaatttta 192420
tgcttgctca tcaaagaaca aaaggctttg tcttactcaa gactttttag gtcactcaca 192480
acacaggatt tctaggggac ataagacaag ttttctgagt taggagaaaa gccatacctt 192540
aggtgggttg cctgtgtcgc tccaactaag tacttaactt caggattaca aataggatat 192600
cattatgatt tctatttcct tttatccttt ggagctcagt cacgtagaag tagattaaat 192660
ataattgtta gatcacagca ccctggcatt atggggccgt tatggtccat tgttattatg 192720
tgaattattc agttaattag tttatttttt aaatgtgata aacacccagg aacccaccag 192780
tcaacacaaa agtccttggc aataatctat atccgatcct tctcatcgaa ccagggcaaa 192840
aactacaaga tggagaccca ctgatatttt tctcattcct tttaaaatcg gcctaaggtt 192900
ggttagcttg ttggttggag ggtagggcat aattgttgct tttttttttt tttttttttt 192960
ttagacaagg tcttgctctg tcacccaggc tacagtaggg tggcccaatc ttggctcact 193020
gcaacctcca cctcccaggt ttaagtgatt ctcatgcctc agcctcccaa gtagctgggt 193080
ttacaggcat gtgtcaccac actggctaat ttttgtattt ttagtagagg cggggtttgc 193140
catgttagcc aggctggtct caaactcctg acctcagttg atctgaccgc ctaggcctcc 193200
caaagtgctg ggattacaga cgtgagccac catgcccagc cagctcttcc tttttaacag 193260
aggggaaact gaggcccatg ggaaggacac cttggacagg gcgtggccac agtgggtcat 193320
gtatataatc ccagcacttt gggaggctgt gctgggagga tcacttgagg ccaggagttc 193380
aagaccagcc agggcaacat agtgagaccc ccatctccac ataaaaattt taaaaagaaa 193440
aaagataagt cagaagttgg gtgtggtgac acatgcctgt agttctagca tgttggaggc 193500
caaatcaggg aaactgtttg aggccaggag tttgaaacca gcctaacagc atagcaagac 193560
ctcatctcta caaaaaataa aaagtttaaa aatgataata aaaggaaagt cagagccacc 193620
tggaacccct accctcagca agcctaacct cctctctgtt tcctccttct cccttctaga 193680
ctatgcagaa ttcatttttct taggactctt tatgtccgaa atgtttataa aaatgtacgg 193740
gcttgggacg cggccttact tccactcttc cttcaactgc tttgactgtg gggtaagtgc 193800
tcttgtttct aagagttcat ttctccagct cttgcctgga atgacagata cctggacaca 193860
ttaaagggag aaaggtaaag tcacccctga atatgagaga ctcagatgga tgcagaagga 193920
atgagaaaac aatcccaaac actggcaagg atacagtgta cccagaaccc tcaaccaccg 193980
ccagtgggag gaaaacgtat agaccccctt tggaaagcta agtgggggac ataagacaag 194040
ttttccaagt tgggagaaaa gccatgcctt aggtgggttg cctgtgtcgc tccaactaag 194100
tacccaactt caggattaca aacaggacat caatatgatt tctatttctt cttttccttt 194160
gtagctcagt catgtggagg tagatgaagt ataattgtta gattacaaca ccctggcatt 194220
atggagccat tatggtcctt tgttattttg tgaattactc agttaattaa tttatttttt 194280
aaatgtgatt aacacccagt aacccactag tccacacaaa acctaagtcc tggagaataa 194340
tctacgtcca atccttctca tcgaaccagg gcaaaaaacta caagatggag atatgaccca 194400
gcattccatt gctaggaatt catcctagaa aatctcaccc agatacctag gagacacagg 194460
ccagaatgtc cctgcagctg gaagtgaaat taaggttgtt cgcaaataag tggagaatgc 194520
ctggcccagg gcagccctaa tcatttacca tagtcctgtt ggtctcagaa aggcttaata 194580
atttatttat ttttttttat tttttgtttt tattttttgt ttttgagatg gagtctcgtt 194640
ctgtcaccca ggctggagtg cggtggcgcc atctcggctc actgcaagct ccgcctccca 194700
ggttcactcc attctcctgc ctcagcctcc cgagtagctg ggactacagg tgcccgccat 194760
catacctggc taattttttg tatttttagt agagatgggg tttcaccgtg ttagccagga 194820
tggtcttgat ctcctgacct cgtgatccac ccgccttggc ctcccaaagt gctgggatta 194880
caggcgtgag ccaccacacc cagccagctt aataatttat aataactgaa tgttgtactg 194940
ttttctgcca ttatagaaaa ttatgttgtt ggagaaaaca aaatacatac aaacaagcaa 195000
accttcccta cataaatgac ccaagtagtt aaagaataaa accaatttct ttccattaaa 195060
aagaaaagaa agccgggtgt gatgcctcat gcctatagcc tcagctattc aggaggctga 195120
ggcagcagaa ttgcttgagc ccaggagttg aaaaccagcc caggcaacat agcaagaccc 195180
tgtctctaca aaaattaata ataattagcc aggtgtggtg gtgcacacct gtagccccag 195240
ctactcagaa ggctaaggtg ggaggattgc ttgagcccag cagtttgagg ctgcagtgag 195300

```
ctatgatcac accactgccc tccagcctgg acaagagagt gagaccccat ctctaagaaa  195360
taaaagtagg ccaggcacag tggctcacac ctataatccc agcactttga gaggcggagg  195420
caggtggatc acctgaagtc aggagttcaa gaccagcctg gccaacatgg cgaaaccccg  195480
tctatactaa aaaaatacaa aaattagcca ggcgtcgtgg cacatgcctg taatcccagc  195540
tacttgggag gctgaggaag gagaatcact tgaactgggg aggcagaggt tgcagtaagc  195600
tgagattgca ccactgcact ccagcctggg tgacagaatg agactccgtc tcaaaaaaaa  195660
aaaaagaaaa attttaaaat gtcctgagca accttgtttg taatagttcc aagtctcaat  195720
atccgtgtat ccctttgctg tagaacagat aaatattttg tggcatatct atataatgaa  195780
atactctgtg acaatcaaag tccaccaaca gcagccacat gcccaacaac aggaatgaat  195840
ctcacccatg taacatggca cagaaggagg caggagctag caacgtaagt ccatacagtt  195900
catgcaaagt tcaagtggac aaaattaaac tctctctctc tctctacata tatatatata  195960
tatatatata tttttttttt tttttttttt tttttttttt tttttgagat cagagtctca  196020
ctctattgcc caggctggag tgcagtggcg caatcttggc tcactacaac ctccacctcc  196080
cgggttcaag ccattctccc gcctcagcct cccaagtagc tgggattaga ggcatgcacc  196140
accacccccg gctaatttg tattttttgt agagaccggg attcagcaat ttgcccaggc  196200
tggtctcgaa atcctgatct caggtgatcc acctgccctg gcctcccaaa gtgctgggat  196260
tacaagcgtg agccaccacg ccccgcctta aactgtattt tttaaggatg atacttgaat  196320
acgttaaaaa ggcgaggacc ttgaaaacac aacgctcggt aaaagaaacc aaacacaaaa  196380
ggtcaagtat tgcataattc catttgtatg aaatgtccag agcaggcaaa tccatagaga  196440
cagaaagtag attagtggtt gctagggtct gggtgaggga gagtggggag taactgctca  196500
tggggacagg gcctcctttg ggggtgatga aaatgttttg gaacttgata gaggtgatag  196560
ttgcagaata ttgtgcatgt acctaaaggc actgaattgt gtaattcaaa gtgtgaattt  196620
tatgttatgt gaatttcacc tcagtttttt ttaaggtaag aaaatggtta ttacaaaatt  196680
caggatggta gttatatcac agtgtctctg gaaacttcca gggtatccac atgtcccttt  196740
ttattttatt ttatttttta ttttatttga gatagggtct tgctctgttg cccaggctag  196800
agtgcagtgg caggatcatg accctctcct gtctcaaatt cctaggctca agctatcctc  196860
cctcctcagc ctcctaagta gctgggacta taggcacatg ccaccatgct tgactaattt  196920
tttttttttt tgtaaagtca gggtttccct gtgttaccca ggctggtctt gaactcctgg  196980
gctcaagtga tctgcccacc tcggcctccc aaagttccag aattacaggc atgagccact  197040
gccctagcct tctcctaatt gttgacatag gtagtagttg catgacattc actttgtaat  197100
tatgtgtttc aggaattctc aggcctgtgg gagctcttaa taaataaaaa agaggccagg  197160
tgtggtggct cacgcctgta atcccagcac tttgggaggc cgaggcaggc ggatcacgag  197220
gtcaggagtt cgagactagc ctggccaaca cagtgaaacc ccgtctctac taaaaataca  197280
aaaaattagc cgggcgtggt ggcgggtgcc tgtaatccca gttacttggg aggctgaggc  197340
aggagaatcg cttgaacctg ggaggcggag gttgcagtaa gctgagatcg cgccactgca  197400
caccagcctg ggtgataaga gcaagactcc atctcaaaat aaatgaataa ataaaaaataa  197460
ataaataaat aagaggccgg gtgcagtggc tcaatgcttt ggaaagtgga ggccaacagt  197520
tggagagacc aaagcaggag gatggcttca gcccagaagt ttgaggccag cctgggcaat  197580
actagcgaga cactatctct ataaaaatgt tttaaaatta gccagatgtg gtggggcaca  197640
cctgtaatcc cagctactca agaggctgag gtgggaggat cacttaagcc caggaggaca  197700
gtgctgcagt gagctatgat tgcgccactg cactccagcc tgggtgacac agtgagaccc  197760
ggtctctata gataaatgaa tggatgaatg agggggtcaa ggatcctcac ccggcttcca  197820
tttggaggga ggagtttggt tgagttcttg caaggttggt acctaggaaa tgcttgccag  197880
ttctggagcc cagacactgt ccctggacat gagaccaggt tctctgccct aggttatcat  197940
tgggagcatc ttcgaggtca tctgggctgt cataaaacct ggcacatcct ttggaatcag  198000
cgtgttacga gccctcaggt tattgcgtat tttcaaagtc acaaagtaag tctttggggt  198060
tcctggacat ttgtacaggg ggtggggatg ggggacatgg tggggccgcc tccagaaagt  198120
tgggaaagtg agcctcgtgt ttcgagggct gactccgggg ccctgcctcc cccgcctggc  198180
ctgagtcctc gcctggcctc tgtcggcagg tactgggcat ctctcagaaa cctggtcgtc  198240
tctctcctca actccatgaa gtccatcatc agcctgttgt ttctcctttt cctgttcatt  198300
gtcgtcttcg ccctttggg aatgcaactc ttcggcggcc agtaagtcct tcacaggaat  198360
tccaactcct ggttccctgg ggtcaggctc agggaacaca cagtcccctc caccgtgcag  198420
gctgccttcc tcgtagccca gacacccatt gcggtcaccc aaatgggcag ggccctgggt  198480
accactcagg gtttcctggg gacagagatg atggagacgt tcgtttcctt ggagatgaga  198540
tactgagcca caccctcaga gcaccccggg tggggccaac gtgaaatgtc tgtgtcctcc  198600
ctgcaggttt aatttcgatg aagggactcc tcccaccaac ttcgatactt ttccagcagc  198660
aataatgacg gtgtttcagg tacagcctcc acctggcccc acgggccaac acctctcagt  198720
gtcacagatg aaagtgcctg ctccacatcc aaggggcttc cctgaactcc tccttctcta  198780
cctggccttt tcacaccact ttgaaacaca gattttatgg ttatcattat tcaattatgg  198840
tgaggccaac agatcaggag atgaatgtca ttggaaagat agtttgtggc tgggcacggt  198900
ggctcacacc cataatccca gcactttggc caggtacggt ggctcacacc tgtaatccca  198960
acgctttggg aagcccaggt gggcggatca cttgagatca ggaattcgag accagcctgg  199020
ccaacatggt gaaaccccat ctctactaaa aatacaaaaa ttagccgggc gtggtagcac  199080
atgcctgtaa tcccagctac tcgggagatg aggcacaaga attgcttgaa cctgggaggc  199140
agaggttgca gtgagccaag atcgcgccac tgcactccag cctgggcaac agagtgagac  199200
tccatctcaa aaaagaaaaa gaaaaaaaaa accactttgg gaggtcaaga tgggaggact  199260
acttgaggcc aggagtttga gacaagtctg ggcaacatag tgagactccg tctctgcaaa  199320
aaaataataa taataattag ctgggcatgg tgatacatac ctcctagcta ctagggcagc  199380
tgaagtggaa ggattgcttg agcccaggag gttgaggctg cagtaagcta caatcacacc  199440
actatactcc agcctgggcg agagagcaaa gccctgtctc aaaaacgaaa agaaagtttg  199500
ttatactcac agatcctcag agaaggagca caccatgcag gaccaagcag agaagcaaca  199560
gggtcaagca ggaagagaag gaaaatgtgg gcaagaggct tgattgtggt ttccatggga  199620
cggaatgggt gaggcagagt aaacagctcg agactggcta gtttggatca tttcagtggg  199680
ctctggggca gaggagctgt tcctacttgt ctaggacctg gccttggggt gattagggca  199740
ggtggatagt gctgggaaga taaaggaggt ggttgggata tgggctggtt gggatattgt  199800
ttggtttgct tttaaaaagc ctgctcaggg ctaaattgtt tactacctct agggactggc  199860
tagtgctgga ccgggcagtc cctccagagt cagcaagacc ccagatgcat cagaataaag  199920
aaaataaaat gcgtggccag gccaatgagg tggttcatgc ctgtaatctc agcactttgg  199980
gagaccaagg cgggaggatt gcttgagccc aggagttcaa ggctgccgtg agctccagcc  200040
```

```
tgcaccacag agcaaggccc tgtctcttaa aaaaaaggca gagaaaaaaa atggctaata  200100
cacccatcaa atctgaagat accttggtct catattccag ggtgatcaac ccaaagcaac  200160
ttctgcaccc atgtgggcgc attccctgag gcttgggact ggcccagccg ggaccttcag  200220
agcatctttg gtggattctt tctctttgag ggactgagag tgtatagaaa atgtgacttc  200280
actctctcct tctcctgggg aggtagtttc taaatgagac cccaagacag ggagttgaag  200340
aggaaacctt ccatgaaggg aagttctgag cccccacata agcgattttt tttttttttt  200400
tgagatggag tctcgctctg ttgcccaggc tggagtgcga cggcacgttc ttggctcact  200460
acaacctctg cctcctgggt tcaagcgatt ctcctgcctc agcctcccga gtagctgaga  200520
ctacaggtgc atactaccat gcctggctaa tttttgtatt tttagtagag acagggtttc  200580
actatgttgg ccaggctggt ctcgaactcc tggcctcgtg atctgcctgc ctcggcctcc  200640
caaagtgctg ggattacagg catgagccac cacacctggc ccataagcga ttattaatag  200700
cactgatcgc tagtcatgta tctttagctc agaggttctc acccaaggac aagtctgtcc  200760
tccaaggaca tgtagcaatg tctgcaagca ttgttggttg tcacagctag ggagagggtg  200820
ctactggcat ctggtgggtg gagactagga atgctgctca atatcctaca atgcacagga  200880
cagccccaaa tagaataatc tggccccaaa tatcagcagt gctgaggctt agaaaccctg  200940
ttttagcaga ttcatgtttt tggagttctt taacatttac tttatcctca tggggatatg  201000
gatagaagga aggaagttgg atcttttta aaggagcatg taggtgctgt ttgaatatcc  201060
ccttggttct ttcagtatgc atcagcacaa cttgcgtctg tcaacaccta atcctttgcc  201120
ttggtctttc tctggtcccc tgctctgccc ccaaggaact gcagtccagc agtactgtga  201180
attttttgtg ccacacctta aaaggagcag ccgttggtgg ataaataccc cagctccctc  201240
accctcaggt gggatgaccc ctagagctcc ccagcaagac caagccccgg ttacctacag  201300
tggaaactcg cttgatcaca tactgtttac gttccaccct cttttccctt ttctcacttc  201360
tcctctcccc tactggtgct tcctgagatc acctcccaga caaaccactt gcacccgaac  201420
ccttgttcca gggtctgcct caggcagggg gaccccaaac gtgtccttgt gctacatttg  201480
tgctatccac gtagtagctt gtttaatcat caccatgacc acatgaggaa cacaggtaaa  201540
tattaaaatc ctgtcttagt ctgctcaggc agccataaca aaataccaca cactgggtgg  201600
cttatacagg aaacatttat tctctcatag ttctggaggc cgggaagtcc aagatcaaag  201660
tgttagcagg gttagttagt tcctggtgag ggccctcttc ctagcttgca gatagccacc  201720
ttcttgctgt gtcctcatat gtcaaagaga gagagagaga gttgtgatgt ttcttcctgt  201780
tctttttttt tttttttttt tgagacaaaa atctcaaaaa aaaatctatt tttttttag  201840
gcaaatcaca tttttttgtc acccagcctg gagtgcagtg gcacaatcat agctcactgc  201900
agcctcaaac tcctaggttc aaacgatcct cccacctcag ccccttgagt agctgggact  201960
acagatgggc accagctaat ttttttaaat tttttgtaaa gatggggtct tgctatattg  202020
cccaggctaa tcttgaactc ctgggctcaa gtgatcctcc caccttggcc tcccaaagtg  202080
ctgggattac aggcatgagc catggcatgc ggtctcttcc tgttcttata agggcactaa  202140
taccatcatg aagtccccca tgacctcatc taaccctagt tacctcttaa aggcccccatc  202200
tccaaatacc atcccatcat aggttagggc ttcaactcat gaatttggag gcgggcacaa  202260
tttagtccat aacaaatccc cttaatcaca tcaagtaaga cagagttaca ggagggtctg  202320
tgactcctcc agggtcccat tttcctagaa gccaggctaa gagccccacg acgcaggaac  202380
ggccctttct actcgcaaac aaagagaaaa gccaaggaga agccaacacg gagtctggct  202440
ctgcaaaccg ggcaggattg ttaaagacct cctgggctcg gggatggggt gggcggattc  202500
cggctccaca gctgcatctc caaggggccc gtggctgaga ggggggttgg ctgtgtgttt  202560
cttcctcccc tttcagatcc tgacgggcga agactggaac gaggtcatgt acgacgggat  202620
caagtctcag gggggcgtgc agggcggcat ggtgttctcc atctatttca ttgtactgac  202680
gctctttggg aactgtatcc ttcatggaga gagagaaggg gacaggcctg gacctctggc  202740
agaggagagg ttgcaggggc tcaagggagg gtactgagag acccagatac ccagggccca  202800
agtggtgtcc caccagtggt tgcttttcct gactcagaca tttgcagaca ccctcctgaa  202860
tgtgttcttg gccatcgctg tggacaatct ggccaacgcc caggagctca ccaaggtgga  202920
ggcggtggga gaatgtttct ctggcaaagt taccacctgc ccatggcaga tcaggacggg  202980
ggtgggggtg ggggtggggg tgggggtggg ggcatgggaa cagggttaga acttttgccg  203040
gggatgcacc atgcaaagag aaggcgcctc tccccccact cccagaaaca gactgtccct  203100
catcaagcaa attctacagc caagagggtg ggaagggggga aggcagtgag gtcgctgcag  203160
gaaacggatg gcaaactcaa ccaaaaggcc gtttacaggg agtaagcagg gtttccaagg  203220
aatggtgtag cccccaggct agtggatggg agagggagtg ctgttatggg gacccagtca  203280
gagctggggc caaggaaaaa gggctgccac cagccctggg accttagaga acccagaacc  203340
atggcaaggc acagatggag tggccaataa atgtccccac cttctctctt cctctggctt  203400
cccgctggag cctcccctta gccaaacgca gcatgttaag agctagcctc cgtccagcct  203460
aagcctctcc ccaaggaccc tattaagtta agattacatg taacaggtac agggtcttcc  203520
tctcagccct ggggtctccc tcagcattgc agccccacct ccagtgcctc gaggtattca  203580
ggacatgttt gtgaaattga accaaaccaa gcagacgttg ccaacgctcc atctgccggc  203640
cctggcagga gggagagaga gtttcccggc cccagctccc agtggaggga agcggaagtc  203700
tctgccatcc caagcacacg gccacaagcc tggccactgt ggagctggct ggcatggctg  203760
agccgagggc tgatccagcc atgagctcat ccaagttcca agagtccatc cttaggggct  203820
ggtgcaggag ggtagcagaa ggggagggag aaaggccagt tcgtttatct cctgggaggt  203880
gtggacattc ctctccagat ccacattctt tctttcattg atcctacaag catttcttgg  203940
tcatttaata cgtgttttta atcctattca gtcctcatgg aaaccttagg agccaagttc  204000
tctgagcccc attttacaga tttcatcatt cagtaagcac ttaatgagca cctactgtgt  204060
gaccaaggcc ctggtctagg acttagggat taagcagtga acaaaaaaag gcaaaaatcc  204120
ctgcctccgt ggagcaggga ttcaagaggg gagacagaca agaaacaaga taaatttgta  204180
aacatacgta gcttgtcagt tggtgataaa cacaacagag aaaaattcag tagggaaagt  204240
cagggagagt tggaatttta gatgagatgt gtgtcgcaca gagaggttga gagacttgcc  204300
caaggccaca cagcagtaag ttgtggagct gggatttgaa cccaggccgt ctgggtctgc  204360
agcttgtgct cttaactgct gtgtaccagt tgcttgaatt tgggcatgtt ttatgctcac  204420
ttgggaacct gtgggaaatg cagattccag ggcccagcac tggttctata gattatttgg  204480
ggagcctgag gatctgcatt ttaggtgttt ctgaggcaga tggtccagag acctagctct  204540
gaaaaatgct gggaatggtg ccaggagggg tgggggtggc cctatgagag cagggtggcc  204600
agccagatcc catctccatg ttgtctctga cagtgtcctg atctgaccat ttccaaggtg  204660
gtaaggttgc tccccgttcc agtgattcgg agcacagcgg gagagctgcc tgcaatggca  204720
tgacttttct tatgggcggg ttcatttctg gccatttctt tctcgttgcc ttttctttgc  204780
```

```
tttttctttg ttggcttttc tgttttacga atgaggccct gcatgaaggc tgaagaagga  204840
tttaaagtcc aaaaacgtct ttttctgtat gtatttttaa aacctcttcc cccattctcc  204900
tcctctctga acctaaccac cagtgagcag cagcaccctg ggcagttggc tgtagcccaa  204960
gtgccctgct ctcctctccc caccgccttc ctgtcatggg ggctgggaat ataaattcct  205020
ctcctcattc tccttctggg ggctgttgac agtgcatggc aggggccatc ggatgccagg  205080
ctcttctgtg tgtgagggta gttggtgttt tttgaaagtt ggttcagaga gttcacatgg  205140
ctcagaaagc ctagtgagag gaaaatcttt gcactgcttt ccagctcatt aagacaggat  205200
gcaggggcca ggcatggtgg cacatgcctg gaatcccagc actttgggag gccgaaatgg  205260
gaggatcatt tgaggccaga agttcaagac cagcctgggc aacatagtga gaccctgtct  205320
ctacaaaaaa aaaaaaaaaa ttaaatgtat acaggcatag tggcatgcac ctgtagtccc  205380
agttgcttgg gaggctgagg tgggaggatt gcttgagccc aggagttcaa ggttacagtg  205440
agctatgatt gtgccactgc actccaggct gggcaaccaa gggagactct gtctctgaaa  205500
acaaacaaaa gaaaaaaaaa taggctgcag gaaagtcttc attgtaggaa gagaagggac  205560
atttttattt tttgttatct ggctgtgtgt taaaataggc ttcataatga gttagatgtc  205620
aaacttatac acagagggga tagcaataca cttaaccaat agcaggtacc cattccaatt  205680
ggggagcctt ggttctgatt ggtcgaaata tttcaaatgt tgcccctggt cagcaacagg  205740
gtcagaagtg agtccccaag gcctagttca tgttttgtga acaaagattc cacgtgcctt  205800
ttaggacgag caagaggaag aagaagcagc gaaccagaaa cttgccctac agaaagccaa  205860
ggaggtggca gaagtgagtc ctctgtccgc ggccaacatg tctatagctg tgtaagtgcc  205920
cctaatccct gggatgctac cctggctcct gaacgtccac actatcccag gcacagattt  205980
gggaagcagt gggggtggtc cttgacagaa ctgagcttta ggaagagaca cttcttgtcc  206040
ttccacccac tttcactcaa taaatatttg gttagcagct gttatgtacc cagcactgtt  206100
ctaacttctg gggatacagc attaacaagg aggaaaaaaa aaatcccacc tgtgtgtagc  206160
cattctagca agggaaggag tcaataaatt agataaataa gtaaattata tattgtgtta  206220
gaaggcgatg gaactacaga gaaagtaggg gagggaaata gcaaatgctg ggagtgaaga  206280
gagttgtgat tttaaacgaa gttgtcaggg aaggcatcac ctagaatagg ggtccccagt  206340
cccggggctg tggactggta ccaggccgag gcctattagg aacggggctg cacagcagga  206400
ggtgaacagt gagcaagcaa gcattaccgc ctgagctcca cctgccgtca gatcagcagg  206460
cagcattaga ttctcatagg aacacaaaca ctattgtgaa cggtgcatct gagggatcta  206520
ggttgcgtgc tccttttaag aatcgaatgc ctgatgatct caggtgaaac agtttcatcc  206580
caaaaccacc ccccacacct aggtctgtgg aaaaactgtc ttccacaaaa ctggcccctg  206640
gtgccaaaaa ggttggggac tgctcaccta gaaggttaca tggcctgaag gaggtgaggg  206700
aggagccact ggggggcctg gggaagggca tcccaggcag agggaacagc ataggcaatg  206760
gccctgaggc aggaacatgc ctgatgtgaa ggaggcctgt gtgactagaa tcgaatagta  206820
agtgtgagga ggtgaaggca aggaggtgac aagcagatta cacagggcct tctgggtcag  206880
gggggaggac ttgggctttt gcccctagcc aggtgggagc catggagggt tcttgagcag  206940
aggaggctgg gacctgactc agatgctcac agactcctag cattcagtgg ggagtagagg  207000
gtggagagca ggagtgggag gctgagatgt gggttggttc gcctgggtca tccatccaag  207060
ctacagtgcc tagcaatgct ctaagtcctg tgaccatgcc actgcaggaa agagcaacag  207120
aagaatcaaa agccagccaa gtccgtgtgg gagcagcgga ccagtgagat gcgaaagcag  207180
aacttgctgg ccagccggga ggccctgtat aacgaaatgg acccggacga gcgctggaag  207240
gctgcctaca cgcggcacct gcggccagac atgaagacgc acttggaccg gccgctggtg  207300
gtggacccgc aggagaaccg caacaacaac accaacaaga gccgggcggc cgagcccacc  207360
gtggaccagc gcctcggcca gcagcgcgcc gaggacttcc tcaggaaaca ggcccgctac  207420
cacgatcggg cccgggaccc cagcggctcg gcgggcctgg acgcacggag gccctgggcg  207480
ggaagccagg aggccgagct gagccgggag ggaccctacg gccgcgagtc ggaccaccac  207540
gcccgggagg gcagcctgga gcaacccggg ttctgggagg gcgaggccga gcgaggcaag  207600
gccggggacc cccaccggag gcacgtgcac cggcaggggg gcagcaggga gagccgcagc  207660
gggtccccgc gcacgggcgc ggacggggag catcgacgtc atcgcgcgca ccgcaggccc  207720
ggggaggagg gtccggagga caaggcggag cggagggcgc ggcaccgcga gggcagccgg  207780
ccggcccggg gcggcgaggg cgagggcgag ggcccccgacg ggggcgagcg caggagaagg  207840
caccggcatg gcgctccagc cacgtacgag ggggacgcgc ggagggagga caaggagcgg  207900
aggcatcgga ggaggaagta agtggaggtg acctcgaatc cgcagaatga cggtaacatt  207960
aataatgaca acagccaaag tagcacgtgc tgtgtatttg tttataaaaa tatattataa  208020
aatgctgtat ttggccaggc gcagtggctc acgcctgtaa tcccagcact ttgggaggcc  208080
gaggcggatg gatcacgagg tcaggagttc aagaccagcc tggccaagat ggtgaaaccc  208140
cacctctaat aaaaatacaa aaattagccg ggcacggtgg caggcgcctg tagccccagc  208200
tactcaggag gctgaggcag gagaatcgcc tgaaaacagg gggcggaggt tgcaatgagc  208260
cgagatcaca ccaccgcact ccagcctggg cgacagagtg agactctgtc tcaaaaaaaa  208320
aaaaaaagtg ctgtatttgg ccaggagcag tggctcatgc ctgtaatccc agcactttga  208380
gaggccgagg cgggcggatc acttgaggtc aggagttgga gaacaggctg gccaacatag  208440
tgaaaccccg tctctactaa aaatacaaaa attagtggtg gtgcccacct gtattcccac  208500
tactcaggag gctgaggcgg gagaatcagt tgaacctggg aggtggaggt aggttgcagt  208560
gagctgagat cgtgccatca cactccagcc tgggcaacag agcaagactc tgtctcaaaa  208620
aaaaaaaaat gctgtatgtt tttgtttttt tgacacaggg tctcgcctgt tgcccaggct  208680
ggagtgcagt ggcagtcata gctcagtgca gcctctacct cccgggctca agccatccgc  208740
ctcagcctca caagtagctg ggaccacaga catgtgccac atgcctggct aatttttgta  208800
gagacagtgt tttgtagaga cagggtttca ctgtgtttcc caggctggtc tcaaactcct  208860
gaactcaagc attccgcctg ccttagcctc cctaaagtgc tgggactaca gggttgagcc  208920
accacactca gcctaatttt tttaccttta gtagaaatga ggcctggctc tgttgcccag  208980
gctggtcccc aactcctggc ctcaagcaat catcccacct cagtctccca aagtgttcgg  209040
attagaggct tcacagatgg ggaaactgag agattgagtg agctcctcaa ggtcattcct  209100
ctaaccagtg tccttgaacc caggctctct ggcaccagag gccttgagca tttcagggaa  209160
actattaaga gaagccccac tgtcgtccag aattatatag tcttctgtgt tcttgctgtg  209220
tgacttttgc aaagtgactt catatctctg ggcctcacac aatggaaata gtgggatcta  209280
attgggtcat tgccaggatt gaatgaggta atgtatgcaa agggcctgga agagcagctg  209340
acacataata agtgctcggt aaatttagag catttttggc cattttcagc caactctatt  209400
tacctaatgc tattctttgg aagtttgaaa agccactctg ttgggaggcc aaggtgggag  209460
gatcacttga taccaggagt tggagaccag tctgggcaat agaggcagac cccatctcta  209520
```

```
taaaatataa aaaattaaac agatgtggtg gcatgcacct gcagtcccaa ctacttggga  209580
ggctgaggca ggagggtcac tggagcccag gatgtctagg ctatgatgag ctatgattgc  209640
accactgcac ttcagcctgg gcgacagagc aaggctttgt ctcaaaaaat aaaataaaaa  209700
ataaagaaaa agaaaaggca ctttgggccg ttagaattga agggagagca gagtttcaaa  209760
gctttggatg cagcgggatg tggtggctca tgcctgtagt cccagcactt tgggaggcca  209820
aggtgggagg atccacttga gccccggagt tcaagaccag cctgcgcaac atagtgagac  209880
ctcacctttt aaaaataaat aaaaatgtta gaaagctttt gaggcatctt ccaggccagc  209940
aacttatcca ttcagaacca gcatcctctt tttcataacg acattttgta atactttcta  210000
gcagatgcta tagtgattct gcatataggg actcaacaac ttacccatta aaatagacat  210060
cgtagacatt gtcctattac aaattaacct gctcttagtc ctcttttata ttaccatcag  210120
ggcataatat tgattttttt aatgatgggt ttaagtgatc ctgttgtatg acatatgagg  210180
taggccagca cttctcaaaa tctaatgtgt atgtgaatcc ccagggatct tgttaaaaca  210240
caaattgtaa ttccgtaggg ctaaggactc agtggagcct gagattctgc atttgcaacg  210300
agctcccaga tgaggctgat actactggtc cagggaccac attttgagta atgagactct  210360
ggaggacata gtgaagtaat tctgatatgt acaccataca caaaatcacc atgaagtgac  210420
aggcacaaat gatggctaac tctgggttgt gtggacaatt caaaccacat gaggggagtt  210480
gccagcagtg tcaagatgtt ccacaatgtt gaacacctct tggcaaagtt ccatatacaa  210540
aagagtctag tctttcttcc atttatttaa tagttgcatt gcaggaaaat gcaatgtata  210600
ttaaaaacat acaaaaaata tgttgtgttc ttatgtaaaa gagttaggtt taaactaaaa  210660
gcacaggatc aggtgcagtg gctcccacct gtaatcccag tgcattggga ggctgaggaa  210720
ggagaatcgc ttgaggccag gagttcgaga ccaacctggg cgacataagg agacctcgat  210780
ctctacaaaa gaagtttttt aattagccag gtgtggcggc aggtgcctgt agttctagct  210840
acttggaagg ctgaagcagg aggattgctt gagcccagga gttcaagatt acagtgagct  210900
atgattatgc cattgcattc caacctgggc aacagaacaa gtccttgtct caaaaaaaaa  210960
aaaaagaaag aaagaaagaa aaaacccaaa caaacaagca aactaaaagc acaggtaatt  211020
acaagcaaga tttttcacct ctttgaggga cattagaaag tcatgaagag gaaaagataa  211080
gtctttccca tatgggactg tcatgtacat ggtagggtat ttagtataac tgcctaccat  211140
tctctaagtg cctgcagtgc ccctcaatca ttatgttatt aggtttccac gtagttctac  211200
aacagttttc tgaaaaccat tgttctaggt cattctttcg cttcaatctt ctcctatggg  211260
tttatgcatt cattcagtta gtatttacta agtgcctact atattctaag ctcatgctgt  211320
gagttcagtc acacaactgc aagtgaagtg gtctgagaca ttctgagaaa tacgaccaag  211380
aaactgctcc cagggtctca gggcaggttt ccagaggagc aatctgagaa gggagtagag  211440
tgtttcagtc taacaacagc atgtgcaaag gccctggggt ggaccagaag gaggccagtt  211500
tgcaggacat gactagtgac gagaaagtga caaagaaatt gaaggtgcat tgatgagact  211560
ctggggctgt cagtcactca ggggaatgag agatcaaaac gggagtttag gtggaataaa  211620
gtgtttacca cagcactctc tgtatagtaa agaccaatga agagccaggt acaggccagt  211680
gtgatggttc acgcctgtaa tcccagcact ttgggaggca gagacaggtg gatcacctga  211740
ggtcaggggt tcagaaccag cttggccaac atggcaaaac cctgtctcta ctaaaaatac  211800
aaaaaattag ccaggcgtgg tggtggacgc ctataatccc agctactcag gaggctgagg  211860
cacaagaatt gtcctgcgag gcagaggtta cagtgagctg agatcacacc actgcactcc  211920
agcctgggca acagaacaag actctgtctc aaaaaaaaaa aaaaaaaaaa aaagccaggt  211980
acagtggtat gcacctgtaa tcccagctac tcaggaggct gaggcaaagg attgcttgag  212040
cccaggagtt cgagaccagc ctgagcattt agagaatggg aggccagtat actaaatacc  212100
ctaccatgta caagacagtc tcatatggaa aagaattatc ctttcctctt catgactttc  212160
tagtgctcct cacacaggtg aaaaatcttg cttataatta tctgtgcctt tagtttgttg  212220
gtttatttag ggttttgttt gttttttttt tttttttgag gcagggtctt gctctgttgc  212280
ccaggttgga ttgcagtagc attgctcatt ttagagatga gcaagacctc atgtctaaaa  212340
aaaaaagaaa gaccaatgat tattaattac tcttgctatt attactaata ttactgttat  212400
tatcagcctt attaacagat ctactgttat tgaaggaggc agagtgacag ggacaaaatg  212460
tctctcccta acaatatgcc aggaagagtt tttgaaagac aacagtaaac attggaaact  212520
acaagagcag caaagcctgg ttgtgaaagg caaggacttt ggggcaggca gtcacattcc  212580
tgccctatca cttccaggct gtgtgacttt cagaatttca ctcctctctg ggcctccatt  212640
tcctcatcta taaaatgaag ataagaatag tagctacctc cttctctggg tataagattt  212700
aactgagccg ggcgcggtgg ctcatgcctg taatcccagc actttgggag gccgaggtga  212760
gcggatcaca aggtcatgag ttcaagacca tcctggctaa tatggtgaaa ccccatctct  212820
actaaaaata ccaaaaaaaa aaaaaattag ccgggcgtag gtggtgcacg cctgtagtcc  212880
cagctactcg ggaggctgag gtaggagaat ggtgtaaaac ccgggaggcg gagcttgcag  212940
tgagccgaga tcgcaccact gcactccagc cggggagaca gagcgagact ccatctcaaa  213000
aaaaaaaaaa aaaaaaaaaa agatttaact gagttagtac gtgtaaaatg ctttgagtgg  213060
ttcctggctt ataccaagag ctcaataaat gttagcaatt ttttgtagca ttttggggtc  213120
tcactatgtt gcccaggctg gtgtcaaact cctggcctca agaaattctc ccactttggc  213180
ctcccaaagt gctggattta cagacatgag acaccatgcc tggccatgtt agctattatt  213240
aatatgaata ttattaagta ctcaatgaat gctattttta gcagtaatag taagcactca  213300
ggaagtgtca gctaatactg ttagtaatac tctcatcaat aaacataaaa agcaataagg  213360
acccagcttg cccaaatccc acagatggtt cctgctccct ctcttcttca gaggaagaaa  213420
ctatctcccc actttcaccc ccatagcctc agctggccag acccccattc tgaaccaggg  213480
gagtactgct aattccatta ttaatagaca catcaaacaa tctggccggg agagacatta  213540
ttcatttggc tgataaagag gttctaaggc tctttggaaa taaaagttca tgaagattca  213600
tgcactttaa gagaaaaaaa ttcaagatca gtcattcatc tgctttaaaa aaagtggcaa  213660
agataaaact ttatttgaga atataaaata ataaaaagac attttcgttc tctgttgtga  213720
caaagccagt ggccttcgga ggtctgcctt gtacattttt cctcttcttc agtcattcct  213780
tgaggctttt tgcaaacgta ccctgtgttt ttcattctcc agcatattga taattttttt  213840
tttttgagac atggtctcgc tttgtcatcc aggccccgga gtacagtggt acaatcatgg  213900
ctcactgcag ccttgacttc ctgagctcag gtgattctcc cacctcagcc tcccgagcag  213960
ctgggactac aggtgtgcat gaccatgcct agctaatctt ttgtattttt tgtagacaca  214020
gggttttgcc acattgccaa ggctggtctc caactcctgg gttcaagcga tcctcccacc  214080
tcagcctccc aaagtgctgg gattacagga gcgagctacc ttgccaggcc gatcatattt  214140
ttttcctttt tattcacttt gtcttctcct cattcctacc ttcatctgtc tttcagtggc  214200
tcactccagt gaaaagtgga ctgacgcaca ttctatttca tataattcaa tggctgctgg  214260
```

```
ccccagatcc cccataccag gtggccgagc ccagtggccc tgcagggtgg acaaaatgag  214320
ggtggaactt tcccagactg tcagtaaaaa tctatggagg acagagcttc tgcctctccc  214380
ttgcaaccag gcagtgcctt ctcccaggcc tatctgcttg caaagggaac ttttgccaag  214440
acctgctcca ctctagaatt cttatctctg ctgttcgcat cctaattcca cctgcatctg  214500
tcaccatgac aacctgctcc ccaaaaggaa caggaagaga gatgctggac ttttgagctc  214560
cacagtttat cctgcatggg ggtagggagt ggttaattac ttagcactct aattcttacg  214620
gtacccccaa tgggcccaag ttggtttttt taaaaaaaaa cagtcttgct ctgttaccca  214680
ggctggagtg cagtggcaca atcatagctc actgtagcct caaactcctg gactcaaatg  214740
atcttcccac ctcagcctcc caagtaactg gaacaacagt ctcgtgcaac tacgcccagc  214800
taattttttt tttttttttt ttttttttaga gatggggtct cactatgttc cccagactga  214860
tctcaaactc ctgggctcaa gcgatcttcc ttcctcagcc tcccaaagtg ctaggattac  214920
aggcgtaagc cactgtacca agctgcccca ttaaagcttt gaacaccaga gagcccagct  214980
cagctgtttt ccagctgggt aactctgggt aactttgcct ctctgaacct cagtctcctc  215040
ctgtgtgaaa tggggctgat cactataccc atctcggatg gtggtagttg cagggattaa  215100
atgagttaat acgtgaggtc cttaggacag gggggtggggga cacgagataa gcaataaaca  215160
ggaactgctg ttattatcac ccccacataa tccgatctca gggtctgagt gtgccccagg  215220
caaggtgtcc acagccctct gcagaaggat gcccaagtga tcagctggca caagaacgcc  215280
acgcacagca ggtgttatgc aactggccac ctattccagg cagaggatgc cagatcccca  215340
gggagaaggg ggtaggggtg cagcttcaaa gttttctgcc ccttttgagt tctccttgga  215400
gacactttgg aaatgaaacc tcccggaaat tgatattagg cctctgcagg ctgagcttgt  215460
taaaatttcc caacaaacag agccaacaga cgctctacaa ggaagcaaaa acaagacaaa  215520
acacattggc agaccctttt ccatctgctc ttggtagatg gtattcctct aagaaaatgc  215580
cgccacgagt ttctccatgg cttcttgagc tggtggccaa aggatttagg ttctctttga  215640
aattataact taactgggcc tgctttatgg cagggatatc actctctgaa atgtgtatat  215700
atatgtgtat gtatatatat acacatatat acacatatac atacacaggg ccaggcgtgg  215760
tggctcacac ctgtaatccc agcactttgg gcggccaagg caggtggatc tcttgagccc  215820
caggagttca ataccagcct gaacaacata gtgagaccct gtctctacaa aaattaataa  215880
aaataaccag gcatggcagt gtgtgcctgc aatcccagct acccagggtg ggaagatcgc  215940
ttgagcccag gagttaaaag ttgcagtgag ctatggtcat accactgcac ttcagcctgg  216000
gcaacagagc aagaccctgt ctcttaaaaa tatattatta ttattataca cacacagaca  216060
cacacagaca cacacacaca ttacagatga tgagaaaata ctctcagcca ggttttcatg  216120
atacacaact tctcaaaaag catcacaagc aggttagaat tagggatttc tttgtggact  216180
gtccaagatg ttgaggaaat attggtttag aatttacctc atttaggcca gaaatggtgg  216240
ctcacgcctg taatcctaac actttgggag gccaaggcca atggatctct tgaagccagg  216300
agttttagcc tggccaacat ggcaaaatcc tgtctctact aaaactacag aaaaaaaaaa  216360
aaaaattagc cgggtgtggt ggcacaggcc tgtagtccca gctactctgg aggctgaggc  216420
aggagaatca cttgaacctg ggaggcagag gttgcagtga gccgagatcg tgcattacac  216480
ttcagcctgg gtgacagagc aagactccat ctcaaaaaat aagatagata agataaatat  216540
atataatata tatgttatat atataatata gaaactacag aacaagtgat ctttgtatgt  216600
ttccagaata taacagcggg acaggcatag gatagacgtt cccattgcaa aagggagaaa  216660
ttggaaggga taaagaggtc accagtccta agcaagtgct aaatccagca agacaaatcc  216720
cattaggttt caaggcctga gaataatcct cggtgactct cagctcatta acatacttag  216780
ttctcagagc cagactcaat gaggttacgg cccgcatgtt atgggtcagg aactgaggct  216840
aagtaactca ctggagatta tgtggtaaag aaggtccagg atcattgctt cagtctccag  216900
gatatgggga aggttctact cctgttatcc caaattttaa aatgtgggaa ctaaggctca  216960
gagaggttaa gcaaatcaca cagggttgca cagctagtga tgttgctgag atttccctgt  217020
gtgtagtggc tcatgcctat aatcccagca ttttgggagg ctgaggcaag agggtcgctt  217080
gatcccagga gtttgagacc agcctgggca atatagtgag acctcatctc tacaaaaaga  217140
aaaattaaaa agttagccag gcgtggtggc aggcacctga agtcccagct actgggaagg  217200
ctgaggtggg aggattgcct gagcctggga ggtggcgatt acagtgagct gagatcgcgc  217260
cactgcacta caacctgggc gacagagtga gaccctgtct caaaaaaaaa aaaaaaaaaa  217320
gacattgccg agattcaaac ccaggtcagc ctgtcttctg aaatgtccct ctatgaccca  217380
ctcacaaaac tgagaaggca gaaagttgct tggacctgtc tatttcccct gtgcagtctc  217440
agagaaacag tggaactgcc tcggtttctc cttccgggaa gtattcatag aagcatccca  217500
cttacctact ttggtctgaa aataaattag cttgtctctc ttccacttac taaaaacacc  217560
gtgggttttt gcaagttaaa atgcaaaaat aaaatgagga gaatggtgct ggtagtttag  217620
ccagtgggaa gccctctggg gaaagccagc cttttattta ttacttattt atttatttat  217680
tctttctaga tagatttatg ggaaaccagg gctgtgttgt ccaggggtct gtagtccaga  217740
aggcatcaga tgggctacta agtgagtctt tgtccacctg tagatggcaa gaggcagggc  217800
ccaggtgtcc atggcttgga gaggcagggg ttgatgggag gtttgaggct gtgggatctc  217860
tcctggggcc tcagtatcct catctggata atggggacat tctggccagg cacggtggct  217920
ctatatatcc agcacttagg gaggcctata atcccagcac tttgggaggc tgaggtgggt  217980
ggatcactgt aggccacgag ttcaagcagc ctgggcaaca tggcgaagcc ctgtctctac  218040
tgaaaataga aaaactagct gggtattgtg gtgcacgctg gtaatcccag ctattcggga  218100
ggctgaggca cgaggatcac ttgaatccac gaggcagagg ttgcagtgag ccaagatcct  218160
gccactgcac tccagcctgg gcaacagagt gaggctctgt ctcagttaaa aaaaaaaaga  218220
aaaaagaaaa agaaagaaag aaaaagaaaa tgggggtatt catttatcat ttgacagtaa  218280
gtttacccag cattgactgt gtgagaggcc ctgtactagg cagtgaaaac tcagctaaga  218340
ataagaaagt taaaaacaag ctgggcattg tggtttacgc ctgtaatccc aacattttag  218400
gaggccgagg aggaagaatc acttgaggcc aggagtttga gaccaccctg ggcaacatag  218460
tgagacgcca gtctctacaa aaaattgtaa aattagccag acatggtggc gtgagcctgt  218520
agcctcagct acctggaggc tgagatggga ggatcactgg agcccagaag ttcaaggctg  218580
cagtaagcta tgatcctgcc actgctctcc agcctgggca acagagtaag accctgtctg  218640
aaaaaaaaaa aaaaaaagag gccaggtgca gtggctcaca cctgtaatct cagcactttg  218700
ggaggctgag gtgggtggat cacttgaggt caggaattcg agaccagcct ggccaaaatg  218760
gtgaaacccc atctctactg aaatacaaaa aattagccgg tcgtagtggt gggcacctgt  218820
aatcccagct actcaggagg ctgaggcaag agaatcgctt gaacctggga gccagaggtt  218880
gcagtgagcc gagatcacgc cactgtacga cagagcaaga aaaaagaaag aaagaaagaa  218940
aagaaataag atgatgggga gttgtggaaa cctgtccatg ggcacgtgaa ggtcttgacc  219000
```

```
tctgaccaag aagtgaacag gctcctctca attccaggca ctgcagggat ctgggacatg  219060
acttctccat gaccaaactg taccctttcc ttttcttttt tgtttttttg gtgacagggt  219120
ctcactctgt cacccagact ggagtgcagt ggggcgatca cggctcactg cagcctcaac  219180
ctcccaggct caagcaatcc tcccacttcg gcctcccaag tagctagaac tacaggcaca  219240
cagcgccacg cccgtcaatt tacacatttt ttgtagaaat agggtctcac tatgttgccc  219300
aagctggtct tgaactcctg gccttaagca atcctcctgc ctccgcttcc caaagtgctg  219360
ggattacagg cgtgagccac tgcgcccagc ccaaattgta ctcttgaaag atggaatctt  219420
agctaggatc ctgaactgtt gccttttatc ctaaatcagt tgttggttct ttttcattca  219480
cttgccttcc tcagagagaa ccagggctcc ggggtccctg tgtcgggccc caacctgtca  219540
accacccggc caatccagca ggacctgggc cgccaagacc caccccctggc agaggatatt  219600
gacaacatga agaacaacaa gctggccacc gcggagtcgg ccgctcccca cggcagcctt  219660
ggccacgccg gcctgcccca gagcccagcc aagatgggaa acagcaccga ccccggcccc  219720
atgctggcca tccctgccat ggccaccaac ccccagaacg ccgccagccg ccggacgccc  219780
aacaacccgg ggaacccatc caatcccggc ccccccaaga cccccgagaa tagccttatc  219840
gtcaccaacc ccagcggcac ccagaccaat tcagctaaga ctgccaggaa acccgaccac  219900
accacagtgg acatcccccc agcctgccca cccccccctca accacaccgt cgtacaaggt  219960
gagaccctct gctctcacat cactgggcag gggacctggc gtccctggag ccagaggctc  220020
tgctgagtga ccctggactg tgaccccatc tctctggcct cagtctcctc ccctggaaaa  220080
tgggcatagg cgtagtttcc taccccacag ggctgtggag ggttcagtga gataatttgt  220140
gcacagtgcc tggcacgggg ttgtgttcag tcgggttagc aatatcttct acgtccttcc  220200
ttcccaaggg gagccaggaa gccaccccat ttgaggagca atagggtcct ctgatggaag  220260
cttgaggggg tcagatgatt gattctctcg gcccagcact gtccaaaaga aatgtaacac  220320
aggccacatg caaatgtcag tttaaactct ctagtcgcca cattaaaaaa ggggccagat  220380
gtactggctc atgcctgtaa tcccagtact tcaggaggcc gaggtagagt gagccaagat  220440
ggcacctctg tactgcagcc tgggtgacaa agcgagactg tctcaaaaaa aaaaaaaaaa  220500
aaaaaaaatg gtgaactgct gggtggatta tgtcttaagt tcatctagtg tcagttctat  220560
gtgagagatt ttcatgagtt tgctggataa aggctttcca tggtcctgag acctaagatc  220620
ctaaggtctt gtcactgtgc ccattttata gatgtaggga ctgaggctca gagaggctca  220680
gcctgcccgt gggcacataa gcaggctggg ctgcagaatg gaagctccag aggctgatgg  220740
ctcctccccc tgagtcaaga gaggggtgct aatgggggca tgccatgcag tttatgggag  220800
gtctcagtat ttctatctgt tcagtgggtc tcttggcact ctccctacct gcctgcaagt  220860
gagggtgtga aggtccaacg aggatagggg caggtctgtg ttaatatccc atgagggccc  220920
caccgcactc aaggctatag agtggttgag agcaggctct cgggggccag gccgcctggg  220980
ttccaaatgc cagctctgcc acttcctgct gtgtgacctt agacaagtca ctttacttct  221040
ctgtgcctca atttcctcat ctgtaaacag gagatcagaa tatatcaacc tcagggctat  221100
acaagggttc agtgatgtca taagatgcct ggtatataca gcaggcactt tagaaatgtc  221160
agccgcttct tgcctgccct gggagtacac aggagttccc agagacttgt gggaaattgt  221220
ggagggagcc ctgtgttggt tcttgtccca acagtgaaca aaaacgccaa cccagaccca  221280
ctgccaaaaa aagaggaaga gaagaaggag gaggaggaag acgaccgtgg ggaagacggc  221340
cctaagccaa tgcctcccta tagctccatg ttcatcctgt ccacgaccaa cccgtgagta  221400
tggcccccag caagggcagg gggggcctgg ggctcccacc agggtggcgg aagtcaggcc  221460
agatagaggg caatgagtga gtgttgacca ccatgagtcc agggatacct ttgaacaagt  221520
tgaaaatgga tgctccttcc gtaagtcagg taagatgatt tgtcacaata tactttgttg  221580
gaagagaccc ctgtcctgcc atccactaga aaatcattgt tatttatgac aataaataaa  221640
caaatttgtc ataaataaac aaataaattt gtcctaaaca acaaataaat ttgtcataaa  221700
taaacaaatc ttcactgtga tgtaagaggc accccccttag aaatggctgc cttgtgcagt  221760
acacagcctg aacaactgca cgtggcagcc ctaggacctg aactctgttt ctaacctaga  221820
ctctgtaagg gtttagattc tgggcggata gtgtctgagt tccatggcct tctgtcttgg  221880
gcatctttga aatggataga ctatttaggg gagaaattta tcccatgaat gtcgtagtgg  221940
ctcggaggtt gttttagaat tgaatgtctc ccagggatat ttcttgaaag cctgaccgct  222000
caaaatgctt cttgacaatg aaggatcatg tcagataaga tgggggagaa gctgctttct  222060
ataatctgcc tcttggcaac tcaccctggg tagtaataaa taaaagtacc tttaaagtac  222120
tttttttattt agttgactta tcgattttac taaggaaaca cttatgtggt atctactcag  222180
tgccaggcac tgttctgagt gccttaaaat tttttttaat ttctctgagg ttgttactat  222240
gcttagctcc atttgacaga tgaaaaaact gaggtccaga gacgtgaatt cacctgccca  222300
aggtcacaca gcaagccagt gggagagctg gagtttgagc ccagacactg gctctagcct  222360
ccttgttctt aaccactcag ctctgctgcc attcacacaa ccttatgaac tatttattat  222420
tggctccact tattaagagg ttaactggca catcccattg gcacattcaa ggctctgata  222480
aggcctgcaa ttcataattt caataactaa ctttttggag cccctatcat gagccaggca  222540
taaattaagt cttgggtctc atgattttgt gaagtaagca ctagtattac ggctatttta  222600
cagatgaggg caccaaggca cagaggggac aagtaacttg cccaaggtca cacagctaat  222660
ttttaaaaag aaagaaagaa atctacttaa cccatagatt cacaatattg tttggccctg  222720
ggacatttaa tatcgaaaag cctttttatc tcctacagaa ttaaggaccg tatttcttca  222780
acctagcttg gggatcaaga tacttcaaga gggtcgtttg ggagtgatag gaactttgct  222840
aaacagggca tgtgaatgtc ttctctcacc gaggtcccct ctgccttctt ggggttccag  222900
gacccagaga gggcccccac ctggaggagt ttaatagttt gttgtgtagg aggccttggg  222960
ggttggagat ctcagtagtg gtaggtaaca tgagattatg gaagaaaagg gtttgtgagc  223020
ctgtggtctg agtggacctc tgcacgccca tctgtctcca acagccttcg ccgcctgtgc  223080
cattacatcc tgaacctgcg ctactttgag atgtgcatcc tcatggtcat tgccatgagc  223140
agcatcgccc tggccgccga ggaccctgtg cagcccaacg cacctcggaa caacgtgagt  223200
cccacagagc acaccccttc ctagcctggc tgctctgcct caggccactt tctcctgcat  223260
ccaaaatgct cataggtagg gtgggatgtt ggggtcaccc ctaggcatag cccttatggc  223320
tgctggttga gaggggaagc tctgattcct tggggatgct cttgggagca agacattcct  223380
tgaggcagtt tctctgtgag cctggtgggg tggaggtggc ccagagtgac tggggctgaa  223440
aattgctgga ttctctaatg gaggcgtgag actagcagga tatggatgtt gcacattctc  223500
tacatggaat aggggggtta ctggggcagg ggcggtgctc agaggtggtc ccctccgcag  223560
tagacatttc cctttgtaca cgaagctttg aaagaaacaa ctatttggct cagaaacaca  223620
gcctaagctt ttggttttta tgaaagcaag cccctttgcg gatggtgggt ctgttgacaa  223680
cccctgttaa ttgagcactt gctgtgtccc aggaagaaac tcagcatgca gtatctcatt  223740
```

```
taatcctcac aatgcgcccc cccaaccccc cgcccaggca tccccatttg acagatggga 223800
aaactgaggc tcaggggaat gagagagtgg taagtggcct gtccagggtc acacagcaga 223860
attccaactc tgcatccccc aaagctccca ctgcttcccc caactgtctg catttactaa 223920
tcacctactg tatgctacgg atgggtgtgc atagcccctt tgagtcctga caagcaggaa 223980
tgagtgcatg cttgtggttg agatggggaa accgaggcac caacaggcaa gggcgtgcct 224040
cagtcatggg ctgcgggcag aggcttgacc ccagggcctg gtagagggtg gactggtggc 224100
tcctgtttcc ctccccagct ccctccccca acccttccct cccaacccag agccaaaaaa 224160
gtgtgttttc tgctggtcca aggctctgct gccctggcta agtaggttag gacccaggca 224220
aagctggcga gccccatccc tcaagcccgc ccacagctta ccatgcactt tcccttcctt 224280
cccaggcctg gcaggccccc ctggggacct gatgggggag atggaaggaa ataattagaa 224340
cgcagctcct ggaggaagct agagccagtg ctcagcctcc tcacagtccg cttagttgct 224400
tcccgcagcc tggtttcccc caggggcctc caggagccag gcgtggggag gaggtgtccc 224460
tggaggggtc cacaaacccc ctgctgacgc gaggatgctg aagaaggcgt tgccttcggc 224520
agggagggca caggcatgga tgatccaggg ggcacggcag ctcccagggc tgaagggaat 224580
ctaggcagtg ctcagaccag gccccaggga ctgtttgcaa agagcgttca gctccccggc 224640
cccctccctc gtccatctcg cagtcgaaac ttctctacaa gaacactgtg gccccataac 224700
gttcacacca cgtaaccacc atccagggca agaaatagaa caaaaacgcc ccacgcggca 224760
tgtgcctcct cgatccccca cccccaccgc cttctttccc tctagagctg ctggggacac 224820
tgtctggaga catttttggt tgtcacgaca ggagggggga ggtgctcctg gcatctggtg 224880
ggtggaggcc agggatgttg ctcagcaccc gccgatgccc aggacagccc ccactctaga 224940
ggatgatcca gacccaaatg tccacagagc ccagcttgag aaaccctgcc ttaccggtaa 225000
ccacgacccc agcttctgga atgagcgttt ttggcttctc tctttttccc acctgcacag 225060
gctttttttt tttttttttt taagagacaa tgtctctctc tgtcgcccag gttggggtgc 225120
agtaacgtga tcatggctca ctgcagcctc aacgtcccgg gctcaagtga tcctcccacc 225180
tcagcccccc aggtagctag gaccacaggc atgcaccacc acacccagct aatttttaaa 225240
tgcttgtaga aacgggcctc gctatgttgc caggctggtc tcgaactctt gacctcaagc 225300
aatcctccct cctcagattc ccagagctct ggaattacag gcatgtaatt ccaattctta 225360
catgcctgta attggccaac actggccaat tcttaaaaac tgaatttatg tttgctcttc 225420
tgtaacattc aataaatgag acacttctat gcttcgcatt aaatgagtac atgttgcttt 225480
tgcaggattg atgggcattc tttttttttt tttttttttt gagatggagt cttgctctgt 225540
cacccaggct ggagtgcagt ggtgcaatct tggctcactg caacctccgc ctcccgggtt 225600
taagcgattc tcctgcctca gcctccagag tagctgggac tacaggcagg cgccaccaca 225660
cccggctaat ttttgtattt ttagtagaga cggggtttca cactatcagc cagactggtc 225720
tcaaactcct gacctcaagt gatccgcccg ccttggcctc ccaaagtgct gggattacag 225780
gcgtgagcca ccacgcccgg tcaatgagca ttctttatga tgctgttttg agatttactg 225840
tgtggcatgg gatgtgttat ccatcccctg ttgacagatg tttgggttgt ttctaagtgt 225900
gaatactgtc cccatgccac gcccctcaac atgtttcctg agtcacctgg acagtaattt 225960
ctccaggagg ccagatgcag tggctcacgc ctataatccc agcacttcga gaggccaagg 226020
tgggagcaat gcttgaggcc aggagttcaa gaccagcttg ggcaacatag tgagaccccc 226080
acctctacca aaaaaaaaaa aaatttttttt ttttttaatt aaccgagcgt ggtggtgcac 226140
acctgtggtc ccagccactt gggaggctga ggtgggagga tcacttgggt ctggaaggtc 226200
aaggctgtag tgatccatgt tcataccact gcactccaac ctgggtgaca gagcgagacc 226260
ctgtctcaat aaataagaat tcctccaggg tataaaccaa aagcgaagtt tctagagcat 226320
ataatttgca agtggttggc ctcagtaaat gcagcttgaa tgtttattgg acaataaaca 226380
cagtgaccct ttgggaggcc aaggcgggtg gatcacctga ggtcaggagt ttgagaccag 226440
cctggccaac atggtgaaac cccgtctcta ccaaaaatac aaaaattatc tgggcgtggt 226500
aacacacaac tgtaatccca gctactcggg aggctgaagc acaagaatca cttgaaccca 226560
ggaggtggag gttgcagtga gccaagatgg cgtcactgca ctctagcctt ggcgacagag 226620
cgagaccctg tctccaaaat atatataaat aaataaaaat aaacacagtg ggccgggcac 226680
agtgggccgg gctcgcacct gtaatcccag cactttggga ggccaaggtg ggtagatcac 226740
gtgaggtcag gagttcgaga ccagactggc caatatggta aaacctggtc tctactaaaa 226800
atacaaaaat tagccgggcg tggtagcatg cgcctgtaat cccagacact tggaggctga 226860
ggcagaagaa ttgcttgaac ccgggaggca gaggttccag tgagccaaga ttgtgccact 226920
gcactccagc ctgggtgaca gagtgagaca ccatctcaaa aaaaaattaa aaaataaatg 226980
aacgcagtgg cccttgcacc agtagctcat gggaactcct gttcttccac atccttgtca 227040
acacttggta ctgtcgactg tttcatttgg ccgatctgct gggtgtggag tgagatctta 227100
ttggggttgt gcttggcatt tccctgtaat gaatgagatc aagcactttt ttggattaga 227160
ctgagccaca ggaaataaca ttttcaaata gatgaaaaag atctaagtat taggaatact 227220
tgaacctaat ttattggtct tttgatttcc tcttgcacag cttattaaga gctccagaat 227280
tagattcacc tgacccccac ggcctgccct ttcccagctc cctctcttcc ttctttcctt 227340
ccattcattc ctttagtaag tatttgataa gcaactacta tgtgccaggt actgagcgag 227400
ccagggagga ttgacagggt atgagatggt ccctgcactc ccagagccca caaaccacca 227460
ggcctttgac caggctgtgc ccactgcctc gtgcacctga aatactctcc caccaccatc 227520
ccctctgccc acccaggtct ttcaagccaa tccccttgca ccagcccctc cctccaggaa 227580
gtcacctcac cctgacccca ggcactctgg tctctgattc ctcttcaagc accacatata 227640
acaggaatat aagttataac cacacagatc acagagccca gctcctccag gacccagtac 227700
agccccaact gttgatgcat tcattcaaca aacatttctt gagcacctac tgtattcctg 227760
accctgtatt ataagctgga gacgccatgg tgacagacag acatccctgt ccttgtgggg 227820
ctgacatttg ggtgggggag atggacaagg agattatcag taactacaac aaatgttcag 227880
ggagtgataa gtggccgggg gtgtggtggg cagagggaag gagagacttc gtaaagagga 227940
tctcaagcac caggagatgg aatttaaaca gccggtcagg ggagtcctca ctgggaaagt 228000
gttatttgag ctaagtcata aaggaggaga aagacggaat caaatgggat gtgggggaaa 228060
gcattccaga gagacagaac agcctgtgca aaggccctga ggtggaagca tcttggggaa 228120
caaaaggaag tgagcaaggg agagaatgag aggaagtgag ggcagggagc tgaatggtca 228180
gatcgtgcag gggcttgagg gcctcgggga ggactttgac ttttatccct gaatgaggtg 228240
ggagccacgg aggattgtaa gcaggggaag gatgtgcctg acttctttgg tgttcacagc 228300
gccctctggt ggccatgttc agtaatgctc agcccttgca gcttctgggt ggatctgatt 228360
tttttttttt tttttttttt agacagtctc tgtctcccag gctggagtgc agtggcacga 228420
tctcggctca ctgcaacctc cgcctcccac gttcaagtga ctgtcacgcc ttggcctccc 228480
```

```
aagtagctgg aattacaggc acacgccacc atgcccagct aatttttat atttttagta  228540
gacacggggt tttgccattt ggttaggctg gtctcgaact cctgacctca agtgatctgc  228600
ctgcctcagc ctcccaaagt gctgggatta caggctcgag ccaccgtgcc cagccggtgt  228660
ccaccccatg tctagcacca gccagacact gtgccggcgc accctcatct tcaggcctgg  228720
gtgacaccag aggtgtgcta tggtgtgtcc tggacagggg ctgggccaga ggacattgct  228780
cgtccaggca gaaacatcag gcctggggag gggcacagga aaaatcaacc taccctggca  228840
ggggcctggc cttgaagcag gaagagatgc cgtggcagga agttggcccc agtgtttaaa  228900
aaaaccacgt agcaactatt tctcgcccag gatgcccagg aaagcaaggg tactggggga  228960
ttagatccat caccaagaag gatacagtca gccctgaact tctctggggc cgcttctaat  229020
ccactacagg gcttggggca aattttaaaa ggtacccttc ccgtgggtta gcgaactggc  229080
ctagtacagt gattttttg ttaggatttg ctgccatctg ctggacaatt tcattcacaa  229140
catacaaatc tgcagtatga aaagagatgg gaggggccct tgtgcagtgc acgccctgcg  229200
caactgtata tagcagctgt gtttcctctt ctgggtagaa actctgctcc ccagtaggcg  229260
atcgttagtt ttaccggggc tctgctggaa caggccagtg atccactgct ctcttgcttt  229320
tatcccttac aggtgctgcg atactttgac tacgttttta caggcgtctt tacctttgag  229380
atggtgatca aggtgagtgc agattataag tgagaacaca cggtaatttt ttttttaag  229440
caagtgcagg gctgggcaca gtggatcatg cctgtaatcc cagcactttg ggaggctgag  229500
gcaggcagat cacttgagat caggaggttg aggccagcct ggccaacatg gtgaaacccc  229560
atctctacta aaaatacaaa aattagccgg gcatggtggc acatgtctgt aatcccagct  229620
actcgggagg ctgaggcagg agaatcactt gaaccctagg ctgcaatgag ccgatgtgga  229680
ggctgcagtg agccgagatc ttgccactgc attccagcct gggtgacaca gcgagactct  229740
gtcaaaaaaa aaaaaaaaaa aaagagctgg gattccagga gatcctgagc ctccaagaat  229800
gccccccttg agaggatgag tctcccagag gattagaaat gcctggtgtg tttgaagagc  229860
agcaaggaag ctggtgtggc tgggcggagt gagagaacag tggggaaacg aaggacagag  229920
agatgagtgg ggaggtgagg gggcaccttg tgccggggat cacagagagg gctcttcggc  229980
tcttactttg agtgaggtga gggccataga gtgttctgag cagaggaggg acttgatcca  230040
ggtgttcaca ggtgcccttt ggcatctgtg ggaagccaga ggacctgtga gcaggtgatc  230100
acactggtcc ccatgggcga tgacggggac aggatcaggc tggtgaccaa agaagaggtg  230160
agaagtggac agattcttgg aaggttctgg aaatagagcc agtgagtttt gctgatagag  230220
ccaccaatga gggatttggg acaaagaggc atcaaagagg atcccaaagt ttggatctaa  230280
gagccggcaa gccagagctg gcttccatca ggcaaagggg ggccgcctca tggggcaggg  230340
gctccccact cctccctgga gtcctctggc cactgcccat ccctgcaaga tgaggtggcc  230400
tcattggctt ccctgcctct ccccgagagg ctagagagtg ggtggcagca ccccagggtg  230460
gggatcaggt gggggttctg agcaccctct cttctccccc acagatgatt gacctggggc  230520
tcgtcctgca tcagggtgcc tacttccgtg acctctggaa tattctcgac ttcatagtgg  230580
tcagtggggc cctggtagcc tttgccttca cgtaagtctc ctcgcaaggg ttcctcttgc  230640
ctcttttccc ccaaccccca gcctgggcca cacatcggat tacaggacat gttctcaggg  230700
tctagggatg gggtgtgtgg gctccgggga cgtgggagat atcagcatgc caccaggaag  230760
agcttcgatg gctttttgca tgatgtccat ggaggaagaa ggagaaggga ccccccctcc  230820
tgccaacctt ctacctcctc acacagcaac gggcctcagc cacatcactg gcccctgct  230880
gtgcagcttc ctgtagacta gcctcgccgg aacatctcat cccccctacta ctccacaagc  230940
gccgcccaaa ccgctgtctc tttggaaagt ccctaaagag acaatcagga aacgaatgtg  231000
catgagaatt ctgacccccct ccctatgcct gaaggccccg tagttgtaga cctggtgact  231060
ccctttgtgt gtctttcact tctcctggca gtcctaggat tctctgccct ctgaaaggcc  231120
atgtgtcatc ctgcagctcc aagatggcgc cccagttgta ggcagccatt tcaggatggc  231180
acccaagctc ttagtagtca tcccaagatg gcatccaagt tctgggtggc cattccaaga  231240
tggcccctga gttctgagct atcattccaa gatggcctct gaatttgggg tggtcattct  231300
tagatggtcc ctgagttcca aggtgacctt caagttctgg gtagccattc caggatggtc  231360
cccaagctct gggtggctat tccaagatgg ccccaagttc taggcagcca ttgcaagatg  231420
gcccctgagt tccagggtgg cccccaagtt ctgggcaacc attccaaggt ggcatccaag  231480
ttctgggtgg ctattccaag atggcctctg atttctgggc taccatgcta agatggcctc  231540
tggattcttg gtggccattc ttacatggtc cctgagttcc aaggtggcct tcaagttctg  231600
ggtagccatt ccaagacggt ccccaagtct tggatggcta ctcgaaggtg acccccaagt  231660
tctgggcagc catctcaagg tggcacccta gttctgggta accattccaa aatggcaccc  231720
aagttctagg gcaaccattt caaaatggcc cccaagttct gggtgactat ttcaagatgg  231780
tacccaacag gtgagtggcc attagccctt agggccctga tagcagactt agcagtacat  231840
tcctgaagtt gtagacattt ggagcgggat gaaaaatatc taatcagtct ttaatcaaga  231900
aacaaatctt ggggaccctg gctgtgccca tcatggtgaa tgattccctg acaggttttg  231960
aaaggatctt gacacattca ctcccatcgt gagagaatca ggggcttcct cctgtgcctc  232020
tgcctctagg ctccctcctg agccaatctg gaggggccct tgaatggtct ccctcaccaa  232080
acaatgagga cttggtttgt caggagggcc aaaatagtgg cccatttcca gtagaagggc  232140
tgttaagtag gccacactta gattcttctc tgggaacaca atgaggtcaa gttgtgttag  232200
aacaaaaaat ctccagagtt tttggatgcc tcagagctgg agatgtatca tgaaggttgg  232260
gaggctgatt atacttcttc ctctttctct ttcactcctt cctcctcttt ctcctctctt  232320
tttgttcgtt tactcttttc tttttctctt ctcctctccc tccccacatc cttccctctc  232380
ctcaaagctt ttcagtgtct atttgactac tagagcaatg cacggtggct tacacctgca  232440
atcccagcac tttgggaggc tgagacaggc agattgcttg agcccaggag gccaagacca  232500
gcctgggtaa catagggaga ccccatctct aaaaaaaaaa aaaaacaatt agccaggcat  232560
ggtagtatgc ctgcactagc agctacacgg gaggctgagg tgggagaatt gcttgagccc  232620
aggaggttca aggctgcagt gagccgaaat cgcaccactg caccccagtc tggggaacac  232680
aggaagaact tgtctcaaaa aaataaaaag tttaaaaaat taaaaatcaa tgaatttgct  232740
atttagaata ttatgcttta tatggttact gaataatttt aatagtgatg agtacaaaaa  232800
aaacaggttt agcaagctgt tctgtaggtt aaaaagtaaa taaataaata attaattaaa  232860
caaaatacaa tgcacatcaa attaggggac aaagattgtg acgaataaga caaggagtcc  232920
atgtctttaa aatatgaaaa gcagttacaa atcaataaga aacactactt ctcaatggat  232980
aaatgggcaa aggacataaa cagaaatctg atagaatgct ggcaactagt aaaaatggag  233040
gtaaatcaac ccttggaatt cagagaaatg taaaataaaa acgagataca attcattccc  233100
tatcaagtta gcactgttcc cgccgcaccc ccacacacac acaaaaaatg atttttttag  233160
ctaataaaca gcatatataa gaatgtatta taataggctg ggcacagtgg ctcacgcctg  233220
```

```
taaccctagc atttgggag gccaagggag ggggatcacc tgaggtcagc agttcgagac 233280
cagcctggcc gacatgacaa aaccctgtct ctactaaaaa atacaaaaat tagccaggca 233340
tggtggcgga tgcctgtaat cccagctact caggtgggta aggcaggaga attgcttgga 233400
cccaggagat ggagactgca gtgagccgag atcatgccac tgcactccag cctgggtgag 233460
aaagcaagat tttgtctcaa aaataaaaaa aggaatgtat tataataaaa tatacttttc 233520
tccccctcta tcacctattt aagcaggtcc ttcaagttgt caggtagaca tcatgctatg 233580
agaaaattta aatcctgaaa agccagaatg ttttaccacc ctcagcctgg aatgaatcct 233640
tctcctatgg aaataaccta cgggtttctc cacccctctc tgcctttcag ccccttccct 233700
ccctctcccc tccttttctt tctccctctt tctcttcctc ctttcccctc tcttccctct 233760
ctcttcttcc ctctctctgt ctctttctgt tcgtctttct ccttttaccc cctctcagtt 233820
tctatctttt tattttcctc tttctctctc tctctccctc tctttctctc tcactccctg 233880
cactgttgat gacctatgtc cttgggtgat gtgggcctcc cctggaccgt gtagcttgga 233940
gaaagctgac cctctgtcat cggtctggca acagggactt ggccccccta ccctgcattc 234000
tgatgaggaa tggtattcag acaaaggcag atcccaggac acaggaggac atgctcaggc 234060
agggaccccc gccccttttcc tctggggcaa ggtctgctca gcagcctcca agattcctag 234120
ggctcaagag gtggcaggta gctcagggca ctagggcagg cagtggggtg aatatgtcac 234180
tcatatccac ctgtccacac acaatgctta ccttggccac ctgtgcccag gggaatgggt 234240
tttatcctgt gaatcctccc agtgaccacc actgagtgtg gcacagataa atggtaccaa 234300
gcccaagctg ttcaggtctc caatgtcact ttcctctcag acctctgttg tagctgacat 234360
actgtaatgc tgaggagggc cgggcacagt ggctcatgcc tgtaatccta gctctttcgg 234420
aggccaaggc agatggatca cctggggtca ggagttcaag accagcctgg gcaacatggt 234480
gaaaccccag gcaacatggt aaaaccctgt ctctactaaa aatacaaata ttagccaagc 234540
gtgatagcag gcgcctgtaa tctcagctac tcgggaggct gaggcagaag aattgcttga 234600
acctgggaag tggaggttgc agtgagccaa gattgcacca ctgcactcca gcctgggcaa 234660
cagagcaaga ctctgtctca aaaaaaaaaa aaaatgctga ggaggtgact gtcccacctc 234720
catcctccga gttgaccatc acaatttagg gaggggaatg acctacaaag gacccagaag 234780
caagcctttc aattgttgag cttttgccat tatgggccat cgtttacaac atgctgtttc 234840
taggttctct ggaggtaaaa ttagcctcct cttttaaaca aagctaatct gcaaaagcga 234900
accaaaaatt cttttccacc agagatcaat tagcagaatg agctgggtgc gatggctcac 234960
acctgtaatc ccagcacttg gggaggccga ggcaggtgga tcacttgagg tcaggggtcc 235020
aagaccagca tggccaacat ggtgaaaccc catctctact aaaaatacaa aaactagctg 235080
ggtgtggtgg ggagggcctg tagtcccagc tactcgggag ggtgaggcag gagaattgct 235140
tgaacccagg aggtgaaggt tgcagtgagc caagattgtg ccactgcact ccagcctggg 235200
tgacggagca agactccatc tcaaaaaaaa aaaaaaaaaa aaaaaacagc agaatgattc 235260
ttttggggag ttgacttttt ttttaatttc tgagttttct ttttaaatat caagttatac 235320
aagggcattc aaattggcct acaactcaca ggaatttggc agcctgtttg cagagtcaag 235380
cttttacatt gttctcatga aattggtaca ggcataaagc caccccttcac tcttgaaaat 235440
ccattttgaa tgttgttgtt ttaattctta tgcaagaaaa ggatctggat agggatttca 235500
ggccatcctg tcaaccctgg caggcttgta gatcatgcag gaactgggag gtgtgagatt 235560
ttgccagtag gatcctggca agtgcctggg actctcccag ggttttggaa gagccgacgg 235620
acatgagtcc aacagggagc atctttatat catggccgaa gggatgagag aggagaccct 235680
caaacctcac gcctaccaca ccctccccac cccactgtca agagtccatc tggtactgct 235740
gttcctcccc cagggcaggg ctgcaggccc agcacagctg gccaggtgcc ttgatcaagc 235800
cattcctgca cacctaagag ccaaactgct agaaaaccag aataggagct actgcttttt 235860
tccctaaaaa gttttggaat cttctccccg ttacaggttt ctggcctctt ttgcctgaga 235920
aggtctctca ccctatgagg actttgctta ttgtctttcc ttgttatcgg atagttggca 235980
cattggaagg agcatggatg ctctgaggtt ctcagcctga gcgctgaact ctccacccgc 236040
cccccacccc ccaccccagg gtcctctgct tatttccttt ctggtctttt aacttgcttt 236100
gtctgtcctc tgtgcatatc ccctcataga caaggctgag agccccacaa gtattagatt 236160
gaccttattg ttttaagaaa ttgtccctcc aggtctgttt gatttctctc tagatgtgca 236220
agtcctttag cctctctgtg cctcagtttt tcccatctag atgaggaaac tgcggcccag 236280
agggactgtg gagggaagta agtccgacaa gatcactgag gttgggttca gctgtcagat 236340
gctacccatc tcccagccct gaatacggag gctcacagtg agcagaatga tgctcagcag 236400
cctggccagc ctgggttctt tgaggcctgg caggggctgcg agatccaggg gaagggaata 236460
ggggaaggga gcataaggtt attcccttcc ttgttgaaag gaaccttgcc attctggcct 236520
gttggggtca aagcaaggat tcttcccccca gtgctgtgat tgtggcctcg tctccgatat 236580
gggagaaaac tatccctgtg gtcccaccaa gggatgtatt gaagctcttc tgaagatgtc 236640
cacccctcct gcacctcacc caaatatctg tgtgtgtgtg tcctgctcaa ttcactgact 236700
gtgtcccttg tatccatgcg tctaccataa acaccccatt tcatgagcca tcacacgtgg 236760
tatcacgctc tgtgcccatg catcagggcg gccaactgac atttctcagc agctggcaga 236820
tcatgatcct gccctcaccg ccaagagtcc atctggcgcg gctgttcttc ccccaaaggc 236880
aggaccgcaa ctggcagagc gccttgatca agctgctcct gcatacccag gagccaaact 236940
gtcaggaagc caaagatgga gccctcaggc tgctatctct tgatcctcat cttcaaaaca 237000
gcccccaccc ctgaaggcat tatttttctt gtgtatgatg aaatggaaag aagattagag 237060
tgcgagatac ccacacctgg gtttgaatct tagtctgtct tcccagctgt gtgcctgccc 237120
ttgggcaggt cactcttttt ctctaggcct cagcttcctc atctggaaaa tggtcataat 237180
ggtgctgtct tcccataggc aaatgcagtg atgtccagaa gactcccata ttaaacctaa 237240
agtcagcaga ttaggcaaaa atcactgtca ttgaaaactc cctcaatcat ccgtaaagaa 237300
gctgggtgtg gtgtctctca cctgtagtcc cagctacttg ggaggctgag gtgggagaat 237360
cacttgagcc agggagttca aggctgcggt aagctatgat tgtgctactg cactccagcc 237420
tgggcgacag agcaagacca cgtctctaaa aatataaaat aaagccgggt gcggtggctt 237480
acgcctgtaa tcccagcact ttggaaggct gaggcagcct ggcaacagag tgagaatcca 237540
tcaaaaaaaa aaaaaaaaaa aaaaaaagta gaatctatat gattctacgt atgcaataat 237600
tcctagatac actgaatttg agaaccccaa gtcagactac aggaaaagga gatgaggggg 237660
tgtggaggag aatccacttg gaatatttgt agacatttaa accattctgt gttttaaaaa 237720
atatcacagc cgggcgcggt ggctcacacc tgtaatccta gcactttggg aggccaaggt 237780
gggcggatca cgaggtcaag agatggagac catcctggct aacacggtga aaccccatct 237840
ctactaaaaa tacaaaaaaa attagctggg cgtggtggtg ggcgcctgta gtcccagcac 237900
tcgggaggct gaggaaggag aatggcgtga acctgggagg cggagcttgc agtgagccga 237960
```

```
gatcttgcca ctgcactcca gcctgggcga cagagcgaga ctccgtttca aaaaaaaaaa  238020
aaaaaatcac taacttccag aggggtcgtg gatggaaaat tccatagagt ccgcttggcg  238080
acagggtttc cgccattctg atggcggtca agtctttcta acctggatct ccagtcattg  238140
ttgaaggcgc ctaatgagcc ccaagcctga ttccaatgaa tcacgagagg accagctgct  238200
aggtgctgat agctttcccc aggcccgcat ttgctcagag ggcttcagag ttgcttctaa  238260
ttccatccca agtcagaact ctttgctgac cccctccttc ataaagagca aagccaaggc  238320
catagctttt gttaatcaaa catcagaatt ccacagacct gagttggttg gttgtttgtt  238380
ttaagagaca gagtcttgcc caggatgcag tggctcacac ttgtaatccc agcgctctgg  238440
gaggcctagg caggaggatc acttgagccc aggagtttga gaccagcctg agcaacataa  238500
tgagaccccc gtctctacaa aaaatggaaa aatttgcctg tatttccagc tacttgggag  238560
gctaaggtgg gagaatcacc tgagccctgg aggttgaggc tacagtgagc caagatcccg  238620
ctactgcact gcagcctggg caacagaggg agaccctgcc tcaaaaaaaa aggagagaag  238680
gagagagaca gggtctccct atgttgtcca ggctggtctc gaacttctgg cctcaagcaa  238740
tcttcccaac tcgtcctccc aaggtgctgg gattatagct gtgagccacg gcacccagtc  238800
tgggcctgtt ttgcagatga ggataacgag aggcagagtc aggattcaaa cccaggtccc  238860
ctcaacttca aagctcacaa ccttttagac attctaaaac cttgcagctc cacaacgcct  238920
ggagaagagg ggtttctccg gctcttggca gtgactttcc gtggtgaatt cacctttggt  238980
aactgacagc tttgcagctg tcctgctacc tggaaatttg gctttcttag tgctttcttg  239040
ggcagtgcca ggtgcctgcc aagggcgggg gactgaatgg aggtgggggc ggcttccaga  239100
tggaaggatg gacatcggcc agcgccatga gcctgaggct cccccaactg ctgcccgggc  239160
gggactcggg ggtgctcagg ggtgcgtgtg tgtacgtgcg tgttctgtgt tcttttttct  239220
gaggccactt acgatctgtc tctccctccg atgccacatc accaggagca gtacacggta  239280
aagtctctct ctatctttct ctctctctct ctttctctct ctctctctct catattctgt  239340
ctctcgtgat ctgtcccctg gtgcagcctc gttagttctg ggcctgtttc tgtggccttg  239400
tgtccttgct gccgctgtcc tgtcgcttca aatgaccaga actcactccc tgcgaaggag  239460
gcatcccaaa gggtcttgcc aatgcctccg cccatgcccc accagttctt gcagagaaca  239520
gaaggggcag aggttcagtt tcaataggca agctgggtgg agcagttatc agaagcaatg  239580
aaagtgggcc agacacggtg gctcacgcct ctaatcccag cattttggga ggccgaggcg  239640
ggtagatcac ttgaggtcag gagtttcaga ccagcctggt caacatggtg aaaccccatc  239700
tctactaaaa atgcaaaaaa ttatctgggc ttggtggtgc acacctgtaa tcccagctac  239760
ataggaagct gaggcaggag aatcacttaa acctgggagg tggaggttgc agtgagctga  239820
gattgcacca ctgcactcca ccctgggtga cagagtgaga ctctgtctca aaaaaatata  239880
taaaataaat tgaacaataa aaaaataaaa tggccatgga atcgttttca gatgaggaga  239940
tgcagaatgc ccatggagac atgctcccaa ttgtcacttg tttgggacat caagatttta  240000
gccagttcca tgtgcaacct ggatgtacag ttccttgact ttttttctat caacatgtat  240060
tctaaagttc aatttcaaaa ggaaacttta gccaggtgca gtggtgcatg cctgcagtcc  240120
cagccatttg ggaggctgag actgaaggat cacttgagcc caggagttgg aggctgcggt  240180
gagctatgat cgtgccactg cactcccccc tgagattcca tctctttaat ttaaataaaa  240240
aaaaaggaaa ctatattatc cacttacaac cagcattgct aacctaagat aaatctgcaa  240300
ctgcaaaagt aaatgtaggc cagacatggt ggctcacacc tataatccca gcactttggg  240360
aggccgaggc aggtggatca cttgaggtcg ggagttcgag accagcctga ccaacatgga  240420
gaaaccccgt ctctactaaa aatacaaaat tagccggacg tgatggcaca tgcctgtaat  240480
cccagctact cgggaggctg aggcaaaaga atttcttgaa cccgggaggc agagactgct  240540
gtgagctgag atcacgccat tcactccagc ctgggtaaca agagagaaat gccatctcaa  240600
aaaaaaaaaa aaaaagtaaa tctaacagaa accagacaat gttgttgcct tcaagctggg  240660
ctctttgtta aaaggaaaat tactaagtgt tagggaggtg ttaaaggcct attagcatct  240720
acctgaggct tcctttctcg caaaagcaga gcgtctgaaa gatacgtgga aaagaaactt  240780
aaagtataat aaaaaagaaa gaaagaaaaa gaaatgatta tgcccctctg agatccaatt  240840
atttaatctg tgcccctgtt ctgcctaaaa ttatctcagt gactgtccaa cgtgtgtctc  240900
acacttgggg gcacagcctt gagatgataa tgatgatgtt agttttaaaa agaaaaaaaa  240960
aggttcagag ttctgaatcc tggagtatat ctctgcctag caggctaaaa tacaattatc  241020
gtctttgttc cctgaaaaat gaaaaaaatg gagtccttta aaaagcaaat ggtgtgaaga  241080
atgatgtttt tgcactggat actgagaccc atcgtgatgg gggtctctgg ggcagctctg  241140
ctcatgacct gggaggtcac tgtagggaga tgttttctag gtgacctccc cacccaaata  241200
ctccaaccgg aggcattcac gtgtcctgag accacacgcc aggcgcaggc taggggctag  241260
gacaagaatc aagattaaag gggaaatggc caggtgcggt ggctcatgcc tgtaatccca  241320
gcactttggg agtcaaggcc agtggattac ttgaggtcgg gagttcgaga ccagcctggc  241380
caacacggtg aaaccctgtc tctactgaaa atacaaaaat tagccaggtg tggtgactca  241440
tgcctgtagt cccagctatt cgggaggctg aggtgggaga atcacttgaa cccaggaggc  241500
agaggttgca gtaagccaag atcatgccac tgcactccag cctgggcaat agagcaagac  241560
tccatctcaa aaaaaaaaaa aaagattaaa gggaaaatga acacagagaa gagtagatta  241620
cactgtaagc ctttgaagag ttttctgtct aaaaccagag accgaagaaa caaacaaaga  241680
ttaactccga aatagcacat aggagctggc aggagccaga ggtaggcagt caggaaatgc  241740
tgtcggaggg agcaacaggt aatttgggct ttgaggaccg ggtagttctg tgactggaga  241800
agtggaggaa gggcatttct agcagcggga acagtatatg cataagcaga cagaggcaaa  241860
agaatgtggc tggggcttga gatatgtagc cataaatggg aatgcaaagg tgaaggtaag  241920
ttggactaga ttttcaagag cattgaatgc catgcccaga agtttgcact tgctcttctg  241980
agaattcacg tgctccagaa gaattctgag caagagaaag agtgacaagg tcattggctt  242040
tagccactgt gtgcataaaa catggaagaa aaggcaggga atgaggagca agttgggaga  242100
cgggtgaggg gggatggcac ccaggaatgg atggcgggat gttaaggaag gtgacccact  242160
ggggatgggg atggggatag agggcaggca gttgaccatg actctcaggt ttctggtgtg  242220
gacaactgga tgggtcatga gtgccatgaa ccacaagcta ttcatggtcc cactcaatac  242280
cctcctcttg gggggcctga gtcatggttg gccaagggtg tcatggcatc tctggggtct  242340
gcattgctaa gctcagttcc aacagacctt ggactgaact tctgtgcagt cctctctggc  242400
aaagatgggc tcagagaccc ttggagcaat gcagcagaga ccatggcagc agccacatca  242460
gcatctgaaa acagcggcac ccggttattt tccctccttc agactcaggg aatatggtgg  242520
gggaggggag atttggtata agggccactt taagtatctt ccagaatccc attggaaggg  242580
ggagaaaatc ccattttttt aagagcccac tgataccacc tttaaaaaga atacacaggg  242640
ggccaggcgc agtggctcac acctgtaatc ccaacacttt gggaggccaa ggtgggtgga  242700
```

```
tcacctgagg tcaggagttc aagaccagcc tggccaacat ggtgaagccc catctctact  242760
aaaaatacaa aagttagctg ggcatggtgg cacgcacctg tagtcccagc tacttggaga  242820
ggctgaggca agagaatcac ttgaacctgg gaggtggagg ttgcagtgag ccaagatcat  242880
accattgcac tccagcctgg gcaacaagag tgaaactcca tctcaaaaaa aaaaaagaat  242940
acatagggga ccactaaact cctagaccaa gggctttttt gaaaatagct gtgaccaggt  243000
gtagtggctc acacctgtaa tcccagcact ttgagagggt gaggagggca gattgcttga  243060
gctcaggagt ttgaaaccag cctgggcaac atggtgaaac ctcatctcta caaaaagaca  243120
aaacaattag ccaggcgcag tggcgtgtgc ctgtagtccc agctacttgg gaggctgagg  243180
tgggaggatg gctttagccc aggaggcgga ggttgcagtg agccgagatc gtgccactgc  243240
actccagcct tggtgacaga gccagaccct gtctcaaaaa agaaaaaaga aaagctgtgc  243300
agaaatgggg gtggggaatc agccaacccc cttgtgctgg gtctcaggga cacccaatac  243360
agctgctcag gcccagccag atggcaaagg gccctcaacc aaccctggga ccagaaccac  243420
aaaaagccac gtacttactg gctcccgagc ccaagcttaa caggtgaaat ggaccactct  243480
tcaccaggaa gggcagggct gtgccaagct caccccagac ttctaggcct gggagggtag  243540
ggtcccatgg agctgtgggc tgccccctac ccaacctgac ctctgcttcc tctcttccct  243600
tcttcccacc taaacattcc tccacagtgg caatagcaaa ggaaaagaca tcaacacgat  243660
taaatccctc cgagtcctcc gggtgctacg acctcttaaa accatcaagc ggctgccaaa  243720
gctcaaggtg agattgggag atggtggggt gcggtggggg ggactgtcag ggttatcatg  243780
tacagctgag caggttgtac actgctcaag gacaacacat taaaggaggt gctgataaca  243840
tcctagccat cgtgtatgga tatttgtatt attacaactt cccagcagat ggcagtaaag  243900
tgagctgacc taaaataatc tgtgtattat ggcagttttt ctttagatga agtgtcttgg  243960
ggttaagatc ctttttccta attcgcatga aggcatcata tggatttaaa agggtataac  244020
cgtgatctgg gaagcaggaa ctagatttct tgttccataa aattttgact tttcatctac  244080
ctattctagg ctctagtatc tcccattcca aaatagcatg aaccagcatt tcccaaaagc  244140
ctgtcattca aaaacatata tatatattaa gggaaataaa atccagtcat tagagcaccc  244200
actttcactc tatgcttcac ctgggggtcc ccagtattat ctcttatgta atatgtttct  244260
ttaaatcaag tcacacccgt aatccctgca ttttgaaaga ccaaggcagg agtgttgctt  244320
gagcccagga gaatgagacc agcctgggca acatagttag actctgtctc tactaaaaat  244380
taaagacaga aaacagatac tgttatggaa atctaaccaa atatggctgc ctgcctaagg  244440
ctttgtgcat tgacaactgc tctttcttgg ttaaagaggg aaaatgtcaa tggtaggtgt  244500
taacatggta gcaactaagt aaaaatttct ccttcactca aaaggattga gagagttgga  244560
aaggaagtaa ctttgttacc ttgtttttct gtgttgggct cctgtatcac ttaaaagcat  244620
ctctggtatc ccatctggga gttttagatc catagaatgc caggattgag tccaactcct  244680
ccaacgctta tttctgaaag ctggggggac cttaccctag tgacttgact tatgaccttg  244740
cctgtaaaat gggaatgatc atggcagtat tttggtatga tgggccactg gaggcagaag  244800
gttgggcagg tccccagccc ctcatgctct ctgtcaactc caccccacag gctgtgtttg  244860
actgtgtggt gaactcactt aaaaacgtct tcaacatcct catcgtctac atgctattca  244920
tgttcatctt cgccgtggtg gctgtgcagc tcttcaaggg gaaattcttc cactgcactg  244980
acgagtccaa agagtttgag aaagattgtc ggtgggtctc cactttccag cacattccca  245040
ttggaaccag caggtgggca ggggggaagt ggctagaggc attggccact tgggctcaga  245100
gactggagaa gtgatgagcc ttggaagtga ctcagttgca accagcttgg atcttgggta  245160
gaaagaaaac cggttttaga atttgagtca ccacccagag ccacagaatg agtcataagc  245220
aaattgattg acctttcagc caccgccttt gtcatgtgag ggatattaat acacatccac  245280
agttccttac ttgaaatcgt tacaggcaga tgtgtttcaa agttgagaat attttgagat  245340
tcccatgtgg gacatgacac cctcagctgg gtctaaggca gccctataat caaacacaat  245400
atttctgcca taaaatgtgt aactatttac atcaaatggg gtaaataaca agtataaaga  245460
gcttcatgtc caatcagatc aggtttcatt accaaataag ttaggtaaga ggccaggtgc  245520
agtggctcac acctgtaatt ccaacacttt gggaggctga ggtgggagga tcacttgagg  245580
ccaggagttg gagaccaggt tgggcaacat aatgagagcc catcctacaa aataaatttt  245640
aaaagttagc ggggcatggt agcacacacc tgtagtccca gctacccggg aggctgaggc  245700
gggaggattg tttaaacaca ggagttcaag gctgcaatgc actatgatgg taccactgca  245760
ctccagcctg cgtgacagag tgagaccctg cctctcaaaa atatatacat ataggccggg  245820
cgcagtggct catgcttata atctcagcac tttaggaggc cgaggcgggc ggatcatgag  245880
gtcaggagat cgagaccatc ctggctaaca cggtgaaacc ctgtctctac taaaaataca  245940
aaaacctagc tgggcatggt ggcagacgcc tgtagtccca gctacttggg aggctgagac  246000
aggagaatgg cgtgaacccg ggaggcggag cttgcagtga gcccagattg ggccactgta  246060
ctccagtctg ggcaacagag ccagactcca tctcaaacaa acaaacaaac aaacaacaac  246120
aacaaaaata tatatatata tatatgtata tatatatatg tacacgcaca cacacatatg  246180
tattatatgt gtgtgtgtat atatatgtat gtgtatatat agtgatattg ttaccagtgt  246240
aaagtggcat tttgcaacac atggtagcct gttgttatct tgatggctat ttattgaaat  246300
taggaggatg ccagatgtct ggataggagt ctggaactaa cccttgtttc ctgccttgaa  246360
aaggagtagc aacctccctt agcctgatga acctctaaat gtcccctatg tctctctgcc  246420
tcctcctaaa ctccctccac cccacccccca gcaagcctga ggctctcacc ctgaggacta  246480
gaagttatca cgttggaaga gggtgctgga ccctgggtca gctctcccac caggagtaag  246540
gttgtgccat cacccatgga tttatctcaa agtagatgca cacgtcatcc cctatgaagc  246600
acaggaacac atggtggcag gatggggagt cactgcttcc caagcagtct aggctggtgg  246660
accactcttc ctttccctcc ccctgtctct gataaccaaa gacaagtgca agacagcccc  246720
tctttcccat ttactaacag tccccactct ctgtggcaga ggcaaatacc tcctctacga  246780
gaagaatgag gtgaaggcgc gagaccggga gtggaagaag tatgaattcc attacgacaa  246840
tgtgctgtgg gctctgctga ccctcttcac cgtgtccacg ggagaaggct ggccacagta  246900
agtggcccga ctggaaatct atccaggagg agccctgggg agcaggagga taaagggcct  246960
gagagcttag caataagaaa ggtcttggag gccgggcatg gtggctcacg cctgtaatcc  247020
caacacttta ggaggccaag gcagatgtat cacttgaggc caggagtttg agatcagcct  247080
ggccatcatg gcaaaactcc atttctacta aaaatcccaa aaaaaaaaaa aaaaaaaaaa  247140
aaaaaaaagc tgccaggcat ggtggctcac acctgtggtc ccggctactc aggaggctga  247200
gacacgagaa tcacttgaac ccaggaggca gaggttgcag tgagccgaga ttgcaccact  247260
gcacttcatc ctgagtgaca gagcaagact atggcctccc cgccttcaaa aaaaaaaaaa  247320
agtgaggctg aatcatggac ttagtcttta tttaaaattt tgagccactt gtggtggctc  247380
atacctgtta tcccagctac tcaggaggct gaggtgggag gatcgcttga gcccaagagt  247440
```

```
tcaaggctgc agtgagctgt gattatgcca ttgtactcca gcctagacaa cagaaggaga  247500
cccctatccc tgaaaaaaaa aaagaagaag aaattgatat ttgttcatca tggacttttt  247560
gcattaattt tgatttttta aaatattgga gcaaaagatt atcttgatta ctgagatttt  247620
cagtaccccc ttaatttgca cccaaaacaa atgcctccct ccctcacctc gtccaagtaa  247680
tggtctttct ctcagaggtc ttggaaatgc caggctggaa gcttggtaga ttccagcatg  247740
tgccctcagc atcctcacct ccctccctct ctcagcaaat atgccaacct gaacatgccc  247800
tactacccac tctcagacac atccagtact cacacatgtg ggaataatgc taacccacaa  247860
ggcacctttg agcaaagttt ttttaaacac ctttctcaac agacttcatt tccatctgtc  247920
tgaaaatcat cgcaatagac ttaaatgatt ttgttcaaac aaggcactga aggaccacct  247980
gccaaaaaat tgtcatcatg aatacacaaa tctatcatgc ctatcatgtg aaggtatcgc  248040
ttagacacag agcctttgag cagtgtgcaa cctgcactac tgtacagagc tgctgtgcac  248100
ttacccactc tcatatatat ccccattgta cctcctgagc acccagcacc acctgtgctc  248160
aaatacccac tctacatgca tacacccacc tctactccct ccattgccac aacctgtctt  248220
taaatcccaa cttggccact tataagtggg tggtcttcag cacgtccctt taaattgctg  248280
aacctcaagt tcctcatgtg caaagtggag ccagtaataa cctccctggg agggttgctg  248340
agccggtggg gatgaattgt tgaatattgt ttccagcaca cagcaagccc ttcatgcaca  248400
gcagtagaaa tgactgacat tggccaggcg tggtggctca cacctgtaat ctcaacagtt  248460
tgggagaccg aggcaggtgg atcacctgag gtcaggagtt caagaccagc ctggccaaca  248520
tggtgaaacc ccgtctctac taaaaataca aaaaaattag ccaggcttgg tggcgcatgt  248580
ctgtaatccc agctacttgg gaggctgagg caggagaatc atttgaaccc gggaggcgga  248640
ggttgtagtg acccaagatc acgccgttgc actccagcct gggcaacgag agcgaaactc  248700
catctcaaaa aattaaaatt aaaattaaga aataactgac attgttgtca gcctttcaaa  248760
aaacagcgac tacttaaatt tctttttcat ttccctctgt tcctgttctg ccatctcact  248820
tccaccctct ctccaccttc ctcatcaccc cttgggtccc tgtctctctc cttcctgccc  248880
cttccctctc cctgccccat tccttgcagg gtcctcaagc attcggtgga cgccaccttt  248940
gagaaccagg gccccagccc cgggtaccgc atggagatgt ccattttcta cgtcgtctac  249000
tttgtggtgt tccccttctt ctttgtcaat atctttgtgg ccttgatcat catcaccttc  249060
caggagcaag gggacaagat gatggaggaa tacagcctgg agaaaaatga ggtgccactt  249120
ccaattccat ctgtccttta aaaactgggg acacacacaa actttaaaac acacacaaca  249180
cccaggaacc cctttctagg ggtacctggg ggagggaaca gaagcattgt cccaaccgaa  249240
tccagtcttc agggcagccc ttcatggagt ttccagagga aacacatcat atagtgtatg  249300
tatcagtcag tttagactag gttatgccgc agtaacaagc aaccccagat ttcattgcca  249360
aatatccaca aagggactta ttttttgctc acactgcatg tcaacatcag ttgtggatct  249420
tgccatcttt attctggttc ccaggctggc agagcagcag agcagcctcc ctctgagatg  249480
ctccagatga aaaagagagt atgtcagact gaggttcagt tcttcaggct tgtgctcaaa  249540
aattacacat gtcacttctg ctcacatttc atcagccaaa gcaagtcaca catccattct  249600
gacatcagtg gagtgggcaa atacaatctc ccctagcgaa gggtggtgaa tatttatgaa  249660
tgaaaagcca agccaggtgt ggtggctcac acctgtaatc ccaacatttt gggaagctga  249720
ggcaggagga tcacttgagc tcaggagttt gagaccagcc tggccaacat agcaagaccc  249780
catctctact acaaatcaaa aaaattagcc aggcaggatg gtgcacacct ttagccccag  249840
taacatggga ggctgaggtg ggaggatgct tgagcttggg agttcgaggc tgcagtgagc  249900
tatcattatg ccactgcact acagcctggg caacagagca agaccctctc tcaaaaaaag  249960
aaaaggaaag aaaatccagt cccctgtcta ccagagagta tagacatgac tctttgcctc  250020
tctggcatca tccaagctaa atagaggacc tagaatatat cctctgctcc cttgacccctt  250080
aagacttaat aaccactatt cctccttctc tctccctcaa agagaaggag aagacgcagc  250140
aaagtattca gtaagaaaga atgggctggg cgcagtggct cacgcctgta atcttaacac  250200
tttaggaggc caaggcagga ggattgcttg agcccggaag ttcaagacca gcctgagcaa  250260
catagtgaga ccccatctct atgattaaaa aaaaaaagtt ttaattagct gggtgtggtg  250320
gtgcacgcct gtagtcccag ctactcagga ggctgaagcg ggaggatcac ttgagtccag  250380
gaggtcaagg ctgcagtgag ctgtgattgc actgcactcc agcctgggtg acaaagcaag  250440
cccgtgtcaa agaaaaaaaa aaaaaaagga aggagggagg gagggaggga aggaaggaaa  250500
tgagagagag aaagaaagga gggagggaag gaaggagata gggaagaagg aatgaagaag  250560
aaagaaaggg agcgaaggaa agaaggaaga agagagaaag gaaaggagaa aggggaaagg  250620
gtggaaggaa tgaagggaag gaaggaaaaa ggaaagtgaa ggagggaggg aggaaggaag  250680
gaaaggaggg agggaaggag ggagggaagg agggagggag ggaaggaggg agggagagaa  250740
ggagggaggg agggaaggaa ggagggagga aggaaggaag gagggaggga gcgagggagg  250800
gaggaagggg aagaaggatt aggcttcaat ttgatttggc acactcggta gctgtgtcac  250860
ctcaggcaag tggtttaacc tttctaagcc tctattttgg tgatctgcaa agtgaggcca  250920
ttgatagtac ccacttccca tgtttgtatt agccatgcaa taatggggaa atgtcagtgc  250980
aagttttggc agttggtgac atctcaagca actgtagctg ttgggataag aaagcaatgg  251040
tgagaaggaa gagagagccc aggaatcctg gctgggggca agagaggcag agactcaagc  251100
agaagcactt gagaaccgcg acgagttaga cagagggtgc ccggtgtaca gccaccttcc  251160
tcctgcctct gccgctctca ccactggcct ctctcccgca gagggcctgc attgatttcg  251220
ccatcagcgc caagccgctg acccgacaca tgccgcagaa caagcagagc ttccagtacc  251280
gcatgtggca gttcgtggtg tctccgcctt tcgagtacac gatcatggcc atgatcgccc  251340
tcaacaccat cgtgcttatg atgaaggtaa gtgccccaca ccagccccca gcactactta  251400
acccccacct cgttcctgcc tctaccctga taaaatgaaa ccatctgcag tttcccagac  251460
agaccacact ctggatcacc tctgagattt tgttcctgct gttccctcta cctgacacac  251520
tgttcccacc actcccccgg ccagcttctt cttcccagct gtacctgcag acctcttcct  251580
ccagaaagcc ttccctgacc acccaagact gcttgaggtg cccatcttag caggcatcct  251640
atctttatgt cgcctgccac aaaaatctgc gtcaggttgc atgacagtgt cccccaccca  251700
tttatgatga cctcagccct gaattcctag aggccaacaa ggatctggct cagacggaac  251760
aagaagctct ctataaatgt ttgattaatg aaatgagggg gctgggcgcg gtggctcatg  251820
cctgtaatcc cagaactttg ggaggccgag gcgggcggat cacctgaggt cacgagttcg  251880
agaccagcct gaccaacacg gagaaaccgc atctctacta aaaatacaaa attagccagg  251940
cgtggtggtg cgcatctgta atcccagcta ctcgggaggc tgaggcagga gaattgcttg  252000
aacccgggag gcggaggttg ccatgagccg agatagcgca attgcactct agcctgggca  252060
acaagagcaa gactccatct caaaaaaaaa aagaaaagaa aaagaaagaa atgagggaga  252120
aggggtaggt gaggacccta aaatccccag ggctaaggag cggcttccaa aaaaaaactc  252180
```

```
tgaaaacctt tcaccctgtg ctttggactc caaagcgtgg attcaagccc agctcttcca  252240
tttaattcat ttacctttgt acaagcaacc agtgactttc tggggactca gtttccctgt  252300
caataaaatg ggaatgataa taagagcaca tttgcccccct ccagaggagg tgagaggatt  252360
gaatgagaaa gttcatgcaa ggaccttagc tccttctcgg cacttcaaaa acgatcaata  252420
gtggccgggc aaggtggctc acacctgtaa tcccagcact ttgggaggtc gaggcaggcg  252480
gatcacttga ggccaggtgt tcgggaccaa ctggccaaca tggtgaaatc ccgtctctac  252540
taaaaataca aaaattagct gggcgtggtg gcgcatgcct ataataccag ctgcgtgaga  252600
ggctgaggca tgagaatcgc ttgaacccag ggggcggaag ttgcagtgag ctgagatcac  252660
accactgcac tccagcctgg gtaacagagt gagactccgt ctcaaaaaaa ataaggaagc  252720
cggggacggt ggctcacgcc tgtaatccca gcactttggg aggccgagga gggcgatcac  252780
aaggttagga gatcaagacc atcctggcta acacggtgaa acgctgtctc tactaaaaat  252840
acaaaaagtt agctgggcat ggtggtgggc acctgtagtc ccagctactt gggaggctga  252900
ggcaggggaa tggcatgaac ccaggaggtg gagcttgcag tgagccgaga tcgcgccact  252960
gcactccagc ccgggtgaca gagtgagact cctcaaaaaa aaaaaaaaaa aaaaagtata  253020
attcagccaa gcacaatggc gtatgcctat agtcccgact atcaggaggc taaggtagga  253080
ttgtgagttc aagcccagcc tgggcaaaat aggaagaccc cgtctaccaa aaaaaaaaaa  253140
aaaaggttgg gggaggtttt tgttttttttg gatgtgaaaa gaagagccta gtccggcgga  253200
gagcggggct ttcctgaact gtgcctccta ccagtgaggt tgctcagacc ttgcctgggg  253260
ctggagtgtt gcctggagaa cagccatgaa gctgcctccc cacttcccac ttcccacccc  253320
tgctcgctga cccctgctac tcctgcttct ttcccctagt tctatggggc ttctgttgct  253380
tatgaaaatg ccctgcgggt gttcaacatc gtcttcacct ccctcttctc tctggaatgt  253440
gtgctgaaag tcatggcttt tgggattctg gtaagtacca ccttggggct acagctatgg  253500
gcttgggaga agcccaaggg ggaacaatgg gtcctggatg atggtctccc aacgtggccc  253560
caagaacccc aacctcaagg gtggcttcag tatcctgcca gtggccacag atcctactta  253620
ggcattcttg tgtttgccaa ggagtcccag ggagacccaa cctgtgagtg ttaccatatg  253680
gctgcttatg tatccagttc ctcaaaatga tgggagtcat catggctggg agtctttagc  253740
atccatttta gagataagaa aactgaaatc aggctgggcg aggtgtctca tggctgtaat  253800
tccagcactt tgggaggcca aggtgggcgg atcacctgag gtcgggagtt cgagaccagc  253860
ctgaccaaca tggagaaact ctgtctctac taaaaataca aaattagccg ggtgtggtgg  253920
cgcatgcctg taatcccagc tactcgggag gctgaggcag gagaatcgct tgaacctggg  253980
aggcagaggt tgtggtgagc cgagatcaca tcactgcact ccagcctggg caacaagagt  254040
gaaactctgt ctcaaaaaaa agaaagaaag aaagaaaact gaaatcaggc tgagcacagt  254100
ggctcatgcc tgtaatccta gcacttcagg aggccaaggc aggaggatcg cttgaagcta  254160
ggagttctca accagcctgg gcagcaaagc aagcccctgt ccctacaaaa aaaaaaaaaa  254220
ttttttttta attagccagg catggtaact cgtgcctgta gtgccagtta ctcaggaggc  254280
tgaggtggga agatatttttg agcccaggag gtggaggttg cagtgagcta tgatcatgcc  254340
actgcacccc agcctgggca acagcaagac tccatcttta aaaaacaaac acagaggtca  254400
ggcacagtga ctcacacctg taatcccagc actttgggag gcagaggcag gcaaatcact  254460
tgagcctagg agttcgagac caccctggcc aacatggcaa aaccccatct ctactaaaac  254520
tacaaaaaat tagcctggcg tgcttgtggg tgcccatgat cccagctact caggaggctg  254580
aggcaggaga atcgcttgaa cccacaaagt ggaggttaca gtgagctgag atcacaccac  254640
tgcactccag cctgagcaac agagcaagtc tcaaaaaaat aataataata aaaataaata  254700
tgtctttatt tttcaccagc cactaactaa attttaacat ttccttccat cttaaaggga  254760
gataacaaac ccttagtatt agtattatca acccttaata ttatcaacat gacctgtgtc  254820
acttataaac atcagatatt ttcatactgc attataagag ctgcagatac cttaacattt  254880
aatttgcatt catcattgct ttaaaatgtt gcttgtgatt aaacctacag ctagaatttg  254940
ttactcagtg tttttttgtt gttgttctgt tttgttttgt ttgagacagt ctcgctgttg  255000
cccaggctgg agtgcagtgg cgcaatctcg gctcactgaa agctccaccc cctgggttca  255060
cgccattctc ctgcctcagc ctcccgagta gctgggacta caggtgcctg ccaccacacc  255120
tggctaattg tttgtatttt tagtagagat ggggtttcac catgttggcc aggatggtct  255180
tgatttcctg acctcatgat ccgcccgcct cggcctccca aagtgctggg attacaggcg  255240
ggagccaccg cacccggcct actcagtgtg ttaatggaga agtatattca ttgttagatc  255300
gccattttta aaactttttt tttttttttg agacacagtc ttgctctgtt gcccaagctg  255360
gagtaccgtg gcacaatctt ggctcactga aacctccacc tcctgggttc aagcgattct  255420
cccatctcag ccttctgagt agctgggact acagatgcac accagcatgc caggctaatt  255480
tttatatttt tagtagagac ggggtttcac catgttggcc aggctggtct cgaactcctg  255540
gcatcaagca atctgcctgc ttcagcctcc caaaatgctg ggattacagg catgagacac  255600
tgtgcctagc cttaaaaaat attttgatag ctattttatt acaaaaggta accttgaagc  255660
ccttgctatt ttgttatgca tttacaagcc tttatgcata aaataaaata gccagcacta  255720
ttctcacatg gccaaggttc atagcacaca cacaaaagta tagttggctg agtgcggtgg  255780
ctcacacctg taatcccaac actttgggag acagaggtgg gtggatcatg aggtcaagag  255840
atccagacca cccttgccaa catggtgaaa ccccatctct actaaaaagt acaaaaatta  255900
gctgggtgtg gtggcgcatg cctgtagtct cagctactcg ggaggctgag gcaggagaat  255960
catttgaacg tgggaggcgg aggttgcagt gagccgagat cttgccactg cactccagcc  256020
tgggtgacag agtgagactc catctcaata aataaataaa ttaaattaaa ttaaattaaa  256080
attatttttt aaaaaattgg gggctgagtg tgatggctca cacctgtaat cccggcagtt  256140
tgggagcttg aggagggcag atcccttgag gtcaggagtt caagaccagc ctggacaaca  256200
tggtgaaacc ccgtctctac taaaaataca aaaattagcc aggcatggtg gcgtgtgcct  256260
gtaatcccag ctactcgtga ggctgaggcc caagcatcgc ttgaacctgt gaggcggagg  256320
ttgcagtgag ccaagatggc accagtgcac tccagcctgg gtgacagagt gagactttgt  256380
ctcaaaaaaa aaaaaaaatt aaggtgaaga aggcttatac tagtgggctg ggacttgaag  256440
tgaagtgaat tcttgaaggt ccccagtgag tggccaaggt gggacttgaa ccaggacatc  256500
tgttctcttg accaccagct tagtccatcc ctttgaagag agtgacctac agtctgggtc  256560
tcagccaggg tctcaggaaa ccaggttccc accttggctc acggaggtgg ttaggggcat  256620
cagctttagc accagagttc agatcttgcc tcgtcctata taagctttgt cacctcccca  256680
tcattaaaag gagccatcct ccccctccac ctcagcagag ccctggtaaa cagcaaatgg  256740
actaacgtgc atctagaggg ttgaggatga agcctggcct ggcatgggca ctcaataaat  256800
gctaggggcc aggcacggtg gctgacacct gtaatcgcag cactttggga ggctgaggca  256860
ggtggatcgc ttgagcccag gagtctgaga ccaacctgga caacatagtg agattctgtc  256920
```

-continued

```
tctacaaaaa gtacaaaatt agcctggtgt ggtggcgtgc acctgcagtc ccatctactt  256980
aggaggctga ggtgagagga tggattcagc ccaggatgtc agggctgcag tgagtcgtga  257040
ttgagccgct gcaccccacc ctgggtgaca gagcaagacc ctgtatcaaa ataaataaat  257100
aaatgctagg aaagggatcc tactaatgga ccttttttcct ccaaaacagt ggctttcatt  257160
tggtggagat gctacttatt agaagcactt gaggccaggt gtggtggctc atgcctgtag  257220
tcccagcact ttgggacttc tgccaaggca gaagaattgc ttgaacccag gcgtttcaga  257280
ccagcctggg caacatagca agacctcatc tctagaaaac attgaaaaat tagccagcat  257340
agtggcacat gactgttgtc ctaactactt aggcgaaggc aggaggatta cttgagctca  257400
ggagttcaag gctgcagtga gctgcgatca catcactgcc ctccagcctg agcaacaaca  257460
caagacccgg actctaaaaa tcaaaaaaga agcacttagg gaaatttctt aaaattaaat  257520
gataccctga gcaaacccct agatgttctg attcatttgg tttggtgagg tgggagggaa  257580
tcactgaatc tgtaatttat tattattttt ttttttttga gatggattct cactctgttg  257640
cccaggctgg agtgcagtgg tgcaatcttg gctcactgca acctctgctt cccgggttca  257700
agcaattgtc ctgcctcagc ctcccgacta gttgggatta caggcgccca ccatcacgcc  257760
cggctaattt ttgtattttt agcagagacg gggattcacc acgtcagcca ggttggtctc  257820
caactcctga cctcaggtga tccgcctgcc tcggcctccc aaagtgctgg gattataggc  257880
atgagccacc gtacctagcc tgcagttatt ttattctgag ttgatcttct gctggtgaag  257940
tgagtcttcc actggggcct ggagctgcat ctccctcacc ctgccaatcc tgcaagagcc  258000
agcactgagc ttcccctctg ctttctcttt tttttttttt tttttttttt tgagatggga  258060
tcttactctg ttgcccagcc tgttcttgaa ctcgtggcct caagcagttc tccctccttg  258120
gcctcccaaa gtgctggaat tataggcatg agccaccacg cctggtctcc cctttcagtt  258180
ttaaatgaag ccacaagttc cctgtataac atttgggaga tagaggggag ctctctagcc  258240
taggggttga ggtctgtgac caaacgccta taaagttgtc tttgtttgga ctcccccaga  258300
agcagagcct gagacaagga ttgagtgcaa ggaatttatc tgggatgcag ggcagtaagg  258360
gagagaggaa gtgacacagg gacagaaagg caaccaggaa agagtgtatt attaagccag  258420
ttcctgctgt gaacaaatgg ggctcagttt cagtggatac ctccaggagg caacagagag  258480
cacataccac agagtcatcc cacctcacag ggagggaatt ggagtattta tcctccagtg  258540
cccatcagac ataatcacag gccactccca ggggagctat taattcccta acacttgtgc  258600
agccacagag agaccctggg caaagtagtg tacctcaggt gtgtagttga gctatgggca  258660
gggccccagc aacacctgcc aaaatgccaa aagtgccagt gggacctgaa ttccttttta  258720
tttatttatt tatttattta tttattttta tttatttatt tttgacggag tctcgctctg  258780
tggcccaggc tggagtgcag tggtgcaatc tctgctcact gcaagctctg cctcccaggt  258840
tcacgccatt ctcctgcctc agcctccgga gtagctggga ctacaggcgc gcaccaccac  258900
gcctgcctga tttttgtgtg cgtgtatttt tagtagagat ggggattcac catgttatcc  258960
aggatggtct tgatctcctg acctcgtgat ccgcccacat cggcctccca aagtgctggg  259020
attgcaggcg tgagccaccg cgcccggccc cctgaattcc ttttttaggc agttgtgaaa  259080
caacaacatc ccatctgttg ggcacctact gtatattcca tgctcagcga cgcacattca  259140
ttgtctgatt gctgtgttac cactgccttc cagagaaggg cgcagaggcc ccaggcactt  259200
cgcctaggag ggaagcacag ctctaaggtc aggctccttc tctgtaaggt agaggggcta  259260
cttcagggtc acactgaccg ccccaacccc tgacctggcc tctgcttctg cgaagatgct  259320
gagaaggccc tgtgttttgt gttttgggtc ccactgaccc cagaggggag ggccatctct  259380
ttgacccaga ctcttggatc caaactgggg tgccacccat caccatgtca gtacccggtt  259440
gaggggagtc agagatagca ggagaccttg tgggacttga ggctgtgact gttctccaaa  259500
caatgtggag tatttccata ttttaacaaa agagaggcca ggcgtggtgg ctcacgcctg  259560
taatcccagc actttgggag gccgaggcgg atggatcaca acgtcaggag atcaagatca  259620
tcctggctaa catggtgaaa ccccgtctct actaaaaaat acaaaaaatt agccaggcgt  259680
ggtggtgggc gcctgtagtc ccagctactc aggagactga agcaggagaa tggtgtgaac  259740
ccgggaggca gagcttgtag tgagccgaga acgtgccact gcactccagc ctgggcgaca  259800
gagtgagact ctgtctcaaa aaaaaaaaac aaacagagag gttatgcttg tgtttcccct  259860
tgagccagca cccagcccag gaatgcagca gtcaggatag atcaagtgaa gctgcagtaa  259920
caaacagccc ccacatctca gtgacttaaa ttgatgggaa gggtttttta cattcagcag  259980
ggaagctgtt tgcctcatag ttacccaggg acccaggctc acagagtagc tgccattcaa  260040
aatgttactg gtcgccaagc ccagggttga gaggctagag agtccaacac tgaccagaaa  260100
gtgaccacac tgcttccaca cacagcacat cactgcacct agacacacat ggccccatct  260160
aaacacaagg ggaccaggaa gtgcgtgtgc ctgaaaggcc ccaaagcccc gtccagtgcc  260220
tgttctgcac cctgttactg tccgcctcca gatcaggaaa tggaggccca gagaggttaa  260280
gccacttgcc catagccaca cagctgtggt agcagagctg ggatttgaac ccagagtctc  260340
ctttctttgc gagtatgctg ccaacctagt ggggacctga acacagactg tgggctctct  260400
gaggcctggg ttcaaatcct ggctttacat ctctgtgctg ctagcctcag gcagatgagt  260460
ggcttggtta cctcctagaa aatgggtata cctgggagtg gtggctcacg cctataatcc  260520
caacactttg gaaggccaaa gtgagcagat cacttgaggt cagaagttcg agaccagcct  260580
gaccaacatg gtgaaacccc gtctctacta aaaatacaaa aattagctgg gtgtggtggc  260640
atgcacctgt ggtcctacct acttgggagg ctgaggcagg agaatcgctt gaacccagga  260700
ggcagaggtt acagtgagcc gagatcgtgc cactgcactc cagcctggat gactgagcga  260760
gactccatct caaaaaaaaa aaaaaaaaag agaaagaaag aaaaagaaaa tgggtgataa  260820
cccttccctc caggatcttc atgaggagct cagtgatgtc atttataaag cccctggggt  260880
ctcgggagcc ctcaaaaatg ctggagagac aggccacagc tctgaagagc agccccagcc  260940
ctgtggagct gaagcagggt ctggaggccc cctctggggc caggccaatc atgggaaggc  261000
ccccaggagt tcccagggag ggagactcag cacagatgat gtcgaacagc ctttaccgca  261060
gcccttcgaa caaccataac tgtcccgggc actccgctga tgggcaactg tgcctctaac  261120
atgcacccgg ccagcctagg gggccgggaa ccaagccctc tgttggcatc tctgtcttgt  261180
gggtccccat tctagaatta tttccgcgat gcctggaaca tcttcgactt tgtgactgtt  261240
ctgggcagca tcaccgatat cctcgtgact gagtttgggg taagtctccc tccagcttct  261300
ctctgggtga ctctgggctg gacgaggcag gcggcagggg gcgggggagc ggtcccagag  261360
gcagtgtgtc ccggaagcca tagctgcttg agccagcact tggccatgac cagagaggga  261420
gaactggggc cccggggaca agggcagccc ctcaggaggg cattgtgggg agatgggggt  261480
aaccaaagct tggctgtagg gccagcactg aggggtgggc tttcctgcat cctggcctag  261540
gaattaataa tgcagatgag tacactgagg gaactgagac actcaaaagc tctgaaagct  261600
gagccggctc ccaaacacca ccctatgtca ggagcccaga aagaatgggt ttcaagtcaa  261660
```

```
ttctgtttga accaaccctc tcctagttag tgggcaggag agagccacag ccctcaggcc  261720
agtgtgggga caccactccc agggccatag aggggtcccc agggtgtctt ccctcctcta  261780
gccccgggcc tgggagactc tcaacatggg agtctctgga cctctctgtg gtggccccac  261840
aggccacatt gcccttctcc ttttctggaa gactcagggc cccagaggtc ctgtcctaga  261900
ccctctcctt ggccatctgc caatgagccc aggcttgggg tccctcagga gattgggggg  261960
agggtagaag atccttgcag ggggaagcaa tggtcaaaaa agggtgtcaa agccaagggt  262020
caagggtgat accaatgtca tcttactaac aataaaaata acaatagctc acgagaatcg  262080
cagccttgct gtgtgccagg gaactgtgcc aagtggttta cgtggattgg ctcagggtag  262140
aggtcttggt ctcagctcgt aagagaattc cctcggaggg ttcaactgaa ggcacccaaa  262200
tgcagacctc actggtggag gggaagggaa gggtacccac aagggtggca aggtgtccag  262260
cgaccaccca ccgtggggag ctgtcacctg cccaggtgct gaagtgggga gggaacctga  262320
gccggaggcc aggagaagcc accaagtggg agctgtcctg tcaatgtgga gagacagaga  262380
ccagggccca agcaggcaga gagcaatagg ggagaaacac cccaaccttt ctctcccctc  262440
atcccttatc tcctgccaga gcctcccatg gcccaaagta aaccggaagc aagctgaata  262500
tgatgctcag agcaggcagg gaagtcagga gaatagatct gggtgtggtc gggcctgagg  262560
aagagggtgt tgcctcattt cacagatggg aaaactgacc tcagctgggc acggtggctc  262620
atgcctgtaa tcccagcact ttgggaggcc gaagccggcg gatcacctga ggccaggagt  262680
tcaagaccag cctggccaac atggtgaaac cccatctcta ctgacaatac aaaaaaatta  262740
gccaggtgtg gtggtgcatg cctgtaatcc cagctactcg ggaggctgag gcaggaaaat  262800
tgcttgaacc cggaaggcgg aggttgcagt gagcgacggt cataccattg cactccagcc  262860
tgggtgacaa gagcgaaaac tccatctcaa aaaaaaaaag aaagaaagaa aactgatctt  262920
caatgcctgg ggaagtgaga gacactccca aggtcacaaa gccaggcctg ggtgactcct  262980
gagagtacac tgacagctcc tgggggtgtcc cagtcagatc cccctacaga aaaggatctg  263040
tttgcctgct cttccgtcct agaaggccag gaggggctgg ggaactacac aaaagagggg  263100
gccattcttt gatatgtcct acggcacccg cacccaagtg atacacactt atttgccttc  263160
agctccagtg agccagaatt ttccccttcc cctcacccta tccctgaaac cttcctctag  263220
agggttcttg cccacatggg ggctctctcc actggggtgc ccccacctgg tcattctccc  263280
ctgtcctgag tttctagaga gggctggagc tccagctggc aatcaaaata tcttgccatc  263340
cggctacata caagacagcc ttgaaccaat gtccctttgg gtcaagaggt tagaaggatg  263400
gtccagctcc ccagaagggc aggtggggtg gaggaagtta gctgaaacct tcaatcacca  263460
gtaagagagc tgtagggaca gactccaaca gcctgttctc ctggctggca ggaagatggg  263520
gcatggggtg ttcatgggac atcaggaccc ttgcagtagc caaacagccc ccagccctcc  263580
ctaccagctg tttgatcttg gacaacttgc gctatctctt ctcatgtaga gtggggctaa  263640
ccattgcaac caacctcaga cacttgcaag actcacagtg atgcatgcac tcaaaagaca  263700
ttcattgagc acctactgtg tgcctggtgt gattataagt gctggagaca gaacgagaag  263760
gaggggtgcc aaacaaaaca gaccaagaat acagagtgtc tgctcccata gagctgacat  263820
tctaaggaga gagacgggaa ctttttacaa gtaaaagcat caacaggccg ggcatggtgg  263880
ctcacgcctg taatctcagc actttgggag accaaggcag gtggatcact tgaggtcagg  263940
agttcgagac cagcctggcc aacatggtga aactctgtcc ctactaaaaa tacaaaaatt  264000
agccgggcac ggtggcaggt gcctgtaatc ccagctactc aggaggctga ggcaagagaa  264060
tcacttgatt ctcaggaggc gagaggttgt agtaagccaa gattgtgcca ctgccctcca  264120
gcctgggcga cagagtgaaa ctctgtctca aaaagaaaag gaagaaaaag aaagaaagaa  264180
acgtgaagtg cttggcacag aacctgccag gaaaccagga gtttgaaaat ggtggttgtt  264240
aactattact gctgttgtta ttgttattgt gaatgggtgt gtagttttgt tagccagccc  264300
tgagttacag tcaatttgag ggaaagatag ggggtgggtg tttgggtcct tctgggacaa  264360
ttaactccca acctggagta gggagaggca tgtcctggca ggcaaggagg tctcagttgc  264420
ccctttctgc ctcccaggta agcccactag ttctgaggcc agggcttggc caggctgaga  264480
caggaaatgc cagatgcttg ggcgggcagg tccctggggt ttagggggca gagggcatgc  264540
ggcagtacta accagtgctg tctcagctgc tgcccccaag tggctggggt gatgtgggtt  264600
tgccctgtgt gcaatggata atgactgtgt ttcttgtctt gtctcttttc atgcctgctc  264660
ttaaaactgt atattggcgc aacgccgtct gaaaaactca tccaatcaaa atgcactatg  264720
aaattcattt gttcatccat gacatggtct gtgtgttcat acaccaatga cttatctccc  264780
aacccaccgc caccaccacc cccactcccc gcccgggaac cgaaacccat tggtttttttg  264840
gcactggtta caaatcaacc taaaaaatgc tgaacacgcc tccccaactg cccccgcccg  264900
cccgctcccc ctcatcttca acatctgcat ctagaatccg gttggtctta cttctttctg  264960
aagtctaaat gccttacatt aactgtgaac gcatctcctc gcgtcggcat tgcatgccac  265020
accctgcctc tccaacgtgg gatgcctgac gctctcctca accctccgct ctcctctgtc  265080
tgtctgtcct cccgccccca gcccctgtgc ctcccacttc ctgtagactc tgtctctctg  265140
tttttatcgg gttctgaatg ggggttttct gtttggggtg gtttgcgtct tttgcagaga  265200
aagggatggg ttttcccagc gcagcacctc tctcttgccc catcccgcac acacatcccc  265260
tacactcaga gacaatagag gcaaatccac tcccagccac ctctcaccac tcctgtcccc  265320
cattcagctc catggacccc aggccccagg aaagctgcca actgtctcct cgcccctcca  265380
gctctctcca tcctgctgtc cccaatcctc catctcaagc ccacaagatc tttggccttg  265440
accagcagag acttgactct ccaagtctga taaaggagac ctgaaggcca ggcagtgtgc  265500
cggcaaagac tctcaggcag aggaactcag aagtgccaga cttggatctg gtagcttcat  265560
gtggggctgg cccactgagg ccctctcctg gagccttgaa ctgtacgtgc acacgcagtc  265620
acacagtcac tgcacacaga cactgcacac acagtcactg tgcacacact cagtcactgc  265680
gcacacactg tgcacacagt cactgcacac agacgctgca cgcagtcact gcagtcactg  265740
cacacagtca ctatgcacac acagtcactg cacacagaca ctgcacacac agtcactatc  265800
cacacacaca gtcactgcgc agacactgca cacacactgc acacacacaa tcactgcgca  265860
cacacagtca ctgcacgcag aaactggaca cacagtcact atgcacacac tgcacacacc  265920
actatgcaca cacactgtgc acagtcacta tgtacacaca ctggcactgc atgtagtcac  265980
tatggacaca cactgcacag tcactgtgca cacatacact gcacacactg tcactatgca  266040
aacacagtca ctgcacacag tcactatgca cacacactgc acacacagtc actgcacaca  266100
gagccactat gcatgcacac acagtctgca ttcacacatt gaacacacag tcgctataca  266160
cacacagtca ctgcacacac agtctatgca cccacacact gaacacacag tcactgcatg  266220
tacagacact gcacatagtc atgacctctt ctctttttct cactcattct ccaattctct  266280
ctctctctcg ctcttttttt ttttttttt tagacagagt ctcgctctgt cacccaggct  266340
ggcgtgcagt ggcacaatgt cagctaactg caacctctgc ctccccgttt caagcaatta  266400
```

```
tgatgcctca gcctcctgag tacctgggat tacaagcatg taccaccacg ccaggccact  266460
tcttgtattt ttagtagaga cagggtttca ccatgttggc caggctggtc tcgaactcct  266520
gacctcaagt gatgcacccg cctcagcctc ccaaagtgtt gggattacag gtgtgagcca  266580
ctacacctgg cctctaatcc tcattcactg ttcctgtctc tgtgtctctc acatacagtc  266640
atgcatgcat gcacgcatgc acacacacac acactggccc tctctgctac atctacccac  266700
cctgtacccc cactccagta catactgcac acatctctct ccctccccca cttctcagcc  266760
ccttgcacac cccttgttct gttaaatctc aactgcctct gcccctctcc tacccaccaa  266820
tgaggccctt agagggacgc cccaatggca tctttgccct ggaatcatcc cttccctgct  266880
ggcaatacac atgcattcac ccaccaaaca tttaatgagc ccctatttgg tgccacagat  266940
ggaattatgg gcagaagcag acaccattac tgtcccctct taccacatac agtcaggtgg  267000
gggaggcagg catcggtcaa ataacccctt gactccactt aaaattatac ctgcactgcg  267060
agctgaagga tgagcagcat taacaaggca gagagagatg cacagagcat tccaggccca  267120
ggacagcaca tgcaaaggcc ctgtggtggg acggaacctg tgaggggtca ggatctgcaa  267180
gcgagggaat gtggctgatg caaagacagc cgagaaaggc tggcctggag acagccgaag  267240
aaggcagaag gggacaggac ccggggctgg ggagggcggg gctatattgt ggaatatggg  267300
ctttctccta agcaccagga agggcctggg aggataggaa gcaggggagg cgcgactggt  267360
catgtgacta gacaagctcg ctctggttgc agggcaggga acagcttgac aggaggctgg  267420
gctggaggtg ggcaccagga atcgcagcaa gagatgacag tggaggagag agaacagtgg  267480
gagggttgtc ctctgcagga cccagggaaa gatcaggtct gaactgagat gaggtgcctg  267540
ggagcagtcg ggtctggctt aaaactggga gataggctga gcacggtgac tcaagcctct  267600
aatcccagca ctttgggagg ctgaggcagg aagatcacct gaggtcagga gttcgagacc  267660
agcctgacca acatggtgaa accccatctc tcctaaaaaa tacaaaaatt agccaggcgt  267720
ggtggcaggt gcctgtaatc ccagatcctc aggaggccga gacaggagaa tcacttaaac  267780
ctgggaggtg gaggttgcag tgagccgagg tcgtgccatt gcactccagc ctgggcaaca  267840
gagtgagact ctcttaaaaa aaaaatactg ggtgatagag gtgagcgagt gcaaggaaag  267900
gaccaggttg ggggaagaga ataggtgtgg gcatagcaag tttgaggtgc ctttaggaca  267960
tcccgaaata agtcagatag gcaggtgttg tgggggctgc agcttggagc tgaggtctac  268020
aagtagtagg acttttctgg agcccttagg tgggtggtct ccatatcctt ctgagcactt  268080
gaggaacatc tgagcacagc actggaaaag aaaagaccac aaggacgctg tcctcatgtc  268140
ttccagggc tgtgtcccac ccccatcaca ttctagccag gaagttcagg ggaggtgttg  268200
aagagaggaa gctgcacctc ccaagccatg gattgaaatg tggaaggcag gaagagggaa  268260
cttgtcagaa gttctggggg cagtggaaag aattggtact gatgcaggaa gagatggagg  268320
gtggatgagg gcagactagt acccttcccc cactgcccca aacccttccc gtctccaccc  268380
ctacctgcct catgtgtctc ctccccccact tggctccaag aagggaagca tgtttctgc  268440
acgcatctcc ctgccagatc cctggctttt ttgcatggtt gcaagcttcc cctgctctcc  268500
tccaaacccc cctcctgagg ctgcttccag ggtccgcctg ccttcgcatg cctggccgag  268560
tccacatgtt atgatccgcc ccatgaaagg gatggcttgt actctggggt tgaacgggag  268620
ggggctgggg atacctgagc catcggcccc atccccaggt ggagctgggt ggccaggcag  268680
ggatgggggt cagggcagca gggcacagag agtgactctg ttagccaagc tgggtttggg  268740
gcttgttcga ggcactggag acattctcac agcacttgag cccagtgtgg tcagggtagg  268800
atcccccagc ccccttcccc atcctagagg cctaaggacg cactgatgtg tcccagagag  268860
catcctagac attgccatca aacccagagg cctcagaaat tccttgaact ccagtccttg  268920
cctctcagct cccaggccaa agccagcaca agacacagat ctggcagcca gaaagccctc  268980
tggaagccac caagtaggat gcccatgtca cccaaactag gacacttttg aaacaggagg  269040
gaggctgtga ctgtatggtc accctgtgcc atttgggggg tgaaggttag accaagttaa  269100
atcttgctac gtggcctgta gcaaatccta caaatcccat agaacaagtc tgattaagcc  269160
ccttccctta gtgtggagag accctctact cctcctgcct tcaccctgct gggtactggc  269220
cagcgaagga gggtttccat gtctgcctga ggctggggtc tcaaactcaa atgcctctgg  269280
gggccaggca gacaccagtc aaccaggaaa gcaagtgcca tttctaaaac gtgaggaccc  269340
tggaaaactg gagatcatgt ggcctgcttc cagggagcaa tcgcagcagg cctggggttg  269400
ccagaaagcc agattggtgg gcaaaatctc ttgatttta aacaatggca ataattttta  269460
attaaaaaca aggacaaatg aaaaaacact gctcgggccc aacaaaacag ttttattagc  269520
tagatttggc ccactcgtga cttcgagagt cccacccccc ccaccaaggt cccttgaagc  269580
cccacaatgg ccacttaact ctagctggtc tcctccctga ctctccaact ctctggcccc  269640
ctggttcttc tagcttgggt gggaggaggc agaggcagtg actagacagg gggtttttga  269700
gcagaggcag tggccaccca gggaggtcct gggggcaggg atggccccac ctcccggccc  269760
ccagcacccg ccccttggtg ggcccgggct gatttctgag ctcacccacc catgggagct  269820
gagtgcttcc tgcttcctgc aggcctggtc ccgtgctact ccacccagcc ccagaagctg  269880
agaagccatc cctgagaggg gggaaaaggg ccccaaatgc atcttctccg actcagcggg  269940
cagcgaggac tcaccctgca gccgaacagt cccagctccc tcccgtcctc cccattcccg  270000
ctcgccaagg gggtaagaaa agatgctctt ccgcttctcc caattggctc gagccgctgc  270060
tcctcttggc cgtggggtga ggtcagggcg ggcaggagcg ggtgggcagc tcggcagggc  270120
agggcagggc agggtgcccg gtgagtcccg tgacagatgc atttctggcc cggagcgtaa  270180
catgccctcg gaacccgcac atgtccacca ggcctgactg tgctggcgac ctccaccccc  270240
acccccgccc tggtgtttgt gcatcgtaca cgtatgatag attccgcaac ttgaccggct  270300
tgtgtccttt cgtctcagtg catttggttg ttgggagaaa caaaaaccat ctcgattttt  270360
ttcctgattg gatgattcgg atatatttc tttttcttgt tcttttgtta tttcttcccc  270420
atccccgttc ctttttcctc ctttcttttt cttttctttt ccccattgtg ggtggggctg  270480
gcagggaggg cttatgcttt tgagttgatg cctttcctc cctcccaccc tctctctccc  270540
aacattattc ctttttcgag tttttcctct gcatcattgc attaatagtg ctttctctct  270600
ccctccttat ttggggtctg gcttgctttt ttcctgttgg ttggcttcat gtaggggcct  270660
ctgtgagtgg tgacagctct gagccttttg gggtgggtgg atggtcaccc ctcttcctcc  270720
atctccccag aataacttca tcaacctgag ctttctccgc ctcttccgag ctgcccggct  270780
catcaaactt ctccgtcagg gttacaccat ccgcattctt ctctggacct ttgtgcagtc  270840
cttcaaggtg agtcctcgtc cctgctgctg gcccagggct gagaagacag gtgaccctca  270900
tgctctggct gaatgtagaa gtcagattgg aagtgcctct gtgatgtagt cgtgcagaga  270960
atctgttatc tccaaggctg ttgtcaaact tcctgtccct ggtgtgtctt cagagctgta  271020
agggcctcat cctagagccc ccagagatgc ccaccagccc tggaaggact ctggcacgtg  271080
gcatatggcc acccaaccca gtggggcaga gcactgggac aagggaggaa gacagtgcgg  271140
```

```
ctgagggacc cccagcactc ttcttcattg ccttttttcc caccaggccc tgccttatgt  271200
ctgtctgctg atcgccatgc tcttcttcat ctatgccatc attgggatgc aggtgagtgt  271260
cgtgtcccta aggttcccag agcctcccaa ggagggcagc caccccttaga aaggggtggg  271320
tcagaggagc ctggttcaca gaagcagcca tggaggttga gctgggtttc ccagaagcca  271380
ctggaggaat ggcagcccct ggtcgtcacc ctccaattcc acaggtgttt ggtaacattg  271440
gcatcgacgt ggaggacgag gacagtgatg aagatgagtt ccaaatcact gagcacaata  271500
acttccggac cttcttccag gccctcatgc ttctcttccg gtgagaaggg gacctgctct  271560
gataattctg tttccgtggg gtggggtgcc tgccttcatc cttctgttcc catagaggat  271620
gtaccctcct cttccaatgc aagacgtgcc ctcctccttc tcttctggca ggggcgcgcc  271680
ctcacccttc ttttccggta gggggcgtgc ccttctcttc cggtagggga cgtgccggcc  271740
ttctcttccg ataggggggcg tgccctcctc ctccttttct ggtgtggggg tggccagatg  271800
tgctcttatc cttcttttcc cgtgaggctg gaaatgggtg tcgtgggggg cccaggaatc  271860
ctagcagggc agaagcagag ggccctggga catagtcatc aaggtcattt tccaggcatt  271920
atctctgaat cttcctgacc accctgtgag gaagggattc ttggcagccc tatccgacaa  271980
ataagaaaac aggcttacag accgtgaggc ttgattcttt ggttcatcat cttggctgca  272040
cacaaaagtt ccttcactcg ttcagtgtag gtttttttggg ggggcttttt tttttttttt  272100
tttttttttt ggagatggag tctcgctctg ttccccaggc tggagtacag tggcgcgatc  272160
tcggctcact gcaagctccg cctcccgggt tcacgccatt ctcctgcctc agcctcccga  272220
gtagctggga ctacaggcgc ccgccaccac gcccagataa tttttttgta tttttagtag  272280
agtcggggtt tcaccatgtt agccaggatg gtctcgatct cctgacctcg tgatccgccc  272340
gcctcggcct cccaaagtgc tgggattaca ggcgtgagcc accgtgccca gcccttttttt  272400
tttttttttt ttagatggag tctctctctg ttgcccaggc tggagtgcag tggcgccatc  272460
tcggctcact gcaagctcct cttgtggagg tgtattgagc acctacagca tgccaggcag  272520
ggctgaaaaa cgaggatgca ccaggaaata gagaaaagag acattttaag cactttggaa  272580
gctaacatcc ccatggggaa gacgaataat caggaaacaa attatagagg atgctggaaa  272640
aagataaaat tcaagaataa aggggaatag ggccaggtgc agtgactcgt gcctgtaatc  272700
ctagcatttt gggaggccga ggtgggagga tcgctttagc ccaggagttt gagaccagcc  272760
tgggcaacat agtgagaccc cgtctctaca aaaaaattgt ttttaattaa ctgggcatag  272820
tgccacacac ctgtagtccc agctacttgg gaggctgagg caggaggatt gctcgagccc  272880
aggagttcca ggctacagta agctatgatt gtgccactgc actccagcct cggcaacaga  272940
gcgagactct gtctctaaaa agaaaaatat atttttttaa tttttaaaaa aagttacaga  273000
ggtagatagt ggtgatagtt gcataataat gtgagcttac ttaatgctac tgaattgtac  273060
acttcaaaat ggttaaattg ataaacttca tgctgtgtgt attttgccac agtaaaaaat  273120
aataatgttt ttaatctaac aacaaaaaaa gaatagaggg ccggcaggtt atgcctctct  273180
gaaagtgtga catttgagag aaattggcaa gggagggagt cagtgggtat atggggaagg  273240
gcaggccaag ccgaggggac tgcctgtgta aaggccctga ggcaggagta tggctggcat  273300
gtttgaggac tgtgaggagc ccagcatacc tagaacagag tgatctaggg agaatatagt  273360
atgagatgac tgtcaccttc atggagggga gcttttttttt ttttttaatc tgagacagag  273420
tttcggtctt gttgcccagg ctggagtgca gtggtgcgat ctcggctcgg cgcaacttct  273480
gcctcccagg ttcaagcagt tctcctgcct cagcctcccg agtagctgag attataggtg  273540
cccgtcacca cgcccagcta atttttgtat ttttagtaga gacggggttt tgccatgttg  273600
gtcaggccgt tctcaaactc ctgacctcag gtgatccacc cgcctcagcc acccaaagtg  273660
ctgggattac aggcatgagc cactgcaccc ggcctgaagg gagctttttt ttttttttgc  273720
tttttttga gacagaatct ccctctttgt cacccaggct ggagtgcagt ggcgcgatct  273780
cagctcactg caacctccgc ctcctgggtt caagcgattt tcctgcctca gcctcccaag  273840
tagctgagac tacaggtgag cgccaccaca ccgagcaaat ttttggtatt tttagtagag  273900
atagggtttc accatgttag ccaggatggt ctcaatctcc tgacctcgtg atccacccac  273960
ctcagcctcc caaagtgctg ggattacagg tgtgagccac cgcgcccagc caagagggga  274020
gcttttaaag cataacagtg accagcctga gcaatgcagt gaaaccccat ctctacaaaa  274080
aaaaatagtt taaaaattag ccaggagtgg tggcgtgtgc ctgtagtccc cagctactca  274140
ggaggccgag gcgggaggat cacctgagcc tgggaagttg aggctgcagt gagcagtgat  274200
tgtgccacta cactccaacc tgggtaacag agcaagaccc tgtcaaaaaa aaaaaagaga  274260
gagagagaga aaagaaagga aaagaaagag agagagaagg aaaagaaaag aaaaaaacat  274320
atcagtgtcc tcaaatccca ccctagacca actgaatcca agtctgctgg ggtggggcac  274380
gggcattggt attttttcaa agctctctgt ggacttcagt gcacagccaa gaatgtgaat  274440
tcccttctct cagctcccag taaaaggagg tggtccacct ggggcttgcc tggccagctc  274500
cagagcccaa gtgctcaacg tgtgtgctcc acctcctggg gaggcgttgg tacccagtca  274560
gggctgggtg tccgagtctc tgatttctcc ctgtcctcag gagtgccacc ggggaagctt  274620
ggcacaacat catgctttcc tgcctcagcg ggaaaccgtg tgataagaac tctggcatcc  274680
tgactcgaga gtgtggcaat gaatttgctt atttttactt tgtttccttc atcttcctct  274740
gctcgtttct ggtgagtctg tggacactgt gagggccgtc tgggctccct aagcctggct  274800
tcctttcagg ggagtgggtt tctgtggaat gtggctgtgt cgaaggcttg ttccctccaa  274860
ggcttctctg aaccagcctg ggatcaggtg accctgagcg tctcaaactc agcactgttg  274920
acatttgggg gtggctgatt ctttggggtg gggccatcat gtgcactgca gtgtatggca  274980
gcatccctgt cctcccccca ccagatgctg gcagcacacg ccacccgttc ctcctgttgt  275040
gacaaccaaa aatgtctccg gacattgcca ggtgccccca gggggtgggg gtggggttgg  275100
gagtgggggc cagaattccc ccatttgaga ctcaatgaaa tatttcagct gggcgtagtg  275160
gccgatgcct gtaatcccaa cacttcggga ggctgaggtg ggagggtcac ttgagcccag  275220
gaatacaaga ccagcctgga cagcatggtg tgaaacccat ctctttaaaa aaaaaaaaaa  275280
aaattgaatt agctgcacac gtggtgctgt gcacctgcag tcccagctac tcaggaggct  275340
gaggtgggag gatcacttga gccttggagg tcgaggctgc agtgagccat gatcacacca  275400
ctgcacccca gccagggcga cagaatgaga tcctgtctca aaaacaaaca aaaacaaaca  275460
aaaaaaaaaa aaacattgcg agggaagaaa tacctcactt tggccttgtt gggggcagat  275520
gtgggaggat ttggggtcac agtggttctc ttggtgttgg tccctgtttc agaagcctcc  275580
cctccctctc actgactctg tttctttcca tcattcttgg tctttgtctc tctctctctt  275640
tttttttttt ctttgaaatg gagtctcact ctgttgccca ggctaaagtg cagtggcgag  275700
acctcagctc actgcagcct ccacctccca ggttcaaccg attcttcagc ttcaacctcc  275760
caagtagctg ggattacagg tgcacatgcc accacaccca gctaattttt gtatttttag  275820
tagagacagt gtttcaccat gttgaccagg ctggtctcaa actcctgacc tcaagtgatc  275880
```

```
tgtccacctc ggcctcccaa agtgctggga ttacaggcgt gatccaccgt gcccggccag  275940
tctttgtctc tttgtatctc tctctctcca tctctctctg tttctctctt cctcttcccc  276000
atctctccac ttgatctctc tctcactgga cctccttgtg tgagtgagca tcacctctcc  276060
attccccagt ctctttctgt ctctgtctca tttcctttcc ccatcttctc tctatccctc  276120
tctccatctg ggcctctgtg tacatgtctt tgggtctgtc tgtccgtctg tctgtctgta  276180
tccttctcac tcactcattc attccctcgg tctctgcccc cattctctct tggtccccgg  276240
ggtccccaca gatgctgaat ctctttgtcg ccgtcatcat ggacaacttt gagtacctca  276300
cccgagactc ctccatcctg ggcccccacc acctggatga gtacgtgcgt gtctgggccg  276360
agtatgaccc cgcagcttgg taagaagtca ccccgaatcc tccagccaca atactcacct  276420
ctccctggaa ctggaacacg ggctaggtca ggccccagac tctggagcac tgaactcctg  276480
gggtcctagc aggggtctca caggttcagt caggagagaa gatataagaa tcatcaccct  276540
tgcatacccc agattaaaca cgtagggtgc caaccctgcc caaaccctgg actttctggg  276600
aaatgaggga gggcgtcaac catgagatgt cctgaagagc cctctcctcc tacgagtctc  276660
tcctgtctct cactgtgaag tctccagatg gtgaggatgc attagccagg ctccagggag  276720
aaaaccaaca gcatcccagc ctcagttctc ttgagagtgt ggggaggagg gctggcctac  276780
ccttggcaga caggattggc agcaacatca gagtagcaga actcagctcc cactgggacc  276840
cgtgaacctg ggagtgagag gacatacagg ccaggggagg acgcagagcc tcaggggccc  276900
atgcatcttt gtggccacaa agggagtggg cgctcccatc tgggtagaca ccagaggggt  276960
ccctctccac tgacgggcaa tggtttcaga gggtgggttc caccttgtgc acgtgtattg  277020
agtgcccacc caacaccaag ccttgaagga cactcagagg ctttatctga atacctggaa  277080
cccaccagcc actaactgag gatttagttc aggctggtct tggggcctga agaagcatta  277140
ctggggggcc ctcagcagcc taagccccat cttcctctgg cctcagcacc agagaggagg  277200
ccgtcacgag gaaggtgggc aggaggtggt cttggctatt cccatagcct caaacaagta  277260
ctccatgaga ccgagaggct ggggagagcc gtgggtctgg ggctgggctt tggctggttc  277320
ctaactcttc ctcttttgat tttaggtcac agcaattgga tgctgtcccc aaggcctcta  277380
ttccacaagc cccccccac ccctgtagcc catgtagact gtggaggagg cagatgcaga  277440
gagagcccca ggggaggtgc cctgcagtcc cgaactcgac tgacatccta caccccctggg  277500
tctccccagt gtctgggaat gtactgggga ccttcacttg tccccagtct ctcccactcc  277560
ttcaagccag ggacacccca gcctcgggca tcatgacctc gctgtgtgcc cagggagccc  277620
gtgtgaaccc attgcctgca ctaacccccct ttcttctcct ttcagcggtc ggattcatta  277680
taaggatatg tacagtttat tacgagtaat atctcccccct ctcggcttag gcaagaaatg  277740
tcctcatagg gttgcttgca aggtttgact tccactaaaa cctgctagca tccatggaat  277800
gagtgtggct tggggttctt caatatatat atttcatata tatatatata tatatctctc  277860
tctctctcta aaaaaacaga gccatctctc tttcttgcat taaactagaa aactctctta  277920
gccaacagaa tgcagtcatg tagactcgat aaagcatgga acatatttcc tccttccctt  277980
cagccttcag ccatctttgc ttgctcttag ctgaagctgc ccatcctggg gtctccacgg  278040
caccccaaat cagatacatc ccctggggga ttgtaacttt gcatttctcc cccaaccatc  278100
acctccactc tctcccctc cacccctcac ctcccaaagc ccctagccct cctcccctcc  278160
ctggcactgg cccctgctcc ccacctaggc cccctcagag accagcctca gccaaaccag  278220
agaacgtgac ccaactgtag aaataacagt gatggccggg cgcagtggct catgcctgta  278280
atcccagcac tttgggaggc caaagcagga ggatcgcttg agcccaggag tttgagacca  278340
gcctgggcaa catagcaaga accccccttct ctataaaaaa ttagccaggc attgtggcgc  278400
atgcctgtag tcccagctac ttgggaggct gaggcagaag gattgcttga gcccaggagg  278460
tggaggctgc agtgagctat gatcacacca ctgcactcca acccaggcga cagagagaga  278520
ccctgtctct ttaaaaaaaa aaaaaaaaaa aaaaaaaggc aatgaacaaa agcatggctc  278580
tacgtcttcc aaagtgagaa ttctccctcc cctccgcatc cctccagaac tgtagctcag  278640
agcccacgct gaatctgact tttctctttt ctctctctct ccctgctccc gagcagtgaa  278700
gtaatctttt tttactgacc ttttcttcca ttttttttcc tcctcttttc cattgatttg  278760
aaatatctat tttatcattc tctgcatctt tctctctcta ttttttcggc tcgtgtggat  278820
ttcttttttc tttcttctgt ttctccccac ctctcttcct ttggttctct gttcccattc  278880
ccgttttgtt tttttgtttt tgtttttgtt tttttcattt tcggtgctgc caggggccgc  278940
atgccttacc tggacatgta tcagatgctg agacacatgt ctccgcccct gggtctgggg  279000
aagaagtgtc cggccagagt ggcttacaag gtagactacc cttgccgacc accgacgtcc  279060
aggcactggg tttttttttc ttcttcttct tcttttttttt tagtgctgac cagaaacacc  279120
cggccgactc tctttttcca acgtttctct tcttttttgt ttttgattct ttttttttctt  279180
ttctcgagtc aactgatcat gaccatccct tgattctaag cagcacactg tgtccgtcct  279240
ttctgatgag tgtcttcgtg ttttgagact ccattatggc cgacatgccg gggggagggg  279300
gaggggagcg cccaggtccc cttgcacctg gtctcccagg taccaaattg gaaacaaaca  279360
cgcttcttca gggagtcaaa acccatgctt cccacttctg cccacccaga gcggccccca  279420
tgcccaggct ggggcaggcg ccttgcagag aggggcttta gcccccgaaa gcaggcgagg  279480
tcccgggtcc ccgcccctgc cacgcacacc tgaagctgat ctctgaccta gggccttggg  279540
gattcgagac cttccaagga gcaccaagaa cctctcttcc cctcccttcc ttcccctgga  279600
gtttcgtccc cagcccccgt ccctaatccc cccaagacac cccaacatgc ctctccattg  279660
ttccagagtg ggcaggcggc cgcagctgga cccctggacg gtggcacact gatgcaggcc  279720
atgcacgctg ccttggcggg gcctggggcg ggcaggcacc atggccgacg gggggtggtg  279780
catgctggct gagagagcga gcgtcctgcc gccaagcggc tggcccgggc cacccctcca  279840
gatccctgtc ctggaatctc ccttggtgcc caaggacaga tgctctgttc cctccattca  279900
tccacaagaa gttcagggat gacctttaaa gattctcccc acccaaaaag tattacccca  279960
tcatcctatt ctcccatcca ccttgatctt ccctgcgtcc ctatccatca atgctatttg  280020
tacctgcccc gtgttgccac ctcattcctt tccttcctct gtgcacccct cctcacctaa  280080
cctatatgtc tcccctcctt ctcaatcaaa gccggggaca aggttgtccc accagcatct  280140
cagacaatga gcctctcctg gcacctgtcg ctctgtgccc ctccctgccg cccccccccc  280200
cccccccggt tttcctcaag tcgcttctct cagtctctgc ttagatgaat gtgtgcgcat  280260
gtgcaagaga gggagggcga gcccttcctc tcctggtctt tgtgcaggac caccatgggt  280320
ccataagaca actttgtgca aatttgaaaa aggcaccctt tccacagaac atgcctgttg  280380
gaaaattgtt gcaatctacc aatgtggtga gaacaagaca cttttttttct atcacctggg  280440
aagctgttat atttaatata caaatcgggg gctgggcgtg gtggctcatg cctgtaatcc  280500
tagtgctttg ggaggctgag acgggaggat cacttgagcc cagttcgaga ctagcctggg  280560
caacatagcg agaccccatc tctacaaaaa gaaaaaatat tttaattaat aaataagtac  280620
```

```
ataaatctat catttccaag atgggagccc tttgtgcggt gtacaacctg cacaactgtg  280680
cacagtggcc cagtctatgt gtgtttctct atttcccacc tccttcccca ccctaccccc  280740
agtgtcccct ccagtgtcct gctctggatt taccataccc ctccccatct tcaactctgt  280800
gtttcctgcc cacttgtgtc tgaatcccca cccaagttgc cctcaccccc cttctctgtg  280860
ccacttcagc ctgggctggt gcacaccagc ccagcatcct ctcccatgcc accaagcatg  280920
gtggacagag cccctgcctg ggacatgggg aatcttttct tccctgggct ggaagggagt  280980
gcccctcacc ccttcccccct gccattgcac agagagccaa gatctggaca tgcccctgag  281040
atacacttcc cacggagcta tgaatgagtc tcgagattcc gtctgcatgc gcccctgtct  281100
gtgctgttct gtgtcacagc ctcgctgcat gcctgcgagg ggcctgcccc gtcagtgggg  281160
ggctgcctgc ctgctgcttc tcagaggaat gatgtggtct gtgcccatct gctctgtcct  281220
ggtctgggcc aagccaggga ttgggtgtgg ggagccagtg gcacccccca ccagcggctg  281280
tggtcctggc cccctcagcc ttggctgttg catgcactgc tcaaatccag cttgtgctct  281340
ttttctttgg ggtcagactg aaacggggcc atccagaaga actctggggc agggcggggg  281400
tggggcaagg gttgaggcaa accctggaaa tgccagctct caggtcaagc aggtggggga  281460
aaaaaggaga gggcagggga ccagaagtac aagagagcct tttgtgccct ccctgcgggc  281520
caccaagaga aactgagtac tgggacaggt aacctaagta agagacacct cagccgccac  281580
agctttcaga gttcttcctg ggactccctg ggtaggggcg ggcgcggctc acgggagacc  281640
caggagggat gcctgggaat gactgcgctt gccttgggtt ttctgtagcg gcttctgcgg  281700
atggacctgc ccgtcgcaga tgacaacacc gtccacttca attccaccct catggctctg  281760
atccgcacag ccctggacat caagattgcc aagggtaagg aagggacagg ggcgggcaca  281820
gacaggcgtg acagggtgga accggggatc tccctcccta ccccaaacta gaggatctgc  281880
tgtcaccacc cggatcttca ttcactcttc cattcattcg ttccacaggg tttttggggg  281940
tttggggttt tggtgtttt tttttttttt ttttgagaca gagtcttgct ctgttgccca  282000
ggcagcagtg cggtgacatg atcgcaagtc actgcagcct tgacctccca ggctcaagtg  282060
atccttccac ctcagcctcc ccagtagctg ggactacagg cacacaccac catactcggc  282120
taattttttt ttttttggtg tgacaatttc cctctgtcac ccaggctgaa gtgcagtggt  282180
gtgatcttgg ctcattgcta cctccgcctc ccgggttcaa gcgattctcc tgcctcagcc  282240
tcccaagtag ctgggattat aggtacccac cagcacaccc ggctaatttt ttatattttg  282300
ggtagagatg gggtttcacc atgttggcca ggctggtctc gaactcctga cctctggtct  282360
caaactcctg acctcaagtg atccacctgc ctcgacctct caaagtgctg gattacaggc  282420
gtgagccacc atgcccaacc taattttttta tattttttat agagatgggg tttcatcagg  282480
ttgcccaggc tggtctcaaa ctcctgggct caagcagtcc tcccaccttg gtctcccaaa  282540
atgctggtat tacaggcatg agccaccaca cccggcccat ttggcagata tttagtgcac  282600
tccttcaatg tgccagagac ccgtccaagc aggggaggac ccagcagctt acactttaga  282660
tggatgggga ggccgccact gaggaggtaa ggcagtgtct catggatccc tggggggaag  282720
gtgctccagg cagaaggact ggcaaaggcc ctgacagagg ggtgaacaca ggacacccgg  282780
ggcattgagc tgactcacct tctgagtgag ggcacgccac gcaggttcag agcagaggag  282840
gaacctgacc caactcacat ttgaacaggt tccctccggc cactgagggg atgggagacc  282900
gaaaggaggc cagtgtgggg gctgctgata tcatctgggt ggagacaggg cggcagctta  282960
gatctagggg taggctcgac gtggtggctc acgcctgtaa tctcagcact ttgggaggcc  283020
aaggtgggtg gattacttga ggtcaggatg accagcctgg ccaatgtggt gaaacccccg  283080
tctctactaa aaatacaaaa tttagccaga cgtggtggtg ggtactgtag tcccagctac  283140
tagggaggat gaggcagaag aatcgcttga acctgggagg cggaggttgc agtgagccga  283200
gatcacgcca ctgcactaca gcctgggtga cagagcaaga ctctgtctca aaaattaaat  283260
taaattaaat taactggaca tggtggcata tgcctgtggt cccagctact caggaggcag  283320
agatgagagt attgcttgaa gccaggagtt tgaggctgca gtgagtcatg atcgcaccac  283380
tgcactccag cctgggcgac agaacgagat cctagctcaa aacaacagaa agaaaaagaa  283440
aaaaacattt tttttaaagc tgagaagggg ctgggcgcag tggcttacgc ctgtaatccc  283500
agcactttgg gaggccaagg tgggtggatc acgaggtcag gagttcaaga ccagcctggc  283560
caacatggtg aaaccccatc tctaccaaaa atacaaaaag tagccgggtg tcatggtggg  283620
cgcctgtaac cccagctact ccggaggctg aggcaggaga atcacttgaa cctgggagac  283680
agaggttgca gtgagccaag atcgcgccac tgaactccag cctggatgac agagcaagac  283740
gctgtctcaa aaaaaaaaaa agctgaggcc gggcacgctg gctcacgcct gtaatagcag  283800
cactttggga ggccgaggcg ggcagatcat gaggtcaaga aatcgagacc atcctgggta  283860
acacggtgaa acccccttctc tactaaaaat acaaaaaatt agctgggtgt ggtggcacgc  283920
acctgtagtc cctgctactc agaaggctga ggcaggagaa ttgcttgaac ccgagaggca  283980
gaggttgcag cgagccgagc ttgtgccact gcactccagc ctgggtgaca gagtgagact  284040
tcatctgaaa aaaaaaaaaa aaaaaagccg agaaggctgg acatggtggc tcacacctgt  284100
aatctcagca ttttgttgag gccaggcaca gtggttcacg cctgtaatct gagcacgctg  284160
ggaggccgag gtgggtggat catttgaggt caggagttcg agatcagcct ggccaacgtg  284220
gcaaaaccct gtctctacta aaaatacaaa aattagccgg gtgtcgtggc gtgtgcctgt  284280
aatcccagca ctttgggagg ctgaagcggg tggatcactt gaggtcagga gttcaagacc  284340
agcctggtca acatggcaaa accctgtctc tactaaaaat acaaaaatta gccaggtgtg  284400
gtggcgggta cctgtaatcc cagttactag ggaggctgag gcagaagaat cacttgaacc  284460
cgggaggcag agattgcagt gagccgagat cacatcactg cactttagcc tgggcgacag  284520
agcaagactc catctcaaaa ataaaaataa aaataaaaaa taccgagaaa ttccccccaaa  284580
gacctagctc agggctcact ctccatcatt agggggaaag aagaagagga ggccagggag  284640
gcgggcagag accagggcag tgtgggctcc tggaggcagc ttctatgttt aaaagggcgg  284700
cttcaggagg aaggggacca accgtgtcag gcactgccca gagaccaagg atgacaagga  284760
tcacaagtga ctggtcatca tggtcacttt gaccagtgca gctttggcgg aggggtcagg  284820
ggtcccctgt ctggagtgca tttcggaggc ccgaaagggg atgtgatgtg atttggcagc  284880
tgattaagga cagcagggca gagagacagg cgcacaattg ccagaagaaa cggggacctg  284940
aggctcacgc ctgtaatccc agcactttgg gaggctgagg aaggtggatc acttgaggcc  285000
aggaatttga gaccagcctg gccaacatgg cgaaacccca tctccactaa aaatacaaaa  285060
attagccagg catggtggtg cacacctata atcccaacaa cttgggaagc tgagcacaag  285120
aattacttga acctgggagg cagaggttgc agtgagccga gatcaaacca ttgcactcca  285180
gcctggggga cacagcaaga ctctgtctca aaaaaaaaaa aaaaaagaaa gaaagaaaga  285240
aaagaaaaaa caaatgggac cagaaaaaag gagtgggtgg gagaggagca ggtggatagt  285300
cccacacatg ggaaggtgct gagcccagct gaaaccacta gtaagtcagg aggagggaag  285360
```

```
actgagcctc gagacatatg tgccttccag ggtcttgagg gaaagaaggg aggaagagcc  285420
aaggccacgt ggcaagactc aaggaggaag tggcagggaa ggtgggggac tggaggggtg  285480
gaggacagat attgttaatg ccaggaacaa agtgaaggta aagagagcac aaggaagttg  285540
ggagcagtgg ctcacacctg taatcccagc actttgggaa gccaaggcag gaggatcact  285600
tgaggccagg agttcaagat cagcctggcc aacacagaga gaccccatct ctacagaaaa  285660
ttttaaaatt agccaggtgt ggtgatgtgc acctgtagtc ccaactactt gggaggctgg  285720
agtgggagga tcactgggga ctgggatgtc aaggctgcag tgagctatat gatgaccaca  285780
gacatagcag cttaagacac acctatttgt cagctcacag tcctgtaggt cagaagtcca  285840
aaaagctgga ctgggctgtc tgctgagggt ctcacgaggc tgaaatcaag gtgtcagcca  285900
agctgggctc ctctctggag gatctggggg agaatctact tccaggttca ttcaggtgtt  285960
ggcagaattg aagtccttgt ggctgtagga ctgaggtctt gttttatcac tggcttttta  286020
gctttttgct cctggaagtg catgtaatcc tccatgtgct ctcattctct ctgacttccc  286080
catctgccac ccagcagaga caatactgtg cttttcaagg gctcacctga ttggggcagg  286140
cctaccctga tcatctctgt attttgaggt cagctgactt gatatttttt tttttttcttg  286200
agacagaatt tcactcttgt tgccaaggct ggagtataat agtgtgatct cagttcactg  286260
caatctccgc ctcccaggtt caagcaattc tcctgcctca gcctcctgag tagctgagat  286320
tacaggtgcc caccaccacg cccagctaaa tttttttgta tttttagtag agatggggtt  286380
tcacaaggtt ggccaggctg gttttgaact cctgacctca ggtgatccac ccgcctcagc  286440
ctcccaaagt gctgggatta caggagtgag ccaccatgcc cagcattttc tttcttttttt  286500
ttttttttt tgaaacggag tcttgttctg tcacccaggc tggagtgcag tggcgcaatc  286560
tcggctcact gcaacctcca tctcccgggt tcaagtgatt ctgcctcagc ctcccaagta  286620
ggtgggacta cagatgcgtg ccaccacgcc cggataattt tttgtatttt tagtagaaac  286680
ggggtttcac catgatagca ggatggtctc gatctcccaa cctcgtgatc tgcccacctc  286740
ggcctcccaa agtgctggga ttacaggcgt gagccaccgc accgggcctc cggtatttta  286800
attatatctg caaagtccct tcatagcctg ggcaatggtc cctagattag tgtttgaata  286860
aacagaatct tggcagaagg gcagcttttg aattctgcct accacagttc cttcgtttgt  286920
acaacgggtc taacaacacc cccactcttt gtatgtaatg ccatcgtaac tcagcttctg  286980
tggcactctg agaatctgtg ttcaggggtc ccaaaaccac ccacaggttc agtgattccc  287040
tggaagaact cagaactgag aaaagttttt atactcacag tttattacag tgaaagaata  287100
tagattaaaa tctgcaaagg gccgggcacg gtggctcacg cctgtaatcc cagcactttg  287160
ggagggcgag gtaggcagat cacttgaggt cacgagttca agaccagcct gaccaacatg  287220
gtgaaaccct gtctctacta aaaatacaaa aattagccag gcgtggtggc tggcgccagt  287280
aatcccagct acttggaagg ctaaggtagg agaatcactt gagcccagga ggcagaggtt  287340
gcagtgagcc gagatcccgc cacttcactc caggctggac agagtgagac tctattagaa  287400
aaaaaaaaaa aaaaaaaatc tgcaaagggc ctggcatggt ggcttacgcc tgtaatcctg  287460
gcactttggg agggcaaggc gggcagatca cttgaggtca caagtttgag accagcctgg  287520
ccaacatggc gaaaccccgt ctctaccaaa aatacaaaaa ttaggcatgg tgccagaccc  287580
ctgtaatccc aactactcag gaggctgagg caggagaatc gcttgaccct gggaggcaga  287640
ggttgcagtg agctgagact gtgccattgc actccagcct gtgtgacaag atcaaaactc  287700
tgtccaaaaa gaaaattagc caggtgtggt ggcatacacc tgtagtccca gctactccag  287760
aggctgaggc acaagaatcc tttcaaccca ggagatagag ctacattaag ccaagatcac  287820
gccactgcac tccagcctgg gcaacagagc aagactctgt ctcaaacaaa caaacaaatt  287880
ccaaaaacat aaaatgcgca aaggaagggc atctggggaa gggtccagga gacaccaggt  287940
gcgagcttcc agttgtctgc ctccagtgga gttgcacaga caacgcttaa ttctccctgc  288000
agtgtgtgac aacacgcacc gtgtactgcc aaccagggaa gctcacctga gccttggtgc  288060
cccagggttt ttattgaggg tttgtcatat aggcagggct gacgtagtta ctcagtctcc  288120
agtccctcca gaggtcaaac tgataccacg tggcccaaga ccccaacgat aaatcgcatt  288180
gttagaatga actgtatgga aaattatcca ggcgtggcgg cgggcggctg taatcccagc  288240
tactggggaa gctgaggcag gagaatcact tgaaactagg aggccgaggt tgcagtgagc  288300
caagatcgca ccattgcact ccagcctggg caatagagca aaaacaccat ctcaaaataa  288360
ataaataaat agaatgaact gtattggccg ggtacagtga ctcatgccta taatcccagc  288420
actttgggag gctgaggctg gaggatcgtt tgaggccagg agttcgagac cagcctaggc  288480
aacatagtga gaccctatct cttttttttta aaaaaaaaaa aaaaaaaaaa aaagaatgaa  288540
ctatacagtg tggcccaagg ccccctgcta aataaagaca ctcttcaggc aggacatttc  288600
aaaggcttag agatcacctc ccaggagcaa gtcaatgggc cagtcctttc atcggaatgt  288660
gcagggtttg gacaacacta gcctactgag ctagtcctta ctgcttagca ccccagcttc  288720
tatgacacct actggattcc cttcctgagg gtttcaaaga ctcctggaga tgtctctgaa  288780
tttggctgtc acagttgtta cttgtacccc agatgccact cagttccctg aagacaatga  288840
tcccccagat ttctcagcca ggagcccctc cacctcttgt cctcagtggg tgccaggcct  288900
catcctggag ttccacagct gagccaggct ctcggggtta cggaaggtca agagggtgtg  288960
gggacaacaa tggaagagtg ataacagtgg cagccctttg agcagatgcg ggtctcagga  289020
gaacataacg cgctttcttt tcatagttca gctcactttc taagcacact gagcttcctt  289080
tccagcaggc taaggggctg caaagggggt acagattaac ctcattcttc agattctcaa  289140
aaatggtgtc accattcatt gctggagact gggagaaagg gggcaagtcc atctcattct  289200
ctctgtctct gtctctctct ctctcttccc tgtccatctg tttctctctc ccacccaccc  289260
ctctgttctc tctgcccaga agaatctcta ttttggtttt ggttttgttt gttttgtatt  289320
gttttgagac ggagtctcgt tctgtcgccc aggctggagt gcagtggcgc agtctcaact  289380
caccactgca gcctccacct cccaggttca agcgattctc atgcctcagc ctcccgagta  289440
gttgggatta caggcgcacg ccaccacgcc cagctaattt ttgcattttt actagagact  289500
ggtttcacca tgttgaccag gctggaccct atcctctttc aagcccccca ccccaggcat  289560
tgagggcaga gccaactacc tgcctgaacc aattagcata ttaaacgtaa acccagttag  289620
catatccaaa tagcagccca cagtgacatt ctgactgtca gaatgtggat tgcttgagcc  289680
caggagctca aggcttcggt gaacaaagat tgtgccacag cctgggcaac agagtaagtc  289740
cctgtcgatc gatagataga tgatagatag atagatagat agatagatag atagatagat  289800
agatagatag ataaattttt aaaaaaaata ataggccagg cacagtggct catgcctgta  289860
atcccagcac tttgggaggc cgaggcaggc agatcacctg aggtcaggag ttcgagacca  289920
gcctggccaa catggtgaaa ccctgtctct acaaaaatat aaaaatagcc aggcagatgt  289980
ctgtaatccc agctactcag gaggctgagg taggagaatc gcttgaactc tgaaggtgga  290040
ggttgcagtg agccgagatc atgccattgc actccagcct gagtgacaga gcgagactcc  290100
```

-continued

```
atctcaaaaa taataacaat aataaaaata ataataaatg ctctggcccc aaagtggcac  290160
attacatggt gcacacccca ttagcaagga ctcatcacat ggccctgcca accacaggag  290220
gaacccccccc atgtactcag gtaggagggc caggaaacac cgtcagagag ctttaatgac  290280
tcaccccatg actggggtga gggacgaggg actggctgca ggccaagggc atgtccgtgg  290340
cagtggagac ttgggaaagg ggaaaagacc tcctctgagc cacgcacagt ggctttcatc  290400
tgtaattcca gcactttggg aggctgaggt gggaggatct tgagcccagg aggtcgagac  290460
tgcagtgagc tatgtttgtg ccacggcact ctagcctggg cgacagagca aaaccctgtc  290520
tcaaaaatca aaataaaacc aaaaccaaaa cttcctctgt tggggatgct ccagggcgtc  290580
ccagccttga acagatgggt cactgcagta ataatcctat ggcagacact gtcccaaggc  290640
tgcacgcacg ttactttgat catcaaacaa ccaggtgata gccaggcatg gtggtgcgtg  290700
cctgtagtcc cagctactca ggaagctgaa gcgggagaat ctcttgaacc tgggaggcgg  290760
aggtaacagt gagtcgagat cacatgactg cacttcagcc tgggaacaga gagagactct  290820
gtcaaaaaaa aaaaaaaaac aggccagacg cggtggctca cgcatgtaat cgccagcact  290880
ttgggaggct gaggagggtg gatcacctga ggtcaggagt ttgagaccag cctggccaac  290940
atggtgaaac cccgtctcta ctaaaaatac aaaattagtt gggcgtggtg gtgcacacct  291000
gtaatcccag ctactcggga ggctgaggca ggagaatcgc ttgaacccag gaggcagagg  291060
ttgcagtgag ctgagattgc accattgcac tccagcctgg gcaacaagag tgaaactcca  291120
tctcaaaaaa aaaacaaaaa aaaaacaacc agccaggcgc ggtggcttac gcctgtaatc  291180
ccagcacttt gggaggccga ggcgtgtgga tcacccgagg ttaggagttc gagaccagct  291240
tgaccaacat ggtgaaactc cgtctctact aaaaatacaa aaaattagcc aggcatggtg  291300
gtgcatgtct gtaatcccag ctactcggga agctgagaca ggagaattgc ttgaacccag  291360
gagtcggagg ttgcagtgag ccaagctcgt gccactgcac tccagcctgg gcaacagagc  291420
aagactctgt ctaaaaaaaa aaaaaaaaca cacacacaca cacacaacaa ccaggtgagg  291480
caagtactct tgctatcatc tccatttcac agatggagaa actgagttac taagtggtag  291540
agtaacctaa gtcatgcagc cgataactgg gagacaagat tgggacccag gtcgcccagc  291600
tgttctccat gccgggctgt ctcctgcaca gctgctccat ggtcctggcc ccaccgaaaa  291660
ccagagccca caaggtcatt ccagcagcac tgcccagggc ctcctctggg ccaggccgtt  291720
ggggaactgg agaccccatg gggaccagaa agattggggt ctcgttctcg ggagcctatg  291780
gctttgcagc tgacccagag tccagctgac acccaggcag gcagtcaggg tctgtctaca  291840
cccccattgc aggaggagcc gacaaacagc agatggacgc tgagctgcgg aaggagatga  291900
tggcgatttg gcccaatctg tcccagaaga cgctagacct gctggtcaca cctcacaagt  291960
gtaagagctg agcccagccc tgggatccaa tccaccagga cagatggagg gggagggaaa  292020
ggggaggcct ggggagagtg ttggcctggg ctggtataca cagggaccca ggacaagggc  292080
cccaaagagg cctgcccttg gtgagctcac cgtgtgtgtg cccccagcca cggacctcac  292140
cgtggggaag atctacgcag ccatgatgat catggagtac taccggcaga gcaaggccaa  292200
gaagctgcag gccatgcgcg aggagcaggt gcgctgttcg ccgctctggg gacatctggg  292260
ctggggacag tggcttgcat gtcaccacgg gaaccaactg gaatatgagg gtggctgagc  292320
cccagggcag gtccctgaaa agtaggggct gtgcacagca gctcacacct gcaatctcag  292380
tgctttgaga ggccagggca gagggatcgt ttgagaccag gatgagacca ccctgggcaa  292440
cacagtgaga ctccatctct acaaaataaa acattagcca ggcatggtgg tgcacacctg  292500
tagtcccagc tatttaggag gccaagatgg gaggatcact tgaggccagg agtgggagac  292560
cagtctgggc aacatagaaa gacccatatc tctacaaaaa aaaaataaaa ttagctgcat  292620
gtggcgccat gcacctgtgg tcccagctac ttgggaggct gaggcaggag aatcacttga  292680
acctgggagg tggaggttgc agcaagccaa gatcaagcca ctgcactcca gcccgggtga  292740
taagagcagg actctatctc aaaaaaaaaa aaaaaaaaaa aaaaaaaagt tcttgccaag  292800
gacacatcat gtggattcat tcttcattca gctgctccac caacacttat tgagtattac  292860
tgtgtgcagg gcgctgttct cagtcctcgg ggatgcaccc atggggaaaa taggccagaa  292920
tccctgccct cagggagcag acattccaag tggggaaatg ccaatggtag caaatgactg  292980
aatcgtgcaa catccagcaa agagaaagaa agtgtcgtgg gggaaagtgg agaagaatcc  293040
agaagatagg agtatccagg ggaggagggg atgcggtggg aaatgggtag ttggggagcc  293100
tccctgagaa agtgacatgt gagcaaaggc ttgaaggaaa aggggagagg gagtgagcta  293160
agcaatacct ggaagggtgt tccaggcaga ggaaacagcc agtgcaaagg ctctgaggct  293220
ggaccgtgcc tgggttgttt gggtaacagc aaagaggcca gtgtggtgga aaagagcagg  293280
gaggagacaa gggcaaggag gtgacagggc agatccttca gggccatggg agctgcagga  293340
aggactctgg ctttttcccc aagcaagtgg gagccatgga gggttctaag caaaggaggg  293400
ataggacctg actcaagtgc tcatgggcgc cctctggtgg ctcttgtgga acagtggggt  293460
tgaaggtagg agcgggagac ctgggagaag gtgcctgcag tgagagatga ggacgtggga  293520
ccaggctggg gctatgactt gggtggagga gtgagaagtg gtccagttct gcgtggaatt  293580
ggaagggtct agatggatga gacctgagag agtgtgtgtg tgtgtgtgtg tgtatactgg  293640
ggatgtcgca atgccttctg ggtaccaccg tcccaccacc ccacccttgt ccacacactg  293700
ctctctgccc cattccccag gaccggacac ccctcatgtt ccagcgcatg gagcccccgt  293760
ccccaacgca ggaagggggga cctggccaga acgccctccc ctccacccag ctggacccag  293820
gaggagccct gtgagtgtca cccctgccag ggaggtggag tgtgggggtg ccgtggtccc  293880
cacgttctgg aagctgccca agcgcccact gctaccccgg cctctgtccc ccatgcagga  293940
tggctcacga aagcggcctc aaggagagcc cgtcctgggt gacccagcgt gcccaggaga  294000
tgttccagaa gacgggcaca tggagtccgg aacaaggccc ccctaccgac atgcccaaca  294060
gccagcctaa ctctcaggtg cctctgtccc ccaactcccc aatggctccc agggcccggg  294120
tggttcaggt ggaagggatc tgggcccccc acacacacac acctgcagct ccctccctct  294180
gcagacacca gggatctgga ggtcaggccc cagagctcat ctggctttgc catctgctcc  294240
gcagtccgtg gagatgcgag agatgggcag agatggctac tccgacagcg agcactacct  294300
ccccatggaa ggccagggcc gggctgcctc catgccccgc ctccctgcag agaaccaggt  294360
gagggctttc accactgccc tggggctgga cccctcactc tgcactgggt agggccaggc  294420
ccccccacaa gcagcccagt gcatcccctc cctgccggac tcaggcctgg gtagggactc  294480
cttcagtctc tgaagcagtc tgcaggcccc acccaccacc tggtcacacc tggagcacct  294540
gcagaccctc ctccctcaca gaggacagag aggaaagtgc tccccctggg gcagagggca  294600
gtggccactg caaaatggtc tctggctgcc ctggttggag gctgcagaca ggggaggttg  294660
tggaagattt gtgggtgcag cagggttcaa cagggccagc tgagacctgc cacgaagatc  294720
acccctacac aaacacacac acacatgctc aacatacatg cacacacatg tgcagctgtg  294780
cgcctactca gatgcttgca tacacacacg tgtgtgcacg tgggcatata cacactgcac  294840
```

```
atgtactcac acatgcacac atgtacgtgc acacgtgtct gcatatggga acttggcagg  294900
tcctaggata cagtagcaga gtctggggtg ggtctggggg cagctgggct cgtatttttct  294960
gtctggtctc tgtgggagtc attgggggc acaggggtgt gtgcttgatg tgtgtctgtg  295020
tgtggccgct tcacccagct gccaggccca cctgcaggtg atcccgttgc cttggactca  295080
tgggacagag ggcccagagg catagctggc tgcccacccg gcctgaacag cgggggccca  295140
tgcacgcagc ccgcctctgg aggagaacag ggcatggctg tgagagcctg gcccgggtgc  295200
gtggcatgtg tggctgtggc gagctttccg tgtgccgtgt gtggcgtctg cacggggcag  295260
gaggctgtgc tgtgcctggc tggaccaggg tcacctgagg gcctggcctc tggctgctgg  295320
gaacgtgggt tggggagcac ccagcgtgca tgctgctgct ccctcaggac cgagctgctg  295380
ggccccagga gagggttggg acaagcccag ctgacggcca ccacatggaa gctttgagca  295440
tcggccggag ccaggggttg gggtgtgcat cgcatgaggc agagcccagg gccaggggct  295500
cgaggctgcg ccgtcctgtc tttcggtccc atgcctctgc catttgtctg tctgcatctc  295560
ctgtctgtct cctctgtacc catgggaata gaggacgccc agccccgggg gcctgggaca  295620
cccacccgcc aggactttaa cttttctttt cctccctgcc ttctccctcc gatttctctt  295680
gatgccagtg ccactcccct ccttggcttc ttctccatgc accacctcct cactctccct  295740
cttgcctttt atatttattt tcttctttct gttttttctg tgtgcaccat cccatggggc  295800
tgtgacagag gagaaggggc cggccacgtg ggaataacct cagtgtatgt accgcgcctg  295860
cccagcgccc agcagggctc cggccccctc ttcctcccca cccccctcc agggagtccc  295920
gtcatctctc accgtccccg gaccccaccc tttctttggc aatcgcaccc tctcccctcc  295980
atggagccca atccttgtgt gtggtgtcct gtgtgtgccc ctcacccata agccctggtg  296040
ggcggggcca tccccatcct caccccctacc cccttttctt cagggccccc cacgccggag  296100
gacactggct ctccaagagc ctggcccact ctgcacctct ttctgggggg cttcttctcc  296160
tgacaccacc accaacccct ggtcctgcag ctcctacctg gagcagggcc accagcgctc  296220
agctgggctg gaccctggga ggcgggcgtc tgccccatct ccctccttcc ctcctctgcc  296280
tgctgcagag aaacctgtgt gtcagggctt gacccaggga tgaagcacca gggaaaagag  296340
tgggccccca gagcctccag tgcctgggta tcccccaccc ccacccagag ctccctagct  296400
tgggcctcac cagaaggact cagacttgtg ggggcagcga gcacagcccc gttagccggg  296460
aggacccaaa gctgccatgc cggcacctg gtcctgagcc cataggtcag ccagccacag  296520
tcggaggctt ctcaccctcc caggagagca agctggggca gggatgagtg cggcagtcca  296580
gggctcccag gtttgcaccc tggatgtgga gagggcttcc ctctggccag cctgagcctg  296640
cccaactgtg gctgggcccc caggactgga gagtgaggat cagatctttc tggtcagaac  296700
ccaggatggg ctcaaaagga gcagtcctgt ctctgaggga cagaggaatc ctcaggctcc  296760
accctcagag gcctggccac acccagagcc ctgattgatc aggggggagcc aaggccccat  296820
ggcatcccct ggcccctgcc ccaggatggt cacaccgcag tcaccgaagg ccaccaccag  296880
gctgccacaa tggggcagga aggaccggga ccacttggtg ctagctgctg accccagccc  296940
accggcctgt cccctccccc agaccatctc agacaccagc cccatgaagc gttcagcctc  297000
cgtgctgggc cccaaggccc gacgcctgga cgattactcg ctggagcggg tcccgcccga  297060
ggagaaccag cggcaccacc agcggcgccg cgaccgcagc caccgcgcct ctgagcgctc  297120
cctgggccgc tacaccgatg tggacacagg tgggcagccc tgtggtgctc agggacaagc  297180
agaacagagg agaggagagg ggaggagaag gcagggcgga ggagacacta aggaagaaga  297240
aagggagagg cctccatgga gaggggacag agggggccag gcagcagctg caggaacctg  297300
ggtactaccc cctcccccca acccactgac ctgcctcggt tcaggggatc tctagggccc  297360
ccacaccttc caggtggcct cctgtgtgtg catctgcccc acctctccct cacgaccacc  297420
tgtgtgtctg tctgaccctc acccggccca ggcttgggga cagacctgag catgaccacc  297480
caatccgggg acctgccgtc gaaggagcgg gaccaggagc ggggccggcc caaggatcgg  297540
aagcatcgac agcaccacca ccaccaccac caccaccacc atccccgcc ccccgacaag  297600
gaccgctatg cccaggaacg gccggaccac ggccgggcac gggctcggga ccagcgctgg  297660
tcccgctcgc ccagcgaggg ccgagagcac atggcgcacc ggcaggtggg tgcggctgca  297720
agtgacccca ggctgggctc ggccgggagg cggggaggag agaaggggat accccatcca  297780
acagccactc taggcaaagg tccccggatc ccggctgtga ccacctccca tcctgccccc  297840
aagccaccgg ggtgcccggc ggccggagcg gacacggatc ccccaccacac cagctgccta  297900
tgctgtcccc ccagcccct tgcccacccg ccgcccctc cccgccgccc gcagctgctt  297960
gctcctcggt tgtggatcat atttgagttc tgggccgtgc cgcccgacct ttcactttcc  298020
tttaacccgg cttctgtttt tgtttcaatt atgatttctg tcctctggac gcctgtgagt  298080
aatttttgaa acttctgcta tttttaaccc cgaaacttac aaaactccat ttctcatttc  298140
tcttttcact ttgttgtgtt ggttttcgac tcctcccctc cctgtctcac tcccctcct  298200
cccctccctc ctccctgtgg ctgttgcttt tttccattca atgtcctgtg tcccccctct  298260
cctcctcctc ctcctcctcc ccctcccct cctccctctc ctcccggccc ctctcccttc  298320
gctcccctct cttcctccca atcccgtgtc tcctttgatt ttgttgtatc tttttttttg  298380
atttcctttg tttcaatttt cgtgtagggc agtagttccg taagtggaag cccagccccc  298440
tcaacatctg gtaccagcac tccgcggcgg ggccgccgcc agctccccca gacccctcc  298500
accccccggc cacacgtgtc ctattcccct gtgatccgta aggccggcgg ctcggggccc  298560
ccgcagcagc agcagcagca gcagcagcag cagcagcagc aggcggtggc caggccgggc  298620
cgggcggcca ccagcggccc tcggaggtac ccaggcccca cggccgagcc tctggccgga  298680
gatcggccgc ccacgggggg ccacagcagc ggccgctcgc ccaggatgga gaggcgggtc  298740
ccaggcccgg cccggagcga gtcccccagg gcctgtcgac acggcggggc ccggtggccg  298800
gcatctggcc cgcacgtgtc cgaggggccc ccgggtcccc ggcaccatgg ctactaccgg  298860
ggctccgact acgacgaggc cgatggcccg ggcagcgggg gcggcgagga ggccatggcc  298920
ggggcctacg acgcgccacc ccccgtacga cacgcgtcct cgggcgccac cgggcgctcg  298980
cccaggactc cccgggcctc gggcccggcc tgcgcctcgc cttctcggca cggccggcga  299040
ctccccaacg gctactaccc ggcgcacgga ctggccaggc cccgcgggcc gggctccagg  299100
aagggcctgc acgaacccta cagcgagagt gacgatgatt ggtgctaagc ccgggcgagg  299160
tggcgcccgc ccggcccccc acgcacccca cgcacacacc ccacccgagg agccgcgcag  299220
aggccgcggg ggcccagcac agagggcccg ggagagggcc agccgggaga ccccagactc  299280
tggagaggcc agggctgggc cacaagggtg tcccgcagag accctcggcc aaaagagacc  299340
ctcctgggca gccacggcgc cccccaacca gccccgatcc ccccacccac gacaggggct  299400
ctcgggtggg aggcagggag cagacaaacc acacagccaa gggatttgaa ttaactcagc  299460
catttttgga gaactttggg gaacatgaaa aaaaaaaaaa aaaaaaaaaa aaaaaacatt  299520
tttaaaagaa aaaacgggga gaaaaaaata gcttctattg atgagtttta tcatctcaat  299580
```

```
tgaatctttc ctttccctga tgaagacagc tggtggccga gtgcggcaaa gaagccagaa  299640
ggaaccagaa tcccagtgcc ctacacccac caccagacac actcacaccc acacacgttc  299700
tcagacacac acaagagtgc ttgccggtta taccaaaccc tactattact gcctgcagaa  299760
atcaatttaa aaaaataata ataacaataa acaattttaa aaaggacaaa aaaattaatg  299820
attgagaaaa gaggcatttt tttctgacat ttggtcctgc ttgaaacaac aaaagaagaa  299880
gaaaaaccca ccatcaccac cgattccttt gcttcttttt tcctttttttc ctaccttgtt  299940
tgaaaaccgt gggcttggga ctgtgaatta ttgcatgaca ttcaaaaaga aaaaaaaaat  300000
aaaaaaaagt tgaatcaaa                                                300019

SEQ ID NO: 44          moltype = DNA  length = 1000
FEATURE                Location/Qualifiers
source                 1..1000
                       mol_type = other DNA
                       organism = synthetic construct
SEQUENCE: 44
atttcattta tcaggtgttc agtgaatgct tactatgtaa cagcacagtt atcagcactg  60
gggaaataga tgagtaagat aagatttgca ctttcattag cttacatgcc ataaagaggg  120
aaataaagag aacaccagat gatgataagt ttatgctgag aattaaaatg aagtgatgaa  180
ataatgggaa tgtcaggtgg ctacttttgg tgggatggtc aggaaaggca tctctgggga  240
gataaatttt aagctcagac ctgagtgaaa agaatgagcc agccatggaa acattatgtt  300
aactcacatg gtagtttgaa atgctttatc tgatcaaagg tacttatttt tggtgacttt  360
caacaatatt aagggtctat aaaccaacac tcatttgcat aagaataact accagtgaat  420
ctttttgtat gataggtttt ttgtttgttg ttttttttgag acagagtctc gctctgtcgc  480
ccaggctgga gtgcagtggc gcgatcttgg ctcactgcaa cctctacctc cccggttcaa  540
gtgattctcc tgcctcagcc tcccaaagta gctgggatta caggtgcctg ccaccacgcc  600
tggctaattt ttgtattttt agtagagatg gggtttcacc gtgttgtcca ggctcgtgtc  660
aaacttctga cctcaagcca tccacccgcc tcggcctccc aaagtgctgg gattacaggt  720
gtgagccacc actcctggcc atgataggtt attttgtgat gaaaatacct acctcttaat  780
ttgtctgata aatttaaatt ttatgtctag atttcctaag atcagcactt ccatatttta  840
aagtaatctg tatcagacta actgctcttg cattctttta ataccagtga ctactttgat  900
tcgtgaaaca atgtattttc cttatgaata gtttttctca tggtgtattt attcttttaa  960
gttttgtttt ttaaatatac ttcacttttg aatgtttcag                         1000

SEQ ID NO: 45          moltype = DNA  length = 214
FEATURE                Location/Qualifiers
source                 1..214
                       mol_type = other DNA
                       organism = synthetic construct
SEQUENCE: 45
acagcagcaa aagcagcaac agcagcagca gcagcagcag cagggggacc tatcaggaca  60
gagttcacat ccatgtgaaa ggccagccac cagttcagga gcacttggga gtgatctagg  120
tgatgctatg agtgaagaag acatgcttca ggcagctgtg accatgtctt tagaaactgt  180
cagaaatgat ttgaaaacag aaggaaaaaa ataa                               214

SEQ ID NO: 46          moltype = DNA  length = 135
FEATURE                Location/Qualifiers
source                 1..135
                       mol_type = other DNA
                       organism = synthetic construct
SEQUENCE: 46
aacttgttta ttgcagctta taatggttac aaataaagca atagcatcac aaatttcaca  60
aataaagcat ttttttcact gcattctagt tgtggtttgt ccaaactcat caatgtatct  120
tatcatgtct ggatc                                                    135

SEQ ID NO: 47          moltype = DNA  length = 208
FEATURE                Location/Qualifiers
source                 1..208
                       mol_type = other DNA
                       organism = synthetic construct
SEQUENCE: 47
tccccagcat gcctgctatt ctcttcccaa tcctccccct tgctgtcctg ccccacccca  60
ccccccagaa tagaatgaca cctactcaga caatgcgatg caatttcctc attttattag  120
gaaaggacag tgggagtggc accttccagg gtcaaggaag gcacggggga ggggcaaaca  180
acagatggct ggcaactaga aggcacag                                      208

SEQ ID NO: 48          moltype = DNA  length = 214
FEATURE                Location/Qualifiers
source                 1..214
                       mol_type = other DNA
                       organism = synthetic construct
SEQUENCE: 48
ctacttcttg ccctcggtct tcaggtcgtt gcgcacggtc tccaggctca tggtcacggc  60
ggcctgcagc atgtcctcct cgctcatggc gtcgcccagg tcgctgccca gggcgccgct  120
gctggtggcg gggcgctcgc aggggtggct gctctggccg ctcaggtcgc cctgctgctg  180
ctgctgctgc tgctgctgct gcttctgctg ctgt                               214

SEQ ID NO: 49          moltype = DNA  length = 110
FEATURE                Location/Qualifiers
source                 1..110
```

-continued

```
                        mol_type = other DNA
                        organism = synthetic construct
SEQUENCE: 49
ctgtaaatga atgagaaaac cggtttagaa agtgcacagc tgtcagggaa gtcaacactt  60
cagtgagcat gtgaccatgt ggagtcagct tcctgtttcg tgctgcaatc             110

SEQ ID NO: 50           moltype = DNA  length = 374
FEATURE                 Location/Qualifiers
source                  1..374
                        mol_type = other DNA
                        organism = synthetic construct
SEQUENCE: 50
gtaaggcctg ctcaccattc atcatgttcg ctaccttcac actttatctg acatacgagc  60
tccatgtgat ttttgcttta cattattctt cattccctct ttaatcatat taagaatctt  120
aagtaaattt gtaatctact aaatttccct ggattaagga gcagttacca aaagaaaaaa  180
aaaaaaaaaa gctagatgtg gtggctcaca tctgtaatcc cagcactttg ggaaaccaag  240
gcaggagagg attgctagaa catttaatga atactttaac ataataattt aaacttcaca  300
gtaatttgta cagtctccaa aaattcctta gacatcatgg atatttttct ttttttgaga  360
tggagtcttg ctct                                                    374

SEQ ID NO: 51           moltype = DNA  length = 136
FEATURE                 Location/Qualifiers
source                  1..136
                        mol_type = other DNA
                        organism = synthetic construct
                        note = Target site
SEQUENCE: 51
tttaagctca gacctgagtg aaaagaattt gagacagagt ctcgctctgt cgcctttcct  60
aagatcagca cttccatatt tggtgacttt caacaatatt aagggtctat aaaccaacac  120
tcatttgcat aagaat                                                  136
```